US 11,660,093 B2

(12) United States Patent
Bakos et al.

(10) Patent No.: US 11,660,093 B2
(45) Date of Patent: May 30, 2023

(54) METHOD OF APPLYING BUTTRESS TO END EFFECTOR OF SURGICAL STAPLER

(71) Applicant: Ethicon LLC, Guaynabo, PR (US)

(72) Inventors: Gregory J. Bakos, Mason, OH (US); Michael J. Vendely, Lebanon, OH (US); Mark S. Zeiner, Mason, OH (US); Heather Strang, West Chester, OH (US); Pamela M. Ridgley, Lebanon, OH (US); Christopher A. Denzinger, Cincinnati, OH (US); Christopher Q. Seow, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/022,520

(22) Filed: Sep. 16, 2020

(65) Prior Publication Data

US 2022/0079593 A1 Mar. 17, 2022

(51) Int. Cl.
*A61B 17/00* (2006.01)
*A61B 17/072* (2006.01)

(52) U.S. Cl.
CPC .......... *A61B 17/07292* (2013.01); *A61B 2017/00526* (2013.01); *A61B 2017/07257* (2013.01);
(Continued)

(58) Field of Classification Search
CPC .... A61B 17/07292; A61B 2017/00424; A61B 2017/00477; A61B 2017/0053;
(Continued)

(56) References Cited

U.S. PATENT DOCUMENTS 2,131,093 A 4/1936 Cage
2,467,190 A 10/1945 Cowles et al.
(Continued)

FOREIGN PATENT DOCUMENTS

EP 2 090 248 A2 8/2009
EP 3 072 460 A2 9/2016
(Continued)

OTHER PUBLICATIONS

U.S. Appl. No. 17/022,186, entitled "Apparatus and Method to Apply Buttress to End Effector of Surgical Stapler via Fixed Base," filed Sep. 16, 2020.
(Continued)

*Primary Examiner* — Robert F Long
(74) *Attorney, Agent, or Firm* — Frost Brown Todd LLP

(57) ABSTRACT

A method is provided for applying an adjunct element to a surgical stapler end effector having first and second stapling surfaces using an applicator. The method includes providing the end effector in an open state in which the first and second stapling surfaces are spaced apart. With the end effector in the open state, at least a portion of the applicator is positioned between the first and second stapling surfaces. Without engaging a closure system input feature of the surgical stapler, a portion of the end effector is compressively engaged by the applicator to thereby secure the adjunct element to one of the first or second stapling surfaces. The applicator and the end effector are withdrawn relatively away from one another so that the adjunct element remains attached to the one of the first or second stapling surfaces of the end effector.

20 Claims, 80 Drawing Sheets

(52) U.S. Cl.
CPC ............... *A61B 2017/07271* (2013.01); *A61B 2017/07278* (2013.01); *A61B 2017/07285* (2013.01)

(58) Field of Classification Search
CPC ........... A61B 2017/07264; A61B 2017/07271; A61B 2017/07278; A61B 2017/07285; A61B 2017/00526; A61B 2017/07257
USPC .......................................... 227/175.1–182.1
See application file for complete search history.

(56) References Cited

U.S. PATENT DOCUMENTS

| | | | |
|---|---|---|---|
| 3,117,757 A | 1/1964 | Sampson | |
| 3,809,094 A * | 5/1974 | Cook | A61B 13/00 600/218 |
| 3,904,033 A * | 9/1975 | Haerr | A61B 17/34 206/349 |
| 4,506,267 A * | 3/1985 | Harmuth | H01Q 17/001 343/846 |
| 4,930,674 A * | 6/1990 | Barak | A61B 17/072 227/179.1 |
| 5,358,510 A * | 10/1994 | Luscombe | A61B 17/0643 606/151 |
| 5,372,868 A * | 12/1994 | Prewo | E04C 2/34 428/120 |
| 5,655,698 A * | 8/1997 | Yoon | A61B 17/07207 227/176.1 |
| 5,697,542 A | 12/1997 | Knodel et al. | |
| 5,752,965 A | 5/1998 | Francis et al. | |
| 5,769,892 A | 6/1998 | Kingwell | |
| 5,797,931 A * | 8/1998 | Bito | A61B 17/1285 606/127 |
| 5,810,855 A | 9/1998 | Rayburn et al. | |
| 5,833,695 A * | 11/1998 | Yoon | A61B 17/07207 606/139 |
| 5,901,895 A | 5/1999 | Heaton et al. | |
| 5,902,312 A * | 5/1999 | Frater | A61B 17/07207 606/148 |
| 6,019,791 A | 2/2000 | Wood | |
| 6,099,551 A | 8/2000 | Gabbay | |
| 6,273,897 B1 | 8/2001 | Dalessandro et al. | |
| 6,325,810 B1 * | 12/2001 | Hamilton | A61B 17/07207 227/175.1 |
| 6,592,597 B2 | 7/2003 | Grant et al. | |
| 6,638,285 B2 | 10/2003 | Gabbay | |
| 7,147,138 B2 | 12/2006 | Shelton, IV | |
| 7,377,928 B2 | 5/2008 | Zubik et al. | |
| 7,380,696 B2 | 6/2008 | Shelton, IV et al. | |
| 7,559,937 B2 | 7/2009 | De La Torre et al. | |
| 7,665,646 B2 | 2/2010 | Prommersberger | |
| 7,708,180 B2 | 5/2010 | Murray et al. | |
| 7,845,533 B2 | 12/2010 | Marczyk et al. | |
| 8,052,697 B2 | 11/2011 | Phillips | |
| 8,210,411 B2 | 7/2012 | Yates et al. | |
| 8,317,790 B2 | 11/2012 | Bell et al. | |
| 8,348,130 B2 * | 1/2013 | Shah | A61B 17/07207 227/180.1 |
| 8,408,439 B2 | 4/2013 | Huang et al. | |
| 8,453,904 B2 | 6/2013 | Eskaros et al. | |
| 8,453,914 B2 | 6/2013 | Laurent et al. | |
| 8,464,925 B2 * | 6/2013 | Hull | A61B 50/30 227/179.1 |
| 8,864,009 B2 * | 10/2014 | Shelton, IV | A61B 17/00491 227/175.1 |
| 8,920,444 B2 | 12/2014 | Hiles et al. | |
| 9,186,142 B2 | 11/2015 | Fanelli et al. | |
| 9,211,120 B2 | 12/2015 | Scheib et al. | |
| 9,220,501 B2 | 12/2015 | Baxter, III et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,833,238 B2 * | 12/2017 | Baxter, III | A61B 17/30 |
| 9,839,421 B2 | 12/2017 | Zerkle et al. | |
| 9,844,378 B2 | 12/2017 | Casasanta et al. | |
| 9,925,647 B2 * | 3/2018 | Lafond | G01N 1/02 |
| 9,999,408 B2 * | 6/2018 | Boudreaux | A61B 17/00491 |
| 10,092,292 B2 | 10/2018 | Boudreaux et al. | |
| 10,166,023 B2 | 1/2019 | Vendely et al. | |
| 10,213,198 B2 | 2/2019 | Aronhalt et al. | |
| 10,349,939 B2 | 7/2019 | Shelton, IV et al. | |
| 10,869,663 B2 | 12/2020 | Shelton, IV et al. | |
| 10,932,779 B2 * | 3/2021 | Vendely | B32B 7/05 |
| 10,993,716 B2 | 5/2021 | Shelton, IV et al. | |
| 11,033,269 B2 | 6/2021 | Vendely et al. | |
| 11,045,196 B2 | 6/2021 | Olson et al. | |
| 11,051,812 B2 | 7/2021 | Hopkins et al. | |
| 11,058,418 B2 | 7/2021 | Shelton, IV et al. | |
| 11,065,000 B2 | 7/2021 | Shankarsetty et al. | |
| 11,185,327 B2 * | 11/2021 | Harris | A61B 17/07292 |
| 2005/0070929 A1 | 3/2005 | Dalessandro et al. | |
| 2005/0267325 A1 * | 12/2005 | Bouchier | A61B 17/06004 623/23.72 |
| 2006/0173470 A1 * | 8/2006 | Oray | A61B 17/07207 606/151 |
| 2007/0162056 A1 * | 7/2007 | Gerbi | A61B 17/07207 606/153 |
| 2007/0179528 A1 * | 8/2007 | Soltz | A61B 17/07207 606/219 |
| 2007/0246505 A1 * | 10/2007 | Pace-Floridia | A61L 31/044 227/175.1 |
| 2008/0128469 A1 * | 6/2008 | Dalessandro | A61B 17/07207 227/154 |
| 2008/0169329 A1 * | 7/2008 | Shelton | A61B 17/32 227/180.1 |
| 2008/0203134 A1 | 8/2008 | Shah et al. | |
| 2009/0001122 A1 * | 1/2009 | Prommersberger | A61B 17/072 227/176.1 |
| 2009/0084825 A1 * | 4/2009 | Larson | A61B 17/24 227/176.1 |
| 2009/0206125 A1 | 8/2009 | Huitema et al. | |
| 2009/0206126 A1 * | 8/2009 | Huitema | A61B 50/30 227/175.1 |
| 2010/0087840 A1 * | 4/2010 | Ebersole | A61B 17/07207 606/151 |
| 2010/0163598 A1 * | 7/2010 | Belzer | A61B 17/115 227/181.1 |
| 2010/0243393 A1 | 9/2010 | Mahu | |
| 2011/0017802 A1 * | 1/2011 | Ma | A61B 34/76 227/176.1 |
| 2011/0087279 A1 * | 4/2011 | Shah | A61B 17/07207 606/219 |
| 2011/0248064 A1 * | 10/2011 | Marczyk | A61B 17/07207 227/114 |
| 2012/0018487 A1 * | 1/2012 | Bettuchi | A61B 17/07292 227/175.1 |
| 2012/0080336 A1 | 4/2012 | Shelton, IV et al. | |
| 2012/0145767 A1 * | 6/2012 | Shah | A61B 17/07207 227/176.1 |
| 2012/0265154 A1 * | 10/2012 | Criscuolo | A61B 17/1155 604/258 |
| 2013/0037596 A1 * | 2/2013 | Bear | A61B 17/07207 227/176.1 |
| 2013/0075447 A1 * | 3/2013 | Weisenburgh, II | A61B 17/00491 227/176.1 |
| 2013/0146642 A1 * | 6/2013 | Shelton, IV | A61B 17/068 227/177.1 |
| 2013/0214030 A1 * | 8/2013 | Aronhalt | A61B 17/0644 227/176.1 |
| 2013/0256378 A1 * | 10/2013 | Schmid | A61B 17/068 227/176.1 |
| 2014/0058194 A1 * | 2/2014 | Soletti | B05B 13/0436 600/36 |
| 2014/0131418 A1 * | 5/2014 | Kostrzewski | A61B 17/068 227/176.1 |
| 2014/0131419 A1 * | 5/2014 | Bettuchi | A61B 17/07292 227/176.1 |

(56) References Cited

U.S. PATENT DOCUMENTS

| | | | |
|---|---|---|---|
| 2014/0158741 A1* | 6/2014 | Woodard, Jr. | A61B 17/0401 227/175.1 |
| 2014/0239036 A1 | 8/2014 | Zerkle et al. | |
| 2014/0288386 A1* | 9/2014 | Zand | A61B 5/14556 600/301 |
| 2014/0291379 A1* | 10/2014 | Schellin | A61B 17/068 227/176.1 |
| 2015/0041168 A1 | 2/2015 | Dostinov | |
| 2015/0076212 A1 | 3/2015 | Shelton, IV | |
| 2015/0305743 A1* | 10/2015 | Casasanta | A61B 17/068 227/176.1 |
| 2015/0351758 A1* | 12/2015 | Shelton, IV | A61B 17/0644 606/219 |
| 2015/0351761 A1* | 12/2015 | Shelton, IV | A61B 17/07207 606/219 |
| 2016/0287254 A1* | 10/2016 | Baxter, III | A61B 17/0644 |
| 2017/0055980 A1* | 3/2017 | Vendely | A61B 17/07207 |
| 2017/0056016 A1 | 3/2017 | Barton et al. | |
| 2017/0056018 A1* | 3/2017 | Zeiner | A61B 17/34 |
| 2017/0137155 A1 | 5/2017 | Pape | |
| 2017/0281181 A1* | 10/2017 | Matonick | A61B 17/07292 |
| 2017/0303952 A1* | 10/2017 | Nativ | A61B 17/105 |
| 2018/0235617 A1* | 8/2018 | Shelton, IV | A61B 50/20 |
| 2018/0235626 A1* | 8/2018 | Shelton, IV | A61B 17/07292 |
| 2019/0290267 A1 | 9/2019 | Baxter, III et al. | |
| 2019/0321044 A1* | 10/2019 | Franklin, Sr. | A61B 17/1155 |
| 2019/0343520 A1 | 11/2019 | Williams et al. | |
| 2020/0015817 A1* | 1/2020 | Harris | A61B 17/07207 |
| 2020/0205823 A1* | 7/2020 | Vendely | A61B 17/07207 |
| 2020/0205825 A1 | 7/2020 | Vendely et al. | |
| 2020/0261080 A1 | 8/2020 | Bakos et al. | |
| 2020/0281587 A1 | 9/2020 | Schmid et al. | |
| 2020/0405436 A1 | 12/2020 | Shelton, IV et al. | |
| 2021/0106329 A1 | 4/2021 | Williams et al. | |
| 2021/0177411 A1 | 6/2021 | Williams | |

FOREIGN PATENT DOCUMENTS

| | | | |
|---|---|---|---|
| EP | 3 632 342 A2 | | 4/2020 |
| EP | 3 673 831 A2 | | 7/2020 |
| JP | 2015512723 A | * | 4/2015 |
| JP | 2015513958 A | * | 5/2015 |
| JP | 2016506814 A | * | 3/2016 |

OTHER PUBLICATIONS

U.S. Appl. No. 17/022,209, entitled "Apparatus and Method to Apply Buttress to End Effector of Surgical Stapler via Driven Member," filed Sep. 16, 2020.
U.S. Appl. No. 17/022,214, entitled "Apparatus and Method to Apply Buttresses Separately to Jaws of End Effector of Surgical Stapler," filed Sep. 16, 2020.
U.S. Appl. No. 17/022,414, entitled "Apparatus and Method to Close End Effector of Surgical Stapler onto Buttress," filed Sep. 16, 2020.
U.S. Appl. No. 17/022,419, entitled "Apparatus and Method to Detect Full Seating of Buttress Applicator in End Effector of Surgical Stapler," filed Sep. 16, 2020.
U.S. Appl. No. 17/022,442, entitled "Apparatus and Method to Apply Buttress to End Effector of Surgical Stapler with Authentication," filed Sep. 16, 2020.
U.S. Appl. No. 17/022,186.
U.S. Appl. No. 17/022,209.
U.S. Appl. No. 17/022,214.
U.S. Appl. No. 17/022,414.
U.S. Appl. No. 17/022,419.
U.S. Appl. No. 17/022,442.
Gore Seamguard Bioabsorbable Staple Line Reinforcement, Configured for Endoscopic Surgical Staplers, Instructions for Use, Jun. 2019, 136 pgs.
International Search Report and Written Opinion dated Nov. 30, 2021 for Application No. PCT/IB2021/058337, 16 pgs.
International Search Report and Written Opinion dated Nov. 29, 2021 for Application No. PCT/IB2021/058165, 14 pgs.
International Search Report and Written Opinion dated Dec. 2, 2021 for Application No. PCT/IB2021/058414, 14 pgs.
International Search Report and Written Opinion dated Nov. 24, 2021 for Application No. PCT/IB2021/058239, 12 pgs.
International Search Report and Written Opinion dated Nov. 30, 2021 for Application No. PCT/IB2021/058396, 14 pgs.
International Search Report and Written Opinion dated Dec. 2, 2021 for Application No. PCT/IB2021/058412, 15 pgs.
International Search Report and Written Opinion dated Nov. 25, 2021 for Application No. PCT/IB2021/058400, 15 pgs.
International Search Report and Written Opinion dated Feb. 16, 2022 for Application No. PCT/IB2021/060163, 15 pgs.

* cited by examiner

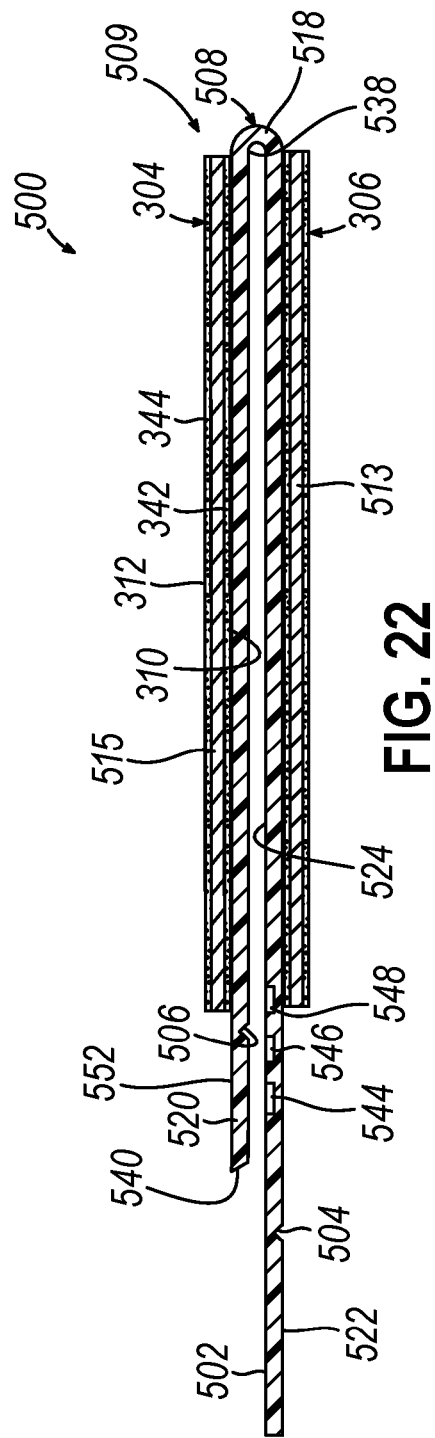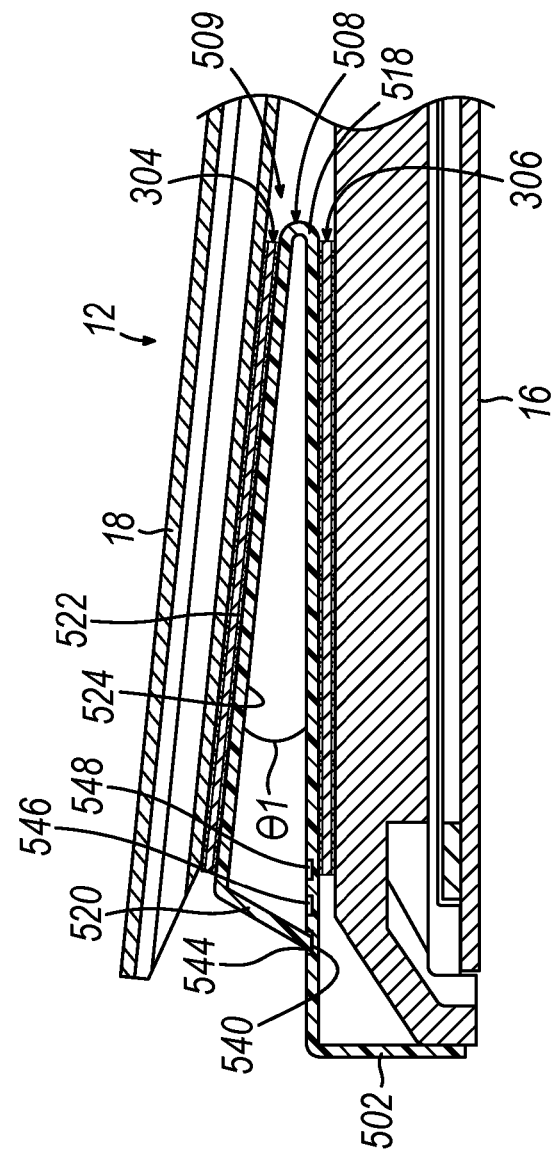

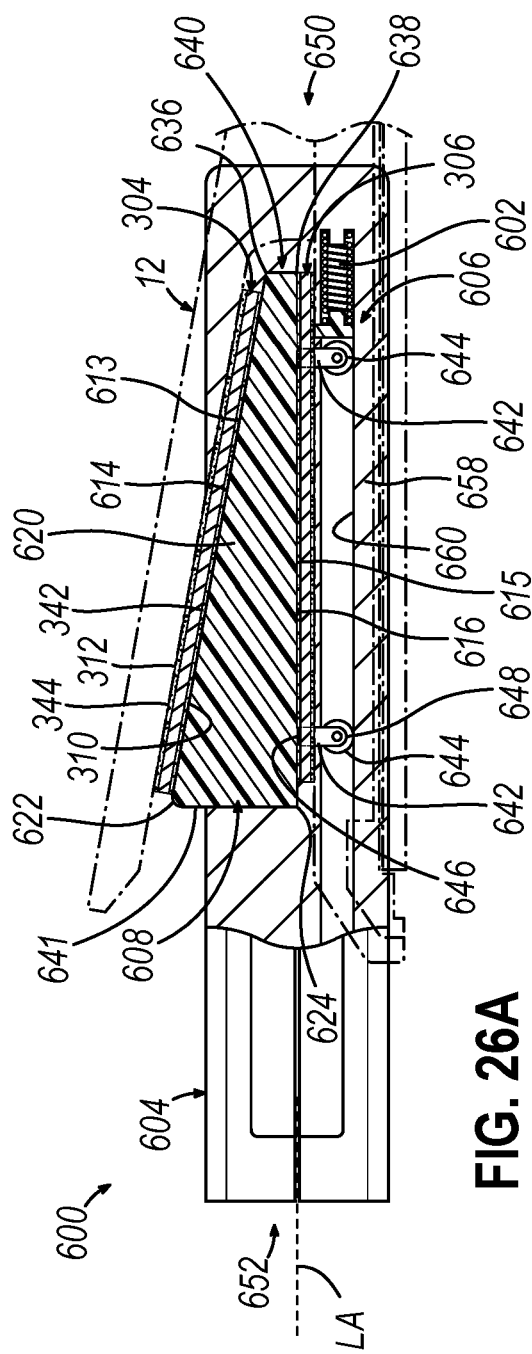
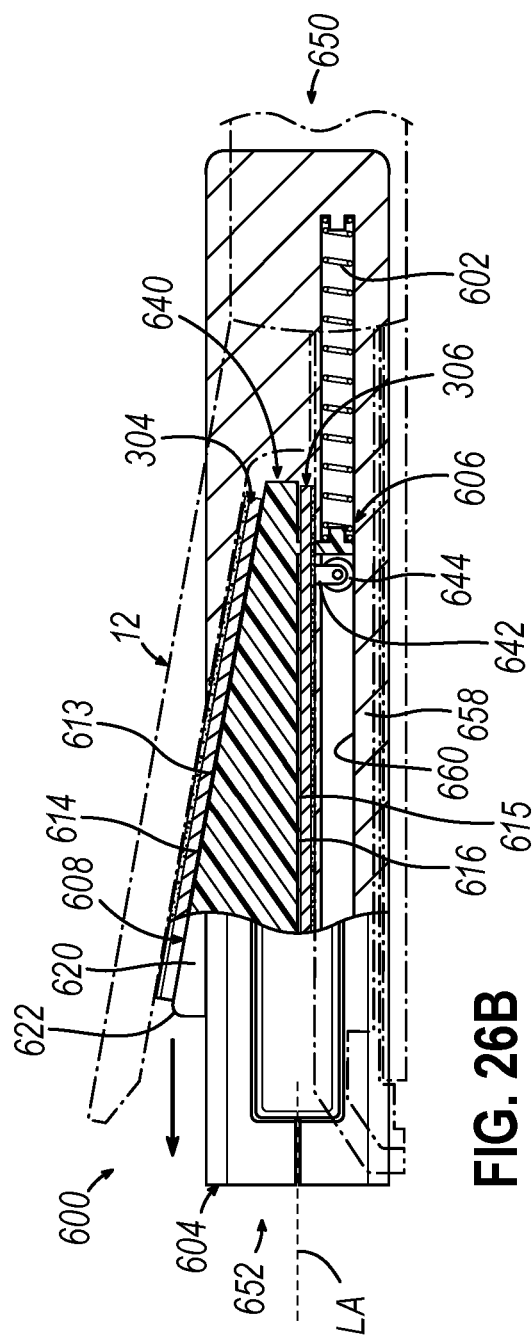

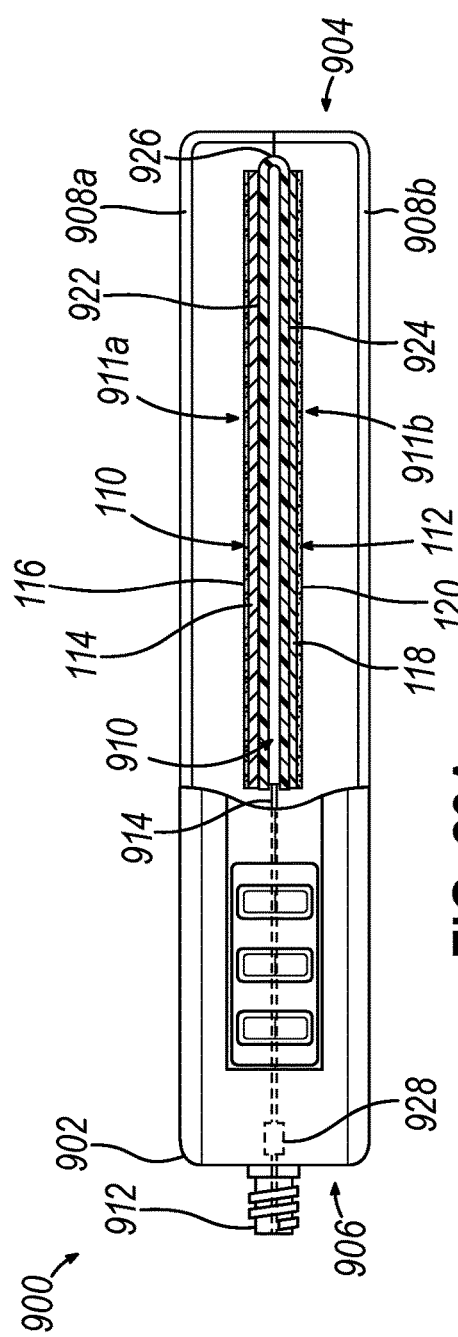
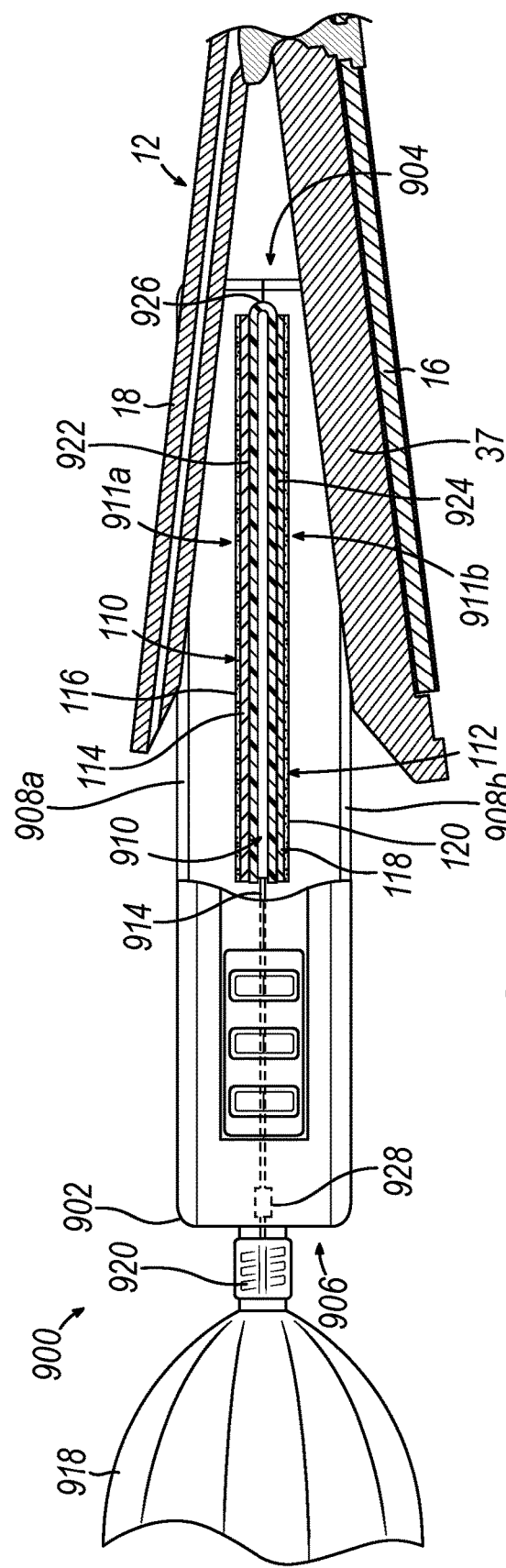
FIG. 29A
FIG. 29B

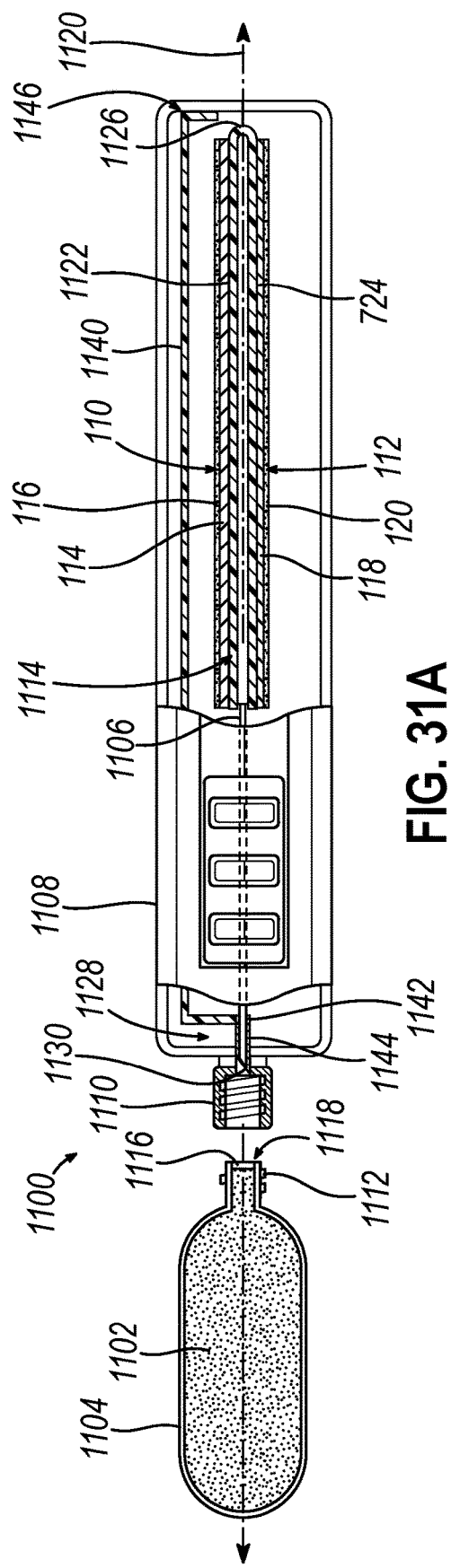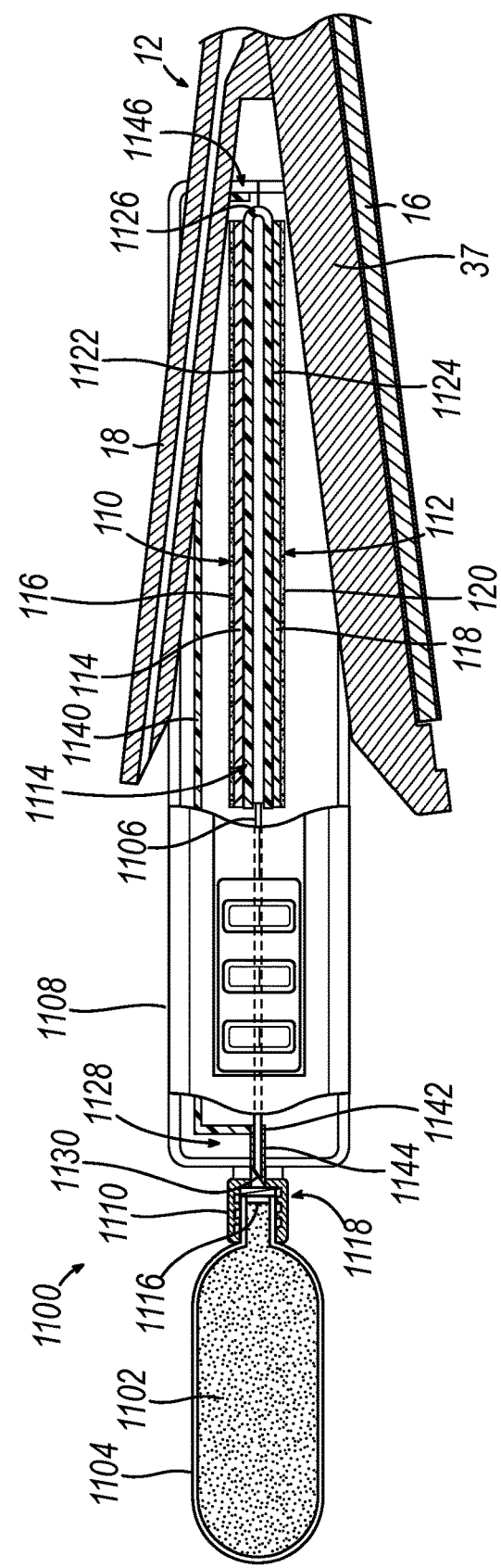
FIG. 31A
FIG. 31B

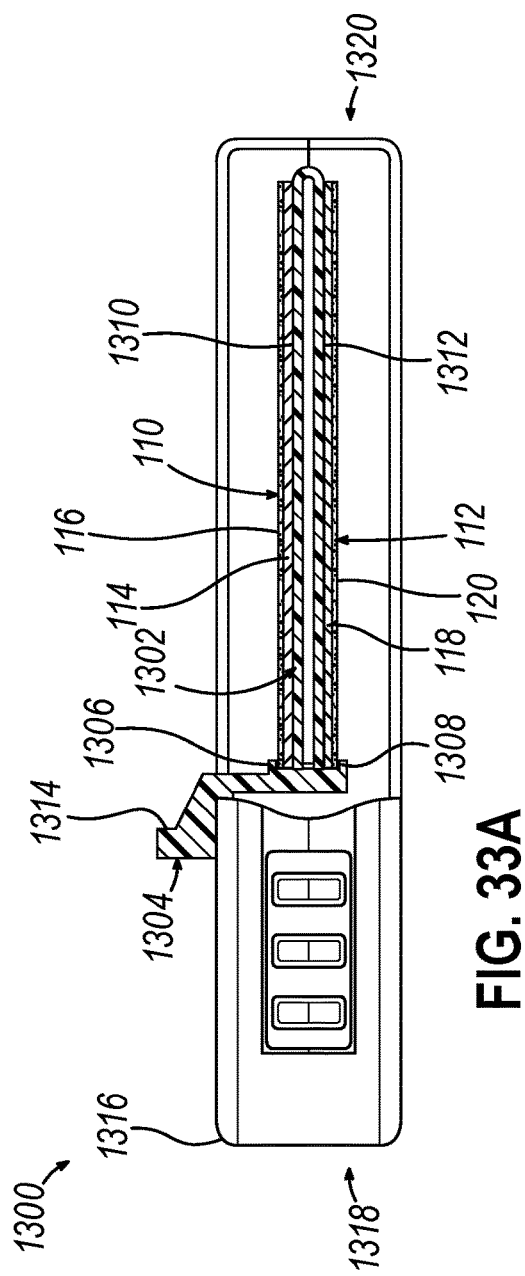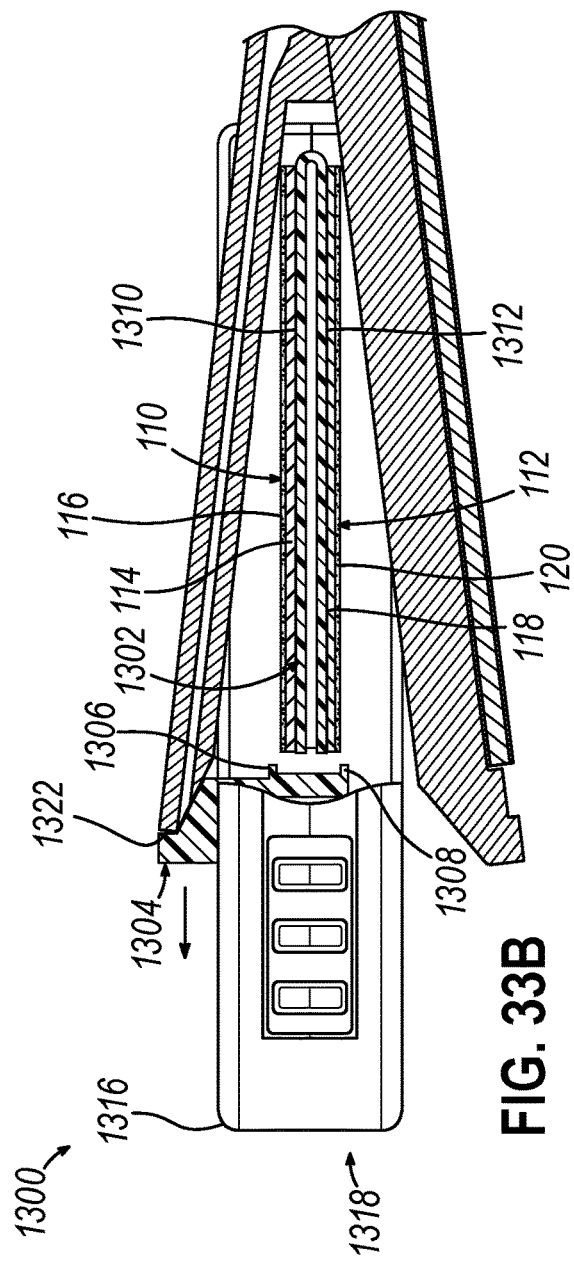

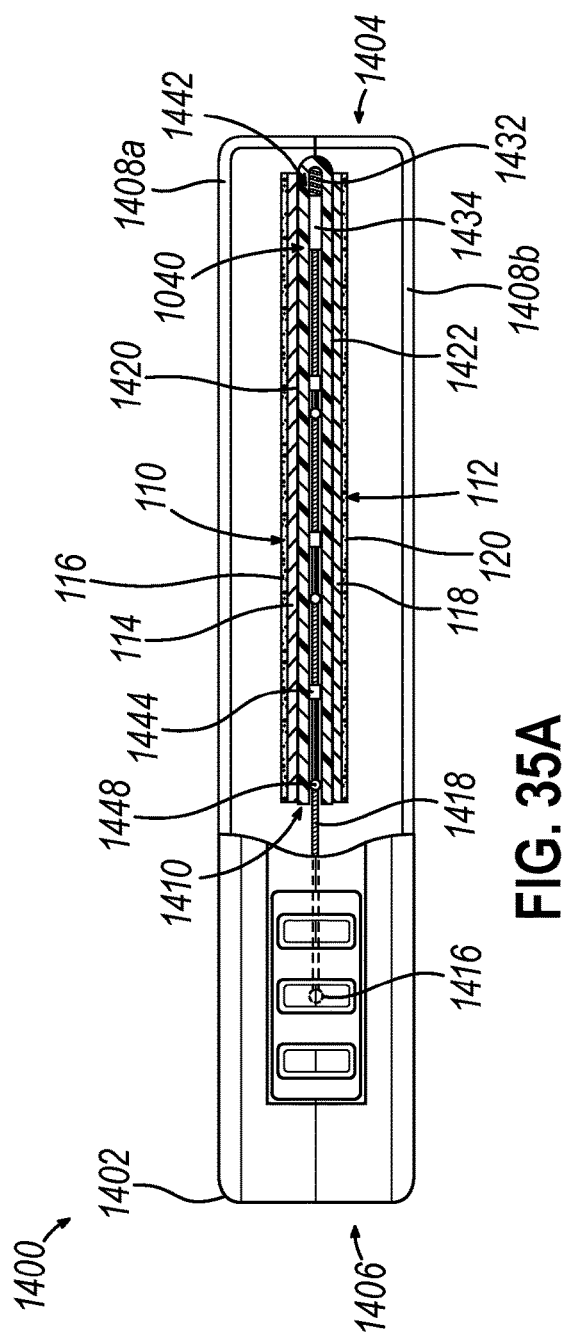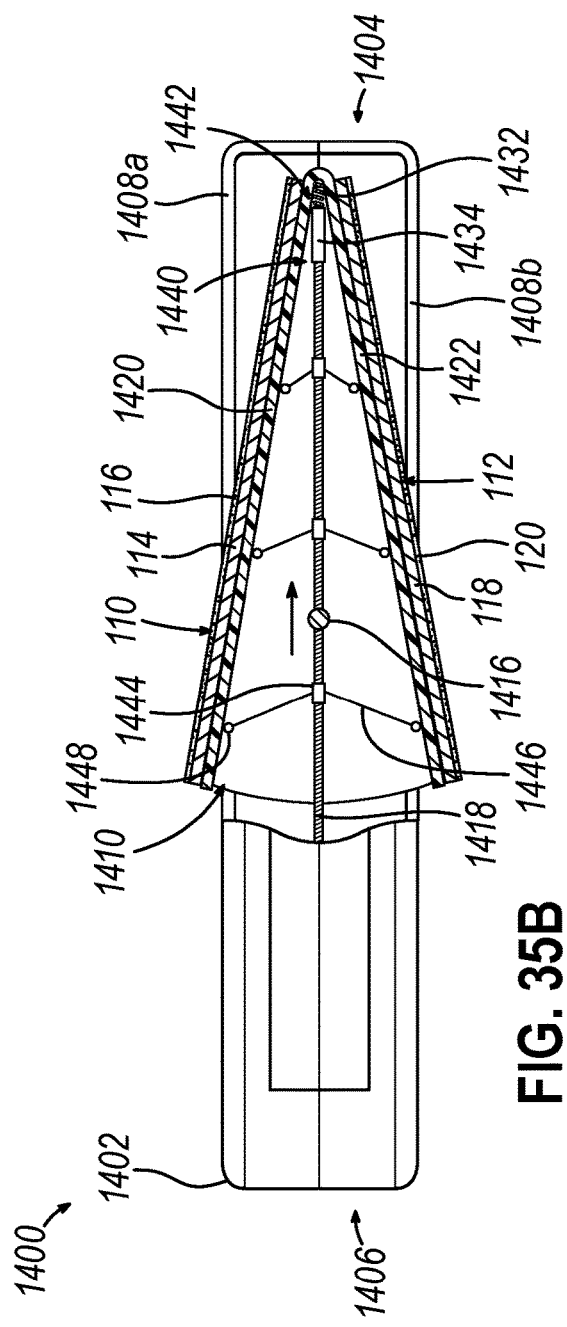

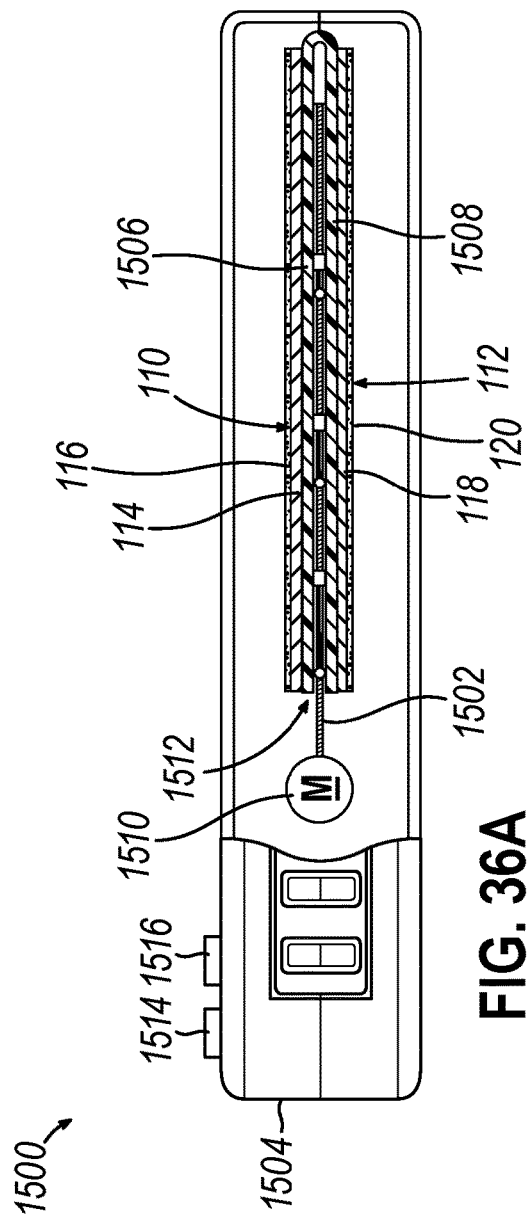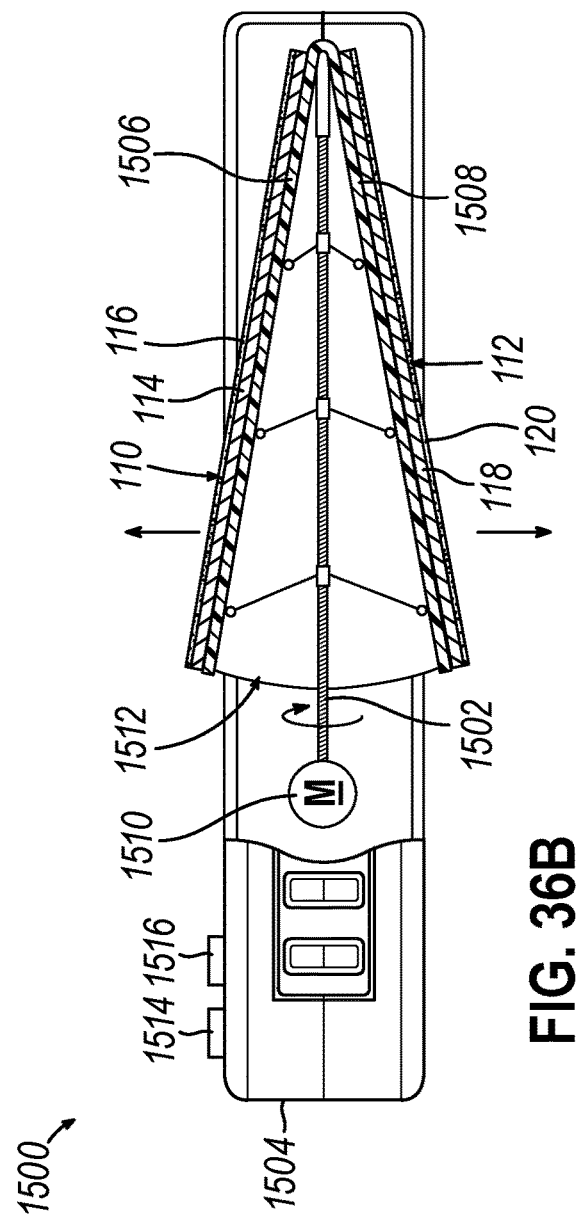
FIG. 36A
FIG. 36B

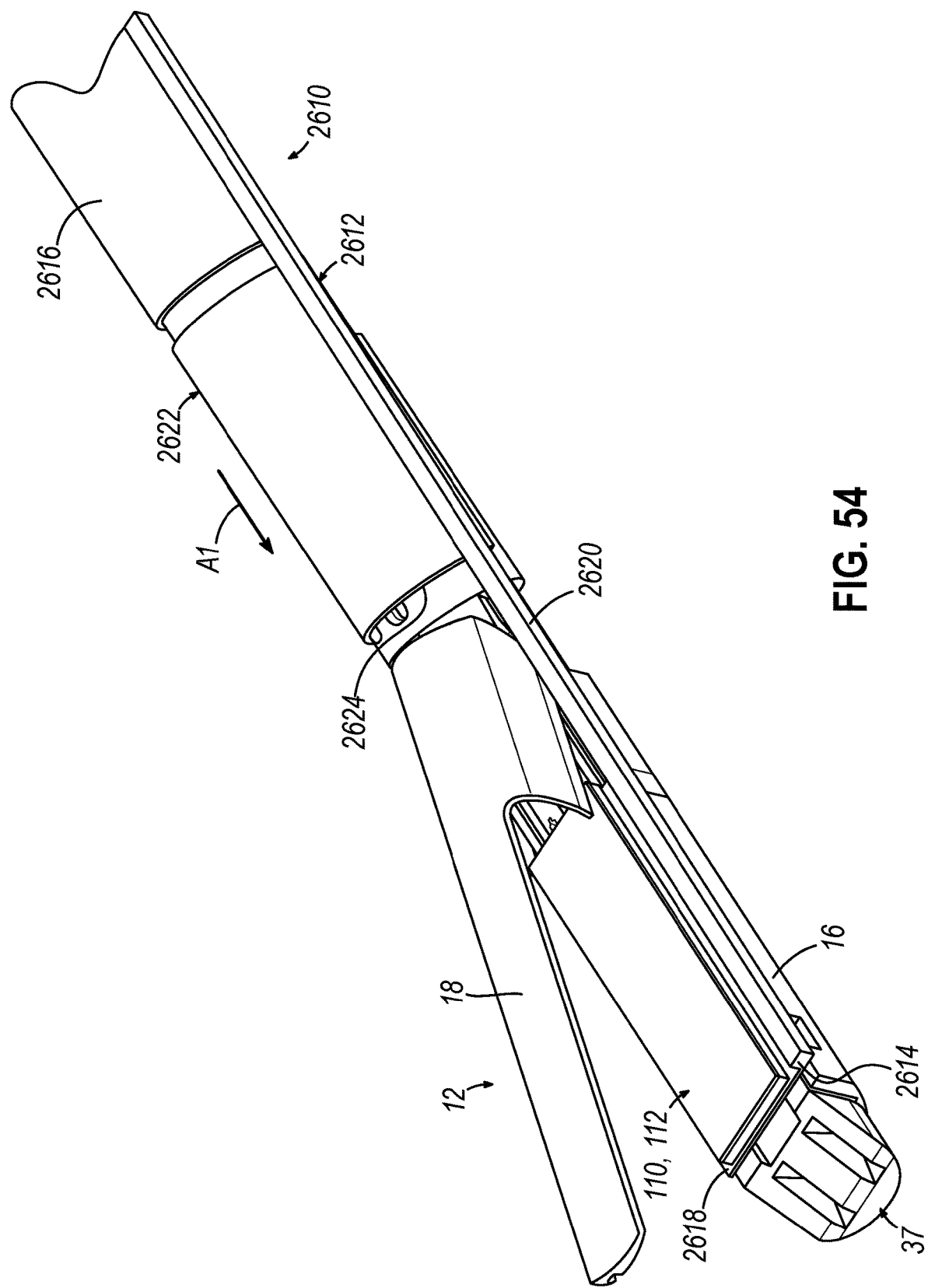

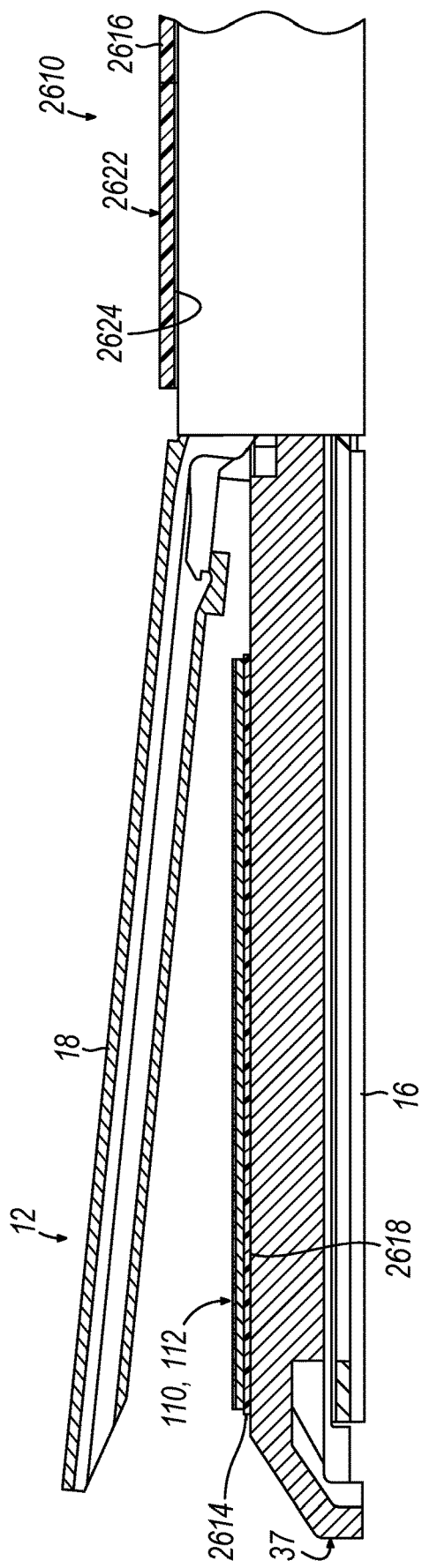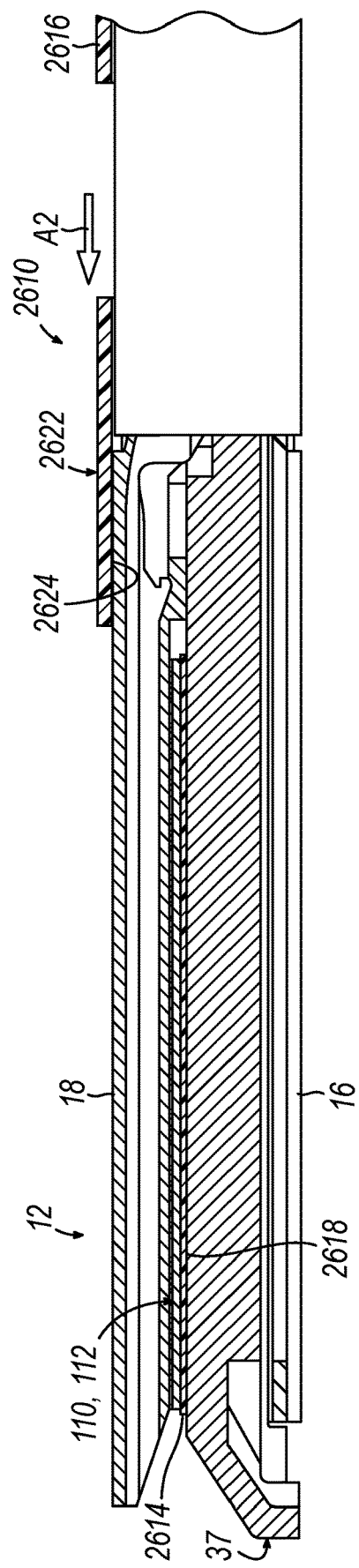
FIG. 55A
FIG. 55B

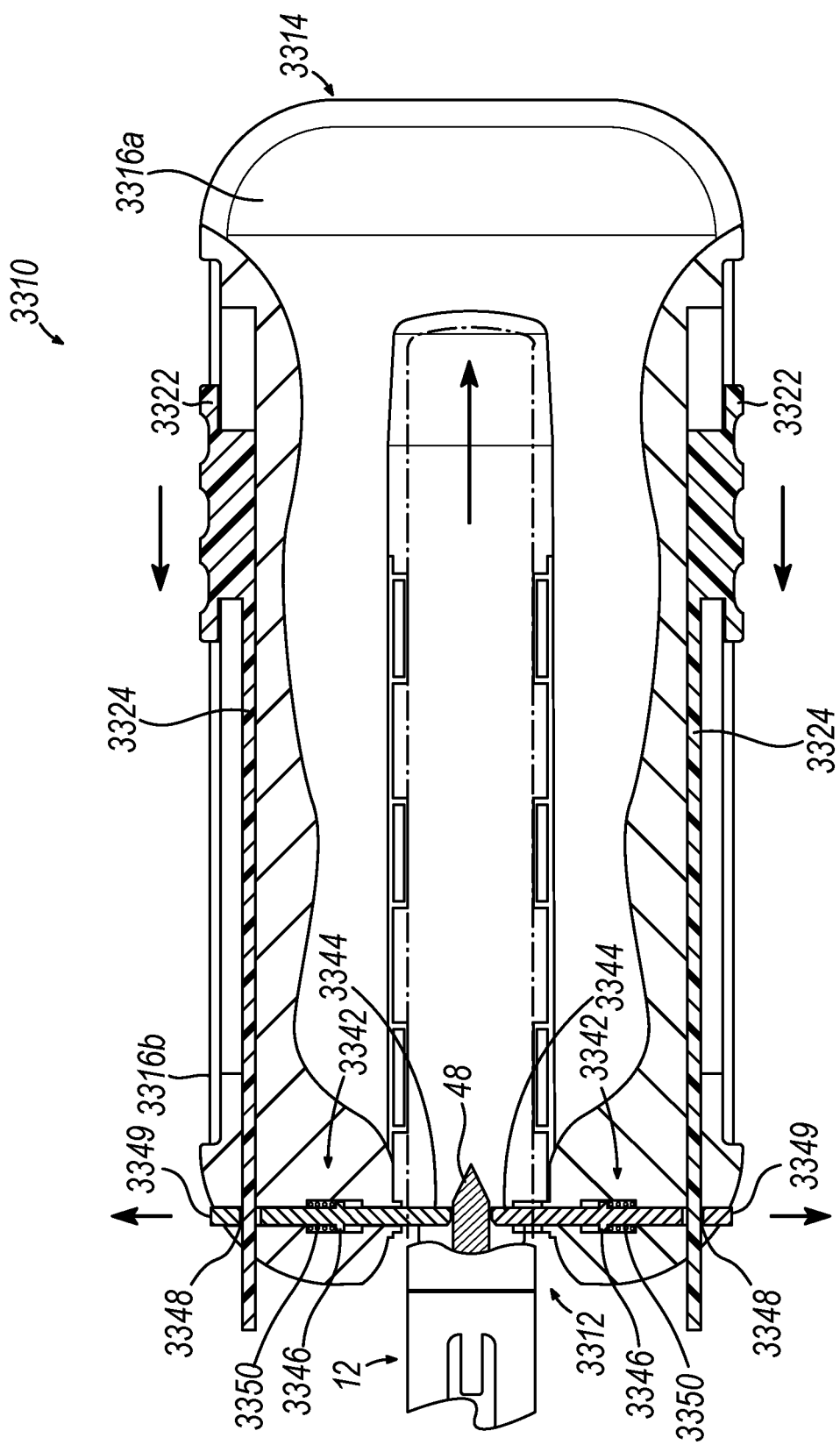

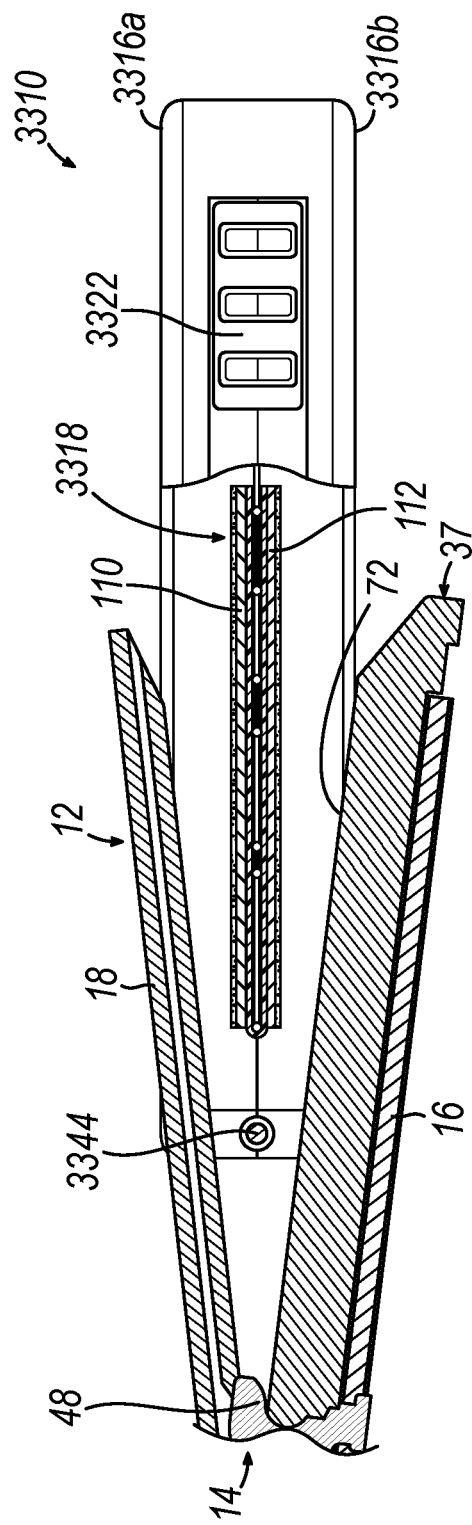
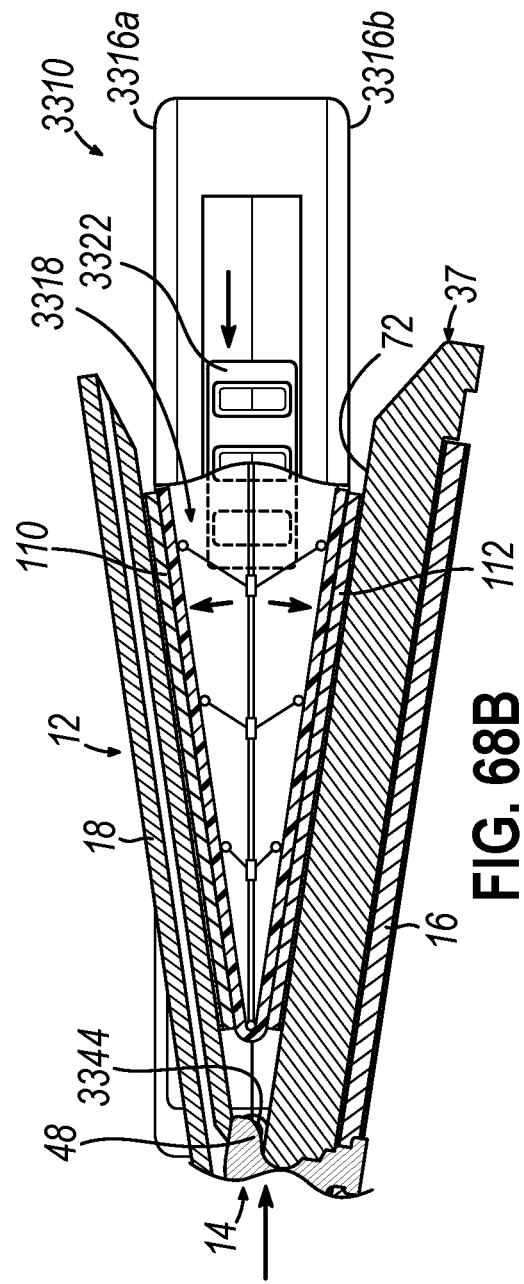

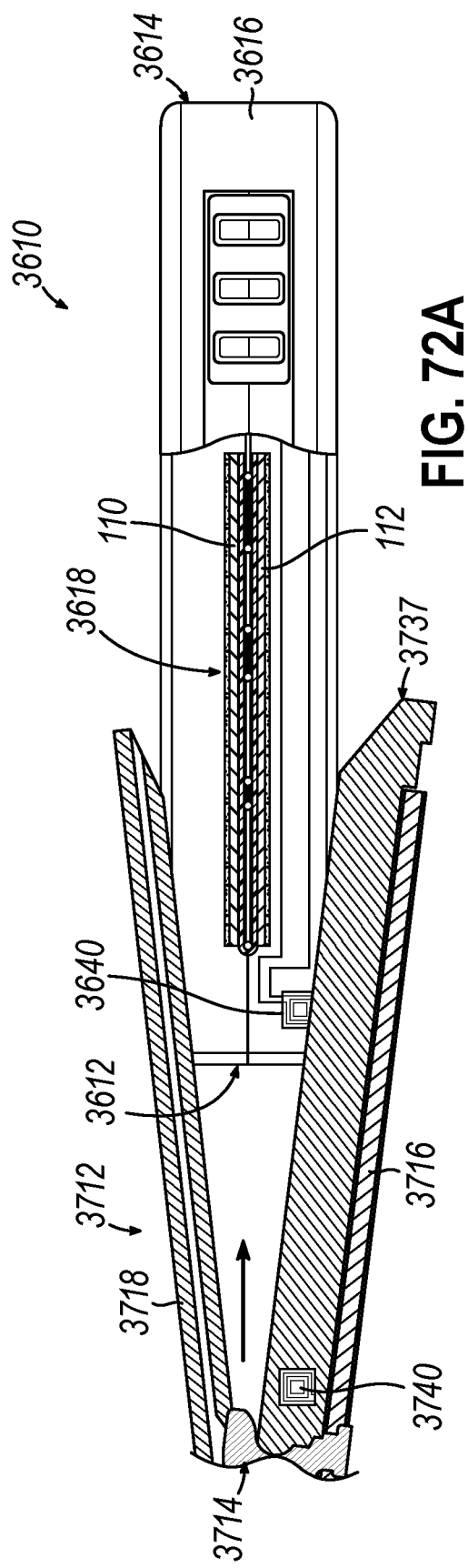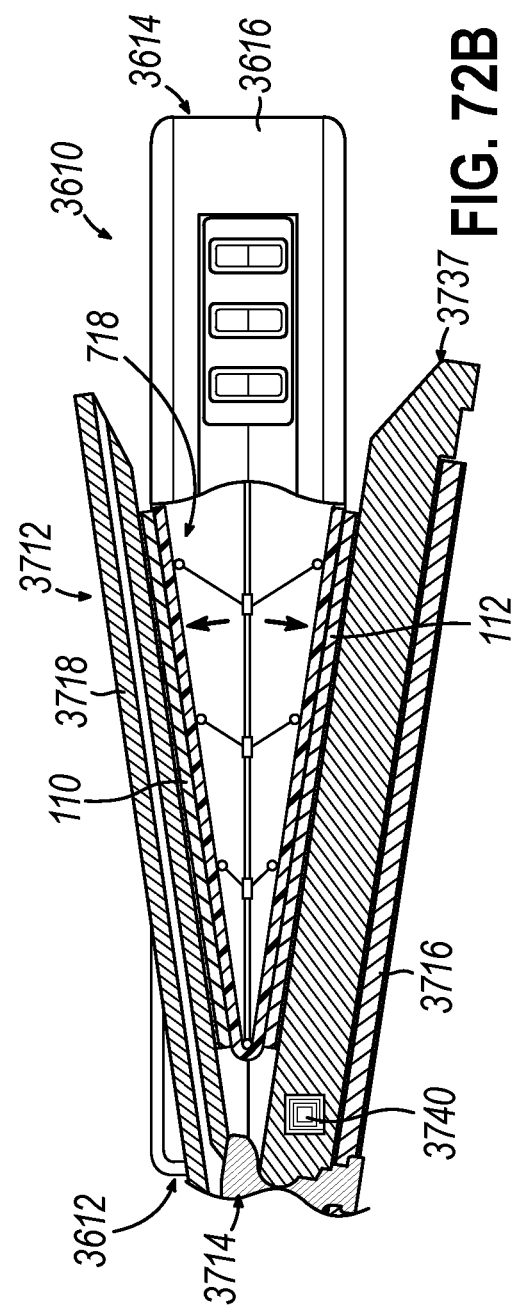

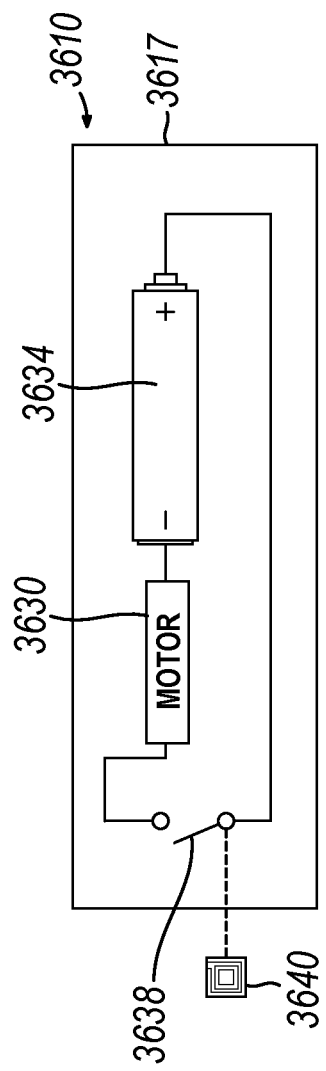
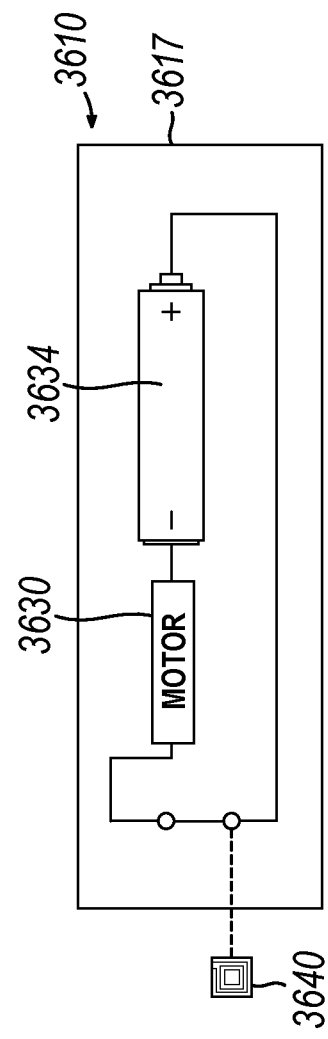
FIG. 73A
FIG. 73B

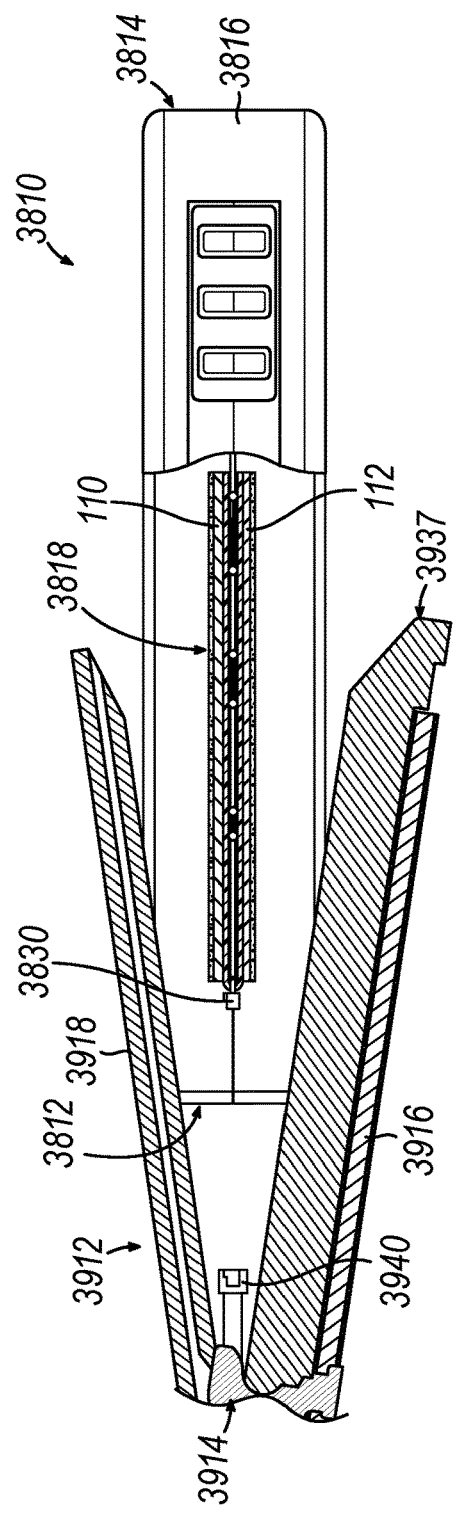
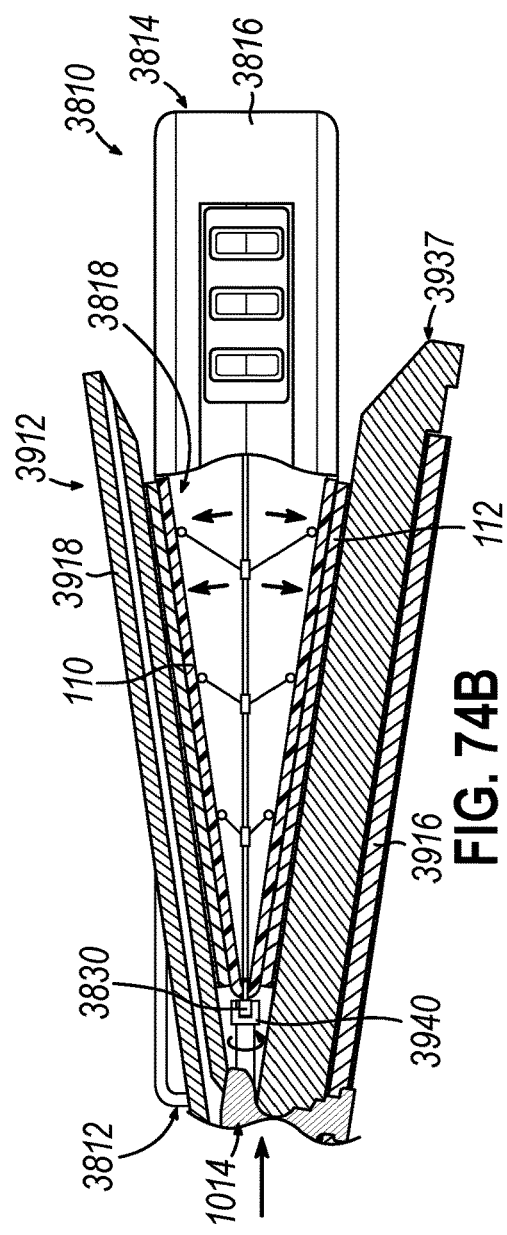
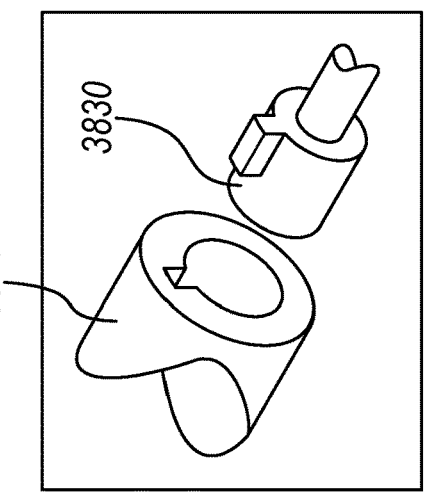
FIG. 74A
FIG. 74B
FIG. 75

METHOD OF APPLYING BUTTRESS TO END EFFECTOR OF SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 22 depicts a side cross-sectional view of another exemplary adjunct applicator device, showing the adjunct applicator device in a non-expanded, storage configuration;

FIG. 23 depicts a side cross-sectional view of the end effector of FIG. 3 engaging the adjunct applicator device of FIG. 22 while the adjunct applicator device is in a first expanded, angular configuration;

FIG. 26A depicts a side cross-sectional view of the adjunct applicator device of FIG. 25, taken along line 26A-26A of FIG. 25, showing the wedge portion of the adjunct applicator device in the proximal position engaging the end effector of FIG. 3, shown in phantom;

FIG. 26B depicts a side cross-sectional view of the adjunct applicator device of FIG. 25, showing the wedge portion of the adjunct applicator device in a distal position engaging the end effector of FIG. 3, shown in phantom;

FIG. 29A depicts a partial side cross-sectional view of another exemplary adjunct applicator device with the buttress assembly of FIG. 8 applied to the adjunct applicator device, showing the adjunct applicator device in a non-expanded state;

FIG. 29B depicts a side partial cross-sectional view of the adjunct applicator device of FIG. 29A, the buttress assembly of FIG. 8, and the end effector of FIG. 3, with an air pump coupled with the adjunct applicator device and in a first state;

FIG. 31A depicts a partial side cross-sectional view of another exemplary adjunct applicator device with the buttress assembly of FIG. 8 applied to the adjunct applicator device, showing the adjunct applicator device in a non-expanded state;

FIG. 31B depicts a partial side cross-sectional view of the adjunct applicator device of FIG. 31A, the buttress assembly of FIG. 8, and the end effector of FIG. 3, with a compressed air injector coupled with the adjunct applicator device and the compressed air being in a first state with the adjunct applicator device in the non-expanded state;

FIG. 33A depicts a partial side cross-sectional view of another exemplary adjunct applicator device with the buttress assembly of FIG. 8 applied to an applicator pad of the adjunct applicator device, with the adjunct applicator device in a first, non-expanded state;

FIG. 33B depicts a partial side cross-sectional view of the adjunct applicator device of FIG. 33A, the buttress assembly of FIG. 8, and the end effector of FIG. 3, with the applicator pad in the first, non-expanded state;

FIG. 35A depicts a partial side cross-sectional view of the adjunct applicator device of FIG. 34A taken along line 35A-35A of FIG. 34A, with the buttress assembly of FIG. 8 applied to the adjunct applicator device, the adjunct applicator device being in the first, non-expanded state;

FIG. 35B depicts a partial side cross-sectional view of the adjunct applicator device of FIG. 34A taken along line 35B-35B of FIG. 34B, with the buttress assembly of FIG. 8 applied to the adjunct applicator device, the adjunct applicator device being in the second, expanded state to thereby secure the buttress assembly to an end effector;

FIG. 36A depicts a partial side cross-sectional view of another exemplary adjunct applicator device, with the buttress assembly of FIG. 8 applied to the adjunct applicator device, the adjunct applicator device being in a first, non-expanded state;

FIG. 36B depicts a partial side cross-sectional view of the adjunct applicator device of FIG. 36A, with the buttress assembly of FIG. 8 applied to the adjunct applicator device, the adjunct applicator device being in a second, expanded state to thereby secure the buttress assembly to an end effector;

FIG. 54 depicts a perspective view of the end effector of FIG. 3 and another exemplary adjunct applicator device that may be used to carry and apply the buttress assemblies of FIG. 8, showing the adjunct applicator device positioned over the end effector with a translatable sleeve of the adjunct applicator device in a retracted position;

FIG. 55A depicts a side cross-sectional view of the adjunct applicator device of FIG. 54 positioned over the end effector of FIG. 3, showing the translatable sleeve of the adjunct applicator device in the retracted position;

FIG. 55B depicts a side cross-sectional view of the adjunct applicator device of FIG. 54 positioned over the end effector of FIG. 3, showing the translatable sleeve of the adjunct applicator device in an extended position for transitioning the end effector toward the closed state;

FIG. 67B depicts another top cutaway view of the adjunct applicator device of FIG. 67A, showing the adjunct applicator device in an unlocked configuration;

FIG. 68A depicts a side partial cross-sectional view of the adjunct applicator device of FIG. 67A, with the end effector of FIG. 3 being inserted into the adjunct applicator device;

FIG. 68B depicts another side partial cross-sectional view of the adjunct applicator device of FIG. 67A, with the end effector of FIG. 3 fully inserted into the adjunct applicator device and a platform of the adjunct applicator device in an expanded configuration;

FIG. 72A depicts a side partial cross-sectional view of another exemplary adjunct applicator device that may be used to carry and apply the buttress assemblies of FIG. 8, showing an end effector being inserted into the adjunct applicator device;

FIG. 72B depicts another side partial cross-sectional view of the adjunct applicator device of FIG. 72A, showing the end effector of FIG. 72A being fully inserted into the adjunct applicator device;

FIG. 73A depicts a schematic view of an interior of the adjunct applicator device of FIG. 72A and a switch in an open circuit configuration;

FIG. 73B depicts another schematic view of the interior of the adjunct applicator device of FIG. 72A, showing the switch in a closed circuit configuration;

FIG. 74A depicts a side partial cross-sectional view of another exemplary adjunct applicator device that may be used to carry and apply the buttress assemblies of FIG. 8, showing an end effector being inserted into the adjunct applicator device;

FIG. 74B depicts another side partial cross-sectional view of the adjunct applicator device of FIG. 74A, showing the end effector of FIG. 74A being fully inserted into the adjunct applicator device;

FIG. 75 depicts a detailed perspective view of a power input and a power output of the adjunct applicator device of FIG. 74A and the end effector of FIG. 74A, respectively;

FIG. 76 depicts a perspective view of another exemplary adjunct applicator device that may be used to carry and apply the buttress assemblies of FIG. 8, showing the adjunct applicator device being positioned onto a staple cartridge of the end effector of FIG. 3;

FIG. 77A depicts a side cross-sectional view of the adjunct applicator device and staple cartridge of FIG. 76 and the end effector of FIG. 3, showing the adjunct applicator device and staple cartridge being inserted into a lower jaw of the end effector;

FIG. 77B depicts another side cross-sectional view of the adjunct applicator device and staple cartridge of FIG. 76 and the end effector of FIG. 3, showing the adjunct applicator device and staple cartridge being fully inserted into the lower jaw of the end effector and a platform of the adjunct applicator device in an expanded configuration;

FIG. 77C depicts a side cross-sectional view of the end effector of FIG. 3 after the adjunct applicator device of FIG. 76 has been removed from the end effector;

FIG. 78 depicts a partial side cross-sectional view of another exemplary adjunct applicator device that may be used to carry and apply the buttress assemblies of FIG. 8;

Figure 3:
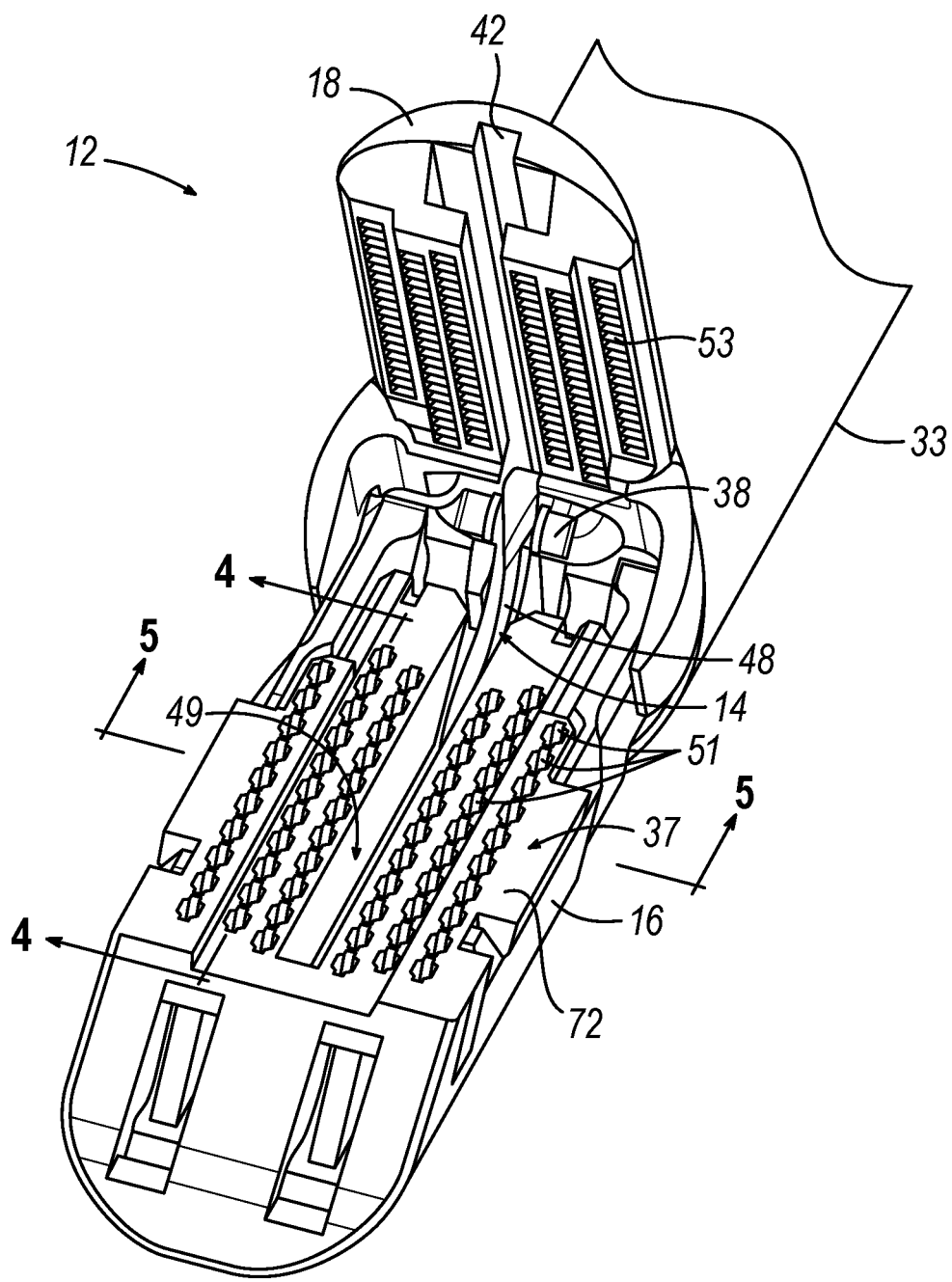
FIG. 3 depicts a perspective view of an end effector of the instrument of FIG. 1 in an open state.
Figure 76:
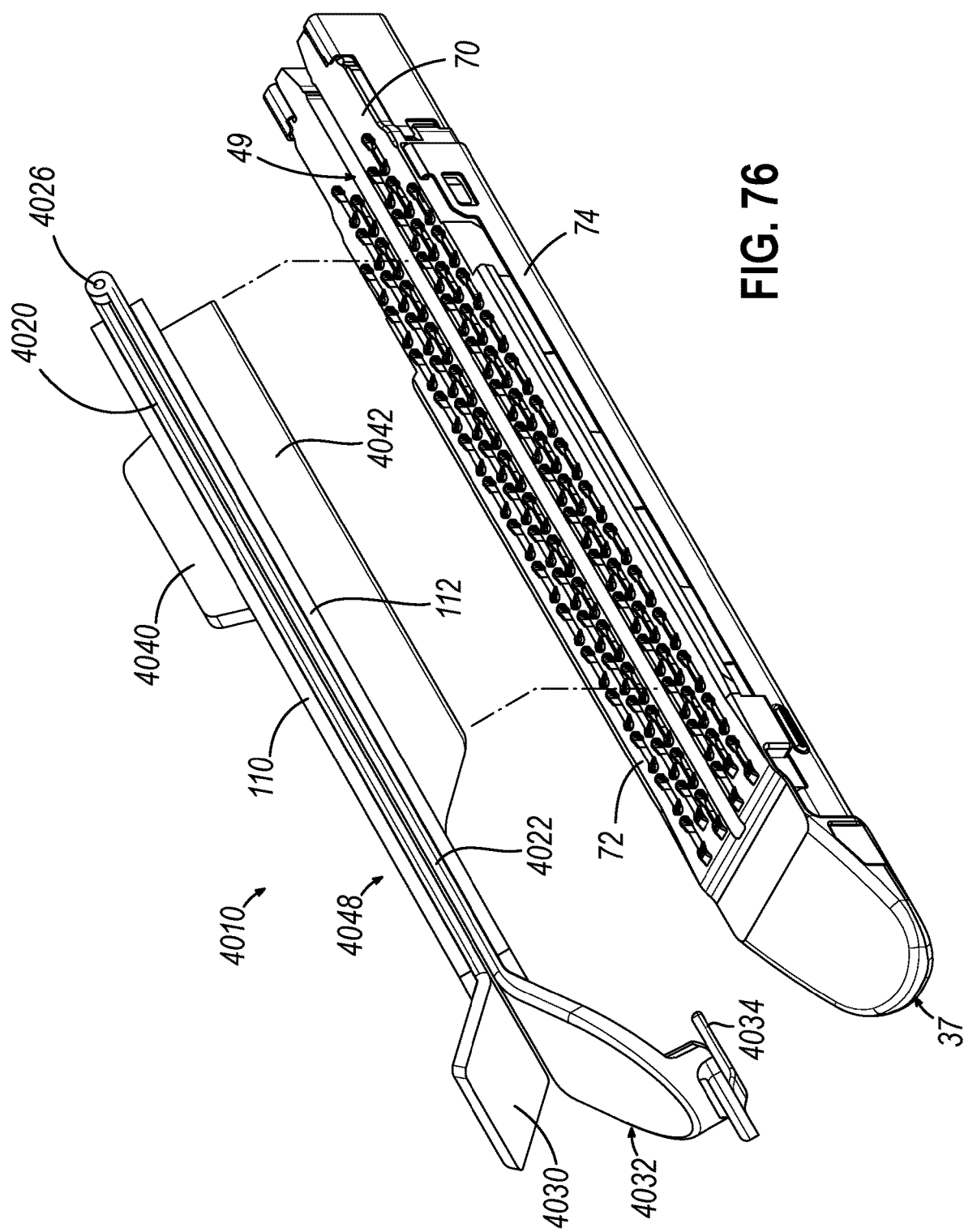
Figure 79A:
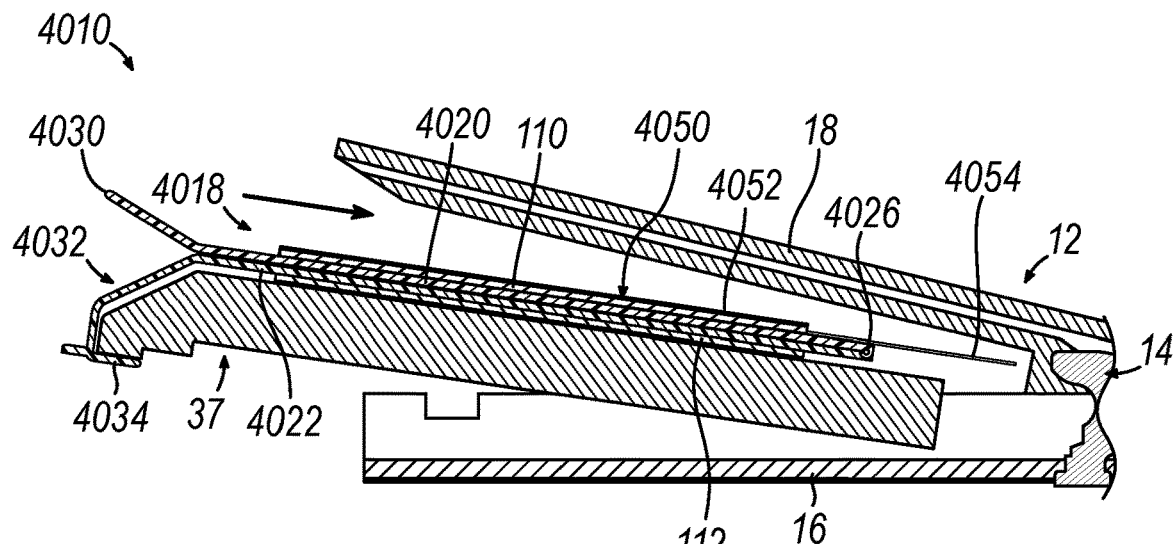
Figure 79B:
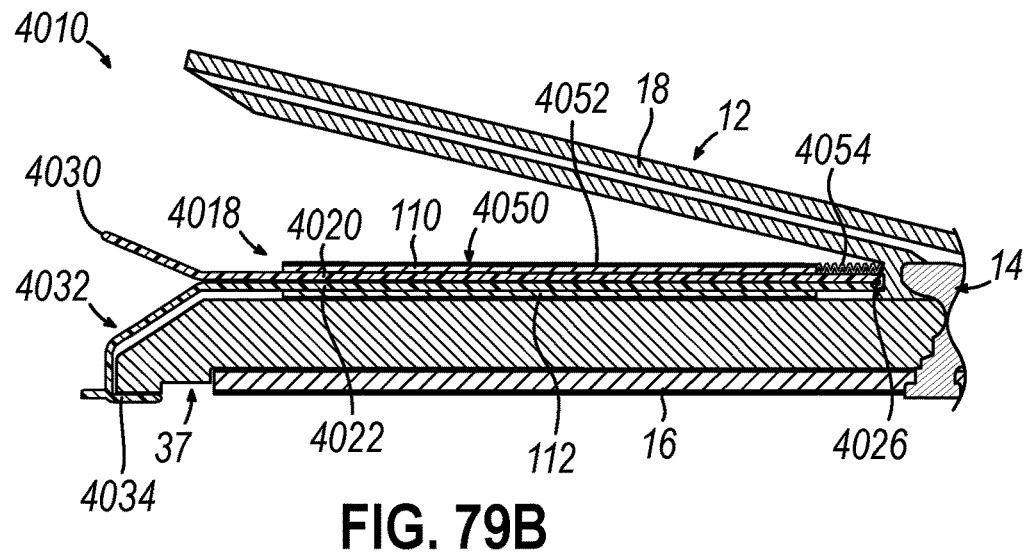

FIG. 79A depicts still another side cross-sectional view of the adjunct applicator device and staple cartridge of FIG. 76, showing the adjunct applicator device and staple cartridge being inserted into the end effector of FIG. 3 with a liner positioned on the adjunct applicator device; and FIG. 79B depicts still another side cross-sectional view of the adjunct applicator device and staple cartridge of FIG. 76, showing the adjunct applicator device being fully inserted into the end effector of FIG. 3 and the liner of FIG. 79A engaged with the end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (α). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 1:
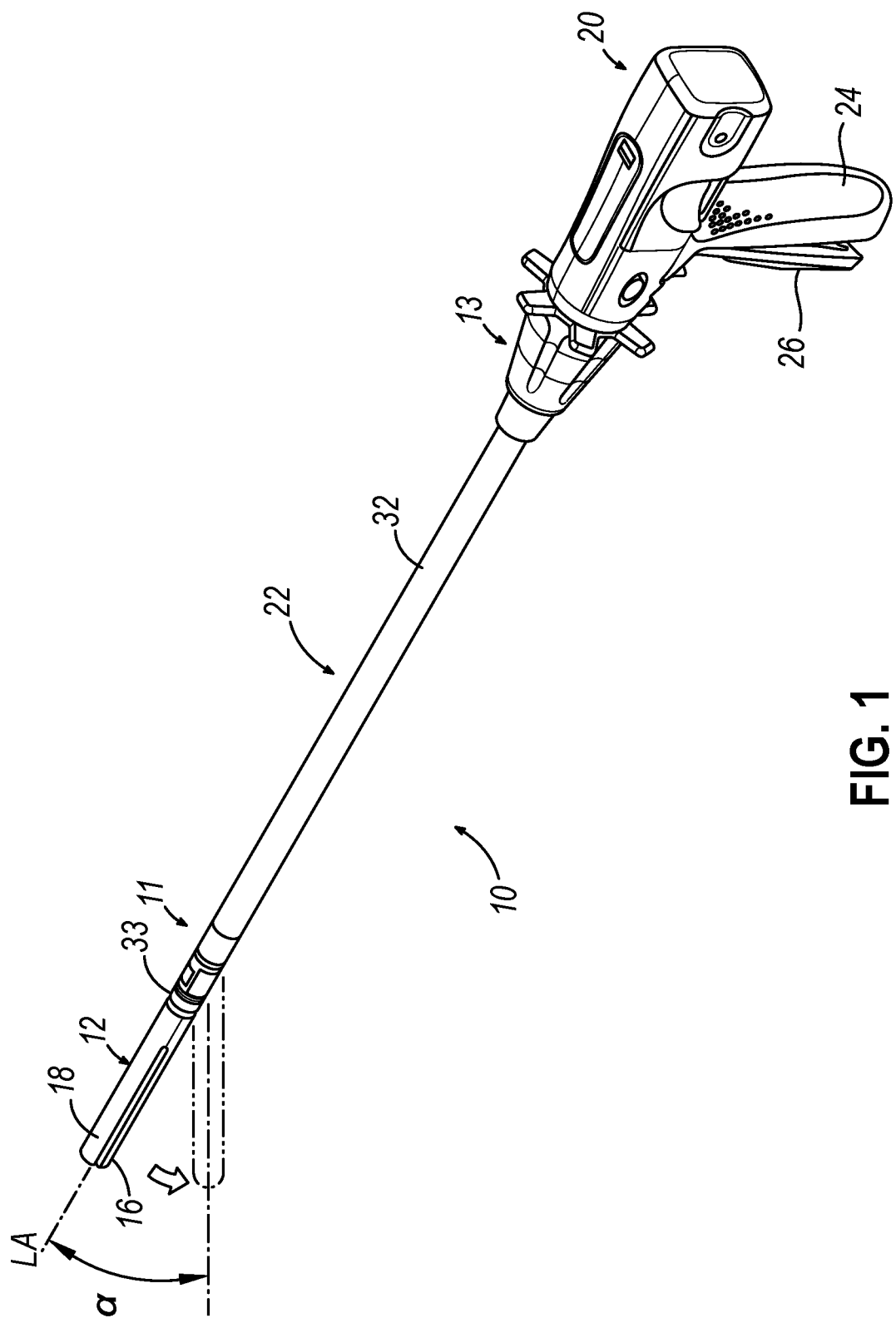
FIG. 1 depicts a perspective view of an exemplary surgical stapling instrument.
Figure 2:
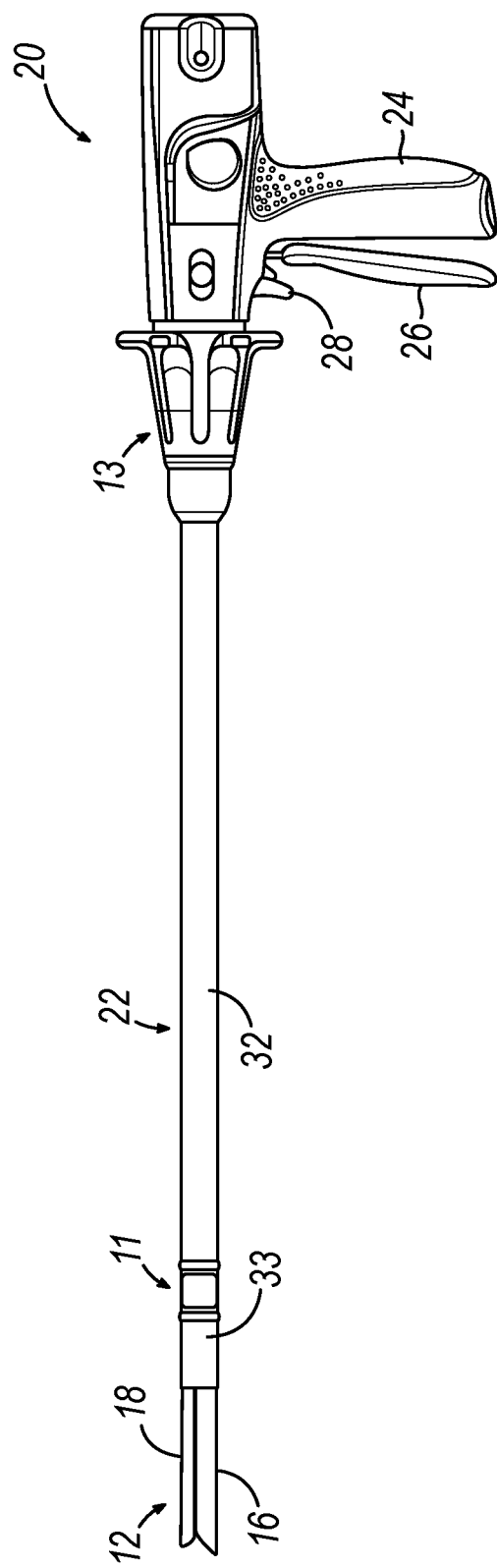
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 4A:
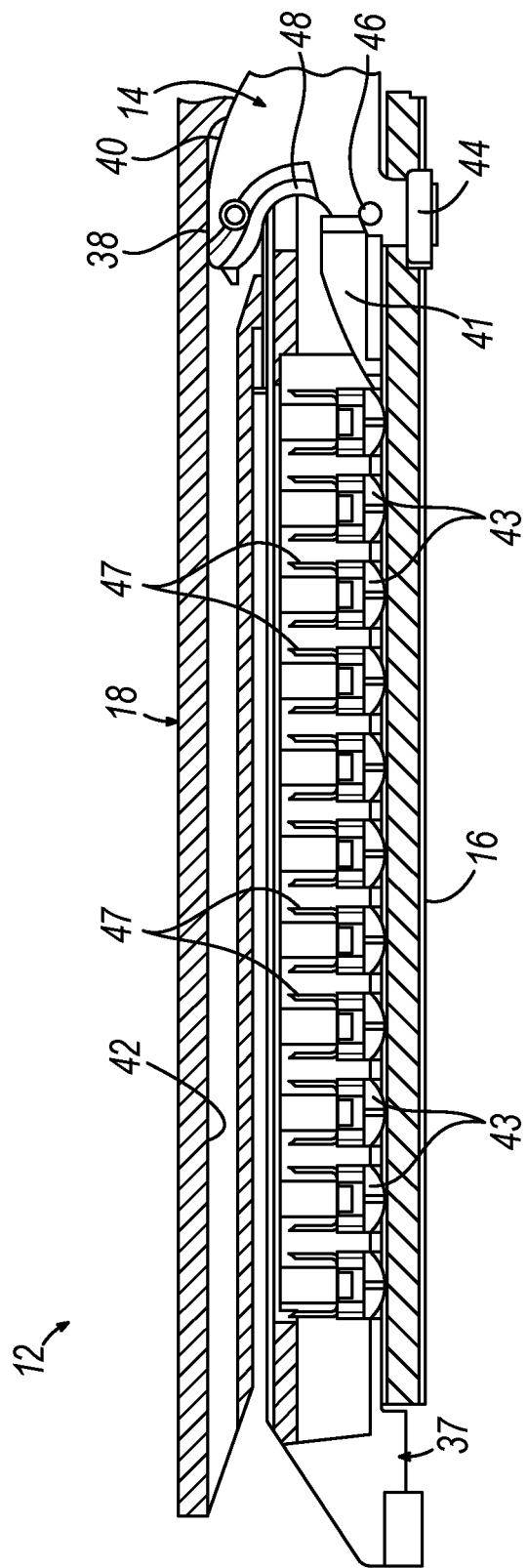
FIG. 4A depicts a side cross-sectional view of the end effector of FIG. 3, taken along line 4-4 of FIG. 3, with a firing beam in a proximal position.
Figure 4B:
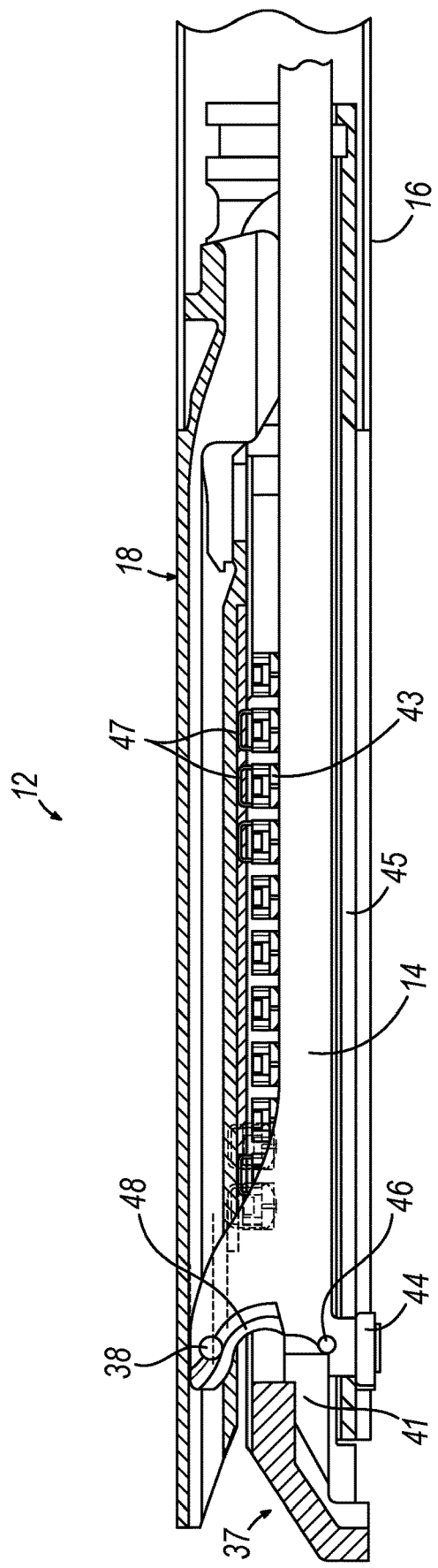
FIG. 4B depicts a side cross-sectional view of the end effector of FIG. 3, taken along line 4-4 of FIG. 3, with the firing beam in a distal position.
Figure 5:
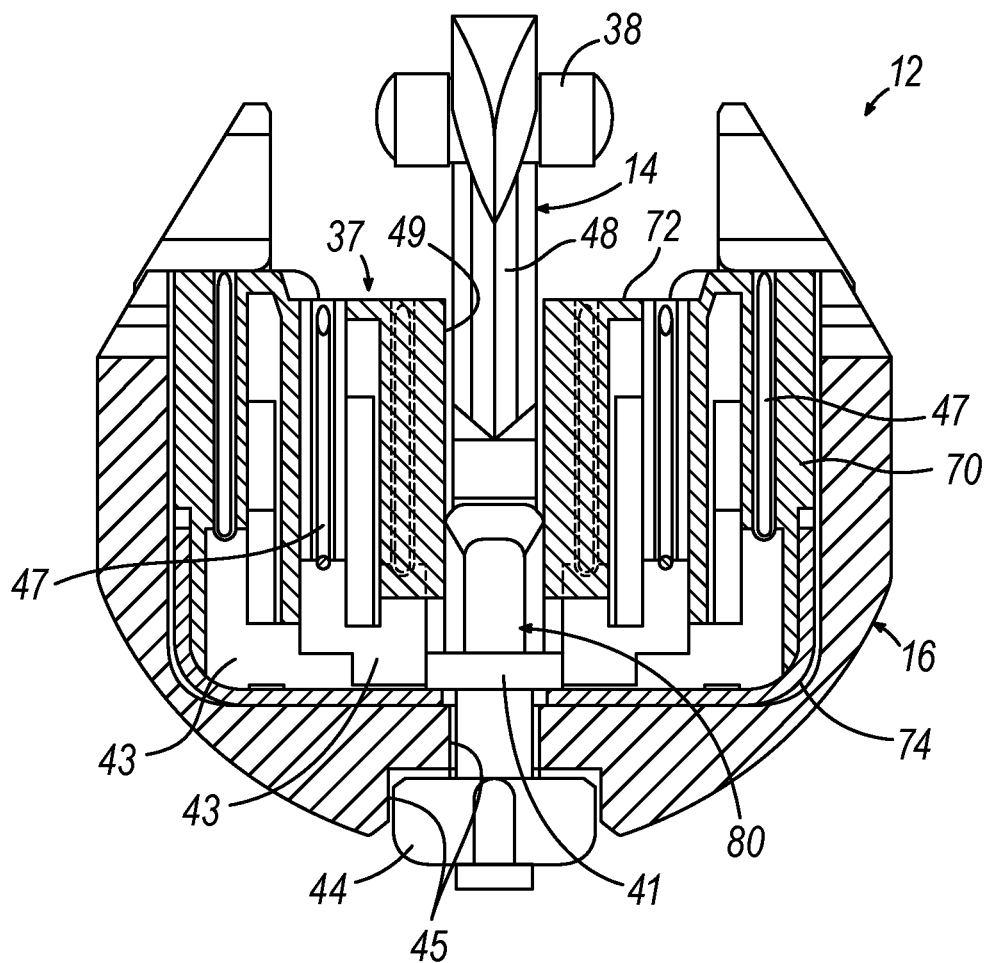
FIG. 5 depicts an end cross-sectional view of the end effector of FIG. 3, taken along line 5-5 of FIG. 3.
Figure 6:
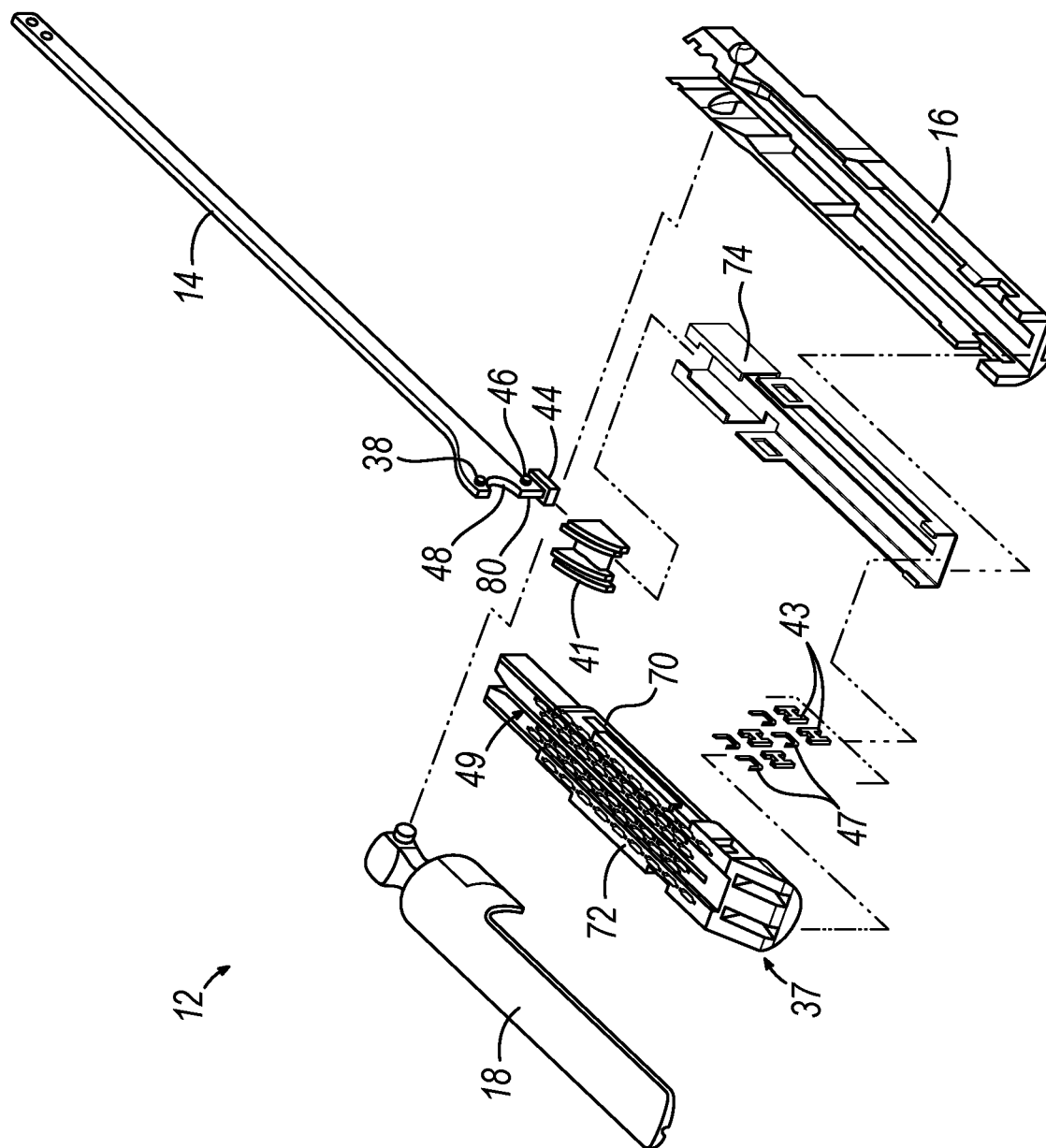
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
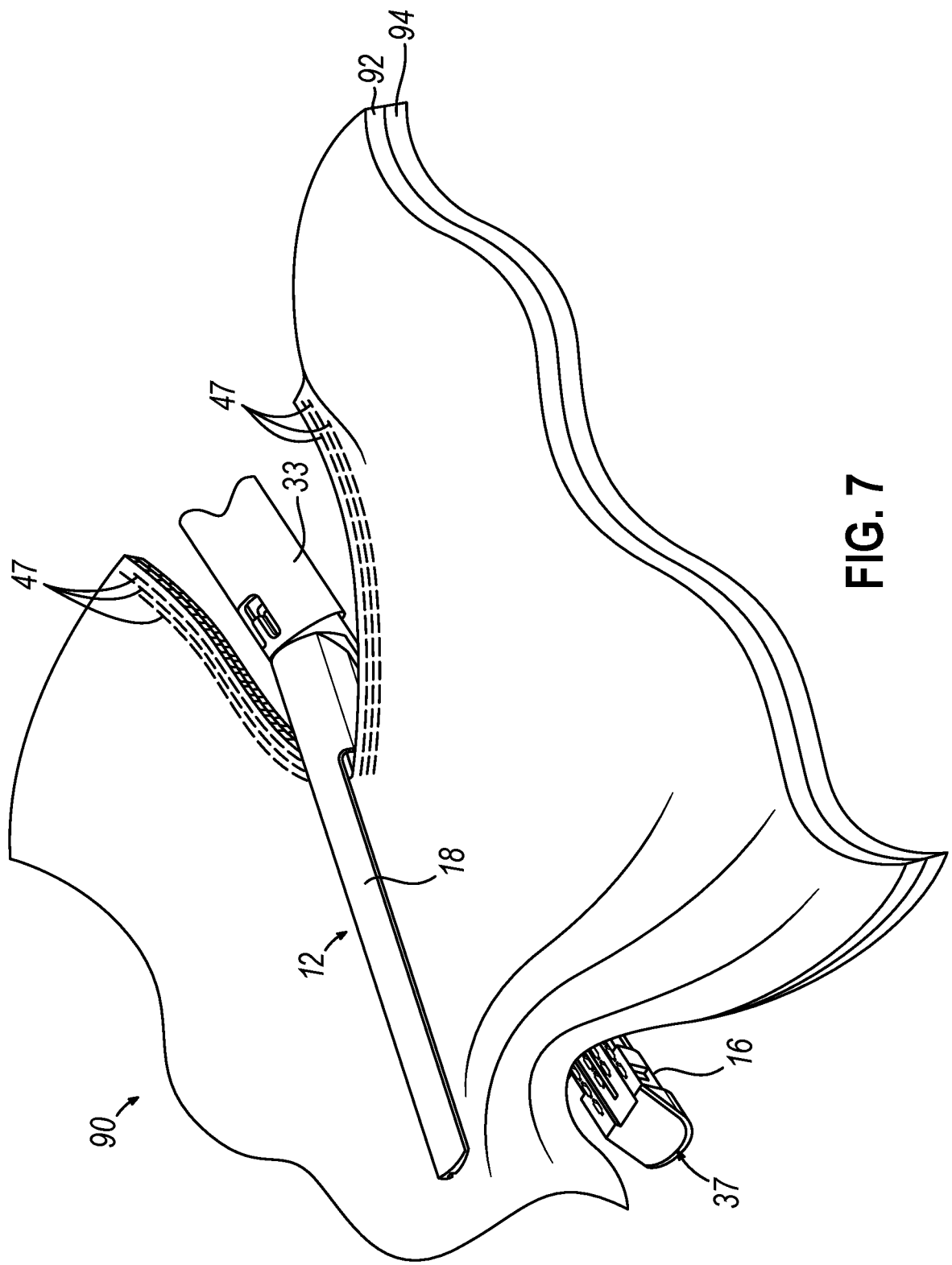
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Applicator Device

In some instances, it may be desirable to equip end effector (12) of surgical stapler (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary applicator devices may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
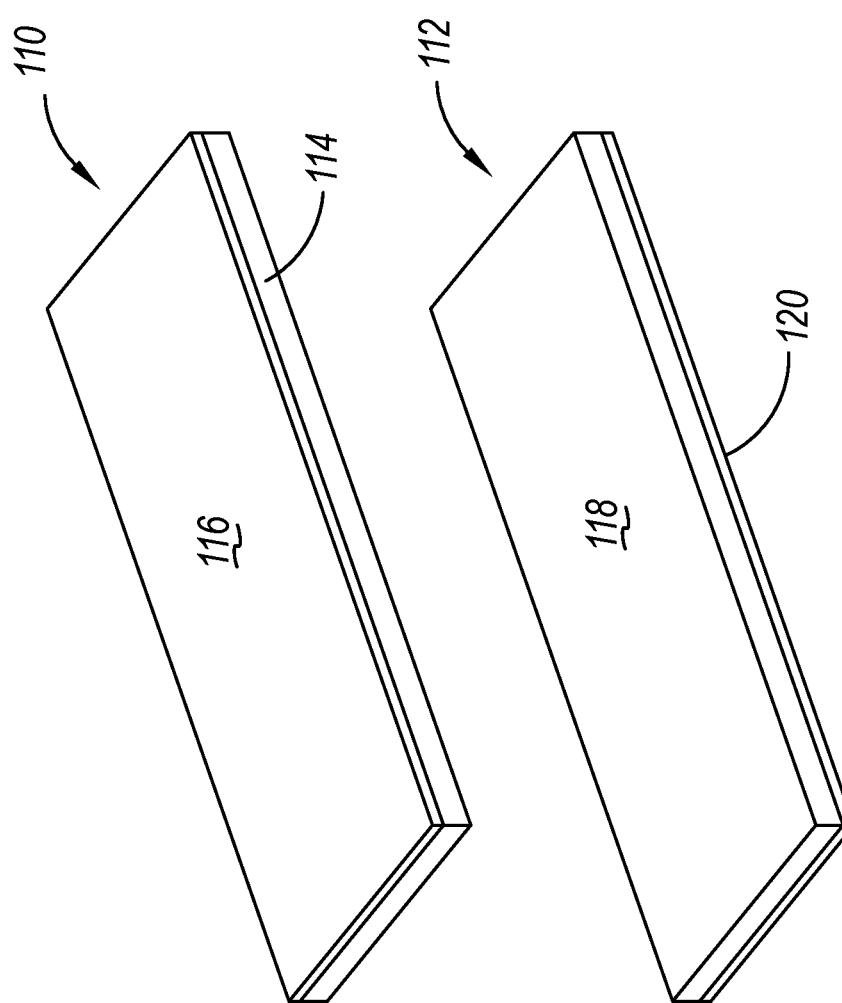
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
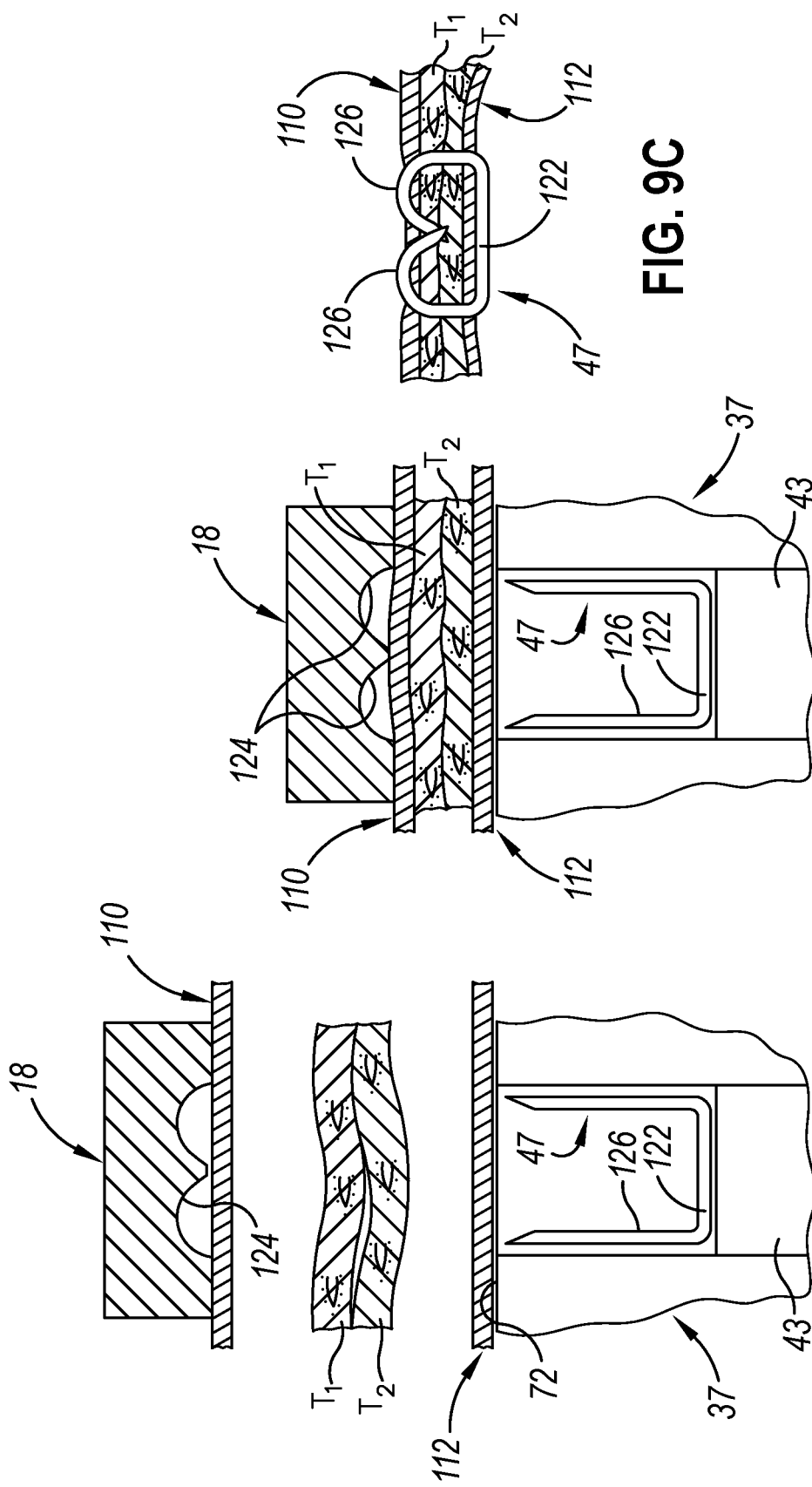
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in open position. Buttress assembly (110) is adhered to underside (424) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
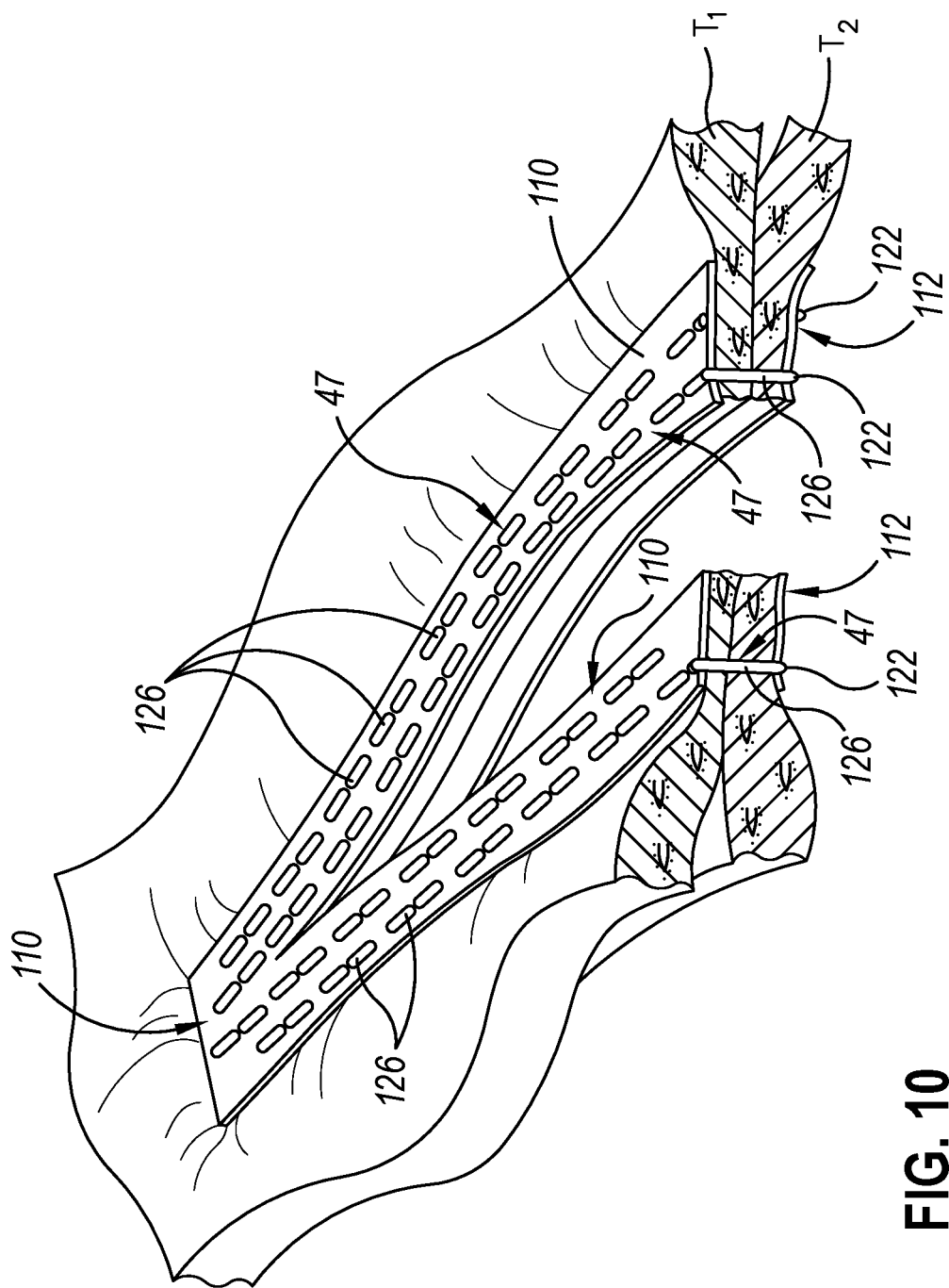
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttress assemblies (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress assemblies (110, 112), separating each buttress assembly (110, 112) into a corresponding pair of sections, such that each section remains secured to a respective severed region of tissue ($T_1$, $T_2$).

C. Exemplary Adjunct Applicator Device with Active Retainer Arms

Figure 11:
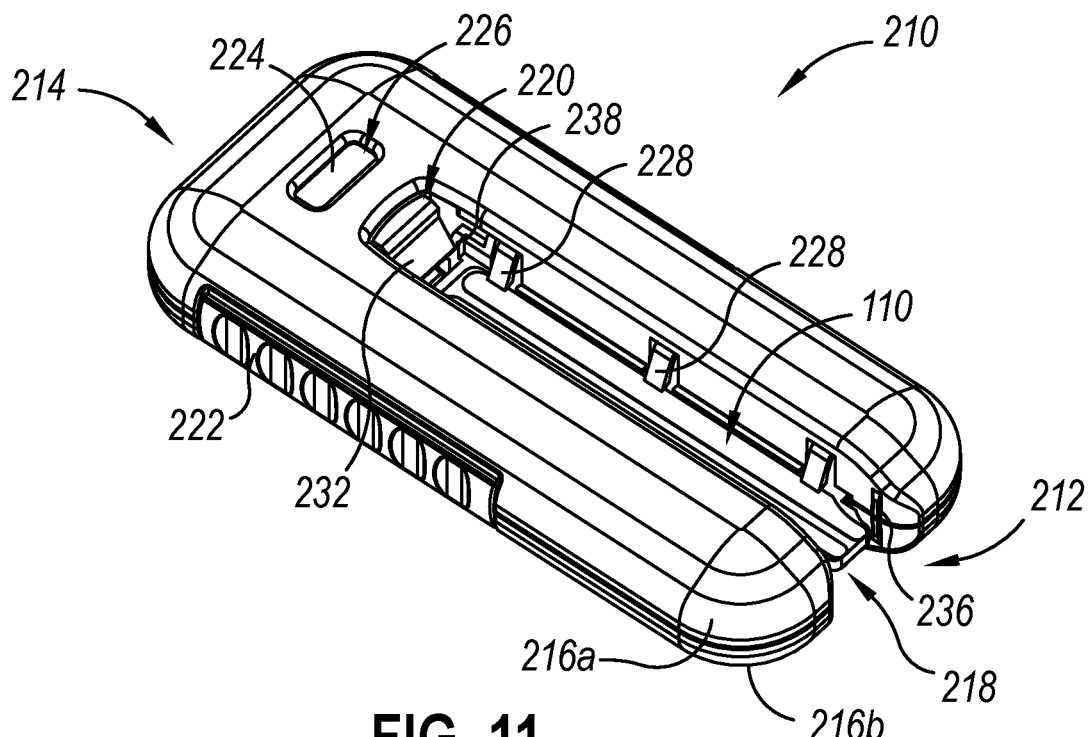
FIG. 11 depicts a perspective view of an exemplary adjunct applicator device that may be used to carry and apply the buttress assemblies of FIG. 8.
Figure 12:
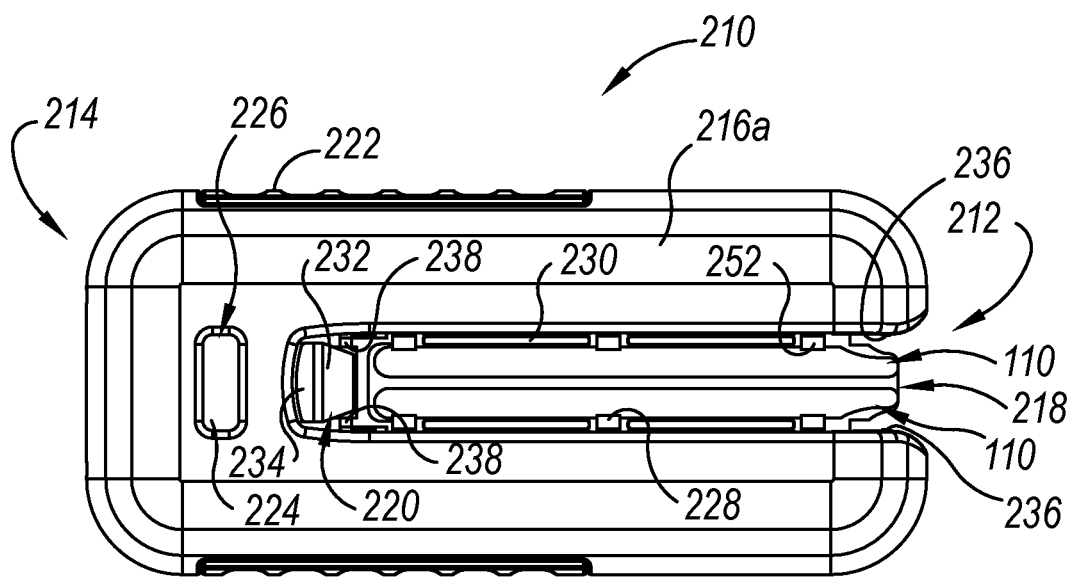
FIG. 12 depicts a top plan view of the adjunct applicator device of FIG. 11.

Because end effector (12) of surgical stapler (10) may be actuated multiple times during a single surgical procedure, it may be desirable to enable an operator to repeatedly and easily load buttress assemblies (110, 112) onto lower jaw and anvil (16, 18) during that single surgical procedure. FIGS. 11-13B show an exemplary adjunct applicator device (210) (also referred to as a "buttress applicator" or a "buttress applier cartridge") that may be used to support, protect, and apply adjunct material, such as buttress assemblies (110, 112), to end effector (12). As best seen in FIGS. 11-12, applicator device (210) of this example comprises an open end (212) and a closed end (214). Open end (212) is configured to receive end effector (12) as will be described in greater detail below. Applicator device (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, outer edges of platform (218) include retention features (530) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Applicator device (210)

includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with applicator device (210).

Figure 13A:
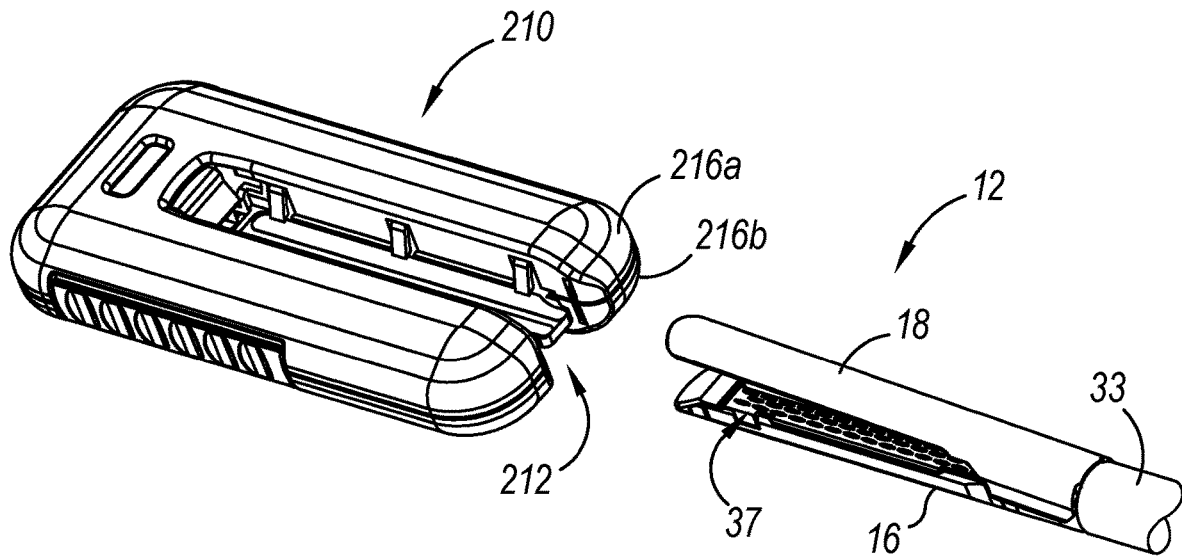
FIG. 13A depicts a perspective view of the end effector of FIG. 3 and the adjunct applicator device of FIG. 11, showing the end effector and the adjunct applicator device being aligned with one another.
Figure 13B:
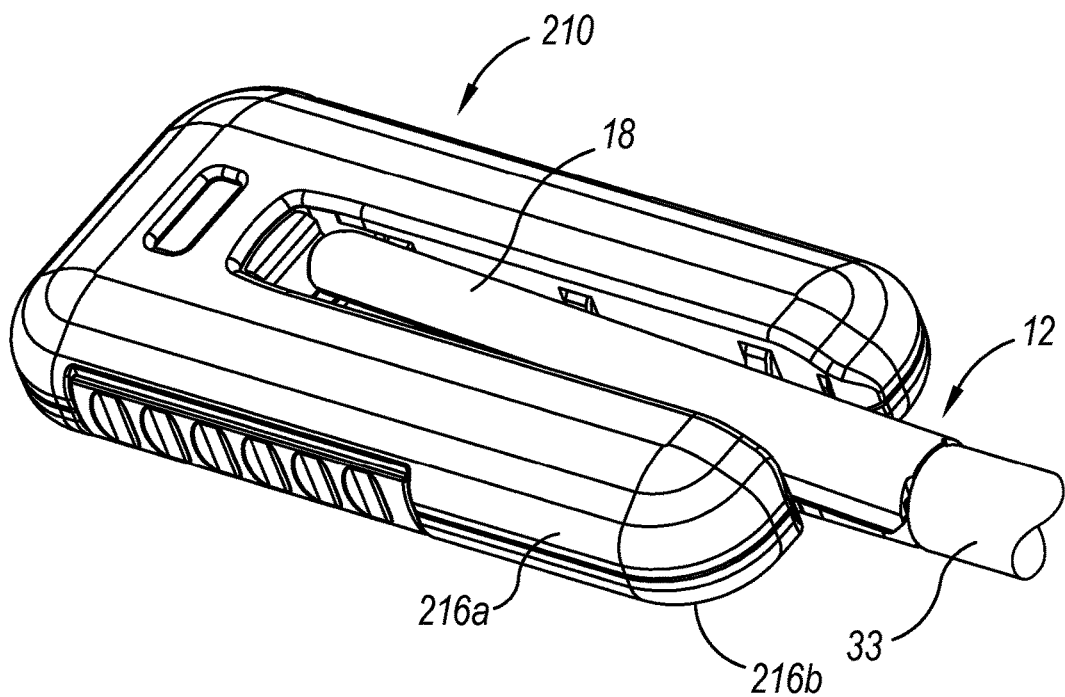
FIG. 13B depicts a perspective view of the end effector of FIG. 3 and the adjunct applicator device of FIG. 11, with the end effectors jaws closed on a platform of the adjunct applicator device.

FIG. 13A shows applicator device (210) in a configuration where retainer arms (228) are positioned to hold buttress assemblies (110, 112) against platform (218); while FIG. 13B shows applicator device (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use applicator device (210) to load end effector (12), the operator would first position applicator device (210) and end effector (12) such that end effector is aligned with open end (212) of applicator device (210) as shown in FIG. 13A. The operator would then advance end effector (12) distally, and/or advance adjunct applicator device device (210) proximally, to position platform (218) and buttress assemblies (110, 112) between anvil (18) and staple cartridge (37) as shown in FIG. 13B. Closure trigger (26) of instrument (10) is then squeezed by the operator to close lower jaw and anvil (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that lower jaw and anvil (16, 18) may be disengaged from platform (218) while buttress assemblies (110, 112) remain adhered to anvil (18) and staple cartridge (37).

III. Exemplary Adjunct Applicator Devices with Static Wedge Configuration

Figure 14:
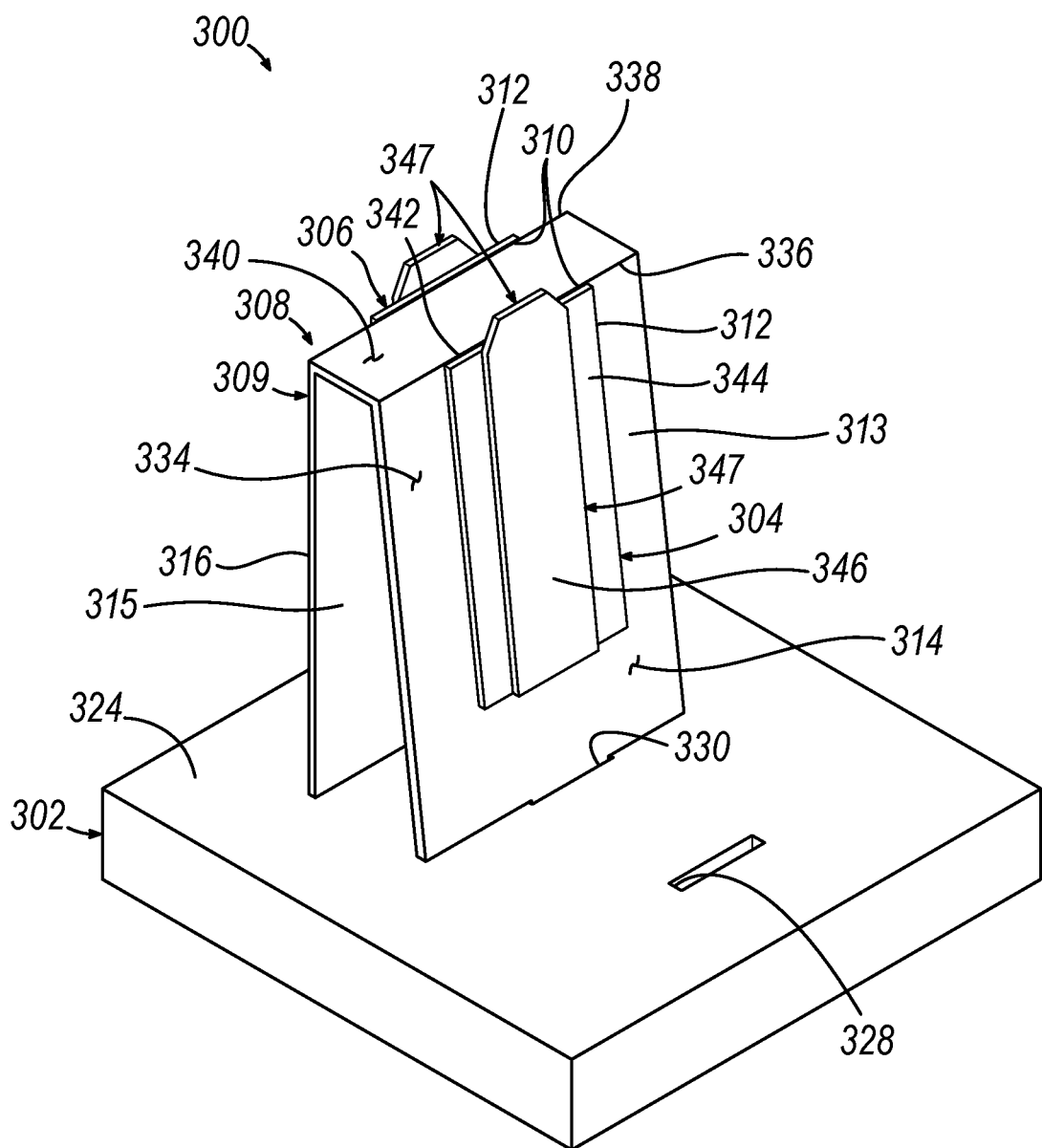
FIG. 14 depicts a perspective view of another exemplary adjunct applicator device, shown in a folded configuration and coupled with a base.

In some instances, it may be desirable to provide an adjunct applicator device that is configured to apply a staple reinforcing adjunct element to one or both jaws of a surgical stapler end effector (e.g., lower jaw (16) and/or anvil (18)) while the jaws remain in an open state, or otherwise without closing the jaws via actuation of the stapler's end effector closure system, such as via actuation of closure trigger (26) input feature of surgical stapler (10). Exemplary applicator devices described below in connection with FIGS. 14-79B provide such functionality, such that each applicator device is configured to be manipulated relative to an end effector to apply an adjunct element to one or both jaws without requiring trigger-actuated closure of jaws like that shown in FIGS. 13A-13B described above. Additionally, each such exemplary adjunct applicator devices may be operable to apply a minimum pressure to appropriately seat the adjunct material on the desired one or more jaws.

It will be appreciated that any of the exemplary adjunct applicator devices described below in connection with FIGS. 14-79B may be configured to apply an adjunct element in the form of a buttress, such as buttress assemblies (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of an adjunct element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein.

Furthermore, any of the exemplary applicator devices described below in connection with FIGS. 14-79B may be suitably constructed for a single use or for multiple uses.

A. Exemplary Static Wedge Adjunct Applicator

In some instances, it may be desirable to provide a compact adjunct applicator device configured to apply a staple reinforcing adjunct element to one or both jaws of a surgical stapler end effector while jaws remain in an open state, or otherwise without closing jaws via actuation of stapler's end effector closure system, such as via actuation of closure trigger (26) of surgical stapler (10).

Figure 15:
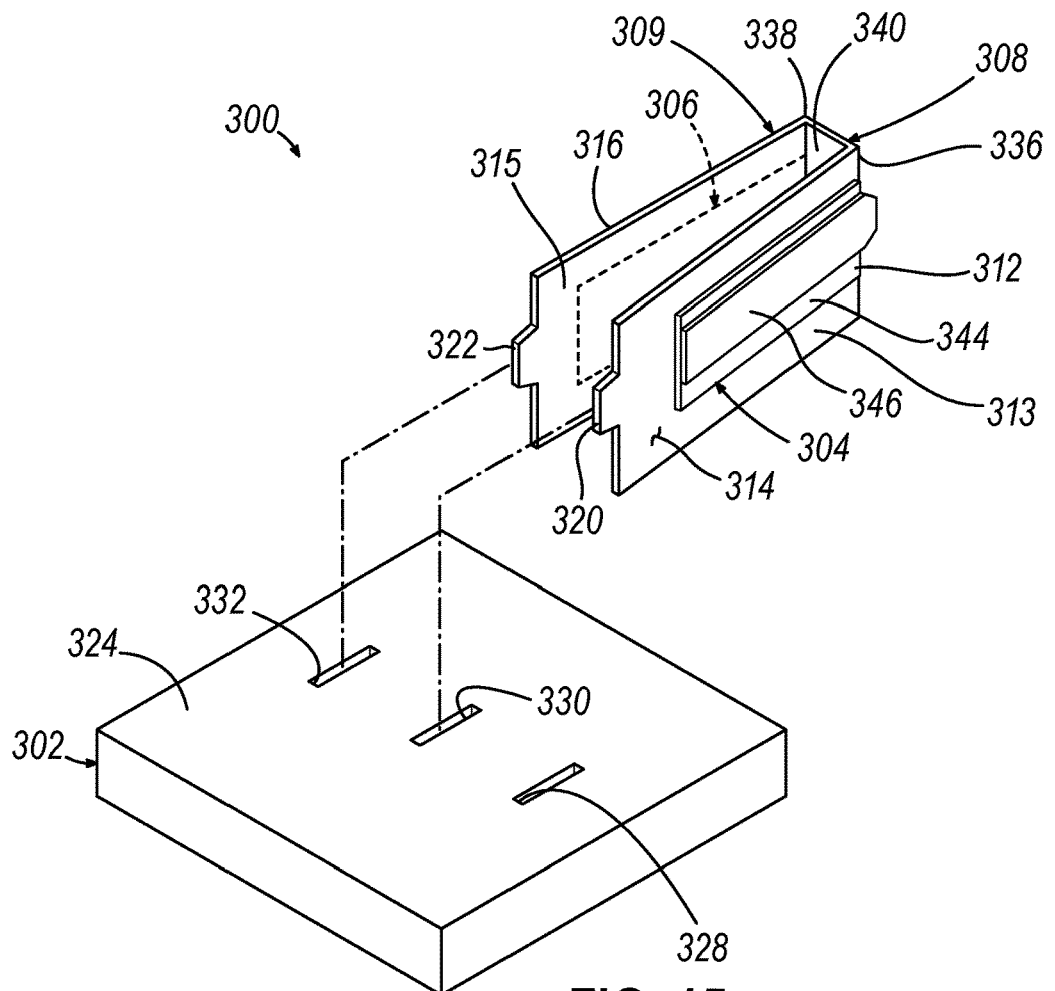
FIG. 15 depicts a perspective view of the adjunct applicator device of FIG. 14 in the folded configuration and being positioned in relation to slots of the base.
Figure 16:
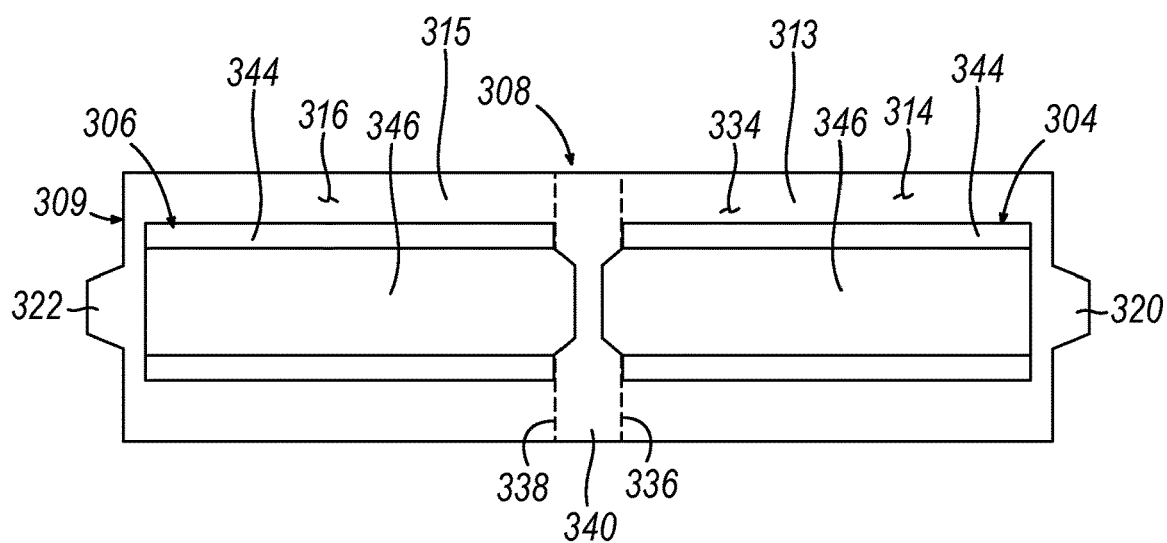
FIG. 16 depicts a plan view of the adjunct applicator device of FIG. 14 in an unfolded configuration.

FIGS. 14-16 show an exemplary adjunct applicator assembly (300) including a wedge-shaped applicator member (308) and a base (302). Wedge-shaped applicator member (308) includes a body (309), a first adjunct element (304), and a second adjunct element (306). Body (309) may be disposable or reusable. In disposable versions, body (309) may be constructed of foamboard, cardboard, plastic or any other low-cost material known in the art that is sufficiently rigid, planar and provides support. Such versions of body (309) intended for disposal may be disposed of after a single use. In some versions, body (309) may be constructed of cardboard that may be treated with a surgically safe surface coating (334). Body (309) may include a corrugated or foam center with a rigid outer layer such as plastic or any other low-cost material known in the art to provide rigidity in a thin layer. In some reusable versions, body (309) may be constructed of a reusable material such as stainless steel or any other material known in the art to provide a sterilizable, sufficiently rigid surface that may be configured to assume different angles. In some versions, such reusable material may be pre-formed into the folded configuration and may be sterilized using a method described further below.

In the present example, body (309) of wedge-shaped applicator member (308) has a first panel (313), a second panel (315) opposed from the first panel (313), and a connecting panel (340) that joins a proximal end of first panel (313) with a proximal end of second panel (315). First panel (313) defines a first contact surface (314). First contact surface (314) is generally rectangular and lies on an exterior face of the first panel (313). The first panel (313) extends from connecting panel (340) to first tang (320). First tang (320) has a trapezoidal shape having the wider base of the trapezoidal shape adjoined to the first panel (313) and the narrower top of the trapezoidal shape extending distally away from the first panel (313) from a central portion of the end opposite the connecting panel (340). Second panel (315) is also generally rectangular and defines a second contact surface (316) located on an exterior face opposite the second panel (315). Second panel (315) extends from connecting panel (340) to a second tang (322). Second tang (322) has a trapezoidal shape having the base adjoined to the second panel (315) and the top extending distally away from the second panel (315).

Each first and second adjunct element (304, 306) has a respective first side (310) and a respective second side (312). In the present version, first side (310) of each first and second adjunct element (304, 306) is configured to be releasably attached to first and second contact surfaces (314, 316), respectively, with a first attachment feature (342). First attachment feature (342) includes an adhesive (not shown) and/or a mechanical attachment such as retainer arms (228) (shown in FIG. 12), for example. First attachment feature (342) is configured to removably couple first and second adjunct elements (304, 306) to first and second contact surfaces (314, 316). In some versions, adhesive may be a glue, a cement, a mucilage, or a paste. In some versions, first attachment feature (342) may be of any type readily apparent to those of ordinary skill in the art to removably couple an adjunct to an applicator assembly in view of the teachings herein.

Second side (312) of each of first and second adjunct elements (304, 306) includes a second attachment feature (344) configured to attach to the open lower jaw and anvil (16, 18) of the end effector (12). Second attachment feature (344) has stronger bonding properties than first attachment feature (342). Second attachment feature (344) may also include a bonding agent (not shown) and/or a second mechanical attachment feature (not shown) similar to first attachment feature (342). Any combination of adhesives or mechanical attachments may be used for first and second attachment features (342, 344) so long as second attachment feature (344) has stronger attachment properties than first attachment feature (342). First and second adjunct elements (304, 306) may be in the form of buttress assemblies, such as buttress assemblies (110, 112) described above; or alternatively a tissue thickness compensator (not shown). Second sides (312) of first and second adjunct elements (304, 306) may have a film (346) that covers and protects second attachment feature (344). Film (346) may include a grasping portion (347) that extends proximally when the wedge-shaped applicator member (308) is in the folded configuration so that a user may easily remove the film (346) without disturbing the attachment properties of the first and second adjunct elements (304, 306).

In some versions, first and second adjunct elements (304, 306) may be a buttress including a three-layer, polymer construction including a core layer sandwiched between two outer layers to be collectively strong yet flexible to support a line of staples. In the present example, core layer is a polyglactin 910 material, whereas each outer layer is a polydioxanone or para-dioxanone (PDO) film material. Adjunct elements (304, 306) of the present example is formed by laminating core layers between outer layers between outer layers under a predetermined time. Adjunct elements (304, 306) is further mechanically cut to size thereby inhibiting abrasive edges, such as burs and or delamination, that could damage sensitive tissues. It will be appreciated that alternative methods of cutting adjunct elements (304, 306) such as a laser cutting, or hot knife cutting may be similarly used.

Base (302) may be constructed of foam, cardboard, plastic, or any other low-cost material known in the art to protect items from damage during shipping and to provide other structure support. Base (302) is configured to be placed on a work surface so that side (324) faces upwards. Side (324) of base (302) includes a first slot, a second slot, and a third slot (328, 330, 332) configured to accept first and second tangs (320, 322). Slots (328, 330, 332) are spaced apart and aligned with one another along a centerline of side (324). Slots (328, 330, 332) run transversely relative to the centerline (not shown) and are sized to accept tangs (320, 322). In some versions, base (302) may include a recess (not shown) configured to accept adjunct applicator assembly (300) and first and second adjunct elements (304, 306) within base (302) to protect adjunct applicator assembly (300) and first and second adjunct elements (304, 306) during shipping.

FIG. 15 shows adjunct applicator assembly (300) after wedge-shaped applicator member (308) has been transitioned from an unfolded position (shown in FIG. 16) into a folded position and is aligned to be fitted to base (302). In the folded position, the transverse distance between the first panel (313) and the second panel (315) gradually increases in a distal direction away from the connecting panel (340), thus providing body (309) with a wedge-like shape that tapers in a proximal direction toward connecting panel (340). In order to transition adjunct applicator assembly (300) from an unfolded position into a folded position, connecting panel (340) is folded so that first panel (313) and second panel (315) define a first angle ($\theta 1$) therebetween, which may range from approximately 20 degrees to approximately 45 degrees, for example. As shown in FIG. 15, adjunct applicator assembly (300) is vertically aligned with base (302) by aligning first tang (320) with a first slot (328), and the second tang (322) with a second slot (330). In other versions, base (302) may include one or more additional slots configured to set first and second panels (313, 315) at a one or more additional angles ranging from approximately 20 degrees to approximately 45 degrees.

In yet other versions, base (302) may include one or more pairs of slots (not shown) similar to slots (328, 330, 332) that are equally spaced apart from each other about a central point (not shown) along a centerline on side (324) so that tangs (320, 322) may be inserted into a first pair of slots. When tangs (320, 322) are inserted into first pair of slots a first angle ($\theta 1$) is formed between a first and second panels (313, 315). The distance between first panel (313) and second panel (315) increases as the first and second panels (313, 315) extend distally away from connecting panel (340). A second pair of slots are further spaced from the first pair of slots about the central point so that the first panel (313) and second panel (315) define a larger second angle ($\theta 2$) when first and second tangs (320, 322) are inserted into the second pair of slots that are further spaced from each other relative to the first pair of slots.

FIG. 16 shows wedge-shaped applicator member (308) in a planar, unfolded configuration. In the unfolded position, wedge-shaped applicator member (308) lies flat and extends longitudinally from the first tang (320) to the first panel (313). First panel (313) further extends distally to the connecting panel (340). Second panel (315) extends from the connecting panel (340) to the second tang (322). Adjunct applicator assembly (300) is configured to be contained within a sealed sterile barrier of product packaging (not shown) during shipping and storage so that body (309), first and second adjunct elements (304, 306), and base (302) remain sterile. By way of example only, such product packaging may be of the type disclosed in U.S. Pat. Pub. No. 2020/0205825, entitled "Method of Applying Buttresses to Surgically Cut and Stapled Sites," published Jul. 2, 2020, issued as U.S. Pat. No. 11,033,269 on Jun. 15, 2021, the disclosure of which is incorporated by reference herein. In order to house these components within a sterile barrier, it may be advantageous to minimize the size of adjunct applicator assembly (300) or otherwise provide adjunct applicator assembly (300) with the ability to be assembled from a collapsed state. It also may be advantageous to have base (302) function as a portion of the packaging material to protect adjunct applicator assembly (300) during shipping.

Connecting panel (340) of the present example is constructed as a joint or hinge that facilitates folding of the wedge-shaped applicator member (308). Connecting panel (340) is flat in the unfolded position and extends from a first crease (336) to a second crease (338). First crease (336) adjoins first panel (313) and second crease (338) adjoins second panel (315). First and second creases (336, 338)

include a perforated or relieved portion that is transverse to a length of the wedge-shaped applicator member (308) The perforated or relieved portion is configured to facilitate flexing of connecting panel (340) relative to each of first panel (313) and second panel (315). As another merely illustrative example, connecting panel (340) may include only a first crease (336) or may include multiple creases and multiple end panels that are used to join first panel (313) with second panel (315). In yet another merely illustrative example, body (309) may be shipped in a partially folded configuration. In the partially folded configuration, first crease (336) is folded to 180 degrees, and second crease (338) remains straight so that a back side of the first panel (313) is folded over and engages a back side of the second panel (315) to conserve longitudinal space within the sterile barrier.

Figure 17A:
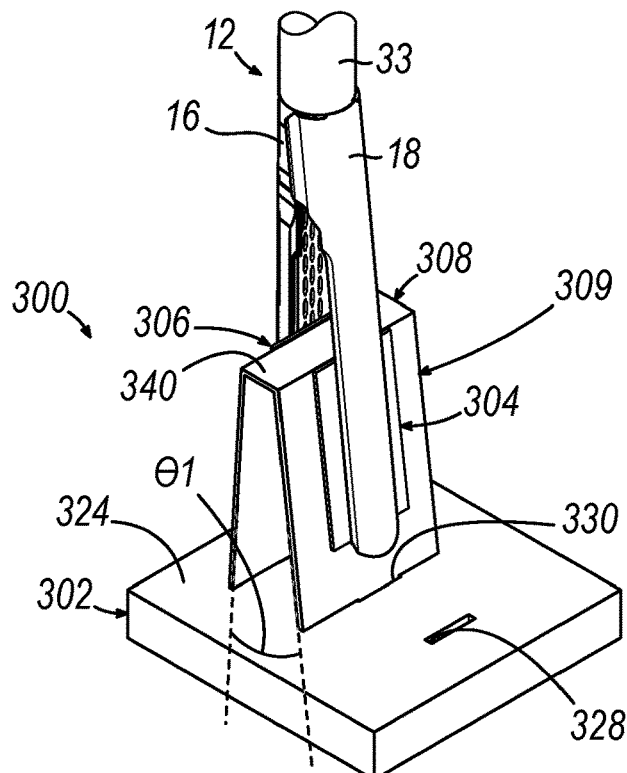
FIG. 17A depicts a perspective view of the jaws of the end effector of FIG. 3 in an open state and engaging the adjunct applicator of FIG. 14 while the adjunct applicator device is in a first folded configuration defining a first angle.

FIG. 17A shows wedge-shaped applicator member (308) coupled to base (302) with the end effector (12) longitudinally aligned with the resulting adjunct applicator assembly (300). Base (302) is positioned on a work surface with side (324) facing upwardly such that slots (328, 330, 332) face upwardly. Wedge-shaped applicator member (308) is coupled to base (302) by inserting first tang (320) into first slot (328) and second tang (322) into second slot (330) and by pressing wedge-shaped applicator member (308) in a downward direction. First and second tangs (320, 322) coupled with first and second slots (330, 332) thereby fix the angular relationship between first and second panels (313, 315) to define a distally opening first angle (θ1). As described above, base (302) may include one or more additional slots configured so that the distally opening first angle (θ1) defined by first and second panels (313, 315) may be set to any desired angle.

Figure 17B:
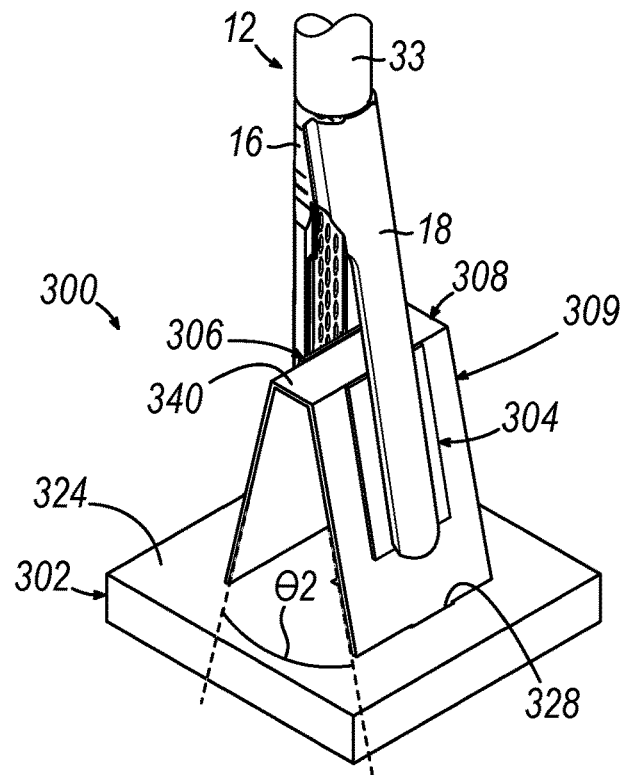
FIG. 17B depicts a perspective view of the jaws of the end effector of FIG. 3 in an open state and engaging the adjunct applicator of FIG. 14 while the adjunct applicator device is in a second folded configuration defining a second angle, showing the adjunct applicator device coupled with the base via a pair of slots.

FIG. 17B shows lower jaw and anvil (16, 18) of the end effector (12) in an open position engaging wedge-shaped applicator member (308) of adjunct applicator assembly (300). Film (346) has been removed from first and second adjunct elements (304, 306) before engaging adjunct applicator assembly (300) with lower jaw and anvil (16, 18) of the end effector (12). Lower jaw (16) of the end effector (12) engages second side (312) of first adjunct element (304) as anvil (18) simultaneously engages second side (312) of second adjunct element (306). Second attachment features (344), described above, of first and second adjunct elements (304, 306) attach to lower jaw and anvil (16, 18), respectively. While remaining in the open position, end effector (12) is then pulled upwardly away from adjunct applicator assembly (300). Second attachment features (344) of first and second adjunct elements (304, 306) remain attached to lower jaw and anvil (16, 18) as first attachment features (342) permit adjunct elements (304, 306) to release from first and second contact surfaces (314, 316) of wedge-shaped applicator member (308). First and second adjunct elements (304, 306) attached to lower jaw and anvil (16, 18) are ready to be used in a surgical procedure. It will be appreciated that by maintaining lower jaw and anvil (16, 18) in an open state while coupling adjunct elements (304, 306) to lower jaw and anvil (16, 18) with adjunct applicator assembly (300), the operator may control the force with which adjunct elements (304, 306) are seated onto lower jaw and anvil (16, 18) by selectively advancing end effector (12) longitudinally toward adjunct applicator assembly (300), which may remain stationary as illustrated in the present example.

B. Exemplary Static Wedge Adjunct Applicator with Angular Wings

In some instances, it may be desirable to modify adjunct applicator assembly (300) described above to include additional structural support to provide additional rigidity to first and second panels (313, 315) to inhibit first and second panels (313, 315) from bowing inwardly or outwardly so that adjunct elements (304, 306) evenly adhere to lower jaw and anvil (16, 18). FIGS. 18-21 show a second exemplary adjunct applicator assembly (400) that has a pair of first and second angular wings (446, 448) that may provide such functional benefits.

Figure 18:
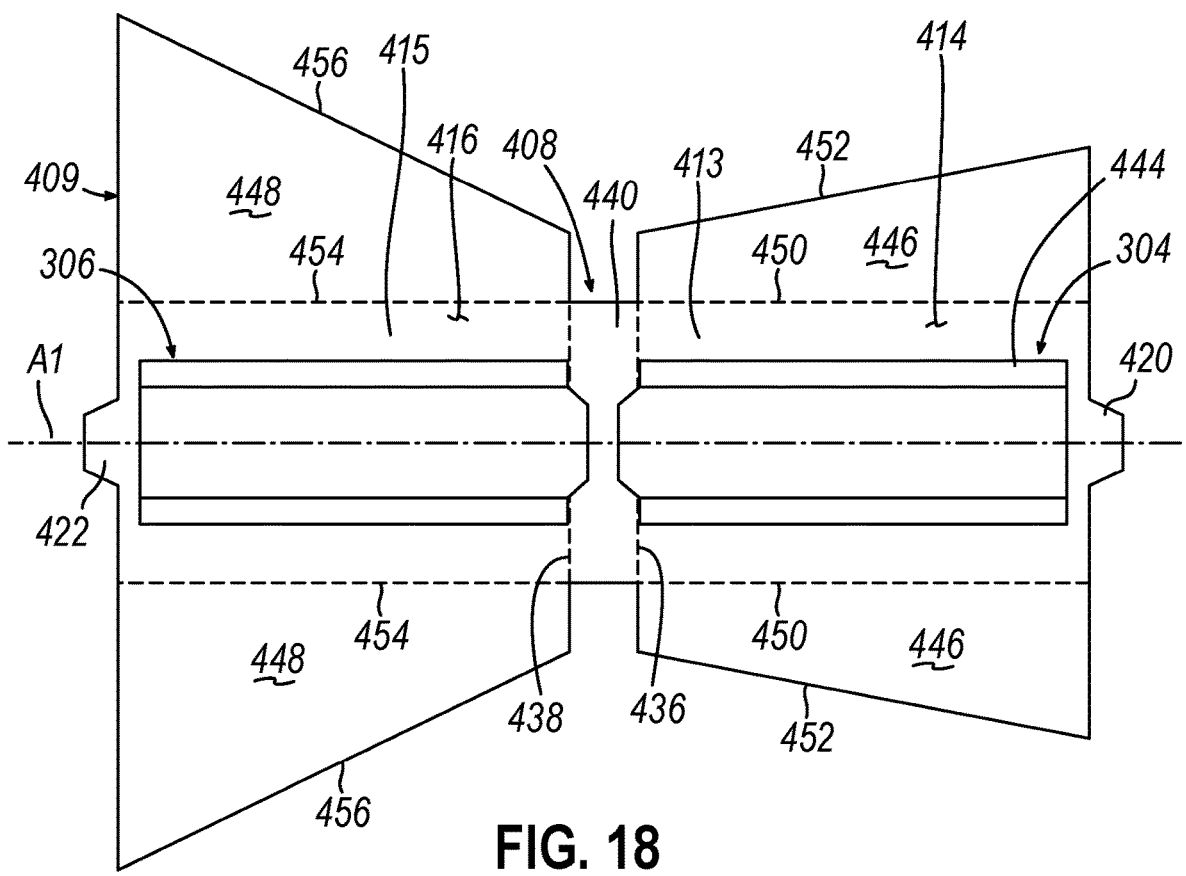
FIG. 18 depicts a plan view of another exemplary adjunct applicator device in an unfolded configuration.

FIG. 18 shows wedge-shaped applicator member (408) of adjunct applicator assembly (400) in an unfolded position. The adjunct applicator assembly (400) is constructed similarly to adjunct applicator assembly (300) described above, except as otherwise described below. The adjunct applicator assembly (400), like the adjunct applicator assembly (300), includes a wedge-shaped applicator member (408) and base (302). Wedge-shaped applicator member (408) includes a body (409) and first and second adjunct elements (304, 306). Wedge-shaped applicator member (408) and base (302) are constructed of similar materials as wedge-shaped applicator member (308) and base (302) of adjunct applicator assembly (300). As shown in FIG. 18, body (409) of adjunct applicator assembly (400) in an unfolded position extends longitudinally from a first tang (420) to a first panel (413). First panel (413) extends towards a connecting panel (440). Second panel (415) extends from the connecting panel (440) towards second tang (422). First and second panels (413, 415) define first and second contact surfaces (414, 416), respectively, similar to first and second contact surfaces (314, 316) of adjunct applicator assembly (300). First and second adjunct elements (304, 306) are attached on their first sides (310) to first and second contact surfaces (414, 416), respectively.

Body (409) of wedge-shaped applicator member (408) differs from body (309) of wedge-shaped applicator member (308) in that body (409) further includes first and second pair of angular wings (446, 448) formed on side portions of first and second panels (413, 415). In particular, a first pair of angular wings (446) is formed on the side portions of first panel (413) and are configured as trapezoidal shaped planar panels that extend transversely from first panel edges (450). First panel edges (450) run parallel to the length of unfolded body (409) along the outside edges of the first panel (413). First panel edges (450) may be perforated or relieved to facilitate bending or tearing of first angular wings (446) relative to first panel (413). In the present version, first pair of angular wings (446) forms a pair of trapezoidal planar panels. A right angle of the trapezoidal shape is located at the end proximate to first tang (420). First angular wings (446) each define a first outer edge (452) that is configured to abut an inside surface of second panel (415) to define a first predetermined angle (θ1) between first and second panels (413, 415) that opens distally and may range from approximately 20 degrees to approximately 45 degrees.

Second pair of angular wings (448) extend transversely from second panel edges (454) of second panel (415) to form trapezoidal planar panels each having a right angle. A right angle of each first angular wing (448) is located at the end proximate to first tang (420). Second panel edges (454) run parallel to the length of unfolded body (409) along an edge of second panel (415). Similar to first panel edges (450), second panel edges (454) may be perforated or relieved to facilitate bending of second pair of angular wings (448) relative to second panel (315) or tearing. Second pair of angular wings (448) is a mirror version of first pair of angular wings (446) and each second angular wing (448) defines a second outer edge (456) to define a second predetermined angle (θ2) (see FIG. 21) between first and second panels (413, 415) from approximately 20 degrees to approximately 45 degrees. Second angle (θ2) may be the same angle or a different angle from first angle (θ1).

Figure 19:
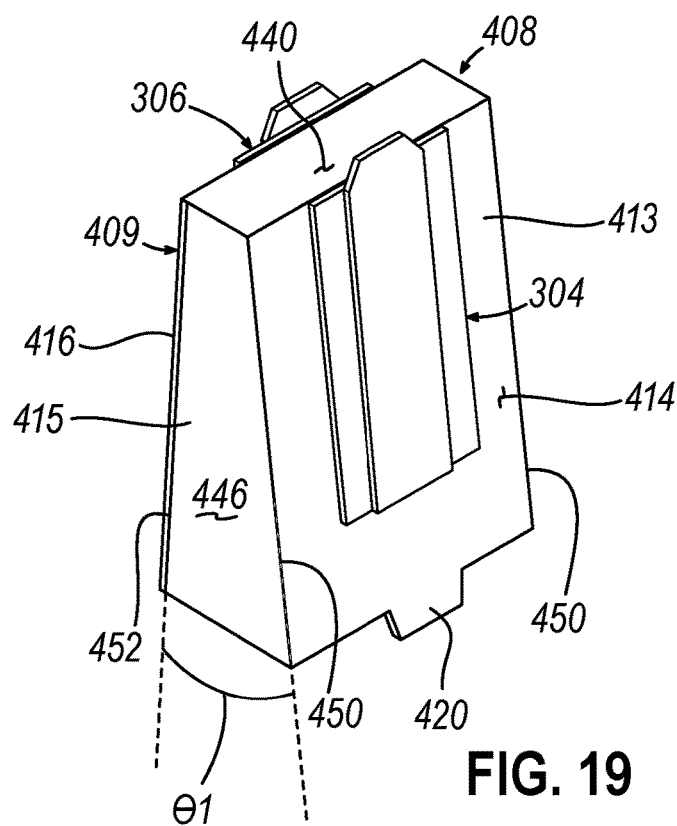
FIG. 19 depicts a perspective view of the adjunct applicator device of FIG. 18 in a first folded configuration defining a first angle.
Figure 21:
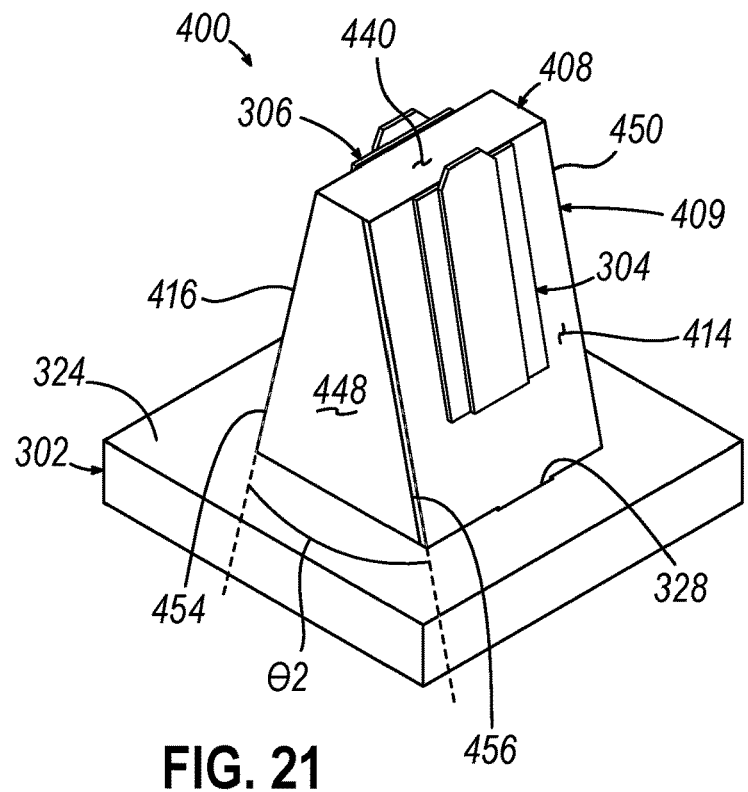
FIG. 21 depicts a perspective view of the adjunct applicator device of FIG. 18 in a second folded configuration defining a second angle, showing the adjunct applicator device coupled to the base via a pair of slots.

In the present example, second pair of angular wings (448) are suitably shaped such that the resulting second angle (θ2) is larger than the first angle (θ1) defined by first wings (446) between first and second panels (413, 415), for example as shown by FIG. 21 upon comparison with FIG. 19. Accordingly, a user may selectively deploy first wings (446) in the manner described above to define a relatively smaller first angle (θ1) between first and second panels (413, 415) for use with an end effector (12) having a relatively smaller jaw opening (also referred to as an "aperture") between the anvil (18) and the deck (72) of the staple cartridge (37) in the open state. Alternatively, the user may selectively deploy second pair of angular wings (448) in the manner described above to define a relatively larger second angle (θ2) between first and second panels (413, 415) for use with an end effector (12) having a relatively larger jaw opening in the open state.

FIG. 19 shows wedge-shaped applicator member (408) in a folded configuration after being transitioned from an unfolded configuration. Wedge-shaped applicator member (408) is transitioned into folded configuration by folding first and second panels (413, 415) relative to connecting panel (440) along first and second creases (436, 438). To transition wedge-shaped applicator member (408) from the unfolded configuration of FIG. 16 to one of the folded configurations shown in FIGS. 19 and 20, either first pair of angular wings (446) or second pair of angular wings (448) is folded along first or second panel edges (450, 454), respectively. First or second outer edges (452, 456) engage inside of the second panel (415) or first panel (413), respectively. For example, if the user desires to set adjunct applicator assembly (400) to first angle (θ1), the user may fold first pair of angular wings (446) inwards along first panel edges (450) to engage inside of the second panel (415). Second pair of angular wings (448) may be folded out of the way, remain unfolded, or be torn off along second panel edges (454) so that second pair of angular wings (448) do not interfere with first pair of angular wings (446) when first pair of angular wings (446) is folded to engage inside of first panel (413).

In order to set adjunct applicator assembly (400) to second angle (θ2), second pair of angular wings (448) are folded inwards along second panel edges (454) so that second outer edges (456) engages inner side of first panel (413). First pair of angular wings (446) may be folded out of the way, remain unfolded, or be torn along first panel edges (450) and discarded so that first pair of angular wings (446) do not interfere with second pair of angular wings (448) when second pair of angular wings (448) is folded to engage inside of the first panel (413).

Figure 20:
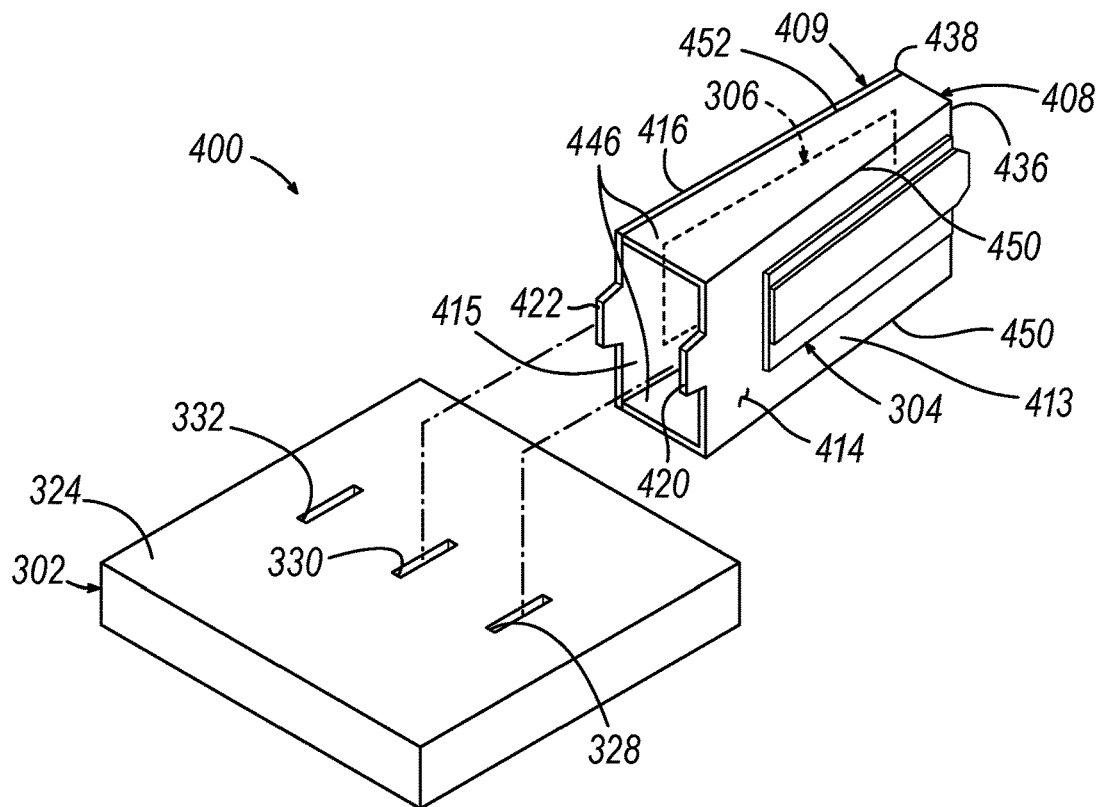
FIG. 20 depicts a perspective view of the adjunct applicator device of FIG. 18 in the first folded configuration and being positioned in relation to a pair of slots of a base.

FIG. 20 shows adjunct applicator assembly (400) with wedge-shaped applicator member (408) in a first folded configuration in which first and second panels (413, 415) define first angle (θ1) therebetween, before wedge-shaped applicator member (408) is coupled to a base (302). Base (302) is placed on a work surface with side (324) facing upwardly. First slot (328) is longitudinally spaced from second slot (330) at a distance equal to the distance between first and second tangs (420, 422) when wedge-shaped applicator member (408) is set to first angle (θ1). First and second tangs (420, 422) are aligned with first and second slots (428, 430), and wedge-shaped applicator member (408) is then pressed downwardly, thereby inserting first and second tangs (420, 422) into first and second slots (428, 430).

FIG. 21 shows adjunct applicator assembly (400) with wedge-shaped applicator member (408) in a second folded configuration in which first and second panels (413, 415) define second angle (θ2) therebetween, and with wedge-shaped applicator member (408) coupled to base (302). First slot (328) in base (302) is spaced from third slot (332) at a distance equal to the distance between first and second tangs (420, 422) when the wedge-shaped applicator member (408) is set to second angle (θ2). Wedge-shaped applicator member (408) is coupled to base (302) by aligning first tang (420) with first slot (328) and inserting first tang (420) into first slot (328), while aligning second tang (422) with third slot (332), and inserting second tang (422) into third slot (332) by pressing wedge-shaped applicator member (408) in a downwards direction.

As described above, it will be appreciated that wedge-shaped applicator member (408) may be suitably configured to assume a variety of predetermined angular, wedge-shaped configurations, and slots (328, 330, 332) of base (302) may be suitably spaced from one another to receive tangs (420, 422) of wedge-shaped applicator member (408) in each of such predetermined configurations. Accordingly, a user may easily modify and adapt wedge-shaped applicator member (408) for use with end effectors (12) having jaw openings between the anvil (18) and the deck (72) of the staple cartridge (37) in the fully opened state.

C. Exemplary Static Wedge Adjunct Applicator with Adjustable Strut

Figure 24:
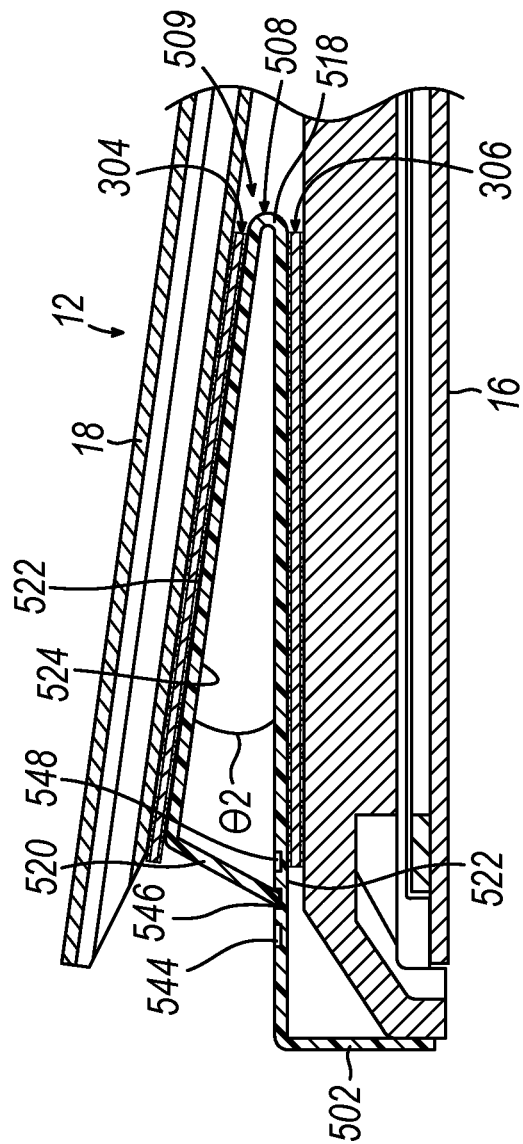
FIG. 24 depicts a side cross-sectional view of the end effector of FIG. 3 engaging the adjunct applicator device of FIG. 22 while the adjunct applicator device is in a second expanded, angular configuration.

In some instances, it may be desirable to attach adjuncts to open lower jaw and anvil (16, 18) of the end effector (12) with a compact, sterile, disposable adjunct applicator assembly. Additionally, it may be advantageous to set such an adjunct applicator assembly to different predetermined angles so that the adjunct applicator assembly may be used with different end effectors, and/or at optimal angles for particular adjuncts. It may also be desirable to have an adjunct applicator assembly that may be manipulated by the user to engage the open lower jaw and anvil (16, 18) of the end effector (12) without a base, such as base (302) described above, that requires a work surface. FIGS. 22-24 show a third exemplary adjunct applicator assembly (500) that may provide such functional benefits.

FIG. 22 shows adjunct applicator assembly (500) in a non-expanded, storage configuration. Adjunct applicator assembly (500) is similar to adjunct applicator assembly (300) described above, except as otherwise described below. Adjunct applicator assembly (500), like adjunct applicator assembly (300), includes a wedge-shaped applicator member (508), a first adjunct element (304), and a second adjunct element (306). Adjunct applicator assembly (500) is also configured to be contained within a sealed sterile barrier of product packaging (not shown) during shipping and storage so that sealed within a sterile bag (not shown) during shipping and storage. Adjunct applicator assembly (500) may be constructed of similar materials as adjunct applicator assembly (300). Adjunct applicator assembly (500) includes a body (509) that may be disposable or reusable. Adjunct applicator assembly (500) is configured to transfer first and second adjunct elements (304, 306) to open lower jaw and anvil (16, 18) of the end effector (12).

Adjunct applicator assembly (500) differs from adjunct applicator assembly (300) in that adjunct applicator assembly (500) is configured to be manipulated by hand and inserted into open lower jaw and anvil (16, 18) of end effector (12) without being coupled to base (302), and body (509) may be folded in a storage configuration to minimize the space that body (509) occupies within the sterile barrier of product packaging.

Body (509) includes a first panel (513), a second panel (515), a third panel (502), a first bending notch (504), a second bending notch (506), a connecting portion (518), and a strut (520). Body (509) extends proximally from third panel (502) to first bending notch (504) when in a non-expanded, storage position. Third panel (502) may serve as a handle configured to be ergonomically gripped by the user with a thumb and/or a finger. Third panel (502) is joined to first panel (513) at first bending notch (504). First bending notch (504) is a v-shaped notch located on an outside surface (522) of body (509) between third panel (502) and first panel (513). The outer surface (522) is an outwardly facing surface of the body (509). First bending notch (504) may include an adhesive (not shown) configured to retain third panel (502) in a transverse position relative to the longitudinally extending first panel (513) (shown in FIG. 23).

First panel (513) includes a first angle notch (544), a second angle notch (546), and a third angle notch (548) located on a distal portion of an inside surface (524). The inside surface (524) is an inwardly facing surface of the body (509). The first panel (513) extends proximally from the first bending notch (504) to connecting portion (518). Connecting portion (518) joins a proximal end of first panel (513) with a proximal end of second panel (515). Connecting portion (518) may be in the form of a flexible u-bend or a v-bend and is configured to enable first and second panels (513, 515) to angularly deflect relative to one another between a plurality of angular configurations. Connecting portion (518) may include one or more flexing features (538), which may be in the form of creases or interconnected panels (not shown) similar to first and second creases (336, 338) and connecting panel (340) of adjunct applicator assembly (300). Second panel (515) extends distally from connecting portion (518) to second bending notch (506). Second bending notch (506) is located on inside surface (554) at second panel (515) and joins strut (520) to second panel (515). Strut (520) extends distally from second bending notch (506) to strut end (540). Second bending notch (506) may be a v-shaped notch located on inside surface (554) of second panel (515). Strut end (540) is configured to selectively engage one of angle notches (544, 546, 548). First and second adjunct elements (304, 306) are releasably attached to the first and second panel (513, 515) on outside surface (522).

FIG. 23 shows adjunct applicator assembly (500) in a first expanded, angular configuration engaging open lower jaw and anvil (16, 18) of the end effector (12). Adjunct applicator assembly (500) has been transitioned from storage configuration (shown in FIG. 22) into the first angular configuration by bending both third panel (502) at first bending notch (504) and strut (520) at second bending notch (506). Third panel (502) is bent transversely downwards at first bending notch (504) relative to first panel (513) towards the outside surface (522). Strut (520) is bent transversely downwards at second bending notch (506) relative to second panel (515) towards inside surface (524) of first panel (513). In the illustrated example, strut end (540) engages first angle notch (544) and is retained by first angle notch (544). First angle notch (544) is distally located relative to second and third angle notches (546, 548). Strut end (540) is retained by first angle notch (544) so that first panel (513) and second panel (515) define a first angle (θ1) therebetween, which may range from approximately 20 degrees to approximately 45 degrees, for example. In the first folded position, the transverse distance between the first panel (513) and the second panel (515) gradually increases in a distal direction away from the connection portion (518), thus providing wedge-shaped applicator member (508) a wedge-like shape that tapers in a proximal direction toward connecting portion (518).

Film (346) is removed from second sides (312) of first and second adjunct elements (304, 306) before the lower jaw and anvil (16, 18) of end effector (12) engage the wedge-shaped applicator member (508). The user may grip or hold third panel (502) between a finger and a thumb of one hand while using the other hand to press the wedge-shaped applicator member (508) into the open lower jaw and anvil (16, 18) of the end effector (12). Open lower jaw and anvil (16, 18) of the end effector (12) will engage first and second adjunct elements (304, 306). Second sides (312) of first and second adjunct elements (304, 306) attach to open lower jaw and anvil (16, 18). The user then removes end effector (12) from wedge-shaped applicator member (508), which results in first and second adjunct elements (304, 306) detaching from applicator member (508) while remaining secured to open lower jaw and anvil (16, 18).

FIG. 24 shows adjunct applicator assembly (500) in a second expanded, angular position engaging and open lower jaw and anvil (16, 18) of the end effector (12). Wedge-shaped applicator member (508) has been transitioned from the storage position (shown in FIG. 22) into the second angular configuration in a manner similar to the first angular position (shown in FIG. 23) described above. In particular, third panel (502) is bent about first bending notch (504) and strut (520) is bent about second bending notch (506). Third panel (502) is bent transversely downwards relative to first panel (513) towards outside surface (522) at first bending notch (504). Strut (520) is bent transversely downwards at second bending notch (506) relative to second panel (515) towards inside surface (524) of first panel (513). Strut end (540) engages and is retained by second angle notch (546). Second angle notch (546) is proximal to first angle notch (544) and distal to third angle notch (548). Once strut end (540) is retained by second angle notch (546), first panel (513) and second panel (515) define a second angle (θ2) therebetween, which may range from approximately 20 degrees to approximately 45 degrees. In the present example, second angle (θ2) is greater than first angle (θ1) (shown in FIG. 23) in the second folded position, and thus the transverse distance between the first panel (513) and the second panel (515) gradually increases distally at a rate greater than in first folded position.

Though not shown, strut (520) may also be placed in third angle notch (548) so that first panel (513) and second panel (515) define a third angle between first panel (513) and second panel (515) that is greater than second angle (θ2) and which may be approximately 20 degrees to approximately 45 degrees. As another merely illustrative example, inside surface (524) of the first panel (513) may include one or more additional angle notches configured to define additional predetermined angles between first and second panels (513, 515) that range from approximately 20 degrees to approximately 45 degrees.

D. Exemplary Static Wedge Adjunct Applicator with Force Limiting Feature

Figure 25:
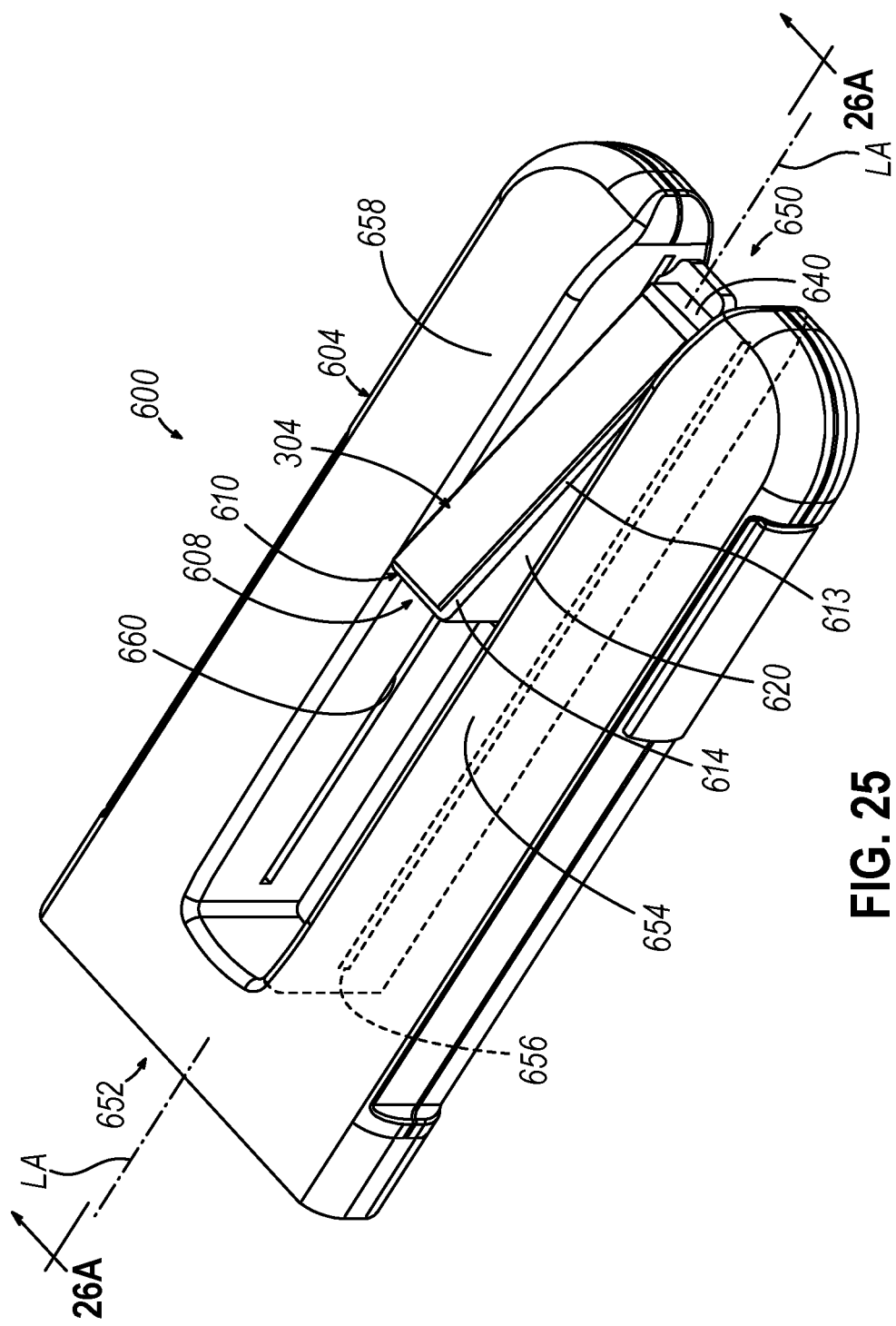
FIG. 25 depicts a perspective view of another exemplary adjunct applicator device, showing a wedge portion of the adjunct applicator device in a first longitudinal position.

In some instances, it may be desirable to limit the amount of force used to attach adjuncts to open lower jaw and anvil (16, 18) of end effector (12) to a predetermined amount of force to thereby avoid excessive application forces that might otherwise damage end effector (12) and/or adjunct elements (304, 306). FIGS. 25-26B show a fourth exemplary adjunct applicator assembly (600) that may provide such functional benefits.

As shown in FIG. 25, adjunct applicator assembly (600) includes a wedge-shaped applicator member (608), which may be similar in construction and function to any of the exemplary wedge-shaped applicator members (308, 408, 508) described above. Applicator member (608) includes a body (610) and first and second adjunct elements (304, 306) disposed on opposing sides of body (610). Adjunct applicator assembly (600) further includes a resilient member in the form of a coil spring (602), a housing (604), and a linking feature (606). Housing (604) may be constructed similar to the combination of first and second housings (216A, 216B) of adjunct applicator device device (210) described above, and in the present example is configured as a chassis that provides a rigid support structure capable of supporting the wedge-shaped applicator member (608). The wedge-shaped applicator member (608) is slidably coupled to housing (604) by linking feature (606). Coil spring (602) biases body (610) proximally to a proximal position, shown in FIG. 26A. Body (610) may be constructed of a surgically safe plastic, stainless steel, or other material known in the art that is capable of being sterilized.

Similar to wedge-shaped applicator member (308) of adjunct applicator assembly (300), wedge-shaped applicator member (608) includes a first contact feature (613) that includes a first contact surface (614), a second contact feature (615) that includes a second contact surface (616), and a connecting feature (640) that interconnects first and second contact features (613, 615) at least at their proximal ends. First adjunct element (304) is mounted to first contact surface (614) of first contact feature (613), and second adjunct element (306) is mounted to second contact surface (616) of second contact feature (615). In some versions, connecting feature (640) may be suitably configured to enable first and second contact features (613, 615) to move toward and away from one another about their proximal ends through a range of angular positions in which body (610) defines a distally opening angle. In other versions, body (610) may be a static structure in which first and second contact features (613, 615) are angularly fixed relative to one another such that body (610) is configured to define a single distally opening angle.

Wedge-shaped applicator member (608) is slidably coupled to housing (604) with a plurality of support arms (642), and a movable member in the form of a roller (644). Each support arm (642) is fixedly attached to wedge-shaped applicator member (608) at a first end (646) and is rotatably coupled at a second end to roller (644). The present version includes up to four support arms (642), with two support arms (642) being attached to each lateral side of the wedge-shaped applicator member (608). Various other quantities and arrangements of support arms (642) may be employed in other versions. In yet other versions, movable member may be in the form of a slider, a puck, a ski, or any other structure known in the art that facilitates linear translation of a body relative to a chassis.

Housing (604) extends longitudinally from an open end (650) to a closed end (652) and has a "U" shape. Open end (650) is configured to receive open lower jaw and anvil (16, 18) of the end effector (12). Housing (604) further includes first and second housing side portions (654, 658) that extend longitudinally. First housing side portion (654) has a first channel (656) and second housing side portion (658) has a second channel (660) laterally opposed from first channel (656). First and second housing side portions (654, 658) collectively define the "U" shape of housing (604). Each channel (656, 660) houses one or more rollers (644). Each channel (656, 660) extends longitudinally along the respective first or second housing side portion (654, 658) and is configured to allow rollers (644) to rotate, thereby enabling wedge-shaped applicator member (608) to translate proximally and distally relative to housing (604).

Coil spring (602), shown in the form of an extension coil spring, is operatively attached between housing (604) and linking feature (606). In the present version, the linking feature (606) connects to a proximal portion of the wedge-shaped applicator member (608) within first housing side portion (654). In other versions, an additional coil spring (602) may be located within second housing side portion (658) and attached between additional linking feature (606) and a proximal portion of the housing (604). In yet other versions, linking feature (606) may be fitted between coil spring (602) and a distal portion of the housing (604). In all such versions, coil spring (602) is in a contracted, relaxed state when wedge-shaped applicator member (608) is in proximal position relative to housing (604).

FIG. 26A shows open lower jaw and anvil (16, 18) of the end effector (12) engaging first and second adjunct elements (304, 306) fitted to first and second contact surfaces (614, 616) with wedge-shaped applicator member (608) in the proximal position relative to housing (604), with the coil spring (602) in the contracted state. In proximal position, coil spring (602) biases wedge-shaped applicator member (608) in a proximal direction to proximal position. Open lower jaw and anvil (16, 18) of end effector (12) are forced distally against first and second adjunct elements (304, 306), which are supported by first and second contact features (613, 615), respectively.

FIG. 26B shows open lower jaw and anvil (16, 18) of end effector (12) being pressed distally with an amount of force that is sufficient to overcome the resilient bias of coil spring (602) and actuate wedge-shaped applicator member (608) from the proximal position (shown in FIG. 27A) to a distal position in which the coil spring (602) is extended. In order to transition applicator member (608) to the distal position, the user applies enough longitudinal input force to overcome the predetermined bias force that coil spring (602) proximally applies to wedge-shaped applicator member (608). Once the distal input force exerted by the user on applicator member (608) via end effector (12) overcomes the proximal bias force exerted on applicator member (608) by coil spring (602), wedge-shaped applicator member (608) moves distally relative to housing (604). This distal translatability of applicator member (608) relative to housing (604) and the resilient bias of extension coil spring (602) effectively limits the magnitude of force that end effector (12) can exert on applicator member (608) in response to a user input force. This configuration may ensure that the longitudinal compressive force mutually exerted between lower jaw and anvil (16, 18) and applicator member (608) is sufficient to effectively seat adjunct elements (304, 306) on lower jaw and anvil (16, 18), while also limiting such compressive force to protect lower jaw and anvil (16, 18) and applicator member (608) from damage due to otherwise excessive compression force.

Rollers (644) facilitate translation of wedge-shaped applicator member (608) distally and keep wedge-shaped applicator member (608) longitudinally aligned so that first and second adjunct elements (304, 306) are not misaligned while being applied to lower jaw and anvil (16, 18) of end effector (12). A portion of the end effector (12) may engage a stop feature of housing (604) to prevent coil spring (602) from being over-extended beyond a designed range of motion and applying more force than the predetermined amount of force to the first and second adjunct elements (304, 306). This allows the coil spring (602) to administer a predetermined amount of force proximally against lower jaw and anvil (16, 18) of the end effector (12). As described above, this predetermined force is enough force to attach second sides (312) of first and second adjunct elements (304, 306) to open lower jaw and anvil (16, 18) of end effector (12). Once a portion of end effector (12) engages the stop feature of housing (604), end effector (12) is moved proximally away from adjunct applicator assembly (600). The attachment force of second attachment feature (344) being greater than the attachment force of the first attachment feature (342) results in attachment of first and second adjunct elements (304, 306) to open lower jaw and anvil (16, 18) of the end effector (12).

IV. Exemplary Adjunct Applicator Devices with Selective Expandability

In some instances, it may be desirable to provide an adjunct applicator device that is operable to selectively transition between a non-expanded state and an expanded state for applying an adjunct element (e.g., a buttress assembly or a tissue thickness compensator) to one or both jaws of a surgical stapler end effector while the jaws remain in an open state. Each of the exemplary applicator devices described below in connection with FIGS. 27A-41B provide such functionality.

A. First Selectively Expandable Adjunct Applicator Device

Figure 27A:
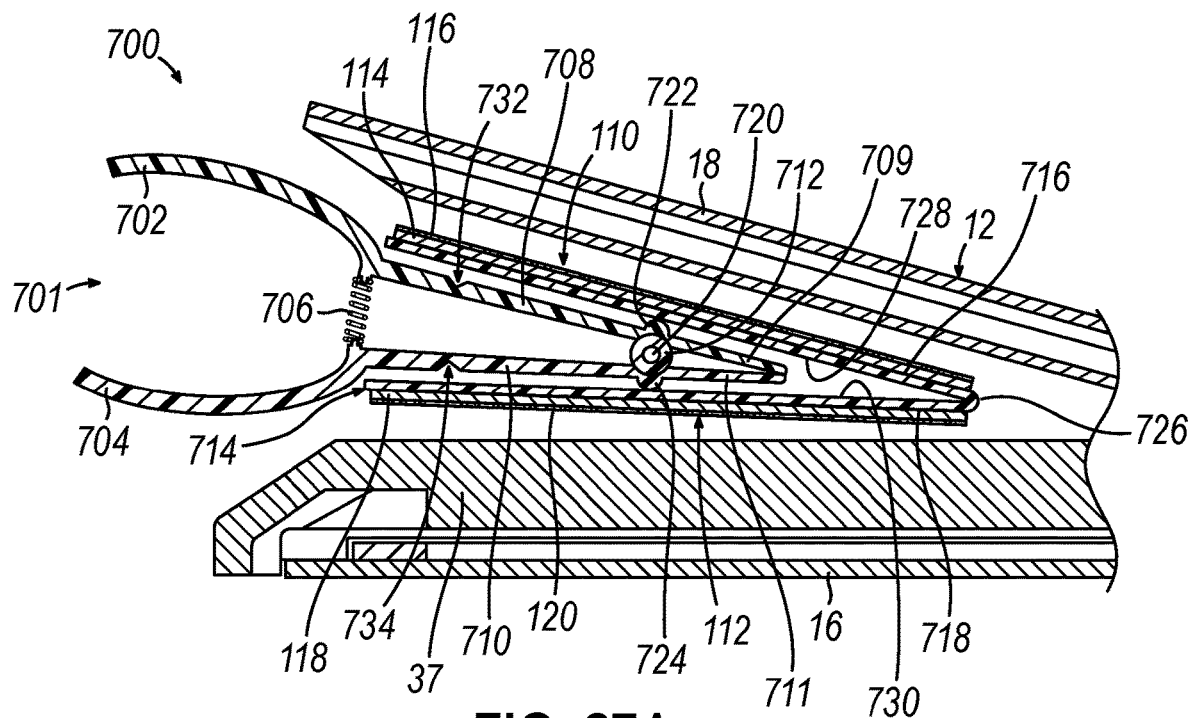
FIG. 27A depicts a side cross-sectional view of another exemplary adjunct applicator device, the buttress assembly of FIG. 8 applied to the adjunct applicator device, and the end effector of FIG. 3, showing the adjunct applicator device in a non-expanded state.
Figure 27B:
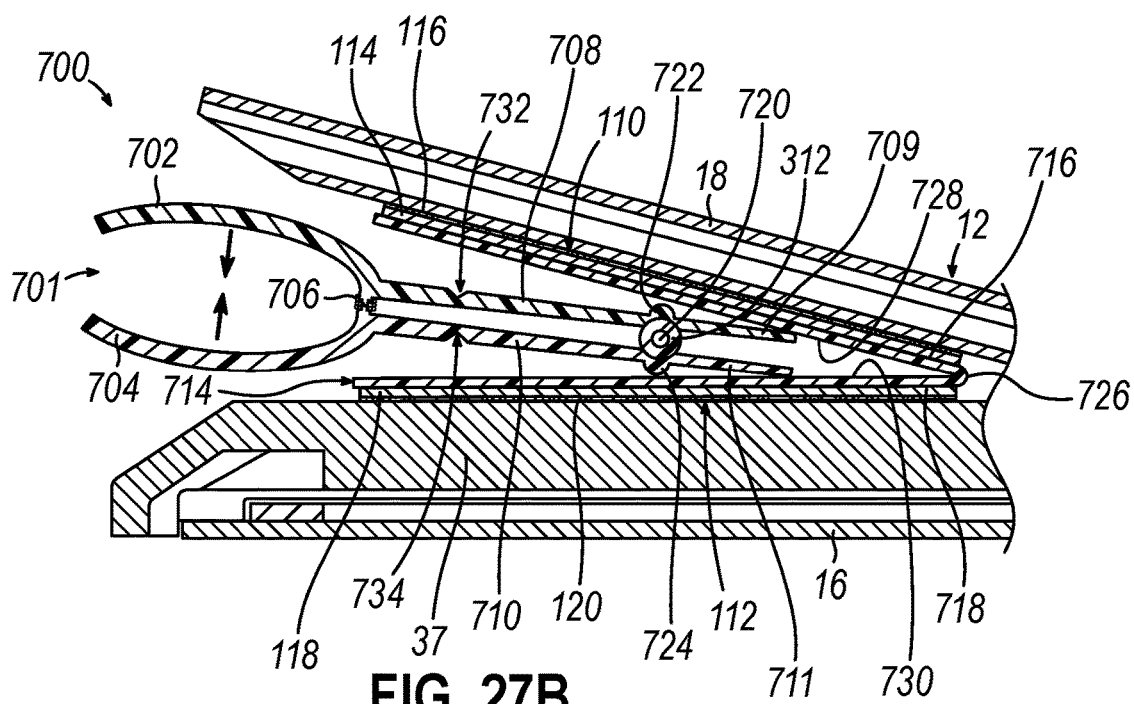
FIG. 27B depicts a side cross-sectional view of the adjunct applicator device of FIG. 27A, the buttress assembly of FIG. 8, and the end effector of FIG. 3, with the adjunct applicator device in an expanded state for securing the buttress assembly to the end effector.

FIGS. 27A-27B show another exemplary applicator device (700) that is configured to apply an adjunct material (e.g., buttress assembly (110, 112) or a tissue thickness compensator) to a jaw (e.g., lower jaw (16) or anvil (18)) of end effector (12) of surgical stapler (10). Applicator device (700) adjusts for the thickness of anvil (18) or lower jaw (16) allowing applicator device (700) to suitably apply adjunct material to both anvil (18) and lower jaw (16) separately. As shown in FIG. 27A, applicator device (700) includes an expansion mechanism (701) and a contact structure shown as an expandable wedge (714). Expansion mechanism (701) of the present example includes handles (702, 704), a compression spring (706), and applicator arms (708, 710).

Wedge (714) of the present example is configured to support a pair of buttress assemblies (110) on one side of wedge (714) and another pair of buttress assemblies (112) on the reverse side of wedge (714). Each buttress assembly (110, 112) is provided in a respective pair of portions that are separated to avoid spanning across slots (42, 49) of anvil (18) and staple cartridge (37) (see, FIG. 3), respectively, though wedge (714) may just as easily support wide versions of buttress assemblies (110, 112) that unitarily span across slots (42, 49) of anvil (18) and staple cartridge (37), respectively. Applicator arms (708, 710) are separated by a pivot member (shown as pin (712)) configured to rotatably couple with applicator arms (708, 710). Applicator device (700) may therefore resemble reverse pliers, that is, compression spring (706) is configured to provide a force biasing handles (702, 704) away from each other, thereby biasing distal portions (709, 711) of applicator arms (708, 710) toward each other via pivoting rotation about axis (720) provided by pin (712). Wedge (714) is configured to contact applicator arms (708, 710) via contact members (722, 724); however, contact members (722, 724) are merely optional and may be omitted in some versions. Further, wedge (714) includes first applicator surface (716) and second applicator surface (718) coupled together at resilient pivoting point (726).

First and second applicator surfaces (716, 718) are each configured to apply adjunct material to end effector (12) of stapling instrument (10). More specifically, first applicator surface (716) is configured to accept buttress assembly (110) thereon for application onto pivotable anvil (18), and second applicator surface (718) is configured to accept buttress assembly (112) thereon for application on to lower jaw (16). Particularly, buttress assembly (110) is placed onto first applicator surface (716) such that upper adhesive layer (116) is facing outwardly away from first applicator surface (716), and buttress assembly (112) is placed onto second applicator surface (718) such that lower adhesive layer (120) is facing outwardly away from second applicator surface (718), thereby allowing lower and upper adhesive layers (116, 120) to adhere to pivotable anvil (18) and lower jaw (16), respectively, upon application of buttress assemblies (110, 112) by applicator device (700). In some versions, first and second applicator surfaces (716, 718) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (716, 718) prior to buttress assemblies (110, 112) being applied to pivotable anvil (18) and lower jaw (16), respectively. However, various suitable methods and structures for securely and removably positioning buttress assemblies (110, 112) on applicator surfaces (716, 718) are also envisioned. In some versions, a user utilizing a separate device (not shown) may initially apply one or both buttress assemblies (110, 112) to applicator surfaces (716, 718).

FIG. 27B shows the adjunct material being secured onto stapling surfaces of pivotable anvil (18) and lower jaw (16) of end effector (12). As described above, the adjunct material may include buttress assemblies (110, 112), tissue thickness compensators, or other suitable materials. The stapling surface is intended to include upper deck (72) of staple cartridge (37) that includes staple apertures (50) or a contact surface (52) of anvil (18) that includes staple forming pockets (53) as shown in FIG. 3. It is also envisioned that anvil (18) may be disposed on the lower jaw and the staple cartridge (37) may be disposed on the upper jaw.

As shown in FIG. 27B, once buttress assemblies (110, 112) are positioned on applicator surfaces (716, 718), handles (702, 704) of applicator device (700) are squeezed together to thereby compress spring (706) and pivot applicator arms (708, 710) about axis (720). As handles (702, 704) transition closer together, distal portions (709, 711) of applicator arms (708, 710) transition away from each other and contact inward-facing surfaces (728, 730) of applicator arms (708, 710) to spread (i.e., separate) applicator arms (708, 710) in opposing directions via resilient pivoting point (726) until buttress assemblies (110, 112) adhere to pivotable anvil (18) and lower jaw (16), respectively. More specifically, wedge (714) defines a distal opening angle that increases as applicator arms (708, 710) of wedge (714) spread, thus advancing each applicator arm (708, 710) toward the respective jaw of end effector (12).

Thereafter, handles (702, 704) may be released by the user thereby reversing the pivoting motion of applicator arms (708, 710), disengaging from buttress assemblies (110, 112) as buttress assemblies (110, 112) remain adhered to pivotable anvil (18) and lower jaw (16). Applicator device (700) may thereafter be removed.

In some versions, a break-away feature may be desired to ensure the applicator device (700) does not apply too much pressure to end effector (12) while applying buttress assemblies (110, 112). For example, one or more breakaway features, such as notches (732, 734) can be included on applicator arms (708, 710). In the illustrated example, notches (732, 734) are included between handles (702, 704) and pin (712), and arms (708, 710) are configured to break at notches (732, 734), respectively, if arms (708, 710) experience force above a predetermined limit while applying buttress assemblies (110, 112).

B. Second Selectively Expandable Adjunct Applicator Device

Figure 28A:
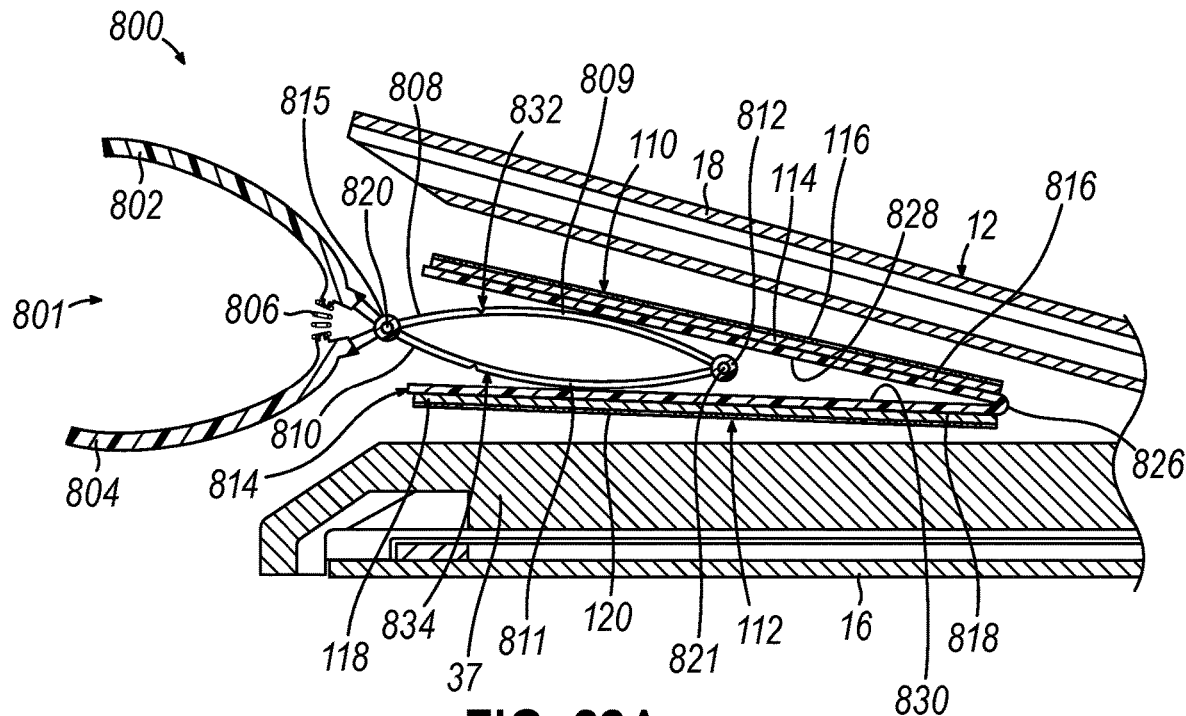
FIG. 28A depicts a side cross-sectional view of another exemplary adjunct applicator device, the buttress assembly of FIG. 8 applied to the adjunct applicator device, and the end effector of FIG. 3, showing the adjunct applicator device in a non-expanded state.
Figure 28B:
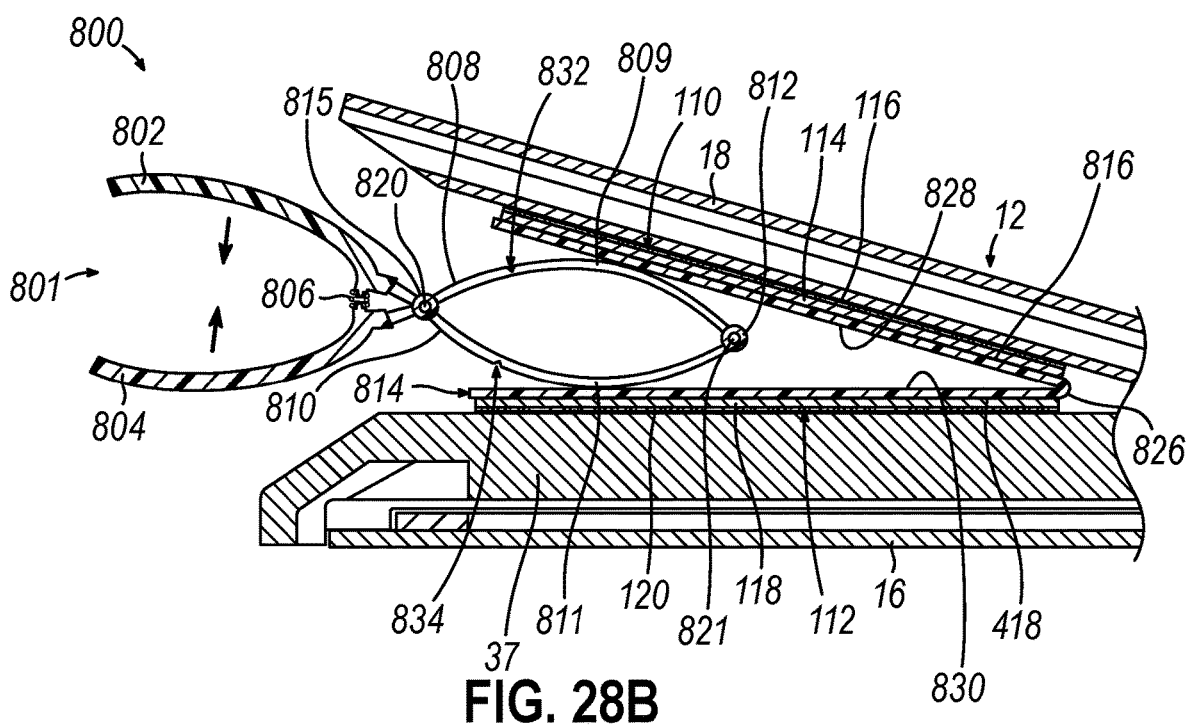
FIG. 28B depicts a side cross-sectional view of the adjunct applicator device of FIG. 28A, the buttress assembly of FIG. 8, and the end effector of FIG. 3, with the adjunct applicator device in an expanded state for securing the buttress assembly to the end effector.

FIGS. 28A-28B show another exemplary applicator device (800) that is configured to apply an adjunct material to a jaw (e.g., lower jaw (16) or anvil (18)) of end effector (12) of surgical stapler (10). Applicator device (810) adjusts for thickness of anvil (18) or lower jaw (16) allowing applicator device (810) to suitably apply adjunct material to anvil (18) and lower jaw (16). As a result, the application of buttress assembly (112) using applicator device (810) to lower jaw (16) that includes staple cartridge (37) may be similar to the application of applicator device (700) described above. As shown in FIG. 28A, applicator device (800) includes an expansion mechanism (801) and a contact structure shown as expandable wedge (814). Expansion mechanism (801) of the present example includes handles (802, 804), a compression spring (806), and applicator arms (808, 810).

Applicator arms (808, 810) are coupled together at first and second pivot members (shown as pins (815, 812)). Compression spring (806) is configured to provide a force biasing handles (802, 804) away from each other, thereby biasing flexible central portions (809, 811) of applicator arms (808, 810) toward each other via pivoting rotation about pivot axes (820, 821) provided by pins (815, 812). Wedge (814) of the present example is configured to support a pair of buttress assemblies (110) on one side of wedge (814) and another pair of buttress assemblies (112) on the reverse side of wedge (814). Each buttress assembly (110, 112) is provided in a respective pair of portions that are separated to avoid spanning across slots (42, 49) of anvil (18) and staple cartridge (37) (see, FIG. 3), respectively, though wedge (814) may just as easily support wide versions of buttress assemblies (110, 112) that unitarily span across slots (42, 49) of anvil (18) and staple cartridge (37), respectively. Wedge (814) is configured to contact applicator arms (808, 810) along flexible central portions (809, 811) of applicator arms (808, 810). Further, wedge (814) includes first applicator surface (816) and second applicator surface (818) coupled together at resilient pivoting point (826). In some versions, flexible central portions (809, 811) may be secured to applicator arms (808, 810).

First and second applicator surfaces (816, 818) are each configured to apply adjunct material to end effector (12) of stapling instrument (10). More specifically, first applicator surface (816) is configured to accept buttress assembly (110) thereon for application onto pivotable anvil (18), and second applicator surface (818) is configured to accept buttress assembly (112) thereon for application on to lower jaw (16). Particularly, buttress assembly (110) is placed onto first applicator surface (816) such that upper adhesive layer (116) is facing outwardly away from first applicator surface (816), and buttress assembly (112) is placed onto second applicator surface (818) such that lower adhesive layer (120) is facing outwardly away from second applicator surface (818), thereby allowing upper and lower adhesive layers (116, 120) to adhere to pivotable anvil (18) and lower jaw (16), respectively, upon application of buttress assemblies (110, 112) by applicator device (800). In some versions, first and second applicator surfaces (816, 818) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (816, 818) prior to buttress assemblies (110, 112) being applied to pivotable anvil (18) and lower jaw (16), respectively. However, various suitable methods and structures for securely and removably positioning buttress assemblies (110, 112) on applicator surfaces (816, 818) are also envisioned. In some versions, a user utilizing a separate device (not shown) may initially apply one or both buttress assemblies (110, 112) to applicator surfaces (816, 818).

FIG. 28B shows the adjunct material being secured onto stapling surfaces of pivotable anvil (18) and lower jaw (16) of end effector (12). Once buttress assemblies (110, 112) are positioned on applicator surfaces (816, 818), handles (802, 804) of applicator device (800) are squeezed together to thereby compress spring (806) and pivot applicator arms (808, 810) about axes (820, 821). As handles (802, 804) transition closer together, flexible central portions (809, 811) of applicator arms (808, 810) deflect away from each other to become more convex to contact inward-facing surfaces (828, 830) of applicator arms (808, 810) and spread applicator arms (808, 810) in opposing directions via resilient pivoting point (426) until buttress assemblies (110, 112) adhere to pivotable anvil (18) and lower jaw (16), respectively. Thereafter, handles (802, 804) may be released by the user thereby reversing the pivoting motion of applicator arms (808, 810), disengaging from buttress assemblies (110, 112) as buttress assemblies (110, 112) remain adhered to pivotable anvil (18) and lower jaw (16). End effector (12) may thereafter be removed from applicator device (800).

In some versions, a break-away feature may be desired to ensure the applicator device (800) does not apply too much pressure to end effector (12) while applying buttress assemblies (110, 112). For example, one or more breakaway features, such as notches (832, 834) can be included on applicator arms (808, 810). In the illustrated example, notches (832, 834) are included between handles (802, 804) and pin (812), and arms (808, 810) are configured to break at notches (832, 834), respectively, if arms (808, 810) experience force above a particular limit while applying buttress assemblies (110, 112).

C. Third Selectively Expandable Adjunct Applicator Device

Figure 29C:
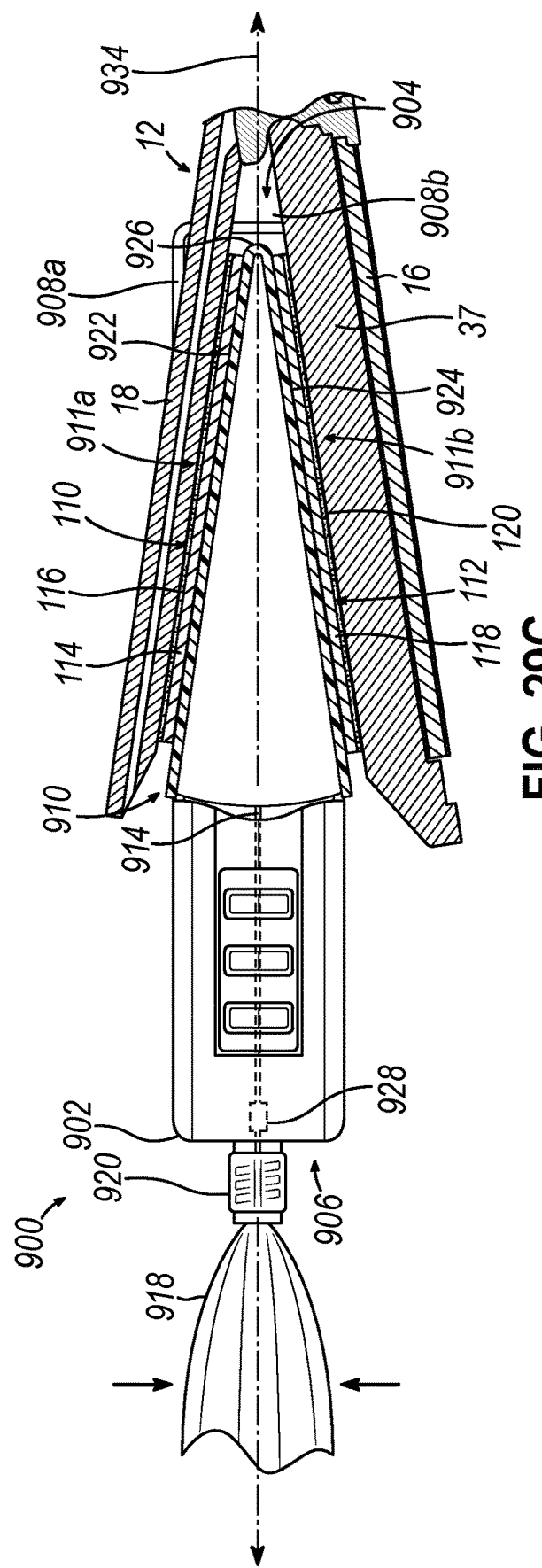
FIG. 29C depicts a partial side cross-sectional view of the adjunct applicator device of FIG. 29A, the buttress assembly of FIG. 8, and the end effector of FIG. 3, with the air pump coupled with the adjunct applicator device and in a second state thereby expanding the adjunct applicator device for securing the buttress assembly to the end effector.

FIGS. 29A-29C show another exemplary applicator device (900) that is configured to apply an adjunct material to a jaw (e.g., lower jaw (16)) of end effector (12) of surgical stapler (10). As best seen in FIG. 29A, applicator device (900) of this example may resemble adjunct applicator device (210) (see, FIG. 11), except for the differences described below. Specifically, applicator device (900) comprises a body (902) defining an open end (904) and a closed end (906). Open end (904) is configured to receive end effector (12) as will be described in greater detail below. Applicator device (900) further includes a first housing (908a) and a second housing (908b), which each collectively generally define a "U" shape to present open end (904). A contact structure in the form of an expandable wedge (910) is interposed between first and second housings (908a, 908b). Wedge (910) of the present example is configured to support a pair of buttress assemblies (110) on one side (911a) of wedge (910) and another pair of buttress assemblies (112) on the other side (911b) of wedge (910). Wedge (910) is exposed in recesses that are formed between the prongs of the "U" configuration of first and second housings (908a, 908b). Each buttress assembly (110, 112) is provided in a respective pair of portions that are separated to avoid spanning across slots (42, 49) of anvil (18) and staple cartridge (37) (see, FIG. 3), respectively, though wedge (910) may just as easily support wide versions of buttress assemblies (110, 112) that unitarily span across slots (42, 49) of anvil (18) and staple cartridge (37), respectively.

As shown in FIG. 29B, applicator device (900) further includes a fluid connector (912) and a fluid conduit (914) fluidly coupled with wedge (910). Fluid connector (912) is positioned at closed end (906) of cartridge body (902) and configured to couple with an applicator expansion mechanism in the form of a pump (918). In some versions, pump (918) may be an inflatable, flexible balloon filled with air, while in other versions pump (918) may be a similar pumping device pre-filled with a liquid, such as water or saline, that is actuatable by a user to expel the liquid therefrom. Fluid connector (912) may be any suitable fluid-tight connector known in the art, such as a luer or snap-fit connector, that is configured to couple with a complementary connector (920) of pump (918). When coupled together, fluid connectors (912, 920) define a lumen configured to communicate a fluid (e.g., air, water, saline, etc.) from pump (918) through fluid conduit (914) in a direction toward open end (904) of cartridge body (902). As will be described in greater detail below, fluid conduit (914) is configured to couple with wedge (910) such that, upon receiving fluid from fluid conduit (914), wedge (910) transitions from a first state (see FIG. 29B) to a second state (see FIG. 29C) to expand opposing sides (911a, 911b) of wedge (910) in opposing outward directions, each away from longitudinal axis (934), to thereby apply buttress assemblies (110, 112) to pivotable anvil (18) and lower jaw (16). In some versions, fluid connector (920) or fluid conduit (914) includes a check valve (928) to ensure fluid pressure remains constant within fluid conduit (914) until the user disengages pump (918) from cartridge body (902).

Wedge (910) includes first and second contact members in the form of first and second applicator surfaces (922, 924) each configured to apply adjunct material to end effector (12) of stapling instrument (10). Particularly, first side (911a) of wedge (910) includes first applicator surface (922) and second side (911b) of wedge (910) includes second applicator surface (924). First and second applicator surfaces (922, 924) join at point (926) of wedge (910) such that surfaces (922, 924) are movably coupled with one another. Wedge (910) may be comprised of any one material or a plurality of materials providing sufficient rigidity at each applicator surface (922, 924) to both accept and apply buttress assemblies (110, 112) while also providing sufficient flexibility to repeatedly expand and contract as pressure is applied from pump (918) to expand each applicator surface (922, 924) outwardly to apply buttress assemblies (110, 112). In some examples, wedge (910) may be comprised of an elastomeric material (e.g., silicone) having a hollow interior that is biased toward a collapsed or flattened configuration, as shown in FIGS. 29A and 29B, and which is configured to expand as it is filled with fluid.

As noted above, first applicator surface (922) is configured to accept buttress assembly (110) thereon for application onto pivotable anvil (18), and second applicator surface (924) is configured to accept buttress assembly (112) thereon for application on to lower jaw (16). Buttress assembly (110) is placed onto first applicator surface (922) such that upper adhesive layer (116) is facing outwardly away from first applicator surface (922), and buttress assembly (112) is placed onto second applicator surface (924) such that lower adhesive layer (120) is facing outwardly away from second applicator surface (924), thereby allowing upper and lower adhesive layers (116, 120) to adhere to pivotable anvil (18) and lower jaw (16), respectively, upon application of buttress assemblies (110, 112) by applicator device (900). In some versions, first and second applicator surfaces (922, 924) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (922, 924) prior to buttress assemblies (110, 112) being applied to pivotable anvil (18) and lower jaw (16), respectively. However, various suitable methods and structures for securely and removably positioning buttress assemblies (110, 112) on applicator surfaces (922, 924) are also envisioned. In some versions, a user utilizing a separate device (not shown) may initially apply one or both buttress assemblies (110, 112) to applicator surfaces (922, 924).

FIG. 29C shows the adjunct material being secured onto stapling surfaces of pivotable anvil (18) and lower jaw (16) of end effector (12). Once buttress assemblies (110, 112) are positioned on applicator surfaces (922, 924), end effector (12) is placed into position for application of buttress assemblies (110, 112), and pump (918) is coupled with cartridge body (902), a user may then grasp and squeeze pump (918) one or more times to expel fluid (e.g., air, water, saline, etc.) from pump (918) through fluid conduit (914). The fluid communicating through fluid conduit (914) pressurizes to expand wedge (910), which thereby inflates and spreads applicator surfaces (922, 924) in opposite outward directions. As applicator surfaces (922, 924) spread apart in opposite outward directions, buttress assemblies (110, 112) may be applied to end effector (12) without requiring any actuation of pivotable anvil (18) or lower jaw (16).

Thereafter, fluid pressure applied to wedge (910) within fluid conduit (914) may be released by the user by disengaging pump (918), thereby releasing the fluid from fluid conduit (914). Releasing the fluid from fluid conduit (914) may function to reverse the spreading of applicator surfaces (922, 924), disengaging from buttress assemblies (110, 112) as buttress assemblies (110, 112) remain adhered to pivotable anvil (18) and lower jaw (16). End effector (12) may thereafter be removed from applicator device (900).

D. Fourth Selectively Expandable Adjunct Applicator Device

Figure 30:
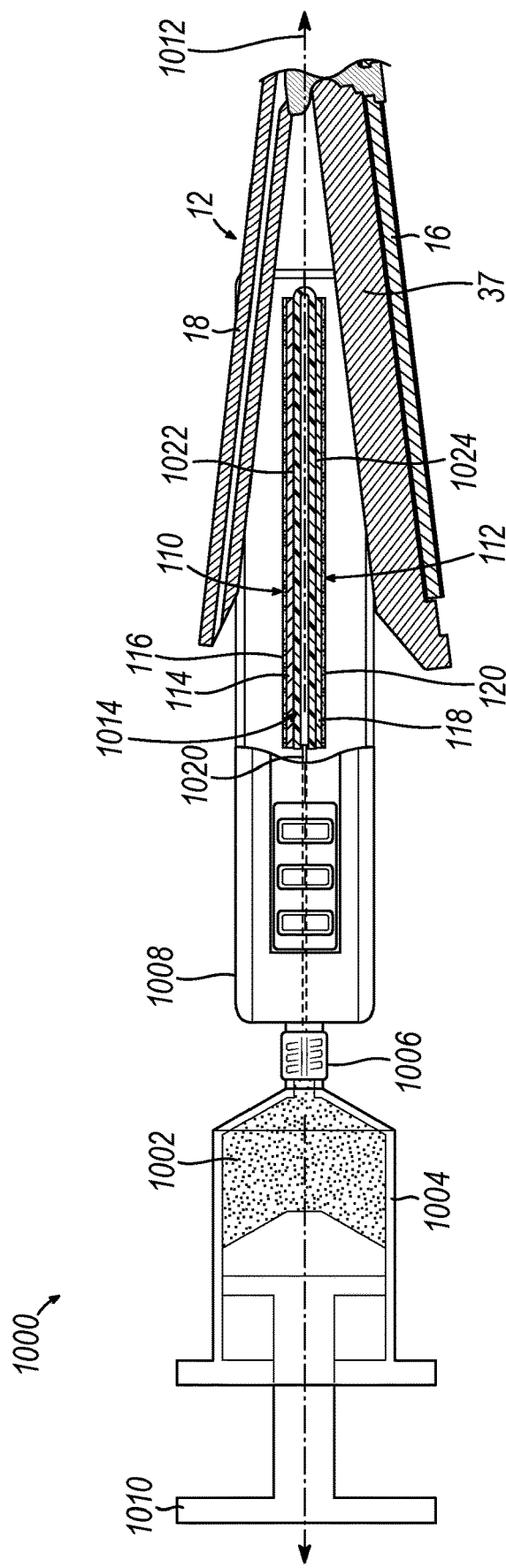
FIG. 30 depicts a partial side cross-sectional view of another exemplary adjunct applicator device, with the buttress assembly of FIG. 8 applied to the adjunct applicator device and with the end effector of FIG. 3 being positioned for application of the buttress assembly, with a fluid injector coupled with the adjunct applicator device, showing the adjunct applicator device in a non-expanded state.

FIG. 30 shows another exemplary applicator device (1000) that is configured to apply an adjunct material to a jaw (e.g., lower jaw (16)) of end effector (12) of surgical stapler (10). Applicator device (1000) is configured with the same structures and functionality as applicator device (900), except for the differences described below. As an alternative to pump (918) of applicator device (900), applicator device (1000) is configured to accept a fluid (1002) (e.g., air, water, saline, etc.) injected using an applicator expansion mechanism in the form of a syringe (1004) or other similar fluid injection device known and used in the art. To operate applicator device (1000) to apply buttresses (110, 112), that is, to inflate expandable wedge (1014) and extend applicator surfaces (1022, 1024) outwardly, a user may couple syringe (1004) to fluid connector (1006) of cartridge body (1008) and actuate the plunger (1010) in a distal longitudinal direction along axis (1012). To retract applicator surfaces (1022, 1024) inwardly, the user may retract plunger (1010) proximally along longitudinal axis (1012) to thereby retract fluid (1002) out of wedge (1014) via fluid conduit (1020) and back into syringe (1004).

E. Fifth Selectively Expandable Adjunct Applicator Device

Figure 31C:
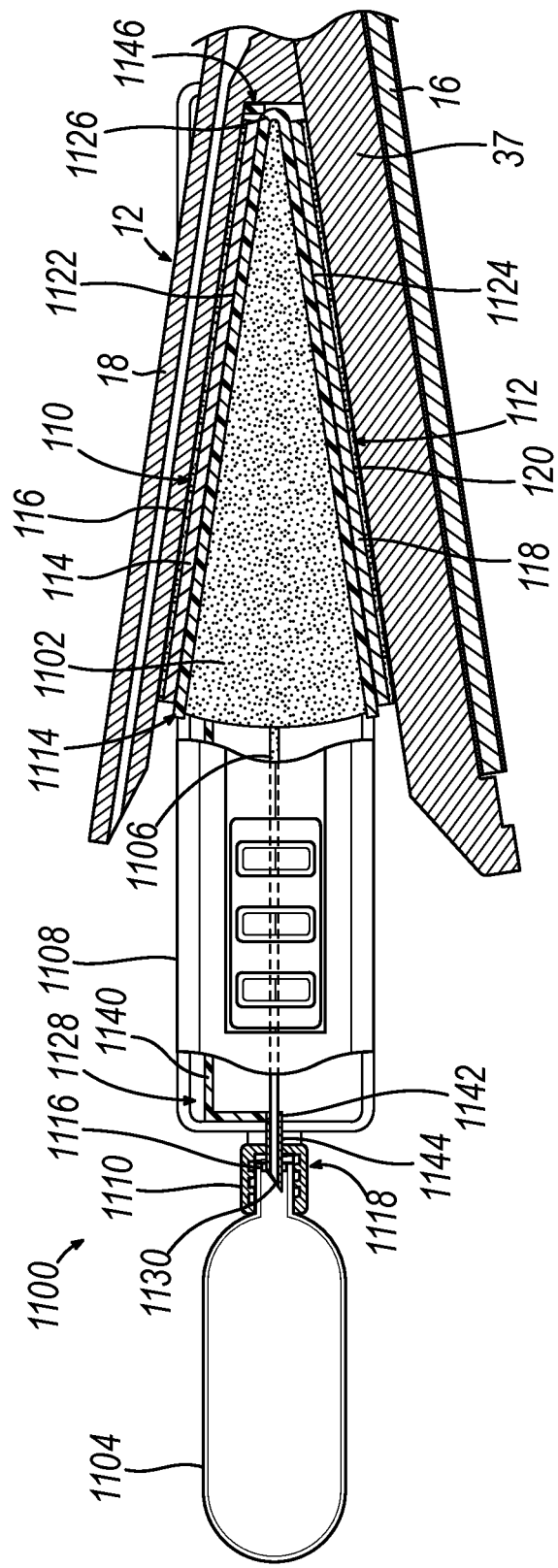
FIG. 31C depicts a partial side cross-sectional view of the adjunct applicator device of FIG. 31A, the buttress assembly of FIG. 8, and the end effector of FIG. 3, with the compressed air injector coupled with the adjunct applicator device and the compressed air being in a second state thereby expanding the adjunct applicator device for securing the buttress assembly to the end effector.

FIGS. 31A-31C show another exemplary applicator device (1100) that is configured to apply an adjunct material to a jaw (e.g., lower jaw (16)) of end effector (12) of surgical stapler (10). Applicator device (1100) is configured with the same structures and functionality as applicator devices (900, 1000), except for the differences described below. As an alternative to pump (918) of applicator device (900) and to syringe (1004) of applicator device (1000), applicator device (1100) is configured to accept compressed gas (1102) (e.g., air, $CO_2$, etc.) injected using an applicator expansion mechanism in the form of a canister (1104) or other similar injection device known and used in the art. To operate applicator device (1100) to apply buttresses (110, 112), that is, to inflate wedge (1114) and extend applicator surfaces (1122, 1124) of wedge (1114) outwardly, a user may couple canister (1104) to fluid conduit (1106) of cartridge body (1108) via fluid connector (1110). Canister (1104) may therefore include a connector (shown as threads (1112)) configured to couple with fluid connector (1110), and a thin seal (1116) configured to be punctured by a sharp tip (1130) formed by the proximal end (1128) of fluid conduit (1106) thereby releasing the compressed gas (1102) from the canister outlet (1118).

In the illustrated example, a user couples canister (1104) with cartridge body (1108) by threading connector (1112) of canister (1104) into fluid connector (1110), thereby translating canister (1104) in a distal longitudinal direction along axis (1120). Once canister (1104) is adequately coupled with cartridge body (1108) and buttress assemblies (110, 112) have been applied to applicator surfaces (1122, 1124) of wedge (1114), end effector (12) may be positioned for application, as shown in FIG. 31B. At this stage, seal (1116) has been positioned adjacent sharp tip (1130) of rigid puncture mechanism (1140), whereby the proximal end of fluid conduit (1106) is disposed within a hollow portion (1144) defined at the proximal end of rigid puncture mechanism (1140). Seal (1142) prevents fluid leakage where fluid conduit (1106) inserts into the hollow portion (1144) of rigid puncture mechanism (1140). To expel the compressed gas (1102) from canister (1104), anvil portions (90a, 90b) (see, FIGS. 3, 6, 31B, and 31C) are configured to press against distal end (1146) of rigid puncture mechanism (1140) near distal tip (1126) of wedge (1114), thereby translating rigid puncture mechanism (1140) proximally (i.e., toward canister (1104)). As rigid puncture mechanism (1140) is translated proximally, sharp tip (1130) punctures through seal (1116) and permits compressed gas (1102) to flow distally through the lumen defined by fluid conduit (1106).

In alternative versions, wedge (1114) may be slidably secured along the longitudinal axis (1120) relative to cartridge body (1108), and sharp tip (1130) may be formed integrally as a proximal portion of fluid conduit (1106). As such, seal (1116) may be punctured by fluid conduit (1106) and buttress assemblies (110, 112) may therefore be applied by a user simply threading canister (1104) into fluid connector (1110).

Thereafter, pressure applied to rod (1132) within fluid conduit (1106) may be released by the user by disengaging canister (1104), thereby releasing the gas from fluid conduit (1106). Releasing the gas from fluid conduit (1106) may function to reverse the spreading or pivoting motion of applicator surfaces (1122, 1124), disengaging from buttress assemblies (110, 112) as buttress assemblies (110, 112) remain adhered to pivotable anvil (18) and lower jaw (16). End effector (12) may thereafter be removed from applicator device (1100).

F. Sixth Selectively Expandable Adjunct Applicator Device

Figure 32A:
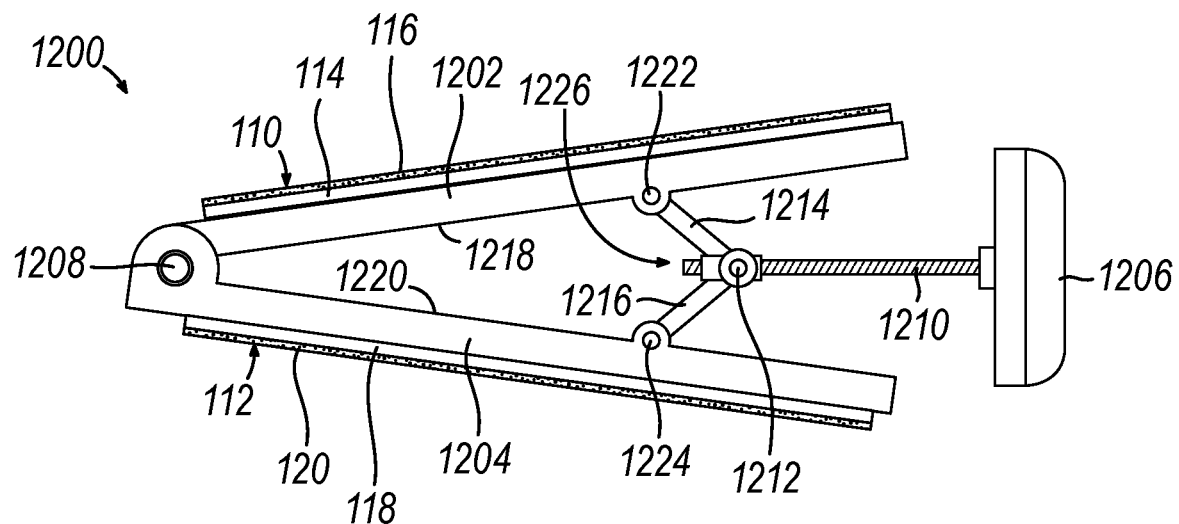
FIG. 32A depicts a side elevational view of another exemplary adjunct applicator device, with the buttress assembly of FIG. 8 applied to the adjunct applicator device and the adjunct applicator device in a first, non-expanded state.
Figure 32B:
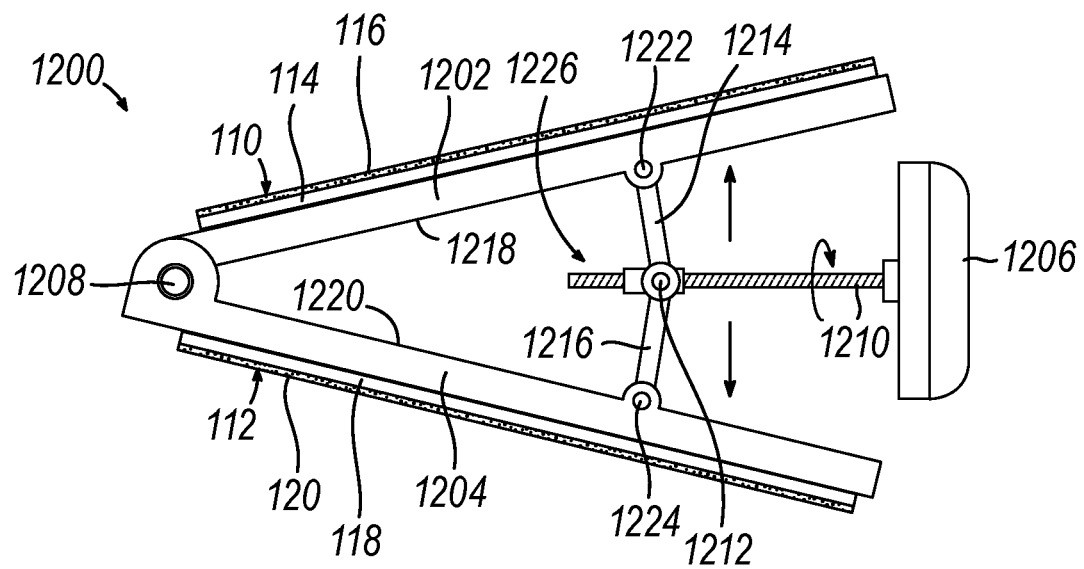
FIG. 32B depicts a side elevational view of the adjunct applicator device of FIG. 32A, with the adjunct applicator device in a second, expanded state to thereby secure the buttress assembly to an end effector.

FIGS. 32A-32B show another exemplary applicator device (1200) that is configured to apply an adjunct material to a jaw (e.g., lower jaw (16)) of end effector (12) of surgical stapler (10). Applicator device (1200) includes a contact structure having first and second applicator arms (1202, 1204) configured to couple with an applicator expansion mechanism in the form of a rotary actuator (1206). Applicator arms (1202, 1204) of the present example is configured to support a pair of buttress assemblies (110) on first applicator arm (1202) and another pair of buttress assemblies (112) on second applicator arm (1204) (first and second applicator arms (1202, 1204) collectively defining a wedge). Each buttress assembly (110, 112) is provided in a respective pair of portions that are separated to avoid spanning across slots (42, 49) of anvil (18) and staple cartridge (37) (see, FIG. 3), respectively, though applicator arms (1202, 1204) may just as easily support wide versions of buttress assemblies (110, 112) that unitarily span across slots (42, 49) of anvil (18) and staple cartridge (37), respectively. Applicator arms (1202, 1204) are coupled together using a pivot member (shown as pin (1208)).

First and second applicator arms (1202, 1204) are each configured to apply adjunct material to end effector (12) of stapling instrument (10). More specifically, first applicator arm (1202) is configured to accept buttress assembly (110) thereon for application onto pivotable anvil (18), and second applicator arm (1204) is configured to accept buttress assembly (112) thereon for application on to lower jaw (16). Particularly, buttress assembly (110) is placed onto first applicator arm (1202) such that upper adhesive layer (116) is facing outwardly away from first applicator arm (1202), and buttress assembly (112) is placed onto second applicator arm (1204) such that lower adhesive layer (120) is facing outwardly away from second applicator arm (1204), thereby allowing upper and lower adhesive layers (116, 120) to adhere to pivotable anvil (18) and lower jaw (16), respectively, upon application of buttress assemblies (110, 112) by applicator device (1200). In some versions, first and second applicator arms (1202, 1204) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator arms (1202, 1204) prior to buttress assemblies (110, 112) being applied to pivotable anvil (18) and lower jaw (16), respectively. However, various suitable methods and structures for securely and removably positioning buttress assemblies (110, 112) on applicator arms (1202, 1204) are also envisioned. In some versions, a user utilizing a separate device (not shown) may initially apply one or both buttress assemblies (110, 112) to applicator arms (1202, 1204).

As shown from the transition from FIG. 32A to FIG. 32B, applicator arms (1202, 1204) may be expanded in opposing outward directions by a user to thereby apply buttress assemblies (110, 112) to end effector (12). To expand applicator arms (1202, 1204) outwardly, a user grasps and rotates rotary actuator (1206) in a first direction. Rotary actuator (1206) is coupled with a threaded rod (1210), and threaded rod (1210) is rotatably coupled with each applicator arm (1202, 1204) via a hinged connector (1212) shown as a hinge pin and translatable legs (1214, 1216). First translatable leg (1214) is rotatably coupled via a hinged connector (shown as hinge pin (1222)) with an underside (1218) of first applicator arm (1202). Second translatable leg (1216) is rotatably coupled via a hinged connector (shown as hinge pin (1224)) with an underside (1220) of second applicator arm (1204). As rotary actuator (1206) is rotated in the first direction, hinged connector (1212) translates distally away from rotary actuator (1206) toward distal end (1226) of threaded rod (1210). As such, as shown in FIG. 32B, translatable legs (1214, 1216) force applicator arms (1202, 1204) in opposing directions relative to each other to apply buttress assemblies (110, 112) to end effector (12). Thereafter, rotary actuator (1206) may be rotated in an opposite, second direction which may function to reverse the spreading or pivoting motion of applicator arms (1202, 1204), disengaging from buttress assemblies (110, 112) as buttress assemblies (110, 112) remain adhered to pivotable anvil (18) and lower jaw (16). End effector (12) may thereafter be removed from applicator device (1200).

G. Seventh Selectively Expandable Adjunct Applicator Device

Figure 33C:
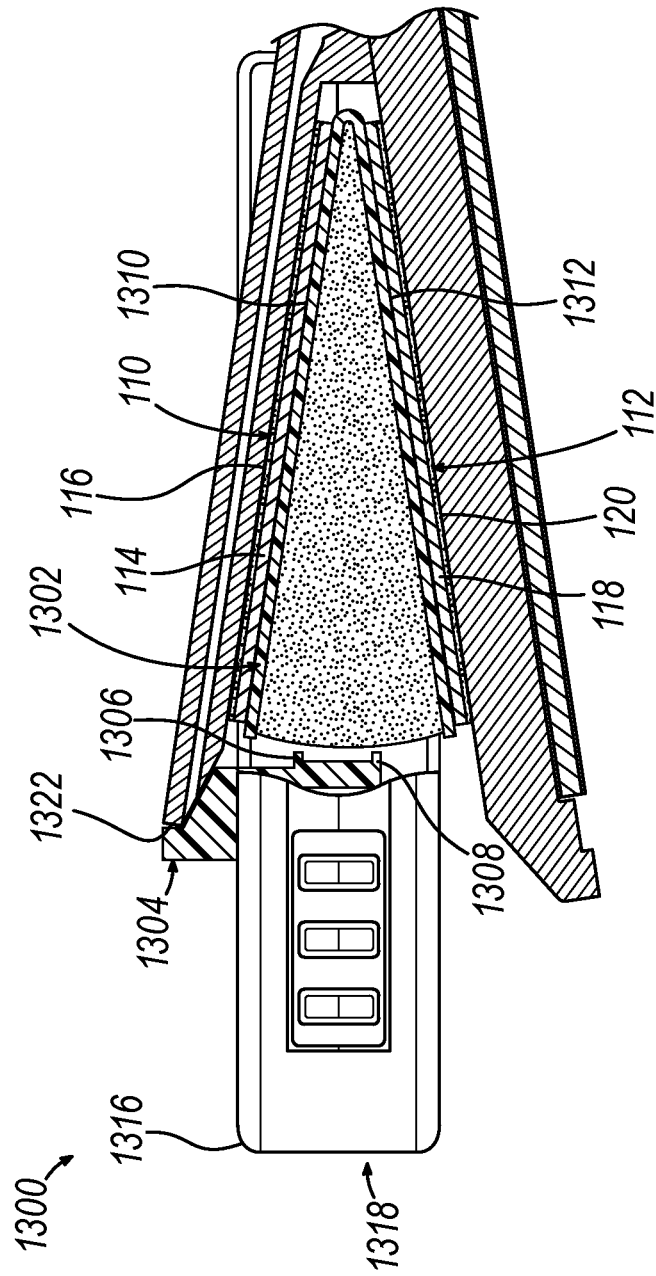
FIG. 33C depicts a partial side cross-sectional view of the adjunct applicator device of FIG. 33A, the buttress assembly of FIG. 8, and the end effector of FIG. 3, with the applicator pad being in a second, expanded state to thereby secure the buttress assembly to the end effector.

FIGS. 33A-33C show another exemplary applicator device (1300) that is configured to apply an adjunct material to a jaw (e.g., lower jaw (16)) of end effector (12) of surgical stapler (10). Applicator device (1300) is configured with the same structures and functionality as applicator devices (900, 1000, 1100), except for the differences described below. As an alternative to pump (918) of applicator device (900), syringe (1004) of applicator device (1000), and canister (1104) of applicator device (1100), applicator device (1300) comprises a contact structure in the form of a selectively expandable applicator (1302) and an applicator expansion mechanism in the form of a removable clip (1304). Applicator device (1300) includes a cartridge body (1316) defining a closed end (1318) and an open end (1320) and a pair of retention members (1306, 1308) operable to compress upper and lower surfaces (1310, 1312) of expandable applicator (1302), as shown in FIGS. 33A and 33B. Expandable applicator (1302) may be comprised of a compressible foam material that is biased to an expanded state. Further, expandable applicator (1302) may be formed into a V-shaped wedge that provides a complementary shape to pivotable anvil (18) and lower jaw (16) that is operable to securely attach buttress assemblies (110, 112) to pivotable anvil (18) and lower jaw (16) when expandable applicator (1302) expands between pivotable anvil (18) and lower jaw (16).

Upper and lower applicator surfaces (1310, 1312) are each configured to apply adjunct material to end effector (12) of stapling instrument (10). More specifically, upper applicator surface (1310) is configured to accept buttress assembly (110) thereon for application onto pivotable anvil (18), and lower applicator surface (1312) is configured to accept buttress assembly (112) thereon for application on to lower jaw (16). Particularly, buttress assembly (110) is placed onto upper applicator surface (1310) such that upper adhesive layer (116) is facing outwardly away from upper applicator surface (1310), and buttress assembly (112) is placed onto lower applicator surface (1312) such that lower adhesive layer (120) is facing outwardly away from lower applicator surface (1312), thereby allowing upper and lower adhesive layers (116, 120) to adhere to pivotable anvil (18) and lower jaw (16), respectively, upon application of buttress assemblies (110, 112) by applicator device (1300). In some versions, upper and lower applicator surfaces (1310, 1312) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator surfaces (1310, 1312) prior to buttress assemblies (110, 112) being applied to pivotable anvil (18) and lower jaw (16), respectively. However, various suitable methods and structures for securely and removably positioning buttress assemblies (110, 112) on applicator surfaces (1310, 1312) are also envisioned. In some versions, a user utilizing a separate device (not shown) may initially apply one or both buttress assemblies (110, 112) to applicator surfaces (1310, 1312).

FIG. 33A shows expandable applicator (1302) in an initial, compressed state with buttress assemblies (110, 112) installed thereon. Further, retention members (1306, 1308) of clip (1304) ensure expandable application (1302) remains in a compressed state until end effector (12) is positioned for application of buttress assemblies (110, 112). FIG. 33B shows end effector (12) being translated into position to apply buttress assemblies (110, 112). Upon translating end effector (12) into position, tip (1322) of pivotable anvil (18) is configured to contact a portion (1314) of clip (1304), thereby translating clip (1304) toward closed end (1318) of cartridge body (1316). As clip (1304) is translated, such as by sliding along the surface of cartridge body (1316), retention members (1306, 1308) release from their positions retaining expandable applicator (1302) in the compressed state. FIG. 33C shows clip (1304) removed and expandable applicator (1302) in its expanded state whereby applicator surfaces (1310, 1312) expand in opposing directions relative to each other to apply buttress assemblies (110, 112) to end effector (12). End effector (12) may thereafter be removed from applicator device (1300).

H. Eighth Selectively Expandable Adjunct Applicator Device

Figure 34A:
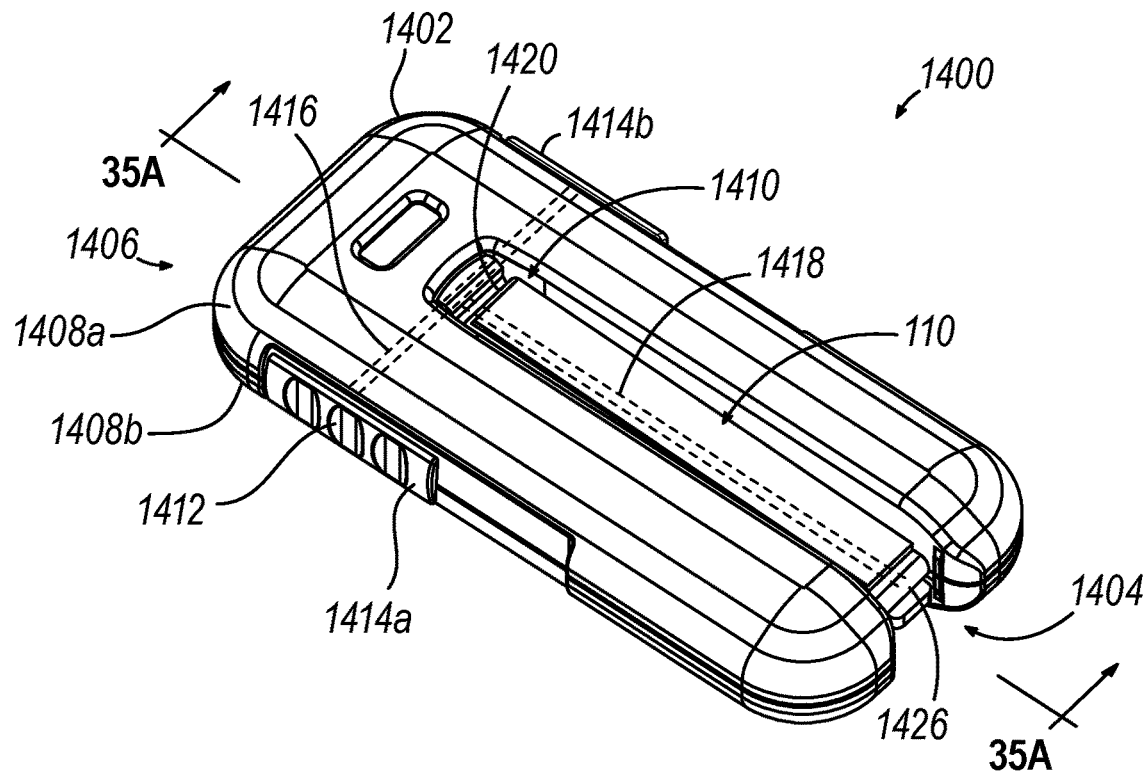
FIG. 34A depicts a perspective view of another exemplary adjunct applicator device, the adjunct applicator device being in a first, non-expanded state.

FIGS. 34A-35B show another exemplary applicator device (1400) that is configured to apply an adjunct material to a jaw (e.g., lower jaw (16)) of end effector (12) of surgical stapler (10). As best seen in FIG. 34A, applicator device (1400) of this example may resemble adjunct applicator devices (210, 900, 1000, 1100, 1300), except for the differences described below. Specifically, applicator device (1400) comprises a cartridge body (1402) defining an open end (1404) and a closed end (1406). Open end (1404) is configured to receive end effector (12) as will be described in greater detail below. Applicator device (1400) further includes a first housing (1408a) and a second housing (1408b), which each collectively generally define a "U" shape to present open end (1404). A contact structure in the form of an expandable wedge (1410) is interposed between first and second housings (1408a, 1408b). Wedge (1410) of the present example is configured to support a pair of buttress assemblies (110) on first applicator arm (1420) and another pair of buttress assemblies (112) on the second applicator arm (1422). Wedge (1410) is exposed in recesses that are formed between the prongs of the "U" configuration of first and second housings (1408a, 1408b). Each buttress assembly (110, 112) is provided in a respective pair of portions that are separated to avoid spanning across slots (42, 49) of anvil (18) and staple cartridge (37) (see, FIG. 3), respectively, though wedge (1410) may just as easily support wide versions of buttress assemblies (110, 112) that unitarily span across slots (42, 49) of anvil (18) and staple cartridge (37), respectively.

Applicator device (1400) further includes an expansion mechanism defined collectively by an actuator member (1412), applicator actuation mechanism (1418), rod (1416), guide rod (1434), and applicator arms (1420, 1422), the expansion mechanism selectively operable to transition wedge (1410) between non-expanded and expanded states as explained in greater detail below. Actuator member (1412) is translatable longitudinally parallel to a guide rod (1434). Actuator member (1412) comprises one or more user grips (1414a, 1414b) coupled together internally through cartridge body (1402) and wedge (1410) via a rod (1416). Actuator member (1412) may further be configured to slide distally and proximally relative to closed end (1406) of cartridge body (1402). As will be described in greater detail below, actuator member (1412), or more particularly, rod (1416), is configured to couple with an applicator actuation mechanism (1418) (see, FIGS. 35A and 35B) such that, upon actuator member (1412) sliding distally relative to closed end (1406) of cartridge body (1402), applicator actuation mechanism (1418) slides distally over guide rod (1434) to transition applicator arms (1420, 1422) from a first non-expanded position (see, FIG. 35A) to a second expanded position (see, FIG. 35B). As will be described in greater detail below, applicator actuation mechanism (1418) is further coupled with first and second applicator arms (1420, 1422) of wedge (1410).

Wedge (1410) includes first and second applicator arms (1420, 1422) each configured to apply adjunct material to end effector (12) of stapling instrument (10). First and second applicator arms (1420, 1422) are coupled together at resilient pivoting point (1426) of wedge (1410). Wedge (1410) may be comprised of any one material or plurality of materials providing sufficient rigidity at each applicator arm (1420, 1422) to both accept and apply buttress assemblies (110, 112) while also providing sufficient flexibility to repeatedly flex at pivoting point (1426) as pressure is applied from applicator actuation mechanism (1418) to expand each applicator arm (1420, 1422) outwardly to apply buttress assemblies (110, 112). In some examples, wedge (1410) may be comprised of a resilient metal or metal alloy that is biased in a "closed" configuration, as shown in FIGS. 34A and 35A.

First applicator arm (1420) is configured to accept buttress assembly (110) thereon for application onto pivotable anvil (18), and second applicator arm (1422) is configured to accept buttress assembly (112) thereon for application on to lower jaw (16). Buttress assembly (110) is placed onto first applicator arm (1420) such that upper adhesive layer (116) is facing outwardly away from first applicator arm (1420), and buttress assembly (112) is placed onto second applicator arm (1422) such that lower adhesive layer (120) is facing outwardly away from second applicator arm (1422), thereby allowing upper and lower adhesive layers (116, 120) to adhere to pivotable anvil (18) and lower jaw (16), respectively, upon application of buttress assemblies (110, 112) by applicator device (1000). In some versions, first and second applicator arms (1422, 1424) and buttress assemblies (110, 112) include corresponding features such as clamp arms and clamp arm fingers (not shown) to hold buttress assemblies (110, 112) and ensure proper and secure alignment and positioning of buttress assemblies (110, 112) on applicator arms (1420, 1422) prior to buttress assemblies (110, 112) being applied to pivotable anvil (18) and lower jaw (16), respectively. However, various suitable methods and structures for securely and removably positioning buttress assemblies (110, 112) on applicator arms (1420, 1422) are also envisioned. In some versions, a user utilizing a separate device (not shown) may initially apply one or both buttress assemblies (110, 112) to applicator arms (1420, 1422).

Figure 34B:
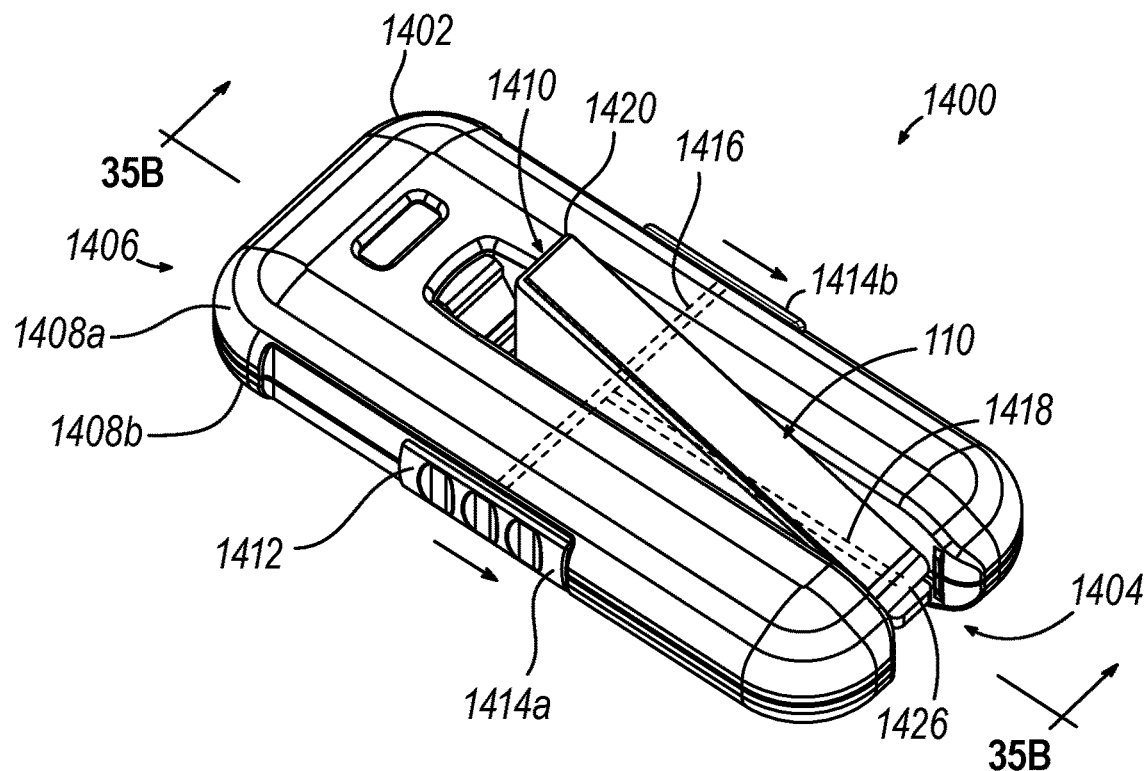
FIG. 34B depicts a perspective view of the adjunct applicator device of FIG. 34A, the adjunct applicator device being in a second, expanded state.

FIGS. 34B and 35B show the adjunct material being secured onto stapling surfaces of pivotable anvil (18) and lower jaw (16) of end effector (12). Once buttress assemblies (110, 112) are positioned on applicator arms (1420, 1422), end effector (12) is placed into position for application of buttress assemblies (110, 112), a user may then grasp grips (1414a, 1414b) and slide actuator member (1412) distally relative to closed end (1406) of cartridge body (1402) to transition applicator actuation mechanism (1418) of wedge (1410) to the distal position. Distal end (1440) of applicator actuation mechanism (1418) abuts a compression spring (1432) disposed over a distal end (1442) of guide rod (1434). Spring (1432) is configured to apply proximal pressure against applicator actuation mechanism (1418) to counteract against the distal pressure provided by applicator actuation mechanism (1418). As such, when pressure is removed from applicator actuation mechanism (1418), such as when user slides actuator member (1412) proximally relative to closed end (1406), applicator actuation mechanism (1418) proximally translates back to its initial position as shown in FIGS. 34A and 35A.

As shown in FIGS. 35A and 35B, applicator actuation mechanism (1418) is moveably coupled to one end (1446) of one or more actuator arms (1444), and the opposing end (1448) of one or more actuator arms (1444) is coupled with wedge (1410). Particularly, each actuator arm (1444) is rotatably coupled with an interior or underside of first applicator arm (1420) or second applicator arm (1422). As such, applicator actuation mechanism (1418), actuator arms (1444), and wedge (1410) are configured to operate in similar fashion as an umbrella. That is, as applicator actuation mechanism (1418) translates in a distal direction over guide rod (1434), actuator arms (1444) force first and second applicator arms (1420, 1422) to spread apart in opposite outward directions via a hinged connection with applicator actuation mechanism (1418) at the first end (1446) of actuator arm (1444) and also via a hinged connection with an interior coupling with wedge (1410) at the second end (1448) of actuator arm (1444). Distal translation of applicator actuation mechanism (1418) further acts to compress spring (1432). As applicator arms (1420, 1422) spread apart in opposite outward directions, buttress assemblies (110, 112) may be applied to end effector (12) without requiring any actuation of pivotable anvil (18) or lower jaw (16).

Thereafter, user pressure applied to applicator actuation mechanism (1418) via actuator member (1412) may be released by the user by sliding actuator member (1412) proximally, thereby disengaging from buttress assemblies (110, 112), as buttress assemblies (110, 112) remain adhered to pivotable anvil (18) and lower jaw (16). End effector (12) may thereafter be removed from applicator device (1400).

I. Ninth Selectively Expandable Adjunct Applicator Device

FIGS. 36A-36B show another exemplary applicator device (1500) that is configured to apply an adjunct material to a jaw (e.g., lower jaw (16)) of end effector (12) of surgical stapler (10). Applicator device (1500) is configured with the same structures and functionality as applicator device (900, 1000, 1100, 1400), except for the differences described below. Similarly, application device (1500) includes an applicator actuation mechanism (1502) configured to longitudinally translate relative to cartridge body (1504) to spread applicator arms (1506, 1508) apart from one another and apply one or more buttress assemblies (110, 112) to end effector (12). Applicator device (1500) of this example includes an expansion mechanism in the form of a user-activatable motor (1510). To operate motor (1510) to apply buttresses (110, 112), that is, to extend applicator arms (1506, 1508) of wedge (1512) outwardly, a user may actuate an actuator, such as a press-button (1514) located on cartridge body (1504). To retract applicator arms (1506, 1508), the user may actuate the press-button (1514) a second time. Optionally, an additional actuator, such as push-button (1516) can be included on cartridge body (1504) to operate motor (1510) in reverse.

J. Tenth Selectively Expandable Adjunct Applicator Device

Figure 37A:
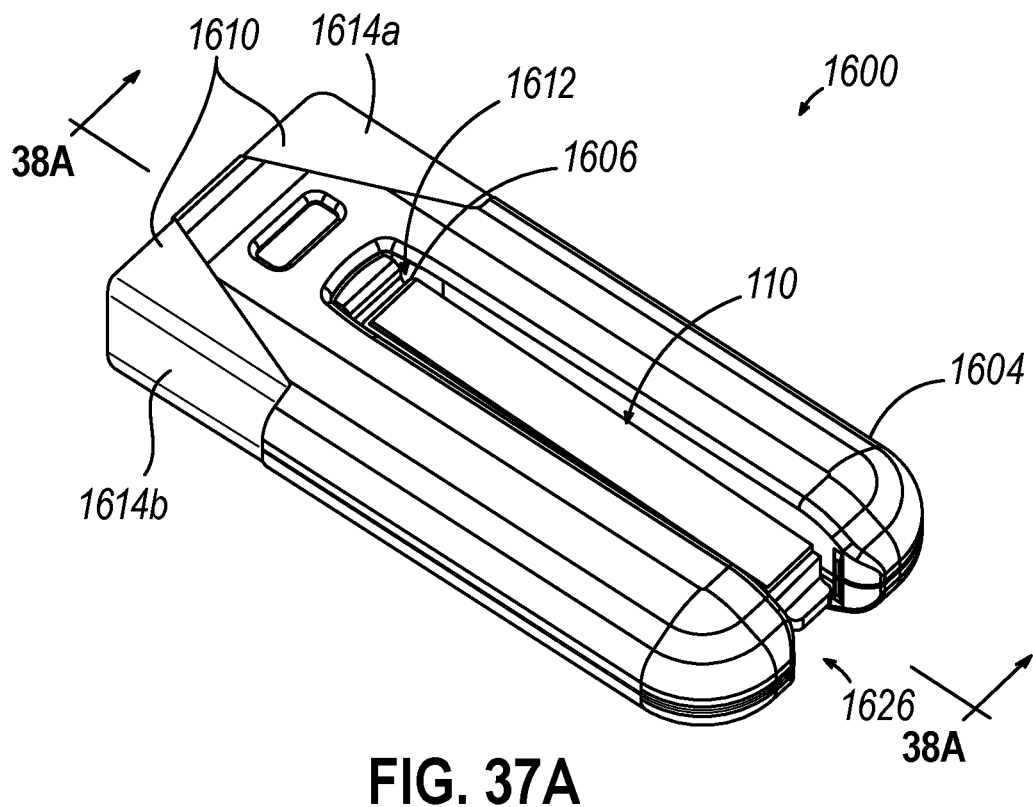
FIG. 37A depicts a perspective view of another exemplary adjunct applicator device, the adjunct applicator device being in a first, non-expanded state.
Figure 37B:
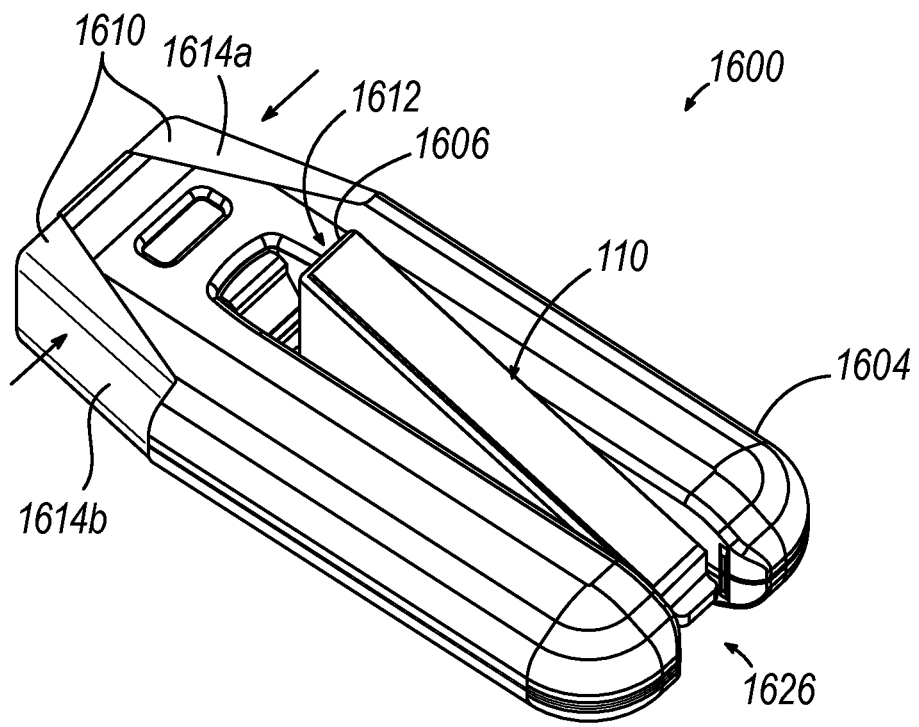
FIG. 37B depicts a perspective view of the adjunct applicator device of FIG. 37A, the adjunct applicator device being in a second, expanded state to thereby secure the buttress assembly to an end effector.

FIGS. 37A-37B show another exemplary applicator device (1600) that is configured to apply an adjunct material to a jaw (e.g., lower jaw (16)) of end effector (12) of surgical stapler (10). Applicator device (1600) is configured with the same structures and functionality as applicator device (900, 1000, 1100, 1400, 1500), except for the differences described below. Similarly, application device (1600) includes an applicator actuation mechanism (1602) coupled with a platform (1620) configured to longitudinally translate relative to cartridge body (1604) to spread applicator arms (1606, 1608) and apply one or more buttress assemblies (110, 112) to end effector (12).

Figure 38A:
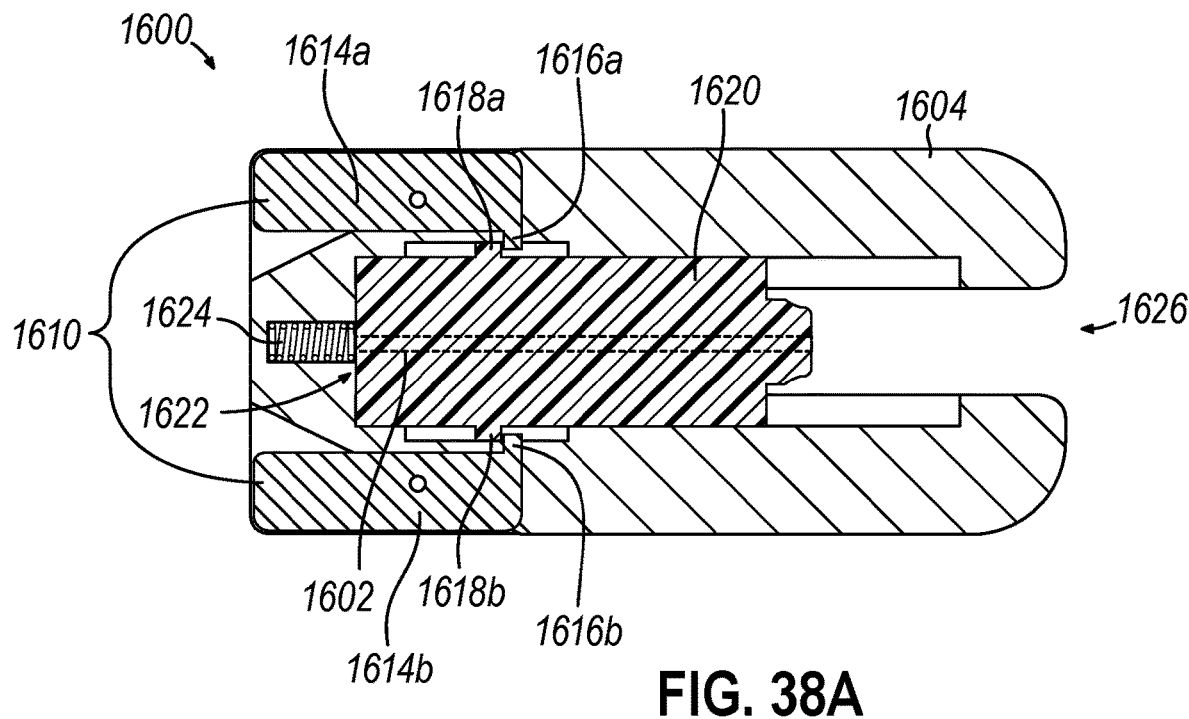
FIG. 38A depicts a top cross-sectional view of the adjunct applicator device of FIG. 37A taken along line 38A-38A of FIG. 37A, the adjunct applicator device being in the first, non-expanded state.
Figure 38B:
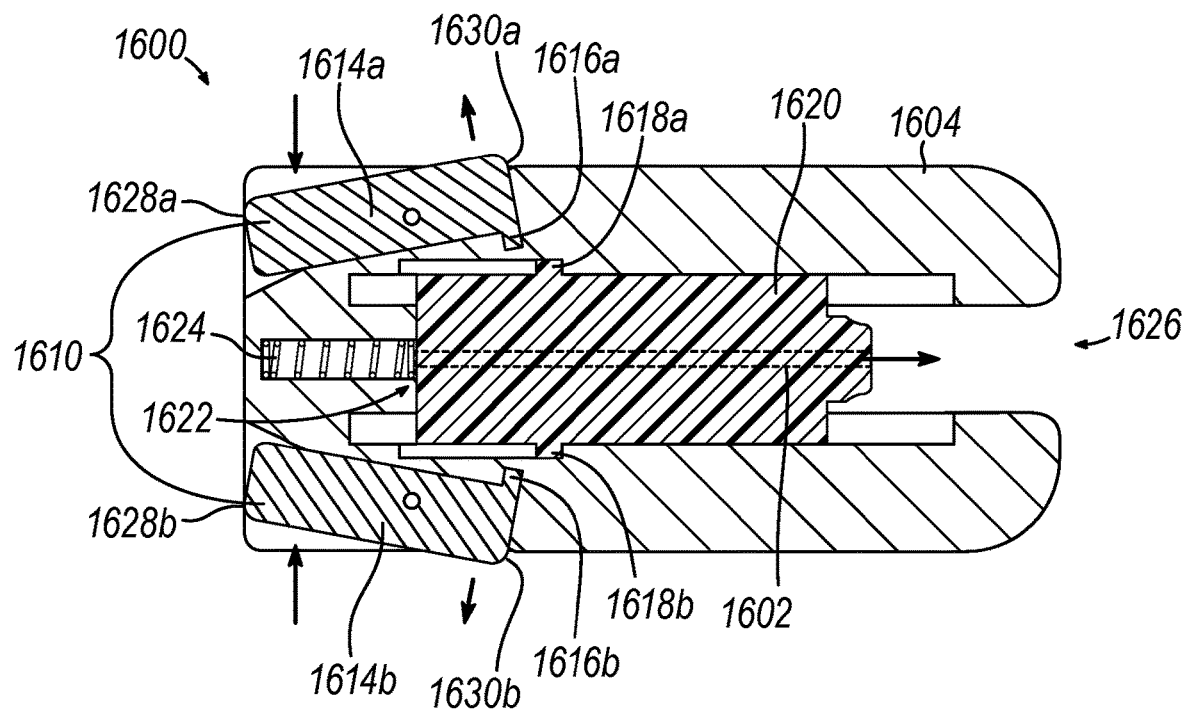
FIG. 38B depicts another top cross-sectional view of the adjunct applicator device of FIG. 37A taken along line 38A-38A of FIG. 37A, the adjunct applicator device being in the second, expanded state to thereby secure the buttress assembly to an end effector.

Applicator device (1600) of this example includes an expansion mechanism in the form of a user-actuatable actuation assembly (1610). To translate applicator actuation mechanism (1610) distally to apply buttresses (110, 112), that is, to extend applicator arms (1606, 1608) of wedge (1612) (i.e., the contact structure) outwardly, a user may manipulate an actuator, such as a squeeze-buttons (1614a, 1614b) located on cartridge body (1604). As shown in FIGS. 37A and 37B, each squeeze-button (1614a, 1614b) includes a retaining distal flange (1616a, 1616b) that is in contact with tabs (1618a, 1618b) of platform (1620). Further, proximal end (1622) of platform (1620) contacts a compression spring (1624), whereby compression spring (1624) biases platform (1620) toward a distal direction (i.e., toward open end (1626) of cartridge body). As such, as proximal ends (1628a, 1628b) of actuators (1614a, 1614b) are squeezed together, distal ends (1630a, 1630b) of actuators (1614a, 1614b) translate apart, releasing tabs (1618a, 1618b) from retaining flanges (1616a, 1616b). Thereafter, spring (1624) forces platform (1620) and applicator actuation mechanism (1602) distally. As applicator actuation mechanism (1602) and wedge (1612) include the same features as applicator devices (1400, 1500) described herein, applicator arms (1606, 1608) spread apart in opposite outward directions to apply buttress assemblies (110, 112) to end effector (12) without requiring any actuation of pivotable anvil (18) or lower jaw (16). To retract applicator arms (1606, 1608), the user may squeeze distal ends (1630a, 1630b) of actuators (1614a, 1614b) to return actuators (1614a, 1614b) and applicator arms (1606, 1608) to their initial positions as shown in FIGS. 37A and 38A.

K. Eleventh Selectively Expandable Adjunct Application Device

Figure 39A:
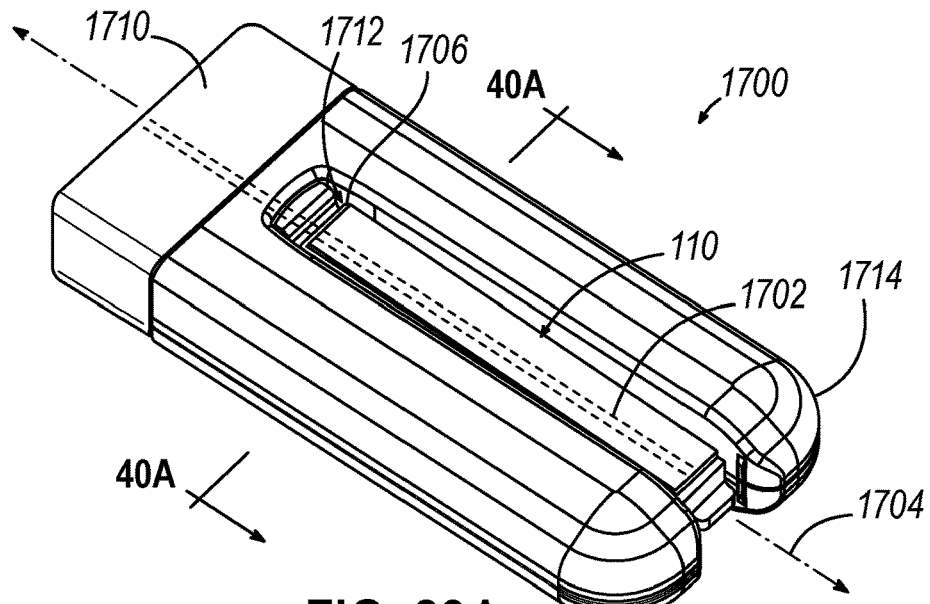
FIG. 39A depicts a perspective view of another exemplary adjunct applicator device, the adjunct applicator device being in a first, non-expanded state.
Figure 39B:
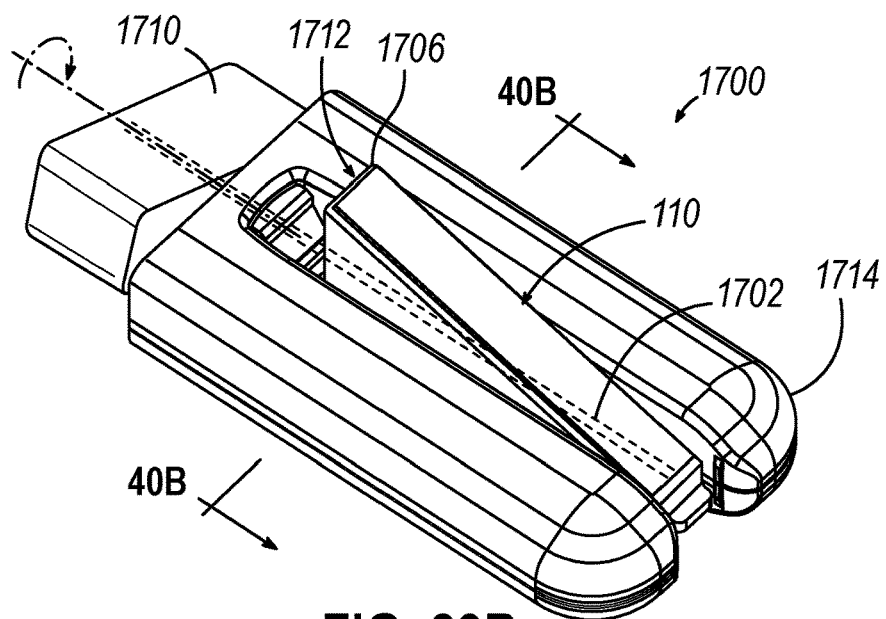
FIG. 39B depicts a perspective view of the adjunct applicator device of FIG. 39A, the adjunct applicator device being in a second, expanded state to thereby secure the buttress assembly to an end effector.
Figure 40A:
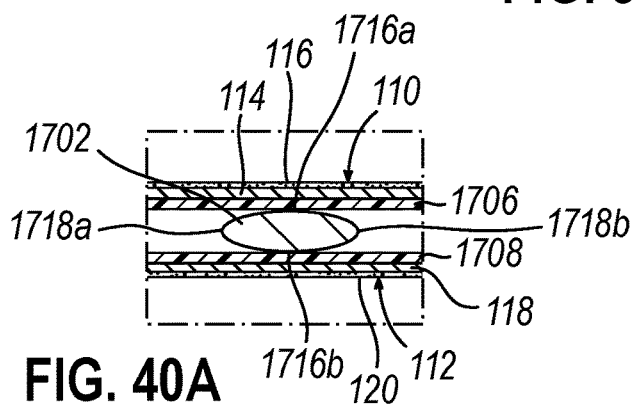
FIG. 40A depicts a partial cross-sectional view of the adjunct applicator device of FIG. 39A taken along line 40A-40A of FIG. 39A, the adjunct applicator device being in the first, non-expanded state.
Figure 40B:
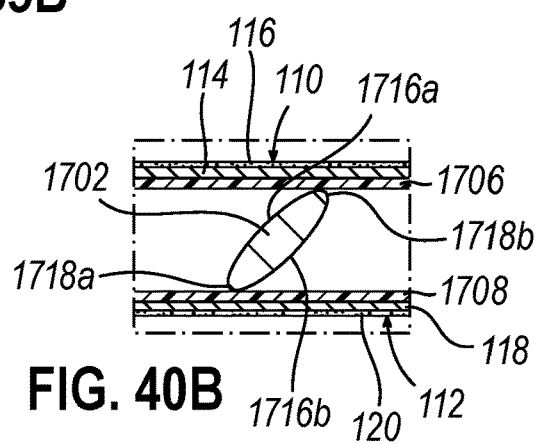
FIG. 40B depicts another partial cross-sectional view of the adjunct applicator device of FIG. 39A taken along line 40B-40B of FIG. 39B, the adjunct applicator device being in the second state, expanded to thereby secure the buttress assembly to an end effector.

FIGS. 39A-40B show another exemplary application device (1700) that is configured to apply an adjunct material to a jaw (e.g., lower jaw (16)) of end effector (12) of surgical stapler (10). Applicator device (1700) is configured with the same structures and functionality as applicator device (900, 1000, 1100, 1400, 1500, 1600), except for the differences described below. Similarly, application device (1700) includes an applicator actuation mechanism (1702) selectively actuatable by a user to spread applicator arms (1706, 1708) of wedge (1712) (i.e., the contact structure of the present version) and apply one or more buttress assemblies (110, 112) to end effector (12). Applicator device (1700) further includes an expansion mechanism defined collectively by an actuator member (1710), applicator actuation mechanism (1702), and applicator arms (1706, 1708), the expansion mechanism selectively operable to transition wedge (1712) between non-expanded and expanded states as explained in greater detail below. Actuation assembly (1710) is configured to be selectively rotated about the longitudinal axis (1704) by a user, and is further configured to couple with applicator actuation mechanism (1702) to thereby rotate applicator actuation mechanism (1702) about longitudinal axis (1704). Applicator actuation mechanism (1702) is formed into an elongate shape, for example an oval shape as shown in FIGS. 40A-40B. Applicator actuation mechanism (1702) is disposed between applicator arms (1706, 1708) and configured to contact and apply radial outward force to applicator arms (1706, 1708) relative to longitudinal axis (1704) upon rotation of applicator actuation mechanism (1702) about longitudinal axis (1704). While an oval shape is illustrated, it has been envisioned that various alternative elongate applicator actuation mechanism (1702) shapes may be utilized.

As shown in FIGS. 39A and 40A, elongate sides (1716a, 1716b) of applicator actuation mechanism (1702) are rotated to an initial position (i.e., prior to extending applicator arms (1706, 1708)) to contact applicator arms (1706, 1708). A user may grip and rotate actuation assembly (1710) located on cartridge body (1714) 90-degrees about longitudinal axis (1704), as shown in FIGS. 39B and 40B, to therefore extend applicator arms (1706, 1708) to apply buttresses (110, 112). As applicator actuation mechanism (1702) rotates, opposing ends (1718a, 1718b) of applicator actuation mechanism (1702) rotate into contact with applicator arms (1706, 1708) of wedge (1712) to push applicator arms (1706, 1708) apart. In some versions, elongate sides (1716a, 1716b) of applicator actuation mechanism (1702) can be shortened or lengthened to thereby respectively decrease or increase the separation distance of applicator arms (1706, 1708) in the expanded state, depending on the separation distance of pivotable anvil (18) and lower jaw (16) of end effector (12). To retract applicator arms (1706, 1708), the user may rotate actuation assembly (1710) 90-degrees in either the same or the opposite direction as before to return applicator arms (1706, 1708) to their initial positions as shown in FIGS. 39A and 40A.

L. Twelfth Selectively Expandable Adjunct Applicator Device

Figure 41A:
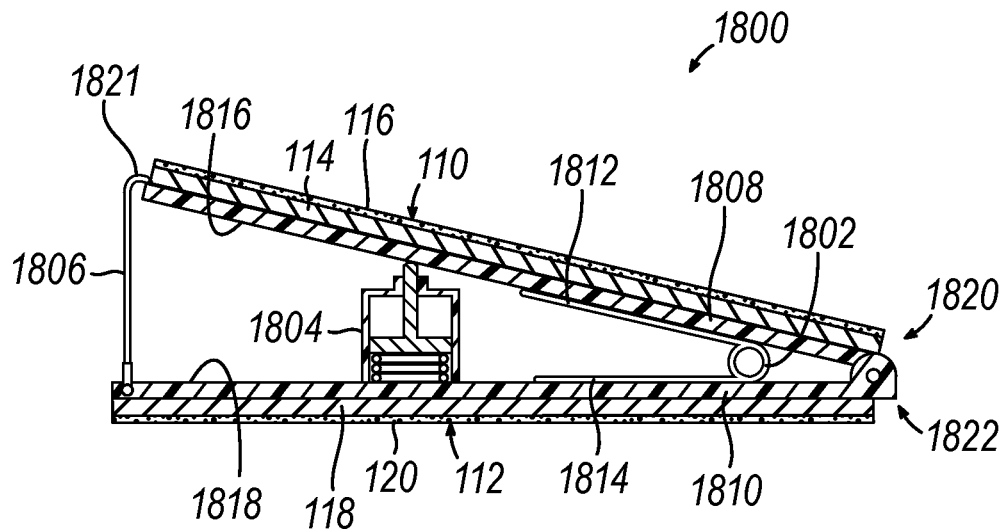
FIG. 41A depicts a side cross-sectional view of another exemplary adjunct applicator device, with the buttress assembly of FIG. 8 applied to the adjunct applicator device, the adjunct applicator device being in a first, non-expanded state.
Figure 41B:
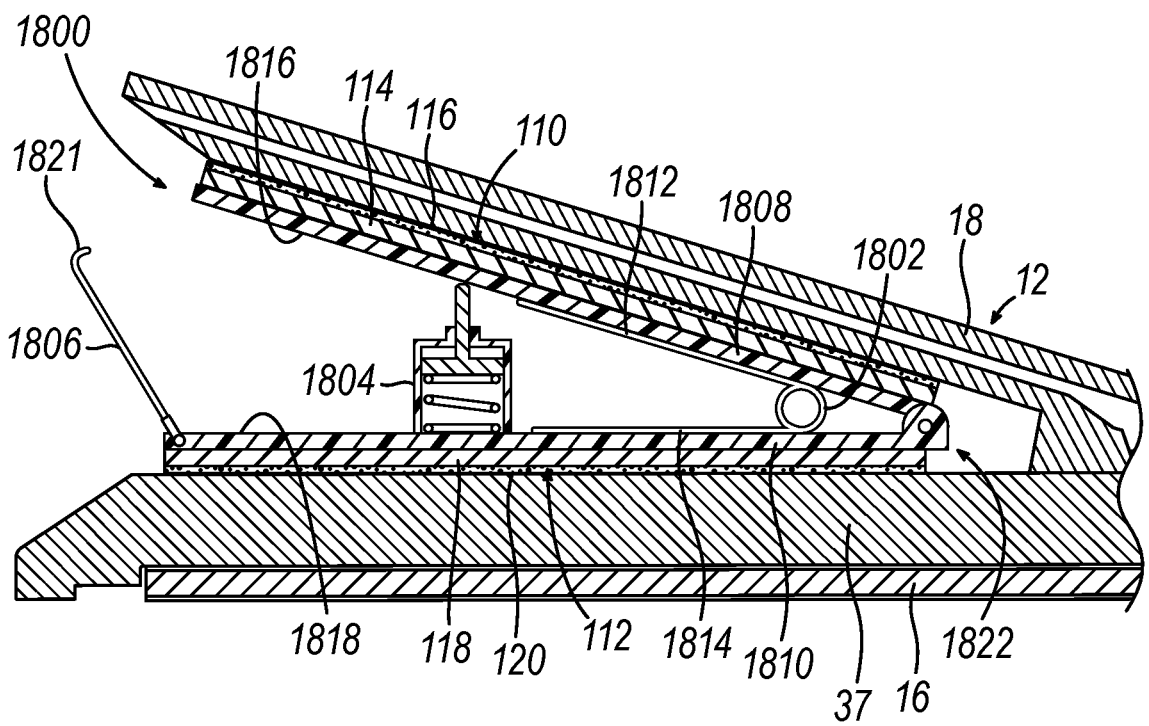
FIG. 41B depicts a side cross-sectional view of the adjunct applicator device of FIG. 41A and the end effector of FIG. 3, with the buttress assembly of FIG. 8 applied to the adjunct applicator device, the adjunct applicator device being in a second, expanded state to thereby secure the buttress assembly to the end effector.

FIGS. 41A-41B show another exemplary applicator device (1800) that is configured to apply an adjunct material to a jaw (e.g., lower jaw (16)) of end effector (12) of surgical stapler (10). Applicator device (1800) is configured with the same structures and functionality as applicator device (900, 1000, 1100, 1400, 1500, 1600, 1700), except for the differences described below. Applicator device (1800) of this example comprises a torsion spring (1802), a dashpot (1804), a latch (1806), and applicator arms (1808, 1810). Applicator arms (1808, 1810) may be formed into a V-shaped wedge that provides a complementary shape to pivotable anvil (18) and lower jaw (16) that is operable to securely attach buttress assemblies (110, 112) to pivotable anvil (18) and lower jaw (16) when applicator arms (1808, 1810) expand apart while positioned between pivotable anvil (18) and lower jaw (16). Applicator arms (1808, 1810) are pivotably coupled together at their proximal ends (1820, 1822), and torsion spring (1802) is disposed adjacent the pivotable coupling at proximal ends (1820, 1822).

Applicator arms (1808, 1810) cooperate to define a contact structure and are each configured to apply adjunct material to end effector (12) of stapling instrument (10). More specifically, upper applicator arm (1808) is configured to accept buttress assembly (110) thereon for application onto pivotable anvil (18), and lower applicator arm (1810)

is configured to accept buttress assembly (112) thereon for application on to lower jaw (16). Particularly, buttress assembly (110) is placed onto upper applicator arm (1808) such that upper adhesive layer (116) is facing outwardly away from upper applicator arm (1808), and buttress assembly (112) is placed onto lower applicator arm (1810) such that lower adhesive layer (120) is facing outwardly away from lower applicator arm (1810), thereby allowing upper and lower adhesive layers (116, 120) to adhere to pivotable anvil (18) and lower jaw (16), respectively, upon application of buttress assemblies (110, 112) by applicator device (1800).

FIG. 41A shows applicator arms (1808, 1810) in a non-expanded, pre-application state with buttress assemblies (110, 112) installed thereon. Applicator arms (1808, 1810) are biased to expand in opposite directions by torsion spring (1802). Torsion spring (1802) is disposed at the base of the "V" defined by applicator arms (1808, 1810) and includes spring arms (1812, 1814) extending across inner surfaces (1816, 1818) of applicator arms (1808, 1810), respectively. Applicator arms (1808, 1810) are further coupled together with latch (1806). Latch (1806) is configured to pivotably couple at one end to applicator arm (1810) and include a hook (1821) at the opposing end. In some examples, latch (1806) may instead be configured to pivotably couple at one end to applicator arm (1808). Hook (1821) of latch (1806) is further configured to releasably couple with the other of first applicator arm (1808) or second applicator arm (1810) to prevent applicator arms (1808, 1810) from spreading apart due to the spreading force provided by torsion spring (1802). Torsion spring (1802) and latch (1806) cooperate to define an expansion mechanism configured to be manipulated by a user to transition applicator device (1810) from a non-expanded state (see FIG. 41A) to an expanded state (see FIG. 41B). Additionally, dashpot (1804), or alternatively another similar energy dampening device, is coupled to inner surfaces (1816, 1818) of applicator arms (1808, 1810).

As shown in FIG. 41B, a user may pivot hook (1821) of latch (1806) away from applicator arm (1808), thereby permitting torsion spring (1802) to force applicator arms (1808, 1810) in opposing directions. As described above, spreading applicator arms (1808, 1810) in opposing directions is operable to apply buttress assemblies (110, 112) to end effector (12). As hook (1821) is removed and applicator arms (1808, 1810) spread apart, dashpot (1804) is configured to dampen the rate of spreading motion of applicator arms (1808, 1810). Dashpot (1804) therefore ensures against applicator arms (1808, 1810) spreading too quickly as to cause damage to end effector (12) when applying buttress assemblies (110, 112). End effector (12) may thereafter be removed from applicator device (1300).

V Exemplary Adjunct Applicator Devices for Applying Adjunct Elements to Surgical Stapler Jaws Individually In some instances, it may be desirable to provide an adjunct applicator device that is operable to apply an adjunct element (e.g., a buttress assembly or a tissue thickness compensator) to each jaw of a surgical stapler end effector separately and individually, while the jaws remain in an open state. Each of the exemplary applicator devices described below in connection with FIGS. 42-53 provide such functionality.

A. First Applicator Device for Individual Adjunct Application

Figure 42:
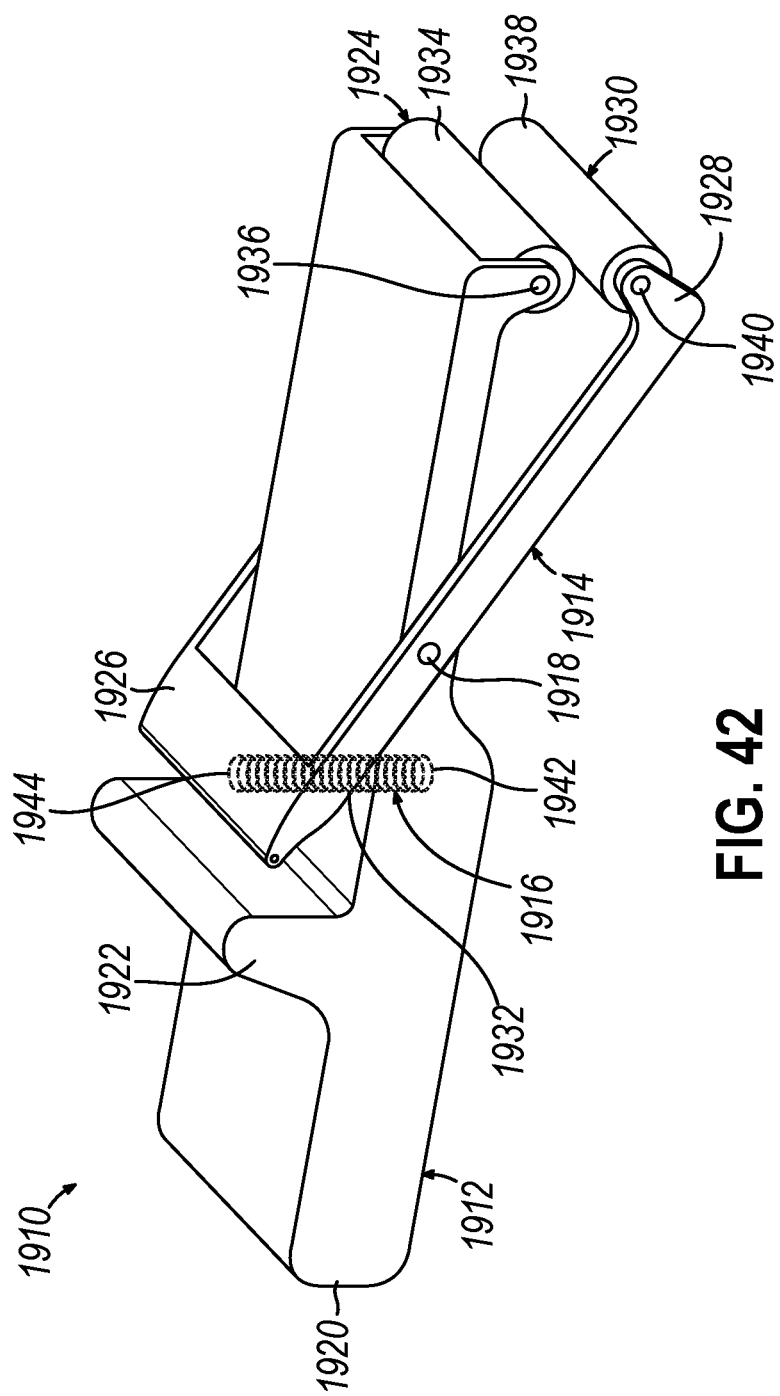
FIG. 42 depicts a perspective view of another exemplary adjunct applicator device.
Figure 43A:
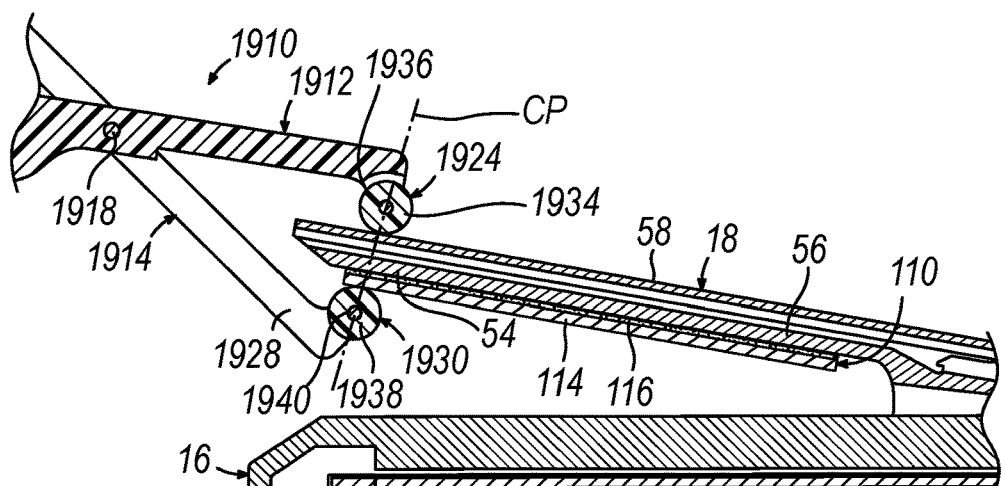
FIG. 43A depicts a cross-sectional view of the adjunct applicator device of FIG. 42, the buttress assembly of FIG. 8, and the end effector of FIG. 3, with the adjunct applicator device securing an already applied buttress assembly to a distal portion of an upper jaw of the end effector.
Figure 43B:
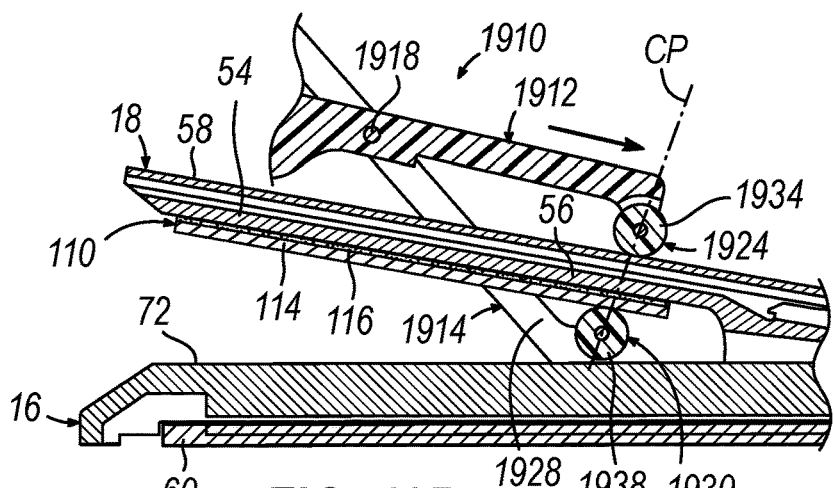
FIG. 43B depicts a cross-sectional view of the adjunct applicator device, the buttress assembly, and the end effector of FIG. 43A, with the adjunct applicator device securing the already applied the buttress assembly to a proximal portion of the upper jaw.
Figure 43C:
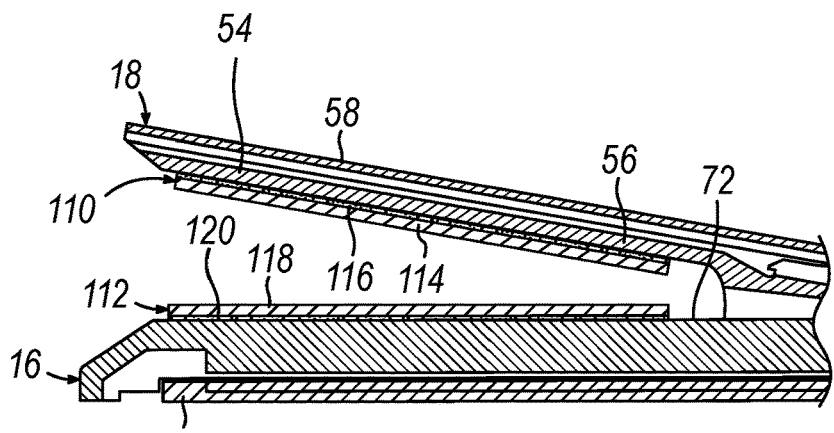
FIG. 43C depicts a cross-sectional view of the end effector of FIG. 43B, with the buttress assembly secured to the upper jaw and a second buttress assembly of FIG. 8 secured to a lower jaw of the end effector.

FIGS. 42-43C show another exemplary applicator device (1910) that is configured to apply an adjunct material (e.g., buttress assembly (110, 112) or a tissue thickness compensator) to a jaw (e.g., lower jaw (16) or anvil (18)) of end effector (12) of surgical stapler (10). Applicator device (1910) adjusts for the thickness of anvil (18) or lower jaw (16) allowing applicator device (1910) to suitably apply adjunct material to both anvil (18) and lower jaw (16) separately. As shown in FIG. 42, applicator device (1910) includes a housing (1912), an arm (1914), a resilient feature (1916), and a coupling feature (shown as a pin (1918)). Housing (1912) includes a body member (1920), a projection (1922) extending from body member (1920), and a first contact feature (1924). First contact feature (1924) may extend from body member (1920) and is translatably fixed relative to body member (1920). Arm (1914) may be coupled with housing (1912) using pin (1918) that extends through a cavity (not shown) disposed in body member (1920) of housing (1912). However, other suitable structures for coupling housing (1912) and arm (1914) are also envisioned. Arm (1914) includes proximal and distal ends (1926, 1928), with a second contact feature (1930) disposed at distal end (1928) of arm (1914).

As shown in FIG. 42, resilient feature (1916) may be coupled with body member (1920) of housing (1912) and proximal end (1926) of arm (1914). Arm (1914) may be rotatably biased toward housing (1912) using resilient feature (1916) and pin (1918). Resilient feature (1916) is configured to bias arm (1914), including second contact feature (1930), relative to first contact feature (1924) to apply a compression force as shown in FIGS. 43A-43B to secure the adjunct material to the desired jaw. Resilient feature (1916) may include at least one spring operatively coupled with housing (1912). As shown in FIG. 42, resilient feature (1916) includes a tension spring (1932). A first end (1942) of tension spring (1932) may be coupled with body member (1920) and a second end (1944) of tension spring (1932) may be coupled with proximal end (1926) of arm (1914). Tension spring (1932) may bias arm (1914), including second contact feature (1930), relative to first contact feature (1924) by applying a compression force. FIG. 42 shows first and second contact features (1924, 1930) being separated by a distance from one another in a neutral configuration (i.e., a resting configuration). Alternatively, it is envisioned that second contact feature (1930) may contact first contact feature (1924) in the neutral configuration, so as to apply a predetermined contact force against first contact feature (1924) prior to applicator device (1910) being used to secure the adjunct material to the jaw of end effector (12).

First contact feature (1924) and/or second contact feature (1930) may include a roller. As shown in FIG. 42, first contact feature (1924) includes a roller (1934) that is coupled with body member (1920) using a coupling feature (1936). Similarly, second contact feature (1930) includes a roller (1938) that is coupled with arm (1914) using a coupling feature (1940). Rollers (1934, 1938) are configured to apply a compression force as rollers (1934, 1938) move along jaw. Particularly, roller (1938) applies a compression force against a jaw of end effector (12), while roller (1934) applies a counter force. As a result, roller (1934) may be static and not deflect relative to body member (1920). While rollers (1934, 1938) are shown as single elongate rollers in FIG. 42, other suitable rollers including rollers having a discontinuous contact surface are also envisioned. Coupling features (1936, 1940) may include, for example, a pin or another suitable coupling along feature that allows for rotation of roller (1934) relative to body member (1920) and rotation of roller (1938) relative to arm (1914). While first and second contact features (1924, 1930) are shown as including rollers (1934, 1938), it is also envisioned that first and second contact features (1924, 1930) may include low-friction elements that may slide along the adjunct material or the outer surface of the jaw.

FIGS. 43A-43C show the adjunct material being secured onto a stapling surface of a jaw of end effector (12). As described above, the adjunct material may include buttress assemblies (110, 112), tissue thickness compensators, or other suitable materials. The stapling surface is intended to include upper deck (72) of staple cartridge (37) that includes staple apertures (50) or a contact surface (52) of anvil (18) that includes staple forming pockets (53) as shown in FIG. 3. It is also envisioned that anvil (18) may be disposed on the lower jaw and the staple cartridge (37) may be disposed on the upper jaw. Applicator device (1910) is shown as securing buttress assembly (110) to anvil (18), where buttress assembly (110) is already at least partially disposed on anvil (18). In some versions, a user utilizing a separate device (not shown) may initially apply buttress assembly (110) to anvil (18), so that applicator device (1910) more securely presses buttress assembly (110) against anvil (18) to secure buttress assembly (110) in place using a desired pressure. In other versions, applicator device (1910) may include or be coupled with a material dispenser that supplies the adjunct material, similar to material dispenser (2030) which is described in detail below with reference to FIGS. 44-45B.

FIG. 43A shows a cross-sectional view of applicator device (1910) of FIG. 42 and end effector (12) of FIG. 3, with applicator device (1910) securing buttress assembly (110) to a distal portion (54) of anvil (18) of end effector (12). As described above, buttress assembly (110) includes upper adhesive layer (116) that is configured to adhere buttress assembly (110), including buttress body (114), to contact surface (52) of anvil (18). As shown in FIG. 43A, anvil (18) includes an outer surface (58) disposed 180 degrees opposite contact surface (52). Roller (1938) of second contact feature (1930) is configured to apply a compression force to pinch buttress assembly (110) against distal portion (54) of anvil (18) to secure upper adhesive layer (116) of buttress assembly (110) with contact surface (52), which secures upper adhesive layer (116) to contact surface (52). As shown in FIG. 43A-43B, rollers (1934, 1938) are disposed opposite one another along a compression plane (CP). Roller (1934) may rotate in an opposite direction relative to roller (1938). Roller (1938) applies a compression force as roller (1934) moves along outer surface (58) of anvil (18) and roller (1938) moves along contact surface (52) of anvil (18). In some versions, roller (1938) may apply the compression force as roller (1934) moves along contact surface (52) of anvil (18) and roller (1938) moves along outer surface (58) of anvil (18).

FIG. 43B shows a cross-sectional view of applicator device (1910) and end effector (12) of FIG. 43A, with applicator device (1910) applying buttress assembly (110) to a proximal portion (56) of anvil (18) after roller (1934) rolls along outer surface (58) of anvil (18) and roller (1938) rolls along buttress body (114) to adhere upper adhesive layer (116) with contact surface (52). While the user may generally secure buttress assembly (110) to distal portion (54) of anvil (18) then secure buttress assembly (110) to proximal portion (56) of anvil (18), it is also envisioned that the user may secure buttress assembly (110) to proximal portion (56) of anvil (18) then secure buttress assembly (110) to distal portion (54) of anvil (18).

FIG. 43C shows a cross-sectional view of end effector (12) of FIG. 43B, with buttress assembly (110) secured to contact surface (52) of anvil (18) and buttress assembly (112) secured to upper deck (72) of lower jaw (16) of end effector (12). As shown, buttress assembly (112) includes lower adhesive layer (120) that is configured to adhere buttress assembly (112), including buttress body (118), to upper deck (72) of lower jaw (16). The application of buttress assembly (112) may be similar to the application of buttress assembly (110) described above. For example, roller (1938) may apply a compression force as roller (1934) moves along outer surface (60) of lower jaw (16) and roller (1938) moves buttress body (118) to adhere lower adhesive layer (120) with upper deck (72) of lower jaw (16). However, it is also envisioned that roller (1938) may apply the compression force as roller (1934) moves along buttress body (114) to adhere lower adhesive layer (120) with upper deck (72) of lower jaw (16) and roller (1938) moves along outer surface (60) of lower jaw (16). Since lower jaw (16) is shown as being thicker than anvil (18), to spread rollers (1934, 1938) further apart, tension spring (1932) may be stretched further. Stretching tension spring (1932) may result in a greater spring force so that lower jaw (16) is interposed between rollers (1934, 1938).

B. Second Applicator Device for Individual Adjunct Application

Figure 44:
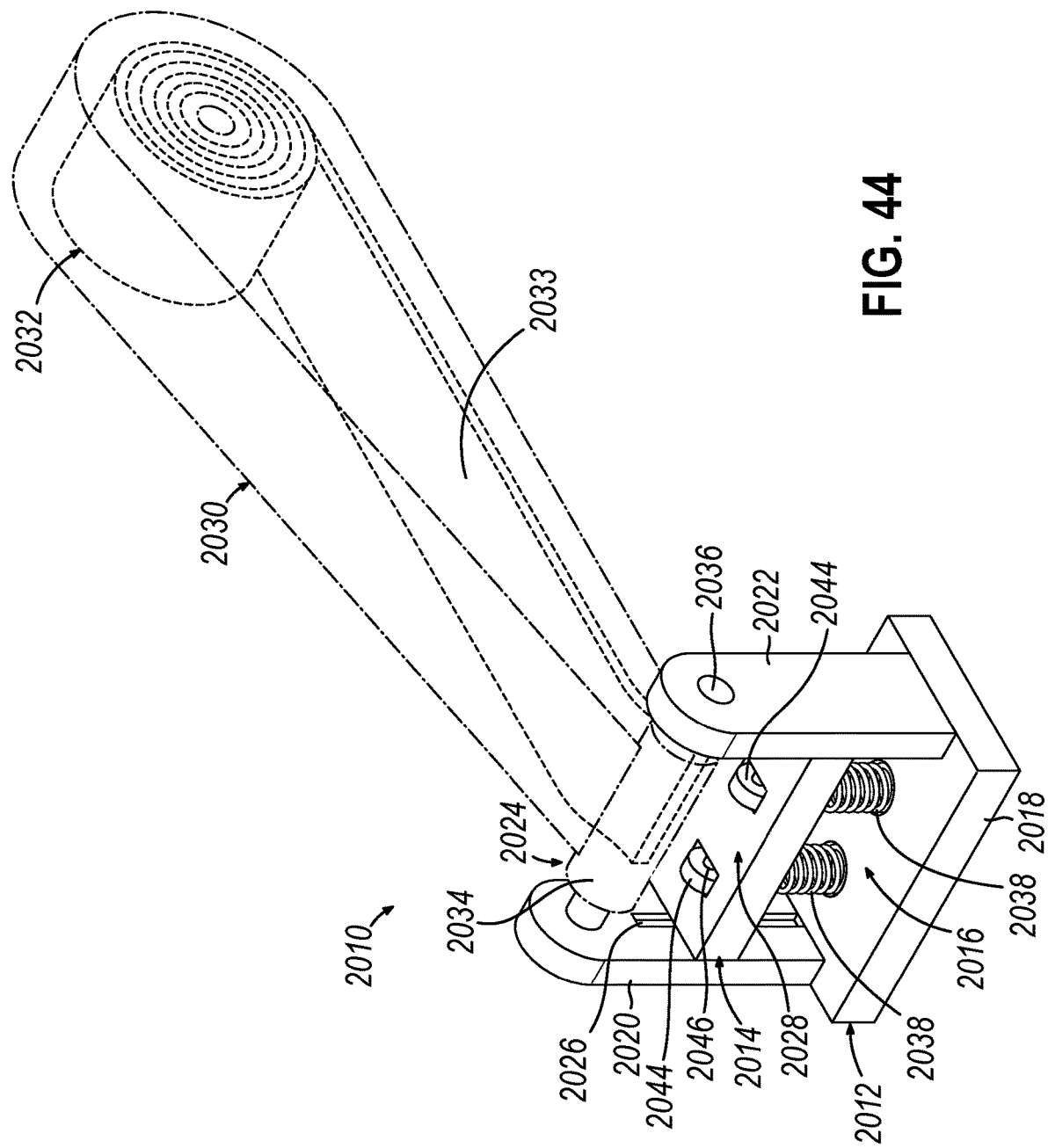
FIG. 44 depicts a perspective view of another exemplary adjunct applicator device, with select internal components being shown schematically in phantom.
Figure 45A:
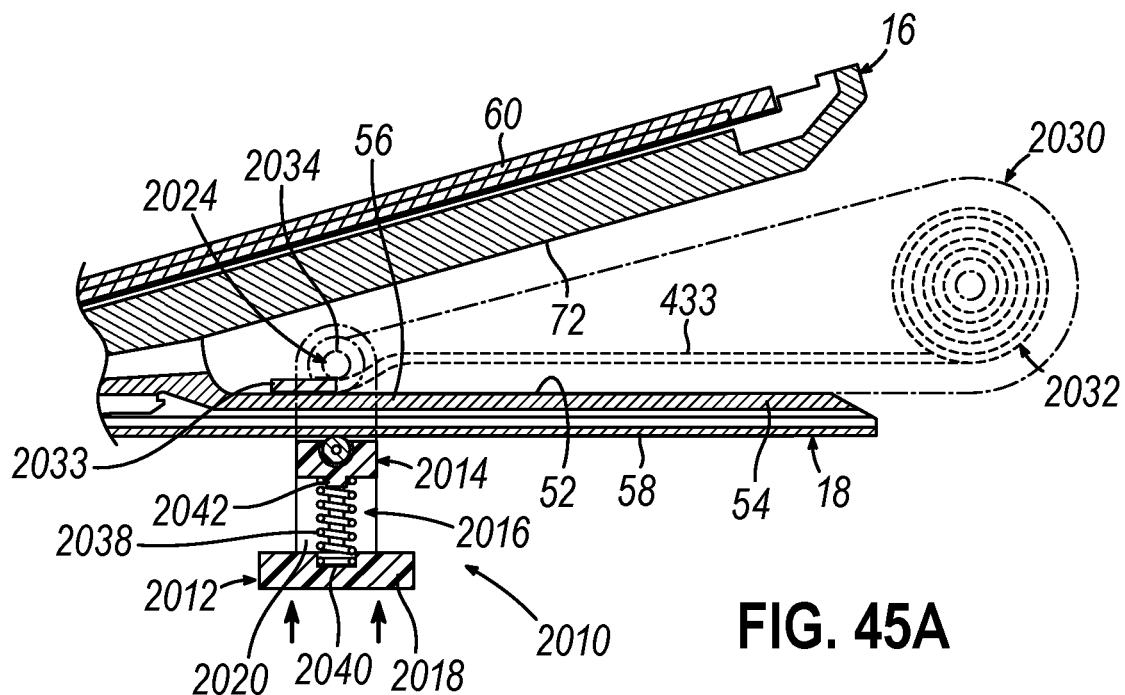
FIG. 45A depicts a cross-sectional view of the adjunct applicator device of FIG. 44 and the end effector of FIG. 3, with the adjunct applicator device applying and securing a continuous buttress assembly from a material dispenser to a proximal portion of the upper jaw of the end effector.
Figure 45B:
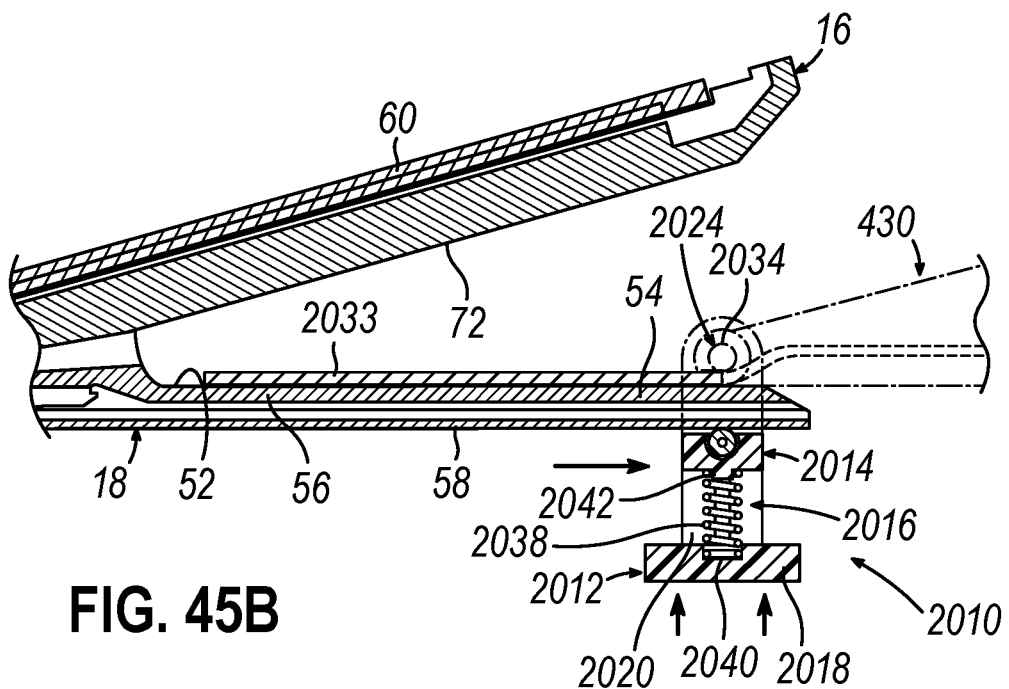
FIG. 45B depicts a cross-sectional view of the adjunct applicator device and the end effector of FIG. 45A, with the adjunct applicator device applying and securing the continuous buttress assembly from the material dispenser to a distal portion of the upper jaw.

FIGS. 44-45B show another exemplary applicator device (2010) that is configured to apply an adjunct material to a jaw (e.g., lower jaw (16) or anvil (18)) of end effector (12) of surgical stapler (10). Applicator device (2010) adjusts for thickness of anvil (18) or lower jaw (16) allowing applicator device (2010) to suitably apply adjunct material to anvil (18) and lower jaw (16). As a result, the application of buttress assembly (112) using applicator device (2010) to lower jaw (16) that includes staple cartridge (37) may be similar to the application of buttress assembly (110) described above. As shown in FIG. 44, applicator device (2010) includes a housing (2012), an arm (2014), and a resilient feature (2016). Housing (2012) includes a base (2018), a first upright (2020), a second upright (2022), and a first contact feature (2024). First and second uprights (2020, 2022) extend outwardly from base (2018). First and second uprights (2020, 2022) are shown as parallel to one another. Optionally, arm (2014) may translate along slots (2026) disposed in first and second uprights (2020, 2022). Arm (2014) includes a second contact feature (2028).

Housing (2012) may include an adjunct material dispenser (2030) that dispenses adjunct material from a spool (2032) using first contact feature (2024). As shown, the adjunct material is a continuous buttress assembly (2033). Buttress assembly (2033) may include an adhesive surface to couple with the stapling surface. It will be appreciated that material dispenser (2030) may be further configured and operable in accordance with the teachings of U.S. Pat. Pub. No. 2015/0076212, entitled "Surgical End Effector Having Buttress Retention Features," published Mar. 19, 2015, issued as U.S. Pat. No. 11,058,418 on Jul. 13, 2021, the disclosure of which is incorporated by reference herein. Continuous buttress assembly (2033) may be dispensed at first contact feature (2024). First contact feature (2024) applies buttress assembly (2033) to contact surface (52). As shown, first contact feature (2024) includes a roller (2034) that is secured with first and second uprights (2020, 2022) and material dispenser (2030) using a coupling feature (2036). Optionally, spool (2032) may be removed from housing (2012) by removing coupling feature (2036) that couples first contact feature (2024) with material dispenser (2030). Material dispenser (2030) may deliver multiple buttresses without reloading. Additionally, material dispenser (2030), utilizing a single product code, may dispense buttresses having varying lengths. This may reduce the number of different buttress sizes that the user has stock or otherwise have on hand.

Applicator device (2010) may control the force with which the adjunct material is applied to the jaw from material dispenser (2030) using resilient feature (2016). Resilient feature (2016) may be disposed between base (2018) of housing (2012) and arm (2014). Resilient feature (2016) may be configured to bias arm (2014), including second contact feature (2028), relative to first contact feature (2024) to apply a compression force as shown in FIG. 45A-45B. Arm (2014) is configured to translate relative to base (2018) using resilient feature (2016). For example, resilient feature (2016) may include at least one spring. As shown in FIG. 44, resilient feature (2016) includes a pair of compression springs (2038). However, more or fewer compression springs (2038), such as a single compression spring, is also envisioned.

As shown in FIGS. 45A-45B, first ends (2040) of compression springs (2038) may be coupled with base (2018) and second ends (2042) of compression springs (2038) may be coupled with arm (2014). Compression spring (2038) is configured to bias arm (2014), including second contact feature (2028), relative to first contact feature (2024) by applying a compression force. In other words, compression springs (2038) push arm (2014) upward onto outer surface (58) of anvil (18). Compression springs (2038) disposed between arm (2014) and base (2018) may provide the desired application pressure to secure the adjunct material with the stapling surface of the jaw. FIG. 44 shows first and second contact features (2024, 2028) being separated by a distance from one another in a neutral configuration (i.e., a resting configuration). Alternatively, it is envisioned that second contact feature (2028) may contact first contact feature (2024) in the neutral configuration, so as to apply a predetermined contact force against first contact feature (2024) prior to applicator device (2010) being used to secure the adjunct material to upper deck (72) of lower jaw (16) or to contact surface (52) of anvil (18).

First contact feature (2024) and/or second contact feature (2028) may include a roller. As shown in FIG. 44, second contact feature (2028) includes a pair of rollers (2044) configured to apply a compression force as rollers (2044) move along the outer surface of the jaw. While a pair of rollers (2044) are shown, more or fewer rollers (2044) are also envisioned. Rollers (2044) of arm (2014) allow smooth application of adjunct material along length of the jaw. Arm (2014), including rollers (2044), is configured to translate relative to base (2018) to simultaneously contact outer surface as spool (2032) applies adjunct material to upper deck (72) of lower jaw (16) or to contact surface (52) of anvil (18). Rollers (2044) may be coupled with arm (2014) using a coupling feature (2046). Particularly, roller (2044) is configured to apply a compression force against a jaw of end effector (12), while roller (2034) is configured to apply a counter force. As a result, roller (2034) may be static and not deflect relative to base (2018). As shown in FIG. 44, rollers (2034, 2044) are disposed opposite one another along a compression plane (CP). While roller (2034) is shown as a single elongate roller in FIG. 44, other rollers are also envisioned including rollers having a discontinuous contact surfaces or multiple discrete rollers.

Coupling features (2036, 2046) may include, for example, a pin or another suitable coupling along feature that allows for rotation of roller (2034) relative to material dispenser (2030) and rotation of roller (2044) relative to arm (2014). While second contact feature (2028) is shown as including rollers (2044), it is also envisioned that second contact feature (2028) may include a low-friction element that may slide along the jaw.

FIGS. 45A-45B show an adjunct material being applied and secured onto a stapling surface of a jaw of end effector (12). Particularly, FIG. 45A shows a cross-sectional view of applicator device (2010) of FIG. 44 and end effector (12) of FIG. 3, with applicator device (2010) securing buttress assembly (110) to a proximal portion (56) of anvil (18). As shown, buttress assembly (110) includes upper adhesive layer (116) that is configured to adhere buttress assembly (110), including buttress body (114), to contact surface (52) of anvil (18). Outer surface (58) of anvil (18) is disposed 180 degrees opposite contact surface (52). As shown in FIG. 45A, rollers (2044) of second contact feature (2028) apply a compression force to pinch buttress assembly (110) against proximal portion (56) of anvil (18) to secure upper adhesive layer (116) of buttress assembly (110) to contact surface (52). Roller (2034) may rotate in an opposite direction relative to rollers (2044). Rollers (2044) apply the compression force as roller (2034) moves along outer surface (58) of anvil (18) and roller (2034) moves along buttress body (114) to adhere upper adhesive layer (116) with contact surface (52) of anvil (18). Applicator device (2010) exerts a clamping force on anvil (18) between proximal tip of roller (2034) and a central point of rollers (2044) of arm (2014) that serves as a bottom force limiting backstop device.

FIG. 45B shows a cross-sectional view of applicator device (2010) and end effector (12) of FIG. 45A, with applicator device (2010) applying and securing buttress assembly (110) to distal portion (54) of anvil (18) after roller (2034) rolled along buttress body (114) to adhere upper adhesive layer (116) with contact surface (52) and rollers (2044) rolled along outer surface (58) of anvil (18). While the user may generally secure buttress assembly (110) to proximal portion (56) of anvil (18) then secure buttress assembly (110) to distal portion (54) of anvil (18), it is envisioned that the user may secure buttress assembly (110) to distal portion (54) of anvil (18) then secure buttress assembly (110) to proximal portion (56) of anvil (18). The application of buttress assembly (112) to lower jaw (16) that includes staple cartridge (37) may be similar to the application of buttress assembly (110) described above.

C. Third Applicator Device for Individual Adjunct Application

Figure 46:
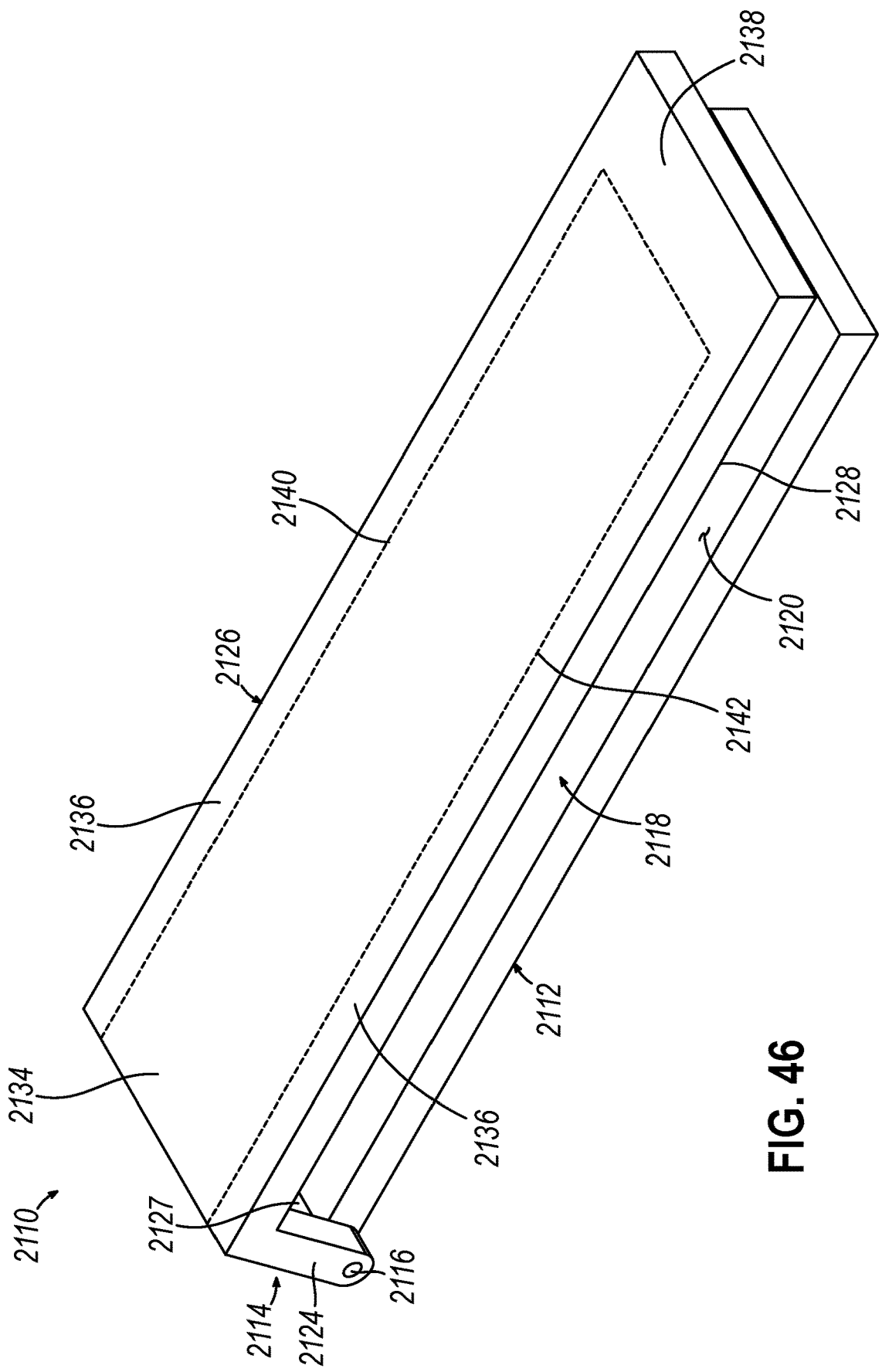
FIG. 46 depicts a perspective view of another exemplary adjunct applicator device.
Figure 47A:
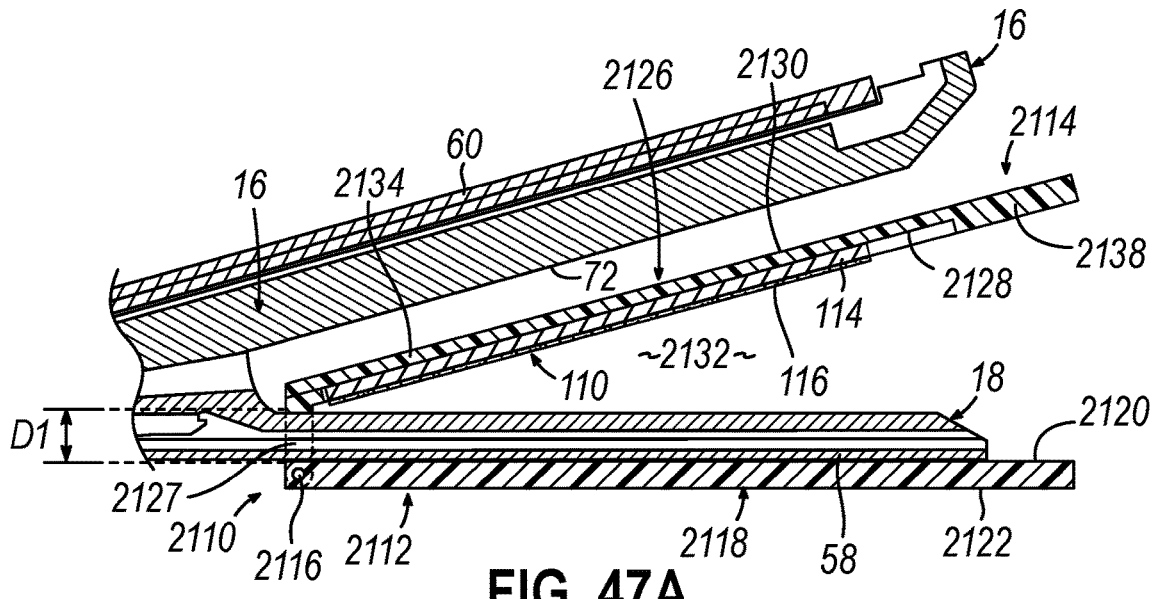
FIG. 47A depicts a cross-sectional view of the adjunct applicator device of FIG. 46, the buttress assembly of FIG. 8, and the end effector of FIG. 3, with an arm of the adjunct applicator device pivoting toward the upper jaw.
Figure 47B:
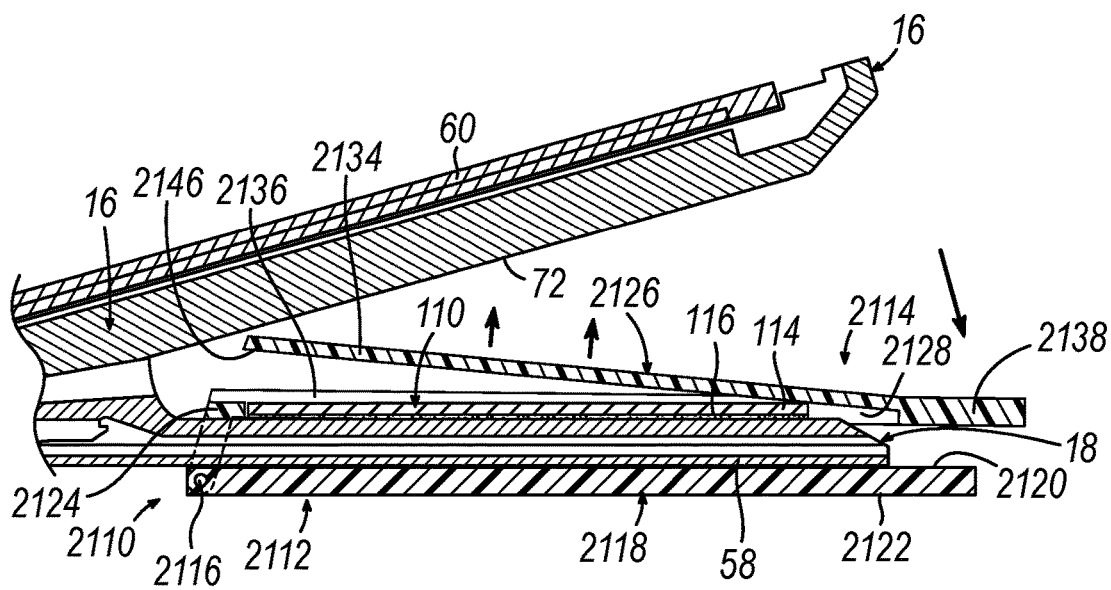
FIG. 47B depicts a cross-sectional view of the adjunct applicator device, the buttress assembly, and the end effector of FIG. 47A, with lateral frangible portions of the arm severing to release the buttress assembly from the adjunct applicator device and apply and secure the buttress assembly to the upper jaw.
Figure 47C:
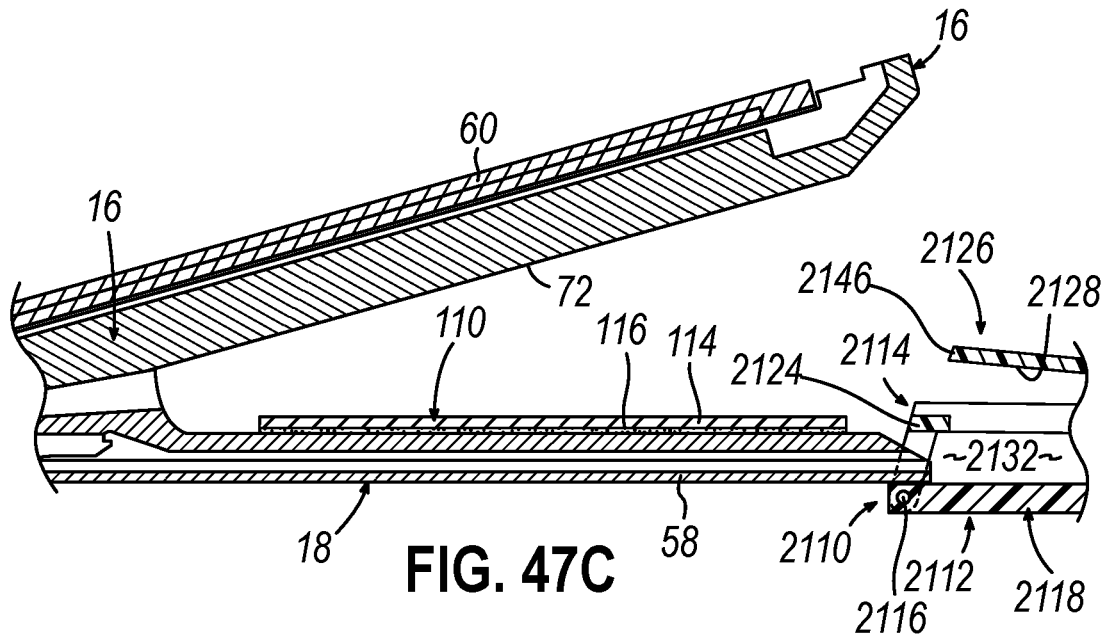
FIG. 47C depicts a cross-sectional view of the adjunct applicator device, the buttress assembly, and the end effector of FIG. 47A, with the buttress assembly secured to the upper jaw and the adjunct applicator device being removed from the upper jaw.

FIGS. 46-47C show another exemplary applicator device (2110) that is configured to apply an adjunct material to a jaw (e.g., anvil (18)) of end effector (12) of surgical stapler (10). As shown in FIG. 46, applicator device (2110) includes a housing (2112), an arm (2114), and a hinge (2116). Hinge (2116) pivotably couples arm (2114) with housing (2112) at a hinge point (HP), so that arm (2114) may pivot relative to housing (2112) to apply and secure the adjunct material (shown as buttress assembly (110)) to anvil (18). Housing (2112) includes a first contact feature (2118) that is shown as a generally planar base. First contact feature (2118) includes inner and outer surfaces (2120, 2122), with inner surface (2120) facing arm (2114). Arm (2114) includes a connecting portion (2124) and a second contact feature (2126) that is shown as a generally planar platform. Connecting portion (2124) has a first thickness (D1) to accommodate the thickness of anvil (18). Connecting portion (2124) may include an aperture (2127) to allow the jaw to extend therethrough as shown in FIGS. 47A-47C. Second contact feature (2126) includes inner and outer surfaces (2128, 2130), with inner surface (2128) facing inner surface (2120) of first contact feature (2118). As shown in FIGS. 47A-47B, a cavity (2132)

is disposed between inner surfaces (2120, 2128) of first and second contact feature (2118, 2126).

Second contact feature (2126) is configured to pivot relative to first contact feature (2118) between an open configuration (shown in FIG. 47A) and a closed configuration (shown in FIG. 47B) where second contact feature (2126) pushes buttress assembly (110) into contact with the stapling surface. As shown in FIG. 46, second contact feature (2126) includes inner and outer portions (2134, 2136) and a retaining portion (2138). Inner and outer portions (2134, 2136) are connected together by lateral frangible portions (2140, 2142). Lateral frangible portions (2140, 2142) are configured to sever when a predetermined pressure is applied to release adjunct material from applicator device (2110). Retaining portion (2138) is disposed an end of second contact feature (2126) disposed opposite to hinge (2116). Lateral frangible portions (2140, 2142) are configured to break to separate inner and outer portions (2134, 2136), except for retaining portion (2138) that keeps inner and outer portions (2134, 2136) coupled together.

FIGS. 47A-47B show adjunct material (shown as buttress assembly (110)) being secured onto the upper jaw (shown as anvil 18) of end effector (12). As shown, applicator device (2110) may load and secure buttress assembly (110) to anvil (18). Particularly, FIG. 19A shows a cross-sectional view of applicator device (2110) of FIG. 46 and end effector (12) of FIG. 3, with arm (2114) of applicator device (2110) pivoting toward an upper jaw (shown as anvil (18)). Outer surface (58) of anvil (18) is disposed 180 degrees opposite contact surface (52). As shown, buttress assembly (110) includes upper adhesive layer (116) that is configured to adhere buttress assembly (110), including buttress body (114), to contact surface (52) of anvil (18). As shown in FIG. 19A, second contact feature (2126) of arm (2114) provides an elongate platform that a first side of the buttress assembly (110) is releasably attached to (e.g., via adhesion). In other words, buttress body (114) may be temporarily attached to inner surface (2128) of second contact feature (2126) using an adhesive or a mechanical coupling feature. Inner portion (2134) of second contact feature (2126) may be perforated along the sides except for retaining portion (2138).

FIG. 47B shows a cross-sectional view of applicator device (2110) and end effector (12) of FIG. 47A, with lateral frangible portions (2140, 2142) breaking to release applicator device (2110) from anvil (18). Second contact feature (2126) applies a compression force to pinch buttress assembly (110) against proximal portion (56) of anvil (18) to apply and secure buttress assembly (110) to contact surface (52). When arm (2114) is rotated toward and compressed against the end effector (12) jaw with sufficient force, lateral frangible portions (2140, 2142) sever. This transforms inner portion (2134) into a flap (2144) with a free end that remains hingedly attached to retaining portion (2138) so that the remainder of arm (2114), such as flap (2144) is not a completely loose piece that may fall onto the patient or the floor. Retaining portion (2138) may include a bendable portion that is configured to bend, but not break when buttress assembly (110) is released from applicator device (2110) as shown in FIG. 47B. Buttress assembly (110) separates from inner portion (2134) of second contact feature (2126) in response to closure of the arm (2114) on the end effector (12) jaw. As a result, applicator device (2110) may control the force with which buttress assembly (110) is applied to contact surface (52) of anvil (18) using lateral frangible portions (2140, 2142).

Lateral frangible portions (2140, 2142) are shown as spaced perforations along respective sides of inner portion (2134), but not at the distal end. For ease of application, lateral frangible portions (2140, 2142) may disposed around the area adjacent buttress assembly (110), so that when buttress assembly (110) is applied, lateral frangible portions (2140, 2142) tear and secure buttress assembly (110) to anvil (18). Lateral frangible portions (2140, 2142) may be altered to increase or decrease the force with which buttress assembly (110) is applied to anvil (18) prior to lateral frangible portions (2140, 2142) severing. For example, the spacing of adjacent perforations and/or the ratio of material to gaps may be altered. Lateral frangible portions (2140, 2142) on applicator device (2110) may prevent re-use after deployment of the adjunct material. Applicator device (2110) prevented from being re-used by the severed lateral frangible portions (2140, 2142). In some versions, arm (2114) may destroys itself or lock into a non-closable state once arm (2114) opens, such that the detent is overcome, but difficult to reset.

FIG. 47C shows a cross-sectional view of applicator device (2110) and end effector (12) of FIG. 47B, with buttress assembly (110) applied to anvil (18) and applicator device (2110) being actively removed. For example, applicator device (2110) may be slid distally relative to end effector (12) using aperture disposed in arm (2114).

D. Fourth Applicator Device for Individual Adjunct Application

Figure 48:
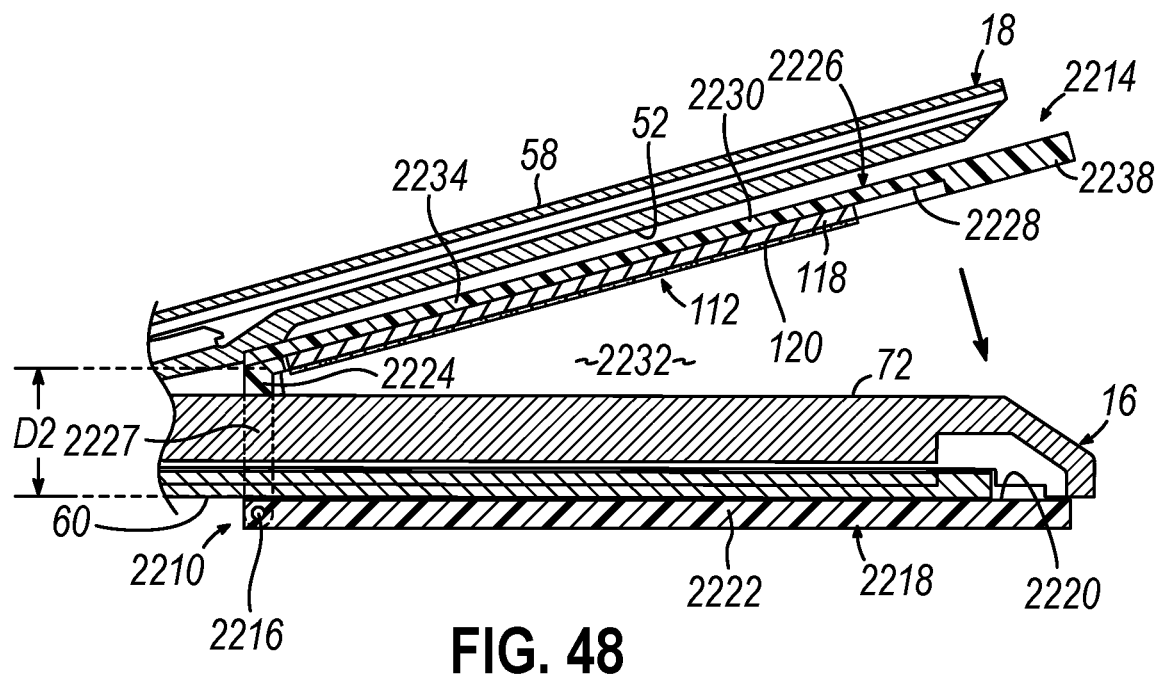
FIG. 48 depicts a cross-sectional view of another exemplary adjunct applicator device, the buttress assembly of FIG. 8, and the end effector of FIG. 3, with an arm of the adjunct applicator device pivoting toward the lower jaw of the end effector.

FIG. 48 shows another exemplary alternative applicator device (2210) that is configured to apply an adjunct material to a jaw (e.g., lower jaw (16)) of end effector (12) of surgical stapler (10). As shown, applicator device (2210) includes a housing (2212), an arm (2214), and a hinge (2216). Hinge (2216) pivotably couples arm (2214) with housing (2212) at a hinge point, so that arm (2214) may pivot relative to housing (2212) to apply and secure the adjunct material (shown as buttress assembly (112)) to lower jaw (16). Housing (2212) includes a first contact feature (2218) that is shown as a generally planar base. First contact feature (2218) includes inner and outer surfaces (2220, 2222), with inner surface (2220) facing arm (2214).

Arm (2214) includes a connecting portion (2224) and a second contact feature (2226) that is shown as a generally planar platform. Connecting portion (2224) has a second thickness (D2) to accommodate the thickness of lower jaw (16). As a result, connecting portion (2224) may be longer than connecting portion (2124), so as to account for the increased thickness (i.e., height) of lower jaw (16) as compared to anvil (18). Connecting portion (2224) may include an aperture (2227) to allow the jaw to extend therethrough as shown in FIGS. 47A-47C. Second contact feature (2226) includes an inner surface (2228) and an outer surface (2230), with inner surface (2228) facing inner surface (2220) of first contact feature (2218). As shown, a cavity (2232) is disposed between inner surfaces (2220, 2228) of first and second contact feature (2218, 2226). Second contact feature (2226) is configured to pivot relative to first contact feature (2218) between an open configuration (similar to FIG. 47A regarding applicator device (2110)) and a closed configuration (shown in FIG. 48) where disposed on second contact feature (2226) pushes buttress assembly (110) into contact with the stapling surface. Second contact feature (2226) includes an inner portion (2234) and an outer portion (not shown) but similar to outer portion (2136), and a retaining portion (2238). Inner portion (2234) is coupled with outer portion by lateral frangible portions (not shown), but which are similar to lateral frangible portions (2140, 2142) described above.

FIG. 48 shows adjunct material (shown as buttress assembly (112)) being secured onto lower jaw (16) of end effector (12). As shown, applicator device (2210) may load and secure buttress assembly (110) to lower jaw (16). Particularly, FIG. 48 shows a cross-sectional view of applicator device (2210) and end effector (12) of FIG. 3, with arm (2214) of applicator device pivoting toward lower jaw (16) that includes staple cartridge (37) of end effector (12). Outer surface (60) of lower jaw (16) is disposed 180 degrees opposite upper deck (72). As shown, buttress assembly (110) includes lower adhesive layer (120) that is configured to adhere buttress assembly (112), including buttress body (118), to upper deck (72) of staple cartridge (37) of lower jaw (16). As shown, when arm (2214) is rotated toward and compressed against the end effector (12) jaw with sufficient force, the lateral frangible portions sever. This transforms inner portion (2234) into a flap (not shown) with a free end that remains hingedly attached to retaining portion (2238).

The application of buttress assembly (112) to lower jaw (16) that includes staple cartridge (37) may be similar to the application of buttress assembly (110) to anvil (18) described above. It may be desirable to package applicator devices (2110, 2210) together or applicator devices (2110, 2210) and buttress assemblies (110, 112) together. For example, a kit may contain one applicator device (2210) and accompanying buttress assembly (110) and one applicator device (2210) and accompanying buttress assembly (112). As shown, applicator devices (2110, 2210) are configured to apply buttress assemblies (110, 112) to the desired jaw of the end effector. Applicator devices (2110, 2210) may include buttress assemblies (110, 112) to be applied, and are fit individually onto each jaw, and closed, then removed to create a force limit. Applicator devices (2110, 2210) may close to different thicknesses to account for the different thickness of each end effector jaw. Optionally, indicia (not shown) may be disposed on applicator devices (2110, 2210) to indicate the desired jaw for use.

E. Fifth Applicator Device for Individual Adjunct Application

Figure 49:
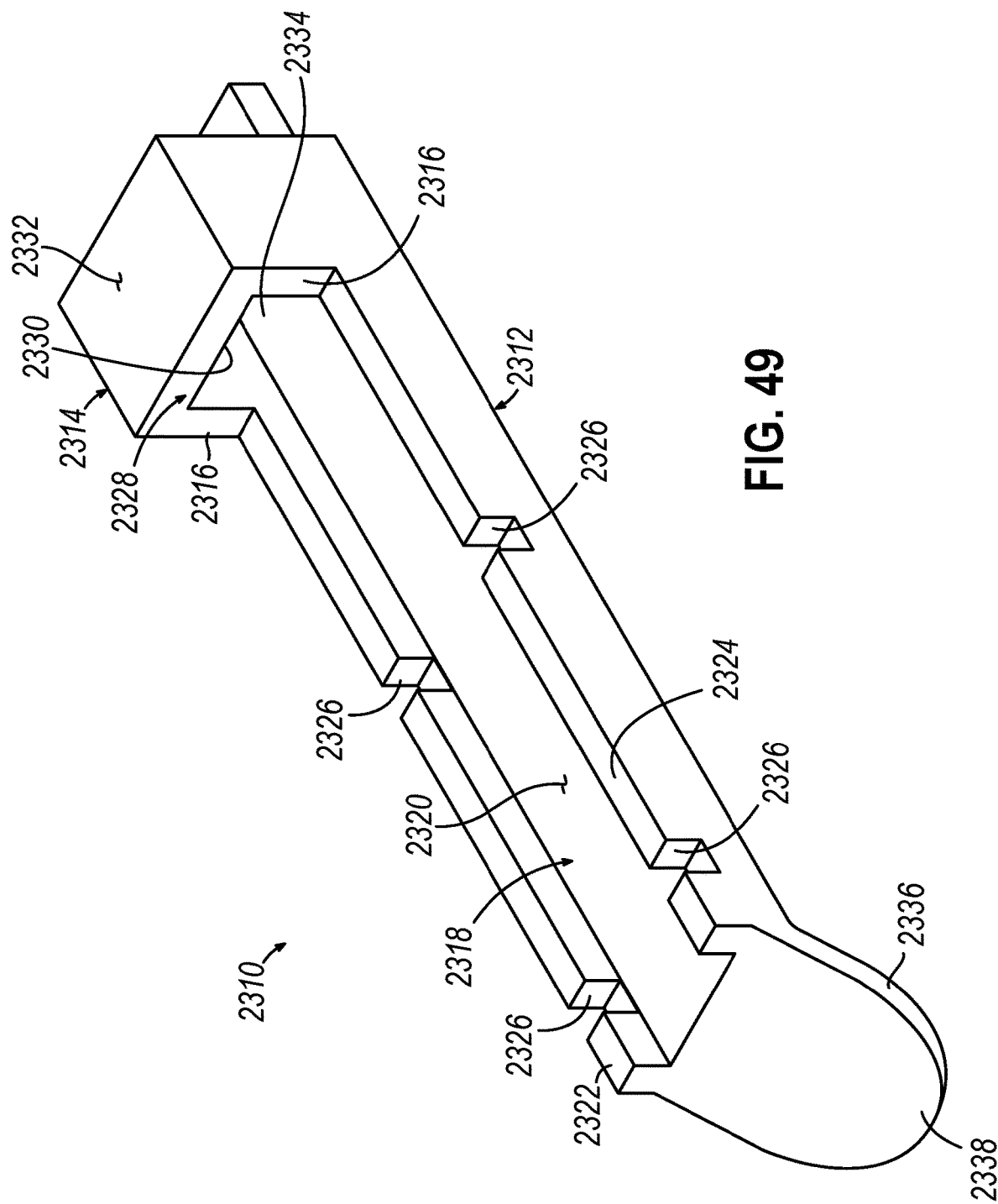
FIG. 49 depicts a perspective view of another exemplary adjunct applicator device.
Figure 50A:
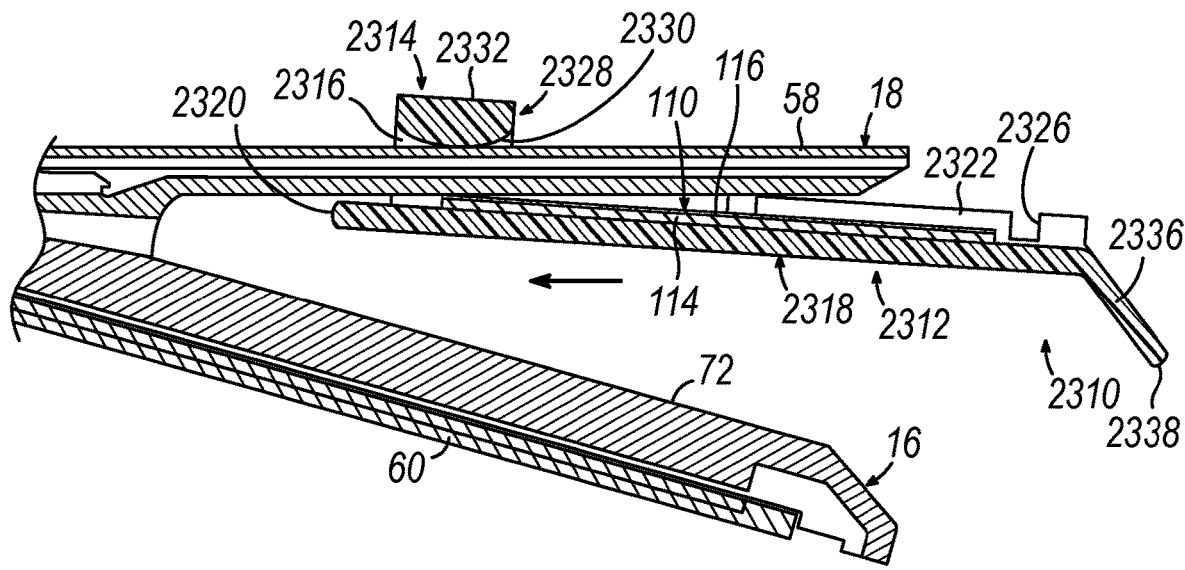
FIG. 50A depicts a cross-sectional view of the adjunct applicator device of FIG. 49, the buttress assembly of FIG. 8, and the end effector of FIG. 3, with the adjunct applicator device being moved proximally along the upper jaw of the end effector.
Figure 50B:
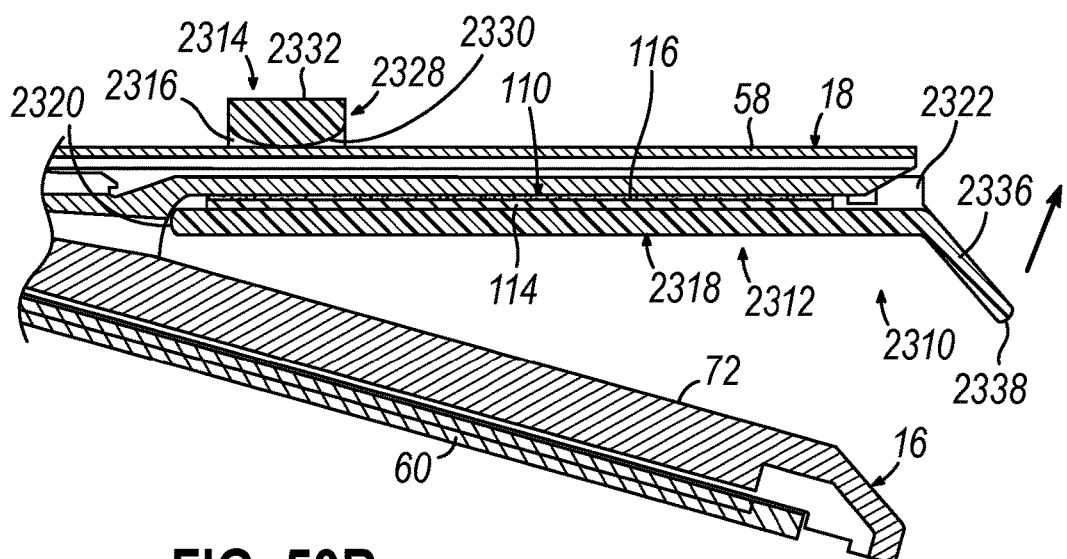
FIG. 50B depicts a cross-sectional view of the adjunct applicator device, the buttress assembly, and the end effector of FIG. 50A, with the adjunct applicator device being rotated via a tab to apply and secure the buttress assembly to the upper jaw.

FIGS. 49-50B show another exemplary applicator device (2310) that is configured to apply an adjunct material to a jaw (e.g., anvil (18)) of end effector (12) of surgical stapler (10). As shown in FIG. 49, applicator device (2310) includes a housing (2312) and an arm (2314). Arm (2314) includes connecting portions (2316) that couple with housing (2312). Housing (2312) includes a first contact feature (2318) that is shown as a U-shaped channel. First contact feature (2318) includes an inner surface (2320) and opposing upward facing walls (2322, 2324). Upward facing walls (2322, 2324) include respective cutouts (2326). Connecting portions (2316) allow arm (2314) to be used as a pivoting element to apply and secure the adjunct material (shown as buttress assembly (110)) to anvil (18). Arm (2314) includes a second contact feature (2328). Second contact feature (2328) includes inner and outer surfaces (2330, 2332), with inner surface (2330) facing inner surface (2320) of first contact feature (2318). As shown in FIGS. 50A-50B, a channel (2334) is disposed between inner surfaces (2320, 2330) of first and second contact feature (2318, 2328). Housing (2312) includes a downward facing tab (2336) that may be used to secure buttress assembly (110) with anvil (18).

FIGS. 50A-50B show buttress assembly (110) being applied and secured onto the upper jaw (shown as anvil 18) of end effector (12). However, it is also envisioned that applicator device (2310) may be modified to apply buttress assembly (112) to upper deck (72) of lower jaw (16). As shown, applicator device (2310) may load and secure buttress assembly (110) to anvil (18). Particularly, FIG. 50A shows a cross-sectional view of applicator device (2310) of FIG. 49 and end effector (12) of FIG. 3, with applicator device (2310) being moved proximally along anvil (18). As shown in FIG. 50A, second contact feature (2328) of arm (2314) provides an elongate platform that a first side of the buttress assembly (110) is releasably attached to (e.g., via adhesion). Outer surface (78) of anvil (18) is disposed 180 degrees opposite contact surface (52). Second contact feature (2328) is configured to be used as leverage to first contact feature (2318), when second contact feature (2328) pushes buttress assembly (110) into contact with the stapling surface.

FIG. 50B shows a cross-sectional view of applicator device (2310) and end effector (12) of FIG. 50A, with a distal end (2338) of applicator device (2310) being rotated to contact anvil (18) to apply buttress assembly (110) to anvil (18). FIG. 50B shows the end effector (12) jaw being rotated downwardly so that anvil (18) is fully received within channel (2334) to compressively contact buttress assembly (110) and induce adhesion using leverage provided by contact between the outer surface (58) of anvil (18) and inner surface (2330) of second contact feature (2328). The application of buttress assembly (112) to lower jaw (16) that includes staple cartridge (37) may be similar to the application of buttress assembly (110) described above, except that a modified version of applicator device (2310) accounts for the additional thickness of lower jaw (16).

F. Sixth Applicator Device for Individual Adjunct Application

Figure 51:
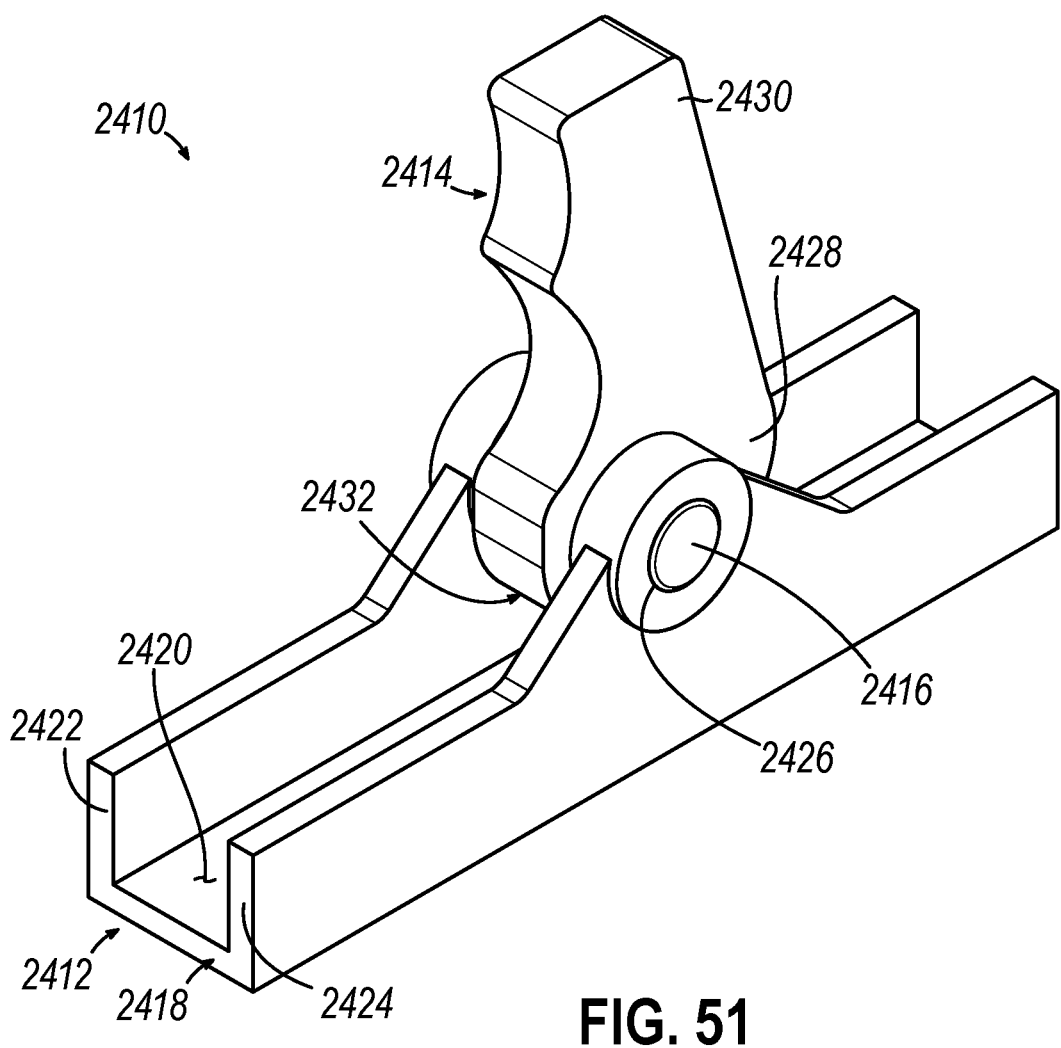
FIG. 51 depicts a perspective view of another exemplary adjunct applicator device.
Figure 52A:
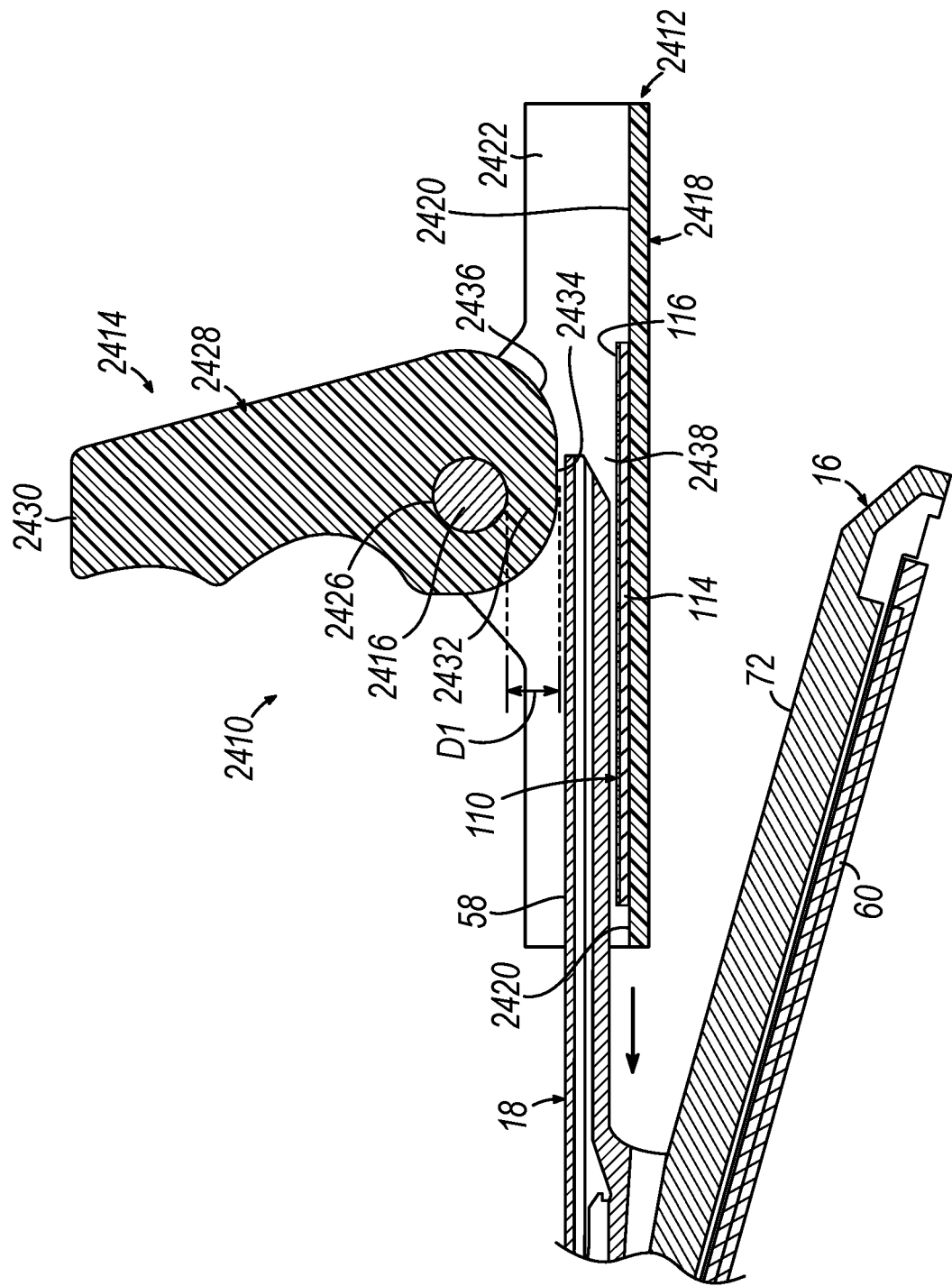
FIG. 52A depicts a cross-sectional view of the adjunct applicator device of FIG. 51, the buttress assembly of FIG. 8, and the end effector of FIG. 3, with the adjunct applicator device and the buttress assembly being moved proximally along an upper jaw of the end effector.
Figure 52B:
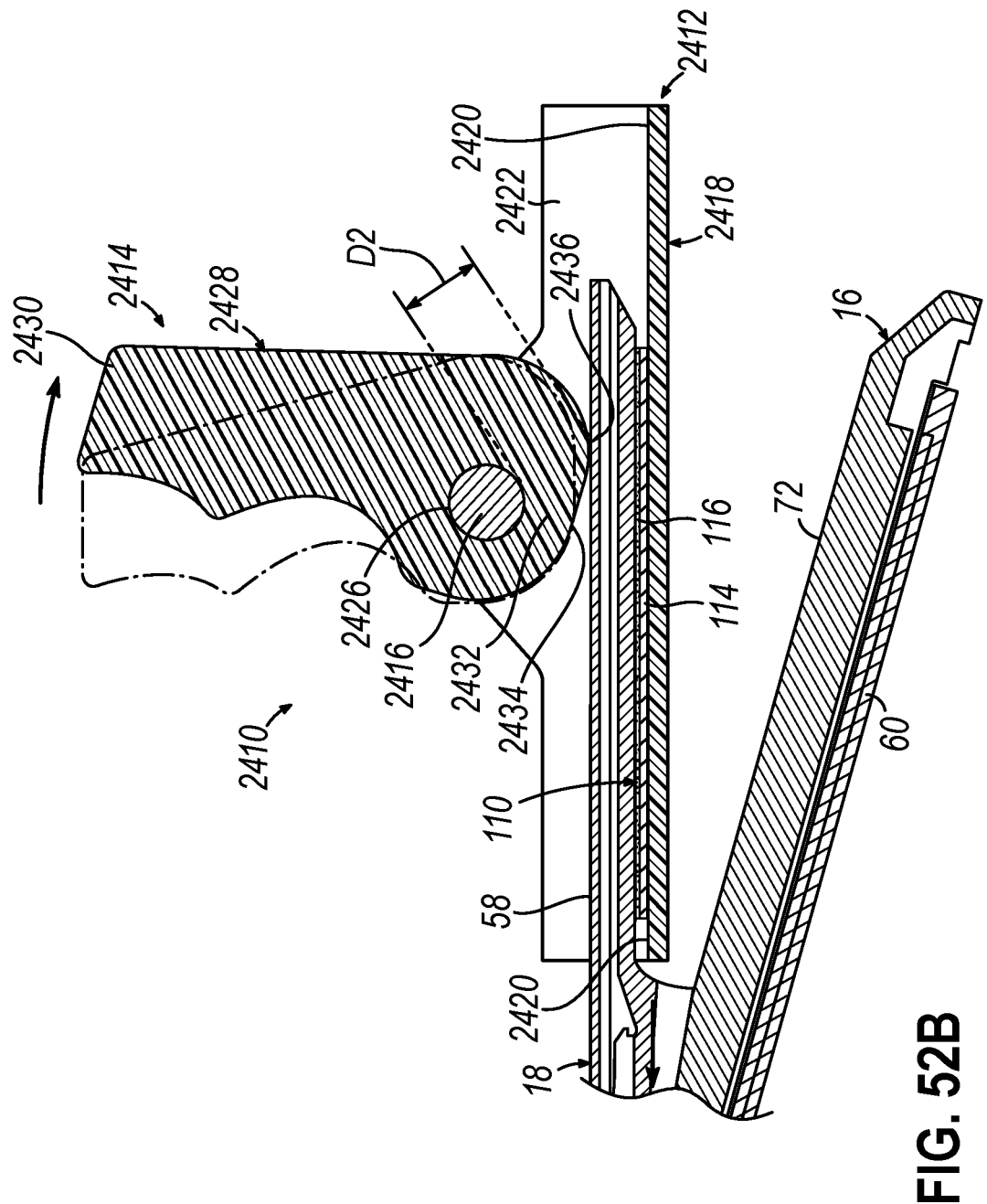
FIG. 52B depicts a cross-sectional view of the adjunct applicator device, the buttress assembly, and the end effector of FIG. 52A, with an arm of the adjunct applicator device being rotated to apply and secure the buttress assembly to the upper jaw.

FIGS. 51-52B show another exemplary applicator device (2410) that is configured to apply an adjunct material to a jaw (e.g., anvil (18)) of end effector (12) of surgical stapler (10). As shown in FIG. 51, applicator device (2410) includes a housing (2412), an arm (2414), and a coupling feature (2416) that pivotably couples arm (2414) with housing (2412). Housing (2412) includes a first contact feature (2418) that is shown as a U-shaped channel. First contact feature (2418) includes an inner surface (2420) and opposing upward facing walls (2422, 2424). Upward facing walls (2422, 2424) include apertures (2426) configured to receive coupling feature (2416). Coupling feature (2416) allows arm (2414) to pivot to apply and secure the adjunct material (shown as buttress assembly (110)) to anvil (18). Arm (2414) includes a body portion (2428). Body portion (2428) includes a handle portion (2430) disposed opposite a second contact feature (2432), shown as a camming feature. Second contact feature (2432) includes first and second camming surfaces (2434, 2436). As shown in FIG. 52A, first camming surface (2434) may be separated from coupling feature (2416) by a first distance (D1). A channel (2438) is disposed between inner surface (2420) of first contact feature (2418) and first and second camming surfaces (2434, 2436) of second contact feature (2432). As applicator device (2410) is being loaded onto anvil (18), first camming surface (2434) of second contact feature (2432) is disposed across channel (2438) from inner surface (2420) of first contact feature (2418)

FIGS. 52A-52B show buttress assembly (110) being secured onto the upper jaw of end effector (12). As shown, applicator device (2410) may load and secure buttress assembly (110) to contact surface (52) of anvil (18). However, it is also envisioned that applicator device (2410) may be modified to apply buttress assembly (112) to upper deck (72) of lower jaw (16). Particularly, FIG. 52A shows a cross-sectional view of applicator device (2410) of FIG. 23 and end effector (12) of FIG. 3, with applicator device (2410) being moved proximally along anvil (18). As shown in FIG. 52A, second contact feature (2432) of arm (2414) provides an elongate platform that a first side of the buttress assembly (110) is releasably attached to (e.g., via adhesion). Second contact feature (2432) is configured to be used as leverage to first contact feature (2418), when second contact feature (2432) pushes buttress assembly (110) into contact with contact surface (52) of anvil (18).

FIG. 52B shows a cross-sectional view of applicator device (2410) and end effector (12) of FIG. 52A, with handle portion (2430) of arm (2414) of applicator device (2410) being rotated to contact distal portion (54) of anvil (18) to apply buttress assembly (110) to anvil (18). FIG. 52B shows the end effector (12) jaw being rotated downwardly so that anvil (18) is fully received within the channel (2438) to compressively contact buttress assembly (110) and induce adhesion using leverage provided by contact between the outer surface (58) of anvil (18) and second camming surface (2436) of second contact feature (2432). As shown in FIG. 52B, second camming surface (2436) may be separated from coupling feature (2416) by a second distance (D2). The application of buttress assembly (112) to lower jaw (16) that includes staple cartridge (37) may be similar to the application of buttress assembly (110) described above, except that a modified version of applicator device (810) accounts for the additional thickness of lower jaw (16).

Figure 53:
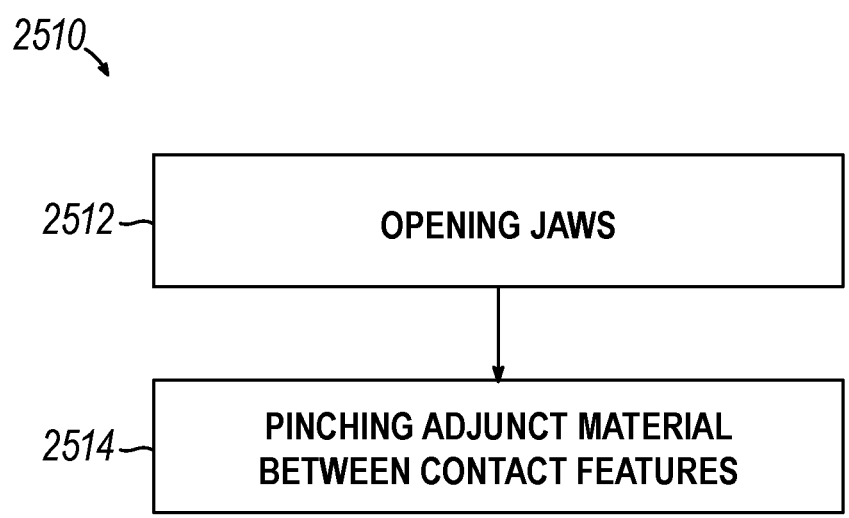
FIG. 53 depicts an exemplary method of applying a buttress assembly.

G. Exemplary Method of Applying Adjunct Material to End Effector Jaws Individually FIG. 53 shows an exemplary method (2510) of applying an adjunct material (e.g., buttress assemblies (110, 112) or a tissue thickness compensator) to a stapling surface (upper deck (72) or contact surface (52)) of a first jaw or a second jaw (e.g., lower jaw (16) or anvil (18)) of an end effector (12) of a surgical stapler (10) using applicator device (1910, 2010, 2110, 2210, 2310, 2410). At step (2512), method (2510) may include opening the end effector (12) jaws, such that the lower jaw (16) and anvil (18) are spaced apart. At step (2514), the method (2510) may include with lower jaw (16) or anvil (18) in an open configuration, pinching the adjunct material between first contact feature (1924, 2024, 2118, 2218, 2318, 2418) and second contact feature (1930, 2028, 2126, 2226, 2328, 2432) to mount the adjunct material to the stapling surface (e.g., upper deck (72) or contact surface (52)) of one of lower jaw (16) or anvil (18) of end effector (12). Buttress assemblies (110, 112) may be pinched by applying a local compression force between rollers (1934, 1938, 2034, 2044) using applicator device (1910, 2010) to mount adjunct material to the stapling surface of one of first or second jaws.

VI. Exemplary Adjunct Applicator Devices for Back-Driving End Effector Jaws Closed onto Adjunct Elements In some instances, it may be desirable to provide an adjunct applicator device that is operable to apply an adjunct element (e.g., a buttress assembly or a tissue thickness compensator) to one or both jaws of a surgical stapler end effector in an open state by directly contacting and forcibly closing (or "back-driving") the jaws onto a portion of the applicator device. Each of the exemplary applicator devices described below in connection with FIGS. 54-62B provide such functionality.

A. Exemplary Adjunct Applicator Device with Translatable Sleeve for Back-Driving End Effector Jaws FIGS. 54-55B show an exemplary adjunct applicator device (2610) configured to force the jaws of an end effector to close onto a portion of adjunct applicator device (2610) supporting one or more buttress assemblies (110, 112), or otherwise "back-drive" the jaws of the end effector for applying buttress assemblies (110, 112) thereon. Adjunct applicator device (2610) is similar to adjunct applicator device (210) described above except as otherwise described below.

Adjunct applicator device (2610) of this example comprises a frame (2612) extending between a proximal end (not shown) and a distal end (2614). Frame (2612) includes a handle (2616) positioned at or near the proximal end of frame (2612), a compression pad or platform (2618) positioned at or near the distal end (2614) of frame (2612), and an elongate rail (2620) extending longitudinally therebetween. In the example shown, rail (2620) extends along lateral sides of handle (2616) and platform (2618) such that rail (2620) is capable of being positioned alongside end effector (12). While a single rail (2620) is shown, frame (2612) may include a pair of opposing rails (2620), for example. Adjunct applicator device (2610) further comprises a movable member in the form of a translatable sleeve (2622) coupled to frame (2612) and configured to translate longitudinally relative to platform (2618) along rail (2620) as indicated by first arrow (A1) in FIG. 14, and to selectively receive end effector (12) as will be described in greater detail below.

Platform (2618) of the present example is configured to support at least one buttress assembly (110, 112) on at least one side of platform (2618). In the example shown, platform (2618) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (2618) is shown supporting buttress assembly (110, 112) on only a single side of platform (2618), platform (2618) may just as easily support buttress assemblies (110, 112) on both sides of platform (2618).

Translatable sleeve (2622) has a generally C-shaped cross section and includes a generally C-shaped inner closure surface (2624) configured to selectively mechanically engage an outer external surface of at least one of end effector jaws (16, 18) to thereby transition end effector (12) from an open state toward a closed state when platform (2618) is positioned between jaws (16, 18). In this regard, sleeve (2622) may be sized and configured relative to end effector (12) such that closure surface (2624) is capable of at least partially circumferentially surrounding or encircling end effector (12) and to be in contact or near-contact with an outer external surface of at least one of jaws (16, 18) for constricting end effector (12) in the closed state. For example, closure surface (2624) may define a cross dimension (e.g., diameter) substantially equal to or slightly greater than a distance between outer external surfaces of jaws (16, 18) when end effector (12) is in the closed state. Sleeve (2622) and/or rail (2620) may also be sized and configured to assist in providing proper alignment of end effector (12) with adjunct applicator device (2610), such as by allowing rail (2620) to abut a lateral side of end effector (12) when adjunct applicator device (2610) is positioned over end effector (12) with platform (2618) properly positioned between jaws (16, 18).

FIG. 55A shows end effector (12) in the open state and adjunct applicator device (2610) in a configuration where sleeve (2622) is in a retracted position relative to end effector (12) such that closure surface (2624) is mechanically disengaged from the outer external surface of anvil (18); while FIG. 55B shows adjunct applicator device (2610) in a configuration where sleeve (2622) is in an extended position relative to end effector (12) such that closure surface (2624) mechanically engages the outer external surface of anvil (18) to thereby transition end effector (12) from the open state toward the closed state. To use adjunct applicator device (2610) to load end effector (12), the operator would first position adjunct applicator device (2610) and end effector (12) such that platform (2618) and buttress assembly (110, 112) are positioned between anvil (18) and staple cartridge (37) and such that end effector (12) is aligned with sleeve (2622) with sleeve (2622) retracted proximally from jaws (16, 18) as shown in FIG. 55A. The operator would then advance sleeve (2622) distally relative to end effector (12) to mechanically engage closure surface (2624) with the outer external surface of anvil (18) as indicated by second arrow (A2) in FIG. 55B. End effector jaws (16, 18) may be back-driven closed on platform (318) by such mechanical engagement (e.g., while closure trigger (26) of instrument (10) remains unactuated), thereby adhesively attaching buttress assembly (110, 112) to anvil (18) (e.g., to the stapling surface thereof). Buttress assembly (110, 112) may be released from platform (2618), such that end effector jaws (16, 18) may be disengaged from platform (2618) while buttress assembly (110, 112) remains adhered to anvil (18). In one example, sleeve (2622) may be sequentially advanced and retracted in a back-and-forth or "pumping" manner to incrementally transition end effector (12) toward the closed state.

While adjunct applicator device (2610) is shown applying buttress assembly (110, 112) to anvil (18), adjunct applicator device (2610) may additionally or alternatively apply buttress assembly (110, 112) to lower jaw (16), such as to staple cartridge (37) (e.g., to the stapling surface thereof).

Figure 56:
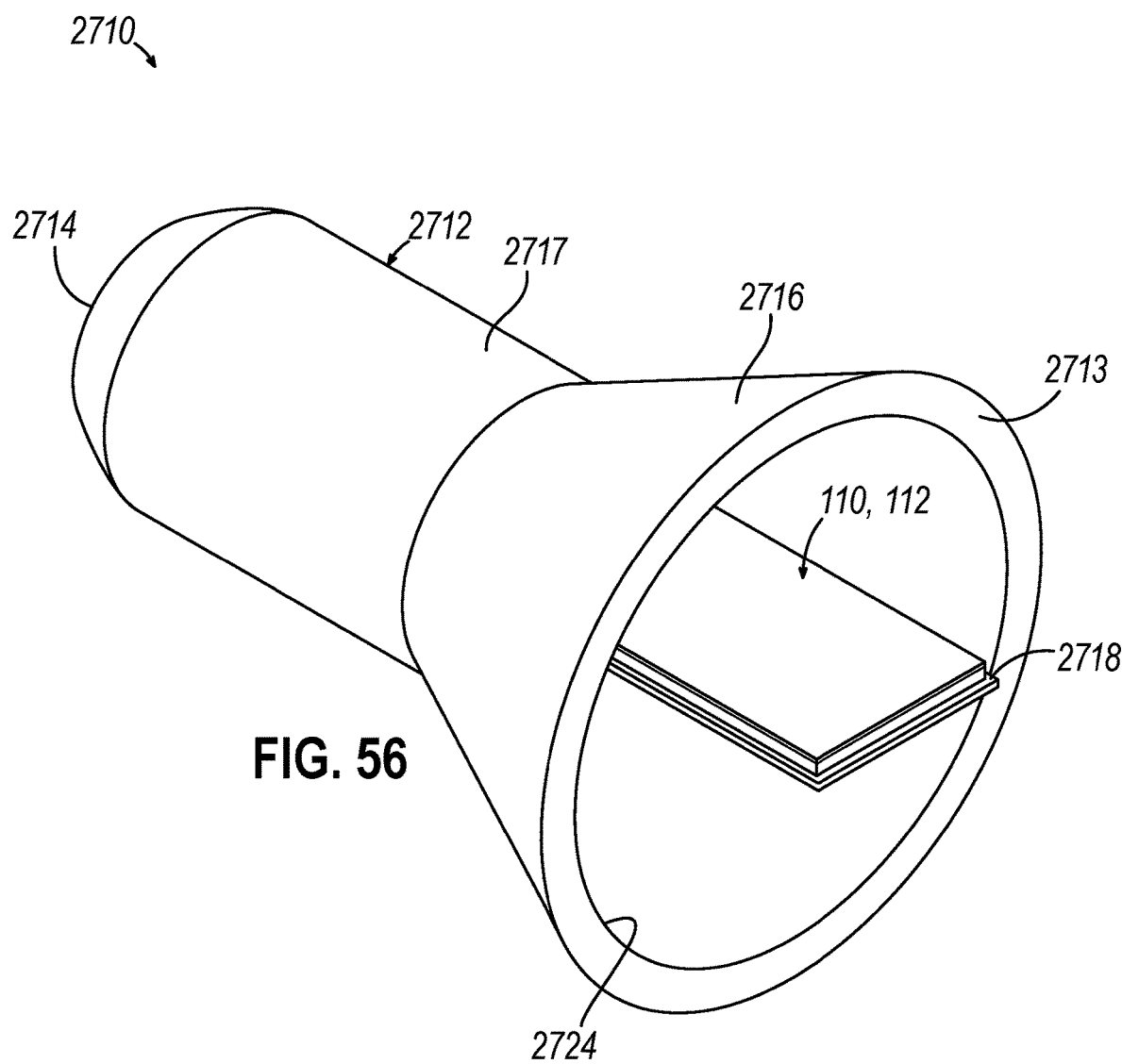
FIG. 56 depicts a perspective view of another exemplary adjunct applicator device that may be used to carry and apply the buttress assemblies of FIG. 8.

B. Exemplary Adjunct Applicator Device with Tapered Camming Surface for Back-Driving End Effector Jaws FIGS. 56-57B show another exemplary adjunct applicator device (2710) configured to force the jaws of an end effector to close onto a portion of adjunct applicator device (2710) supporting one or more buttress assemblies (110, 112), or otherwise "back-drive" the jaws of the end effector for applying buttress assemblies (110, 112) thereon. Adjunct applicator device (2710) is similar to adjunct applicator devices (210, 2610) described above except as otherwise described below.

Adjunct applicator device (2710) of this example comprises a housing (2712) extending between an open proximal end (2713) and a closed distal end (2714). Housing (2712) includes a generally frustoconical proximal portion (2716) and a generally cylindrical distal portion (2717) such that housing (2712) is generally funnel-shaped. A compression pad or platform (2718) extends proximally from closed distal end (2714) within proximal and distal portions (2716, 2717) of housing (2712) and is fixed against movement relative thereto. Housing (2712) is configured to selectively receive end effector (12) as will be described in greater detail below.

Platform (2718) of the present example is configured to support at least one buttress assembly (110, 112) on at least one side of platform (2718). In the example shown, platform (2718) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (2718) is shown supporting buttress assembly (110, 112) on only a single side of platform (2718), platform (2718) may just as easily support buttress assemblies (110, 112) on both sides of platform (2718).

Proximal and distal portions (2716, 2717) of housing (2712) include tapered and untapered inner closure surfaces (2724, 2726), respectively, configured to selectively mechanically engage an outer external surface of at least one of end effector jaws (16, 18) to thereby transition end effector (12) from an open state toward a closed state when platform (2718) is positioned between jaws (16, 18). In this regard, proximal and distal portions (2716, 2717) may be sized and configured relative to end effector (12) such that closure surfaces (2724, 2726) are capable of at least partially circumferentially surrounding or encircling end effector (12) and to be in contact or near-contact with an outer external surface of at least one of jaws (16, 18) for constricting end effector (12) in the closed state. For example, untapered closure surface (2726) may define a minor cross dimension (e.g., diameter) substantially equal to or slightly greater than a distance between outer external surfaces of jaws (16, 18) when end effector (12) is in the closed state; while tapered closure surface (2724) may define a major cross dimension (e.g., diameter) substantially equal to or greater than a distance between outer external surfaces of jaws (16, 18) when end effector (12) is in the closed state, and may taper radially inwardly in a distal direction toward untapered closure surface (2726). It will be appreciated that tapered closure surface (2724) may alternatively be curved radially inwardly in a distal direction toward untapered closure surface (2726). Proximal and/or distal portions (2716, 2717) may also be sized and configured to assist in providing proper alignment of end effector (12) with adjunct applicator device (2710), such as by abutting one or more lateral sides of end effector (12) when adjunct applicator device (2710) is positioned over end effector (12) with platform (2718) properly positioned between jaws (16, 18).

Figure 57A:
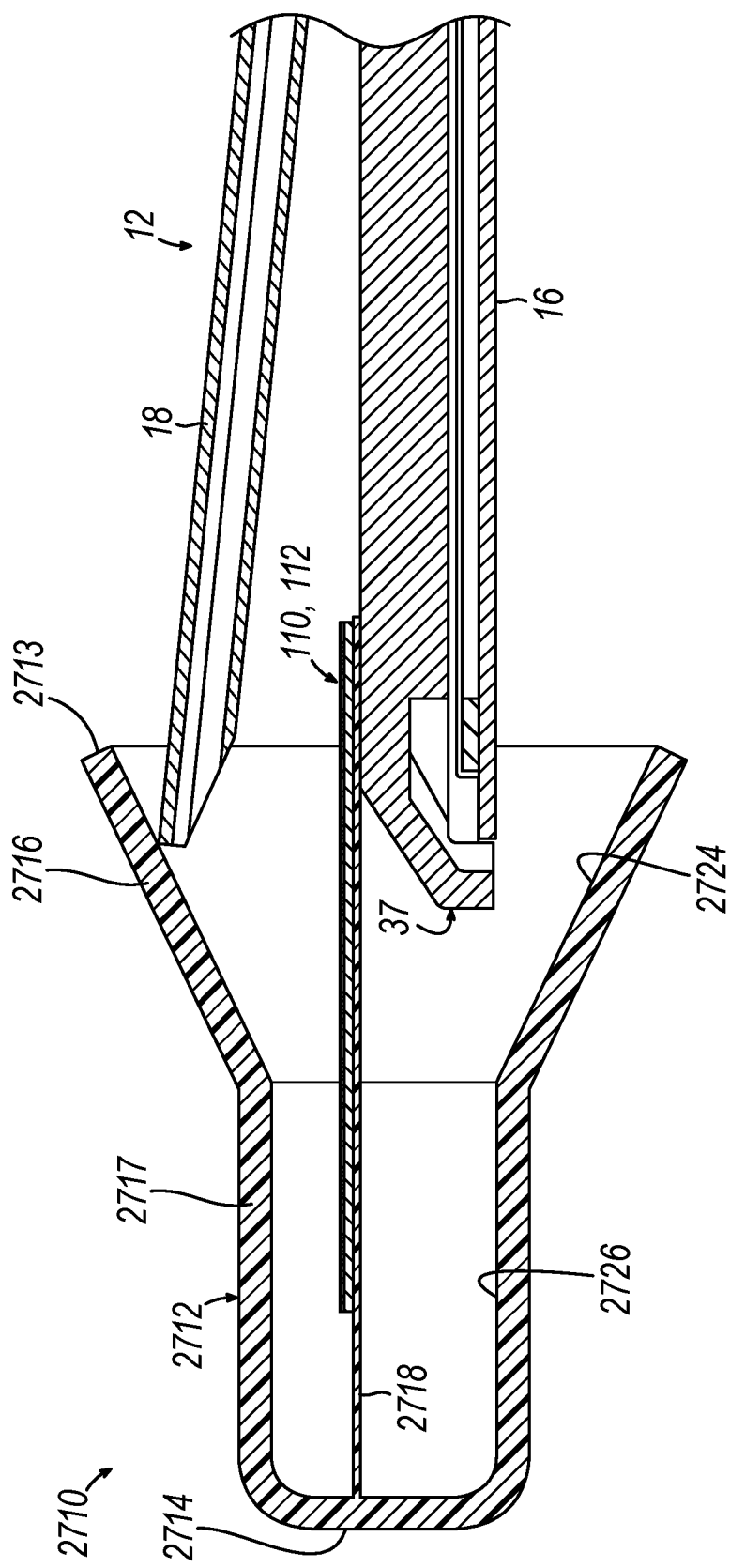
FIG. 57A depicts a side cross-sectional view of the adjunct applicator device of FIG. 56 and the end effector of FIG. 3, showing the applicator axially aligned with the end effector.
Figure 57B:
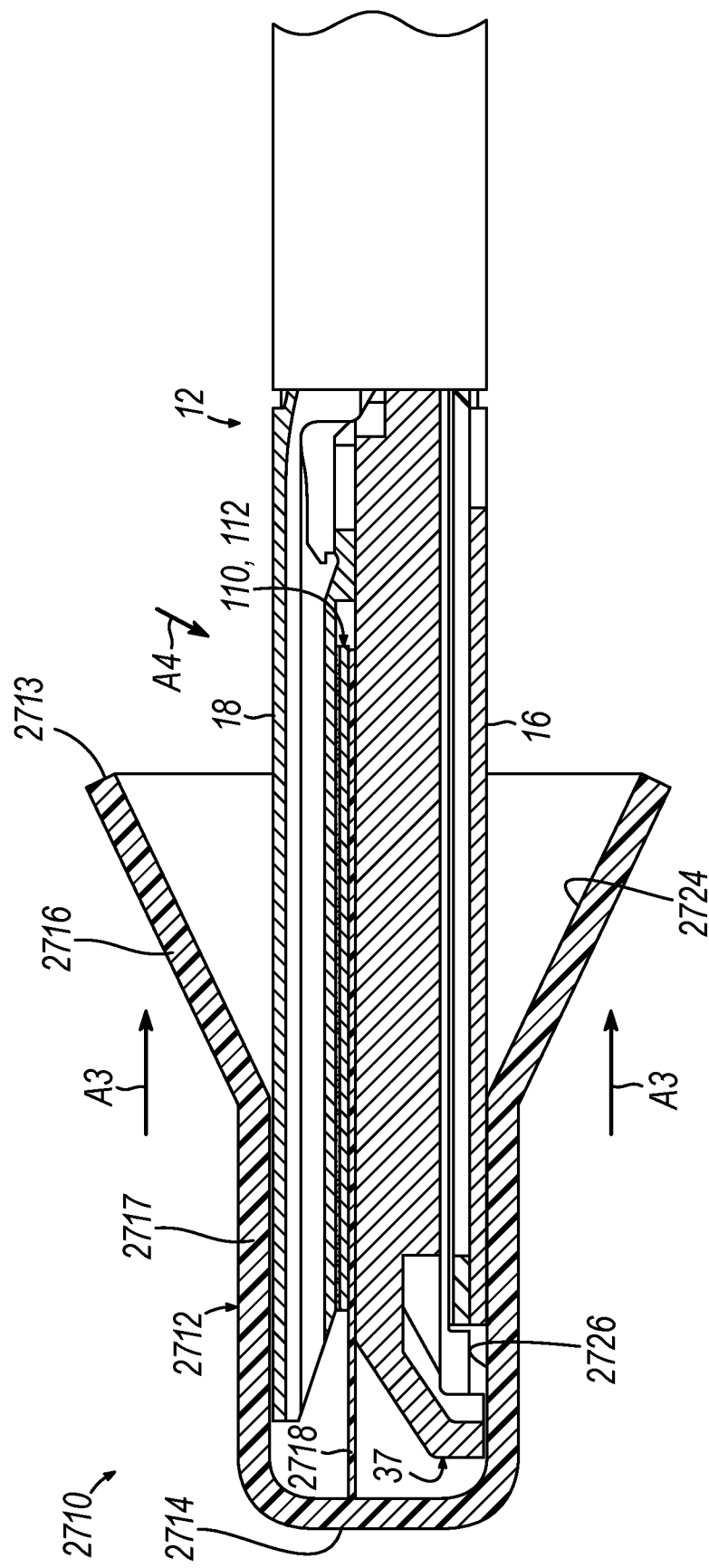
FIG. 57B depicts a side cross-sectional view of the adjunct applicator device of FIG. 56 positioned over the end effector of FIG. 3, showing the adjunct applicator device proximally advanced over the end effector for transitioning the end effector toward the closed state.

FIG. 57A shows adjunct applicator device (2710) positioned relative to end effector (12) such that tapered closure surface (2724) mechanically engages the outer external surface of anvil (18) to thereby transition end effector (12) from the open state toward the closed state; while FIG. 57B shows adjunct applicator device (2710) positioned relative to end effector (12) such that untapered closure surface (2626) mechanically engages the outer external surfaces of both jaws (16, 18) to thereby maintain end effector (12) in the closed state. To use adjunct applicator device (2710) to load end effector (12), the operator would first position adjunct applicator device (2710) and end effector (12) such that platform (2718) and buttress assembly (110, 112) are positioned between anvil (18) and staple cartridge (37) and such that end effector (12) is received by proximal portion (2716) of housing (2712) as shown in FIG. 57A. The operator would then advance housing (2712) proximally relative to end effector (12) to mechanically engage tapered closure surface (2724) with the outer external surface of anvil (18) as indicated by third arrows (A3) in FIG. 57A such that anvil (18) is cammed radially inwardly as indicated by fourth arrow (A4) in FIG. 57A until untapered closure surface (2726) mechanically engages the outer external surfaces of both jaws (16, 18) as shown in FIG. 57B. End effector jaws (16, 18) may be back-driven closed on platform (2718) by such mechanical engagement (e.g., while closure trigger (26) of instrument (10) remains unactuated), thereby adhesively attaching buttress assembly (110, 112) to anvil (18) (e.g., to the stapling surface thereof). Buttress assembly (110, 112) may be released from platform (2718), such that end effector jaws (16, 18) may be disengaged from platform (2718) while buttress assembly (110, 112) remains adhered to anvil (18), such as by retracting housing (2712) distally relative to end effector (12).

While adjunct applicator device (2710) is shown applying buttress assembly (110, 112) to anvil (18), adjunct applicator device (2710) may additionally or alternatively apply buttress assembly (110, 112) to lower jaw (16), such as to staple cartridge (37) (e.g., to the stapling surface thereof).

In one example, platform (2718) may be omitted and housing (2712) may be configured to selectively receive another applicator device, such as applicator device (210) described above, in place of platform (2718). In this manner, adjunct applicator device (2710) may be reusable by selectively inserting a loaded applicator device (210) into housing (2712) and later removing the spent applicator device (210) from housing (2712).

Figure 58:
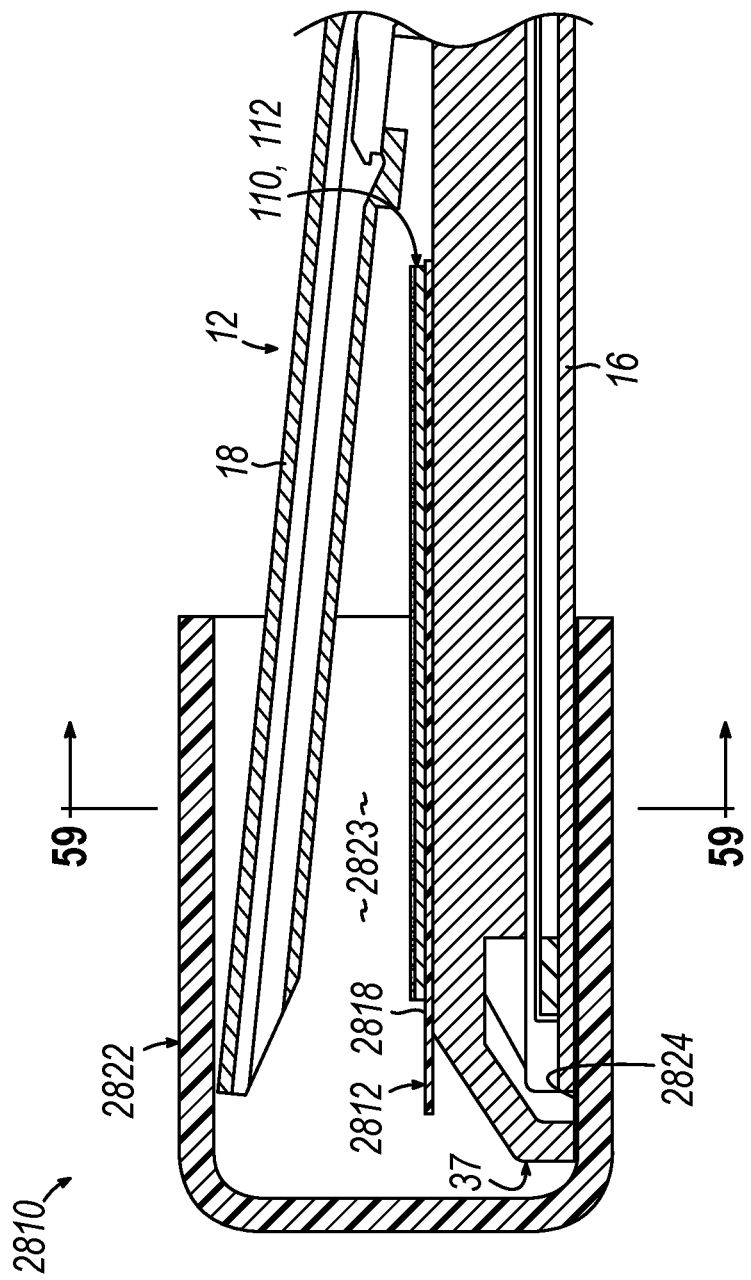
FIG. 58 depicts a side cross-sectional view of another exemplary adjunct applicator device that may be used to carry and apply the buttress assemblies of FIG. 8 positioned over the end effector of FIG. 3, showing a rotatable sleeve of the adjunct applicator device in a first angular (e.g., "unclocked") position.

C. Exemplary Adjunct Applicator Device with Twistable Sleeve for Back-Driving End Effector Jaws FIGS. 58-59B show another exemplary adjunct applicator device (2810) configured to force the jaws of an end effector to close onto a portion of adjunct applicator device (2810) supporting one or more buttress assemblies (110, 112), or otherwise "back-drive" the jaws of the end effector for applying buttress assemblies (110, 112) thereon. Adjunct applicator device (2810) is similar to adjunct applicator devices (210, 2610, 2710) described above except as otherwise described below.

Adjunct applicator device (2810) of this example comprises a frame (2812) including a compression pad or platform (2818). Adjunct applicator device (2810) further comprises a movable member in the form of a rotatable sleeve (2822) coupled to frame (2812) and configured to rotate relative to platform (2818) about a rotational axis (RA) parallel to a longitudinal axis of platform (2818), and to selectively receive end effector (12) as will be described in greater detail below.

Platform (2818) of the present example is configured to support at least one buttress assembly (110, 112) on at least one side of platform (2818). In the example shown, platform (2818) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (2818) is shown supporting buttress assembly (110, 112) on only a single side of platform (2818), platform (2818) may just as easily support buttress assemblies (110, 112) on both sides of platform (2818).

Rotatable sleeve (2822) includes a bore (2823) having a generally oval or elliptical cross section defining a generally oval or elliptical inner closure surface (2824) configured to selectively mechanically engage an outer external surface of at least one of end effector jaws (16, 18) to thereby transition end effector (12) from an open state toward a closed state when platform (2818) is positioned between jaws (16, 18). In this regard, sleeve (2822) may be sized and configured relative to end effector (12) such that closure surface (2824) is capable of at least partially circumferentially surrounding or encircling end effector (12) and to be in contact or near-contact with an outer external surface of at least one of jaws (16, 18) for constricting end effector (12) in the closed state. For example, closure surface (2824) may define a minor cross dimension (e.g., diameter) substantially equal to or slightly greater than a distance between outer external surfaces of jaws (16, 18) when end effector (12) is in the closed state, and may further define a major cross dimension (e.g., diameter) substantially equal to or greater than a distance between outer external surfaces of jaws (16, 18) when end effector (12) is in the closed state. Sleeve (2822) may also be sized and configured to assist in providing proper alignment of end effector (12) with adjunct applicator device (2810), such as by abutting one or more lateral sides of end effector (12) when adjunct applicator device (2810) is positioned over end effector (12) with platform (2818) properly positioned between jaws (16, 18).

Figure 59A:
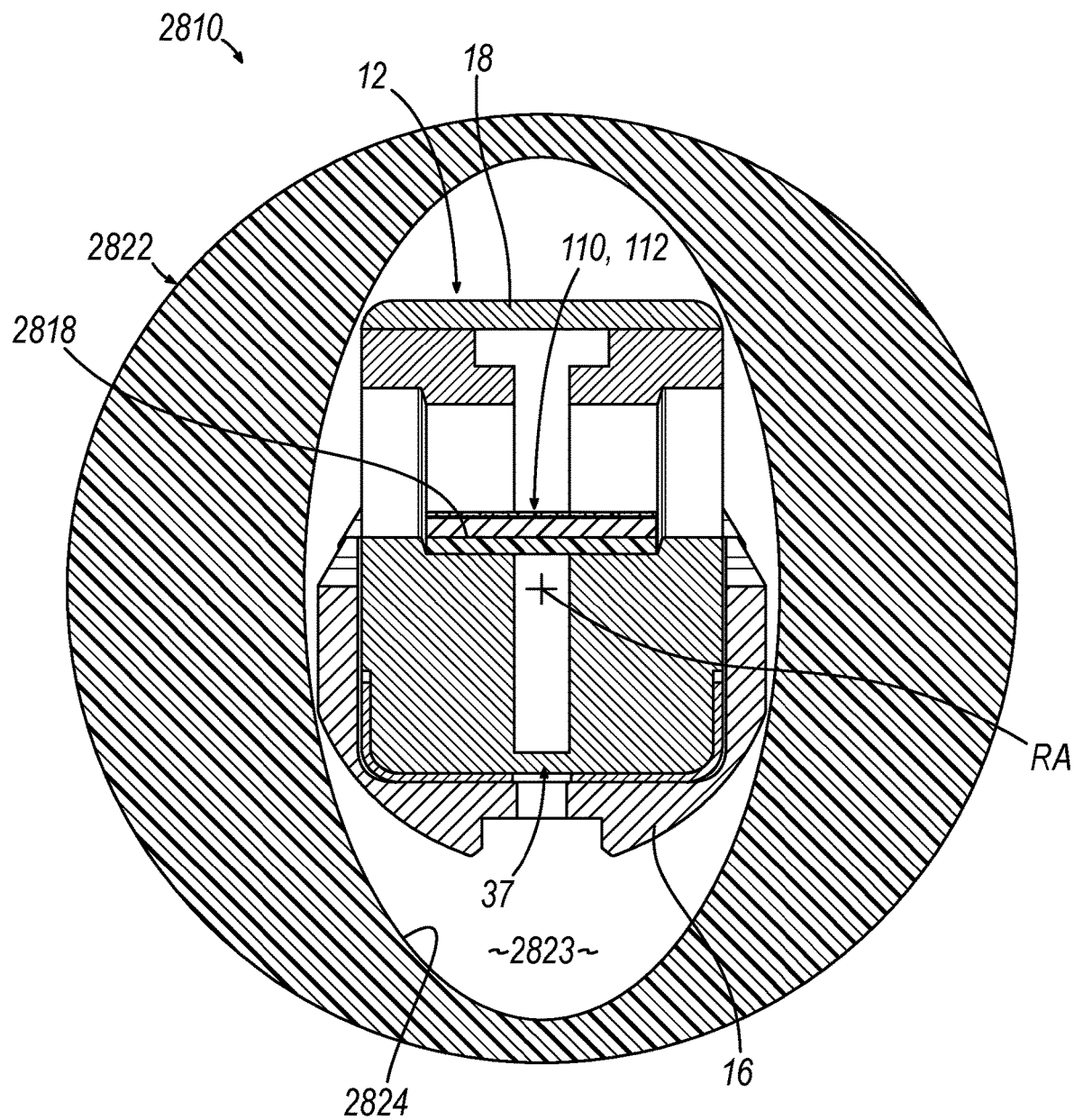
FIG. 59A depicts an end cross-sectional view of the adjunct applicator device of FIG. 58 positioned over the end effector of FIG. 3, taken along section line 59-59 in FIG. 58, showing the rotatable sleeve of the adjunct applicator device in the first angular position.
Figure 59B:
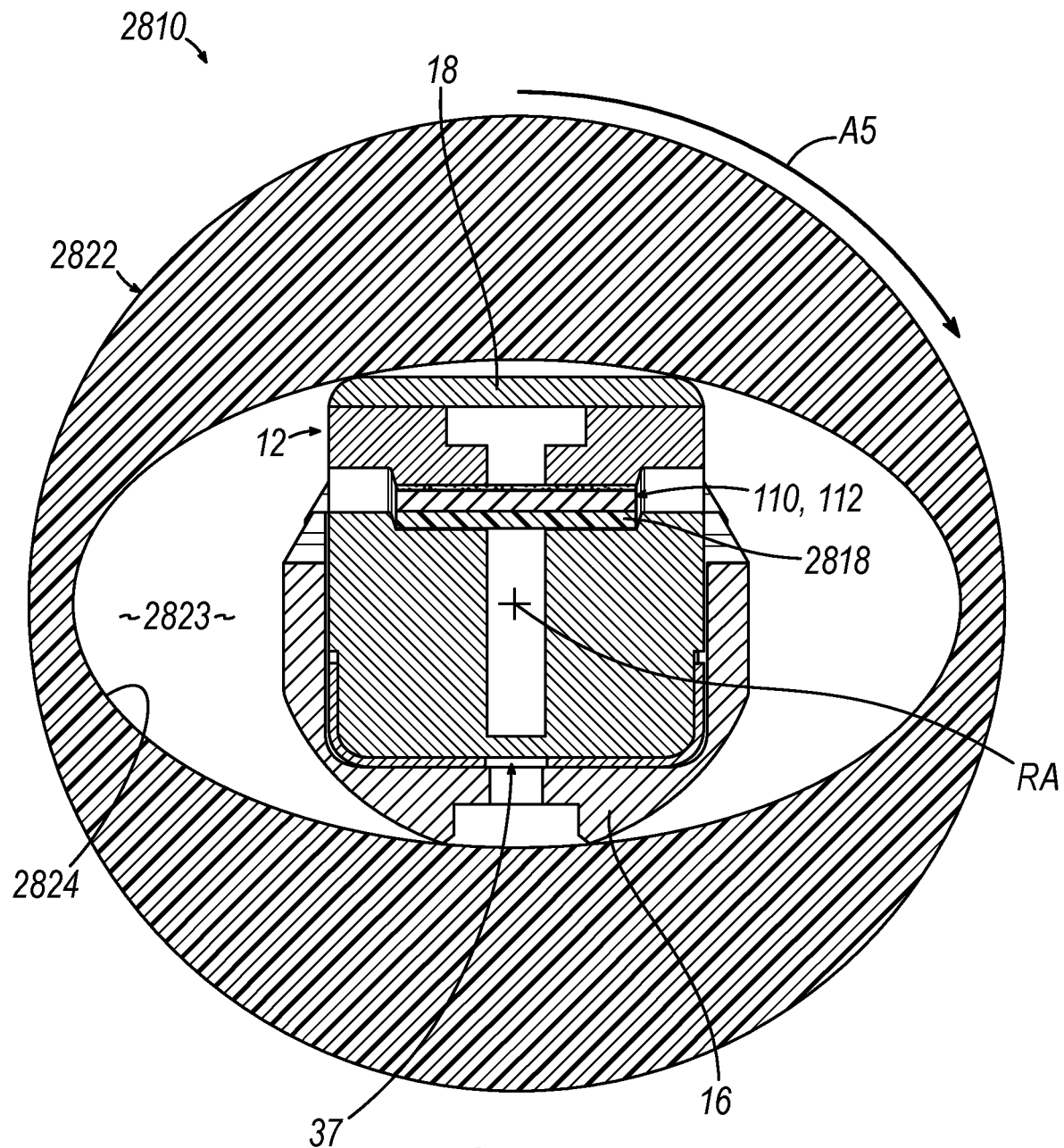
FIG. 59B depicts another end cross-sectional view of the adjunct applicator device of FIG. 58 positioned over the end effector of FIG. 3, taken along section line 59-59 in FIG. 58, showing the rotatable sleeve of the adjunct applicator device in a second angular (e.g., "clocked") position for transitioning the end effector toward the closed state.

FIG. 59A shows end effector (12) in the open state and adjunct applicator device (2810) in a configuration where sleeve (2822) is in a first angular (e.g., "unclocked") position relative to end effector (12) such that closure surface (2824) is mechanically disengaged from the outer external surfaces of jaws (16, 18); while FIG. 59B shows adjunct applicator device (2810) in a configuration where sleeve (2822) is in a second angular (e.g., "clocked") position relative to end effector (12) such that closure surface (2824) mechanically engages the outer external surfaces of jaws (16, 18) to thereby transition end effector (12) from the open state toward the closed state. To use adjunct applicator device (2810) to load end effector (12), the operator would first position adjunct applicator device (2810) and end effector (12) such that platform (2818) and buttress assembly (110, 112) are positioned between anvil (18) and staple cartridge (37) and such that end effector (12) is received by sleeve (2822) with sleeve (2822) oriented about the rotational axis (RA) relative to end effector (12) in the first angular position as shown in FIG. 59A. The operator would then rotate sleeve (2822) relative to end effector (12) about the rotational axis (RA) toward the second angular position to mechanically engage closure surface (2824) with the outer external surfaces of both jaws (16, 18) as indicated by fifth arrow (A5) in FIG. 59B until the narrow or minor cross-dimension portion of closure surface (2824) mechanically engages the outer external surfaces of both jaws (16, 18). End effector jaws (16, 18) may be back-driven closed on platform (2818) by such mechanical engagement (e.g., while closure trigger (26) of instrument (10) remains unactuated), thereby adhesively attaching buttress assembly (110, 112) to anvil (18) (e.g., to the stapling surface thereof). Buttress assembly (110, 112) may be released from platform (2818), such that end effector jaws (16, 18) may be disengaged from platform (2818) while buttress assembly (110, 112) remains adhered to anvil (18), such as by rotating sleeve (2822) relative to end effector (12) about the rotational axis (RA) to the first angular position.

While adjunct applicator device (2810) is shown applying buttress assembly (110, 112) to anvil (18), adjunct applicator device (2810) may additionally or alternatively apply buttress assembly (110, 112) to lower jaw (16), such as to staple cartridge (37) (e.g., to the stapling surface thereof).

Figure 60:
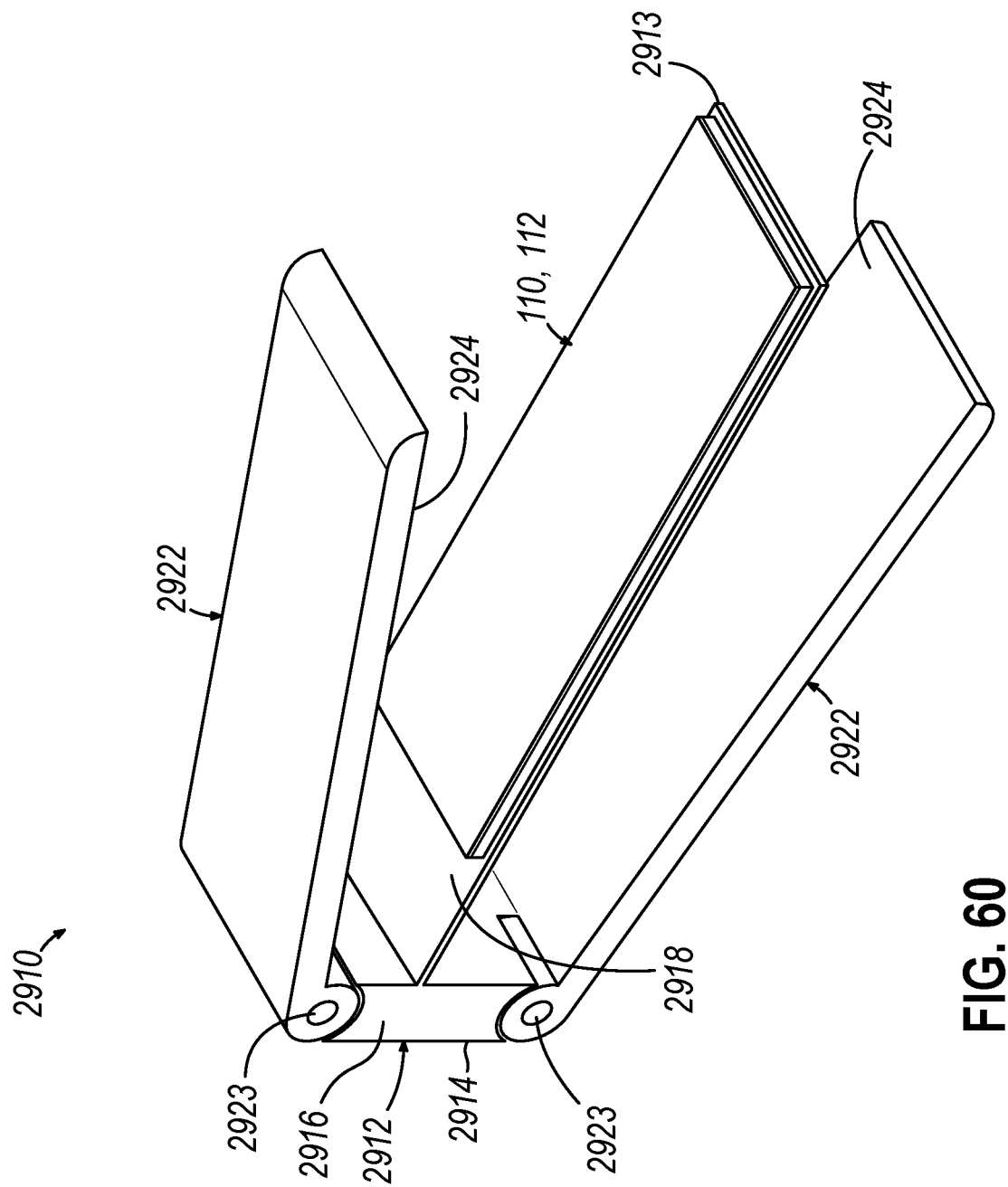
FIG. 60 depicts a perspective view of another exemplary adjunct applicator device that may be used to carry and apply the buttress assemblies of FIG. 8.

D. Exemplary Adjunct Applicator Device with Hinged Lever Arms for Back-Driving End Effector Jaws FIGS. 60-61B show another exemplary adjunct applicator device (2910) configured to force the jaws of an end effector to close onto a portion of adjunct applicator device (2910) supporting one or more buttress assemblies (110, 112), or otherwise "back-drive" the jaws of the end effector for applying buttress assemblies (110, 112) thereon. Adjunct applicator device (2910) is similar to adjunct applicator devices (210, 2610, 2710, 2810) described above except as otherwise described below.

Adjunct applicator device (2910) of this example comprises a frame (2912) extending between a proximal end (2913) and a distal end (2914). Frame (2912) includes a dual hinge knuckle (2916) positioned at or near distal end (2914) of frame (2912) and a compression pad or platform (2918)

extending proximally from knuckle (2916) to proximal end (2913). Adjunct applicator device (2910) further comprises a pair of movable members in the form of opposing pivotable lever arms (2922) coupled to knuckle (2916) via respective hinge pins (2923) and configured to pivot relative to platform (2918) about respective lateral pivot axes (PA) extending in a direction perpendicular to a longitudinal axis of platform (2918), and to selectively receive end effector (12) as will be described in greater detail below.

Platform (2918) of the present example is configured to support at least one buttress assembly (110, 112) on at least one side of platform (2918). In the example shown, platform (2918) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (2918) is shown supporting buttress assembly (110, 112) on only a single side of platform (2918), platform (2918) may just as easily support buttress assemblies (110, 112) on both sides of platform (2918).

Lever arms (2922) are each generally flat and include respective generally flat inner closure surfaces (2924) configured to selectively mechanically engage respective outer external surfaces of end effector jaws (16, 18) to thereby transition end effector (12) from an open state toward a closed state when platform (2918) is positioned between jaws (16, 18). In this regard, lever arms (2922) may be sized and configured relative to end effector (12) such that closure surfaces (2924) are collectively capable of at least partially circumferentially surrounding or encircling end effector (12) and to be in contact or near-contact with respective outer external surfaces of jaws (16, 18) for constricting end effector (12) in the closed state. For example, closure surfaces (2924) may collectively define a variable cross dimension capable of being substantially equal to or slightly greater than a distance between outer external surfaces of jaws (16, 18) when end effector (12) is in the closed state. In one example, hinge pins (2923) may be spaced apart from each other by a distance substantially equal to or slightly greater than the distance between outer external surfaces of jaws (16, 18) when end effector (12) is in the closed state.

Figure 61A:
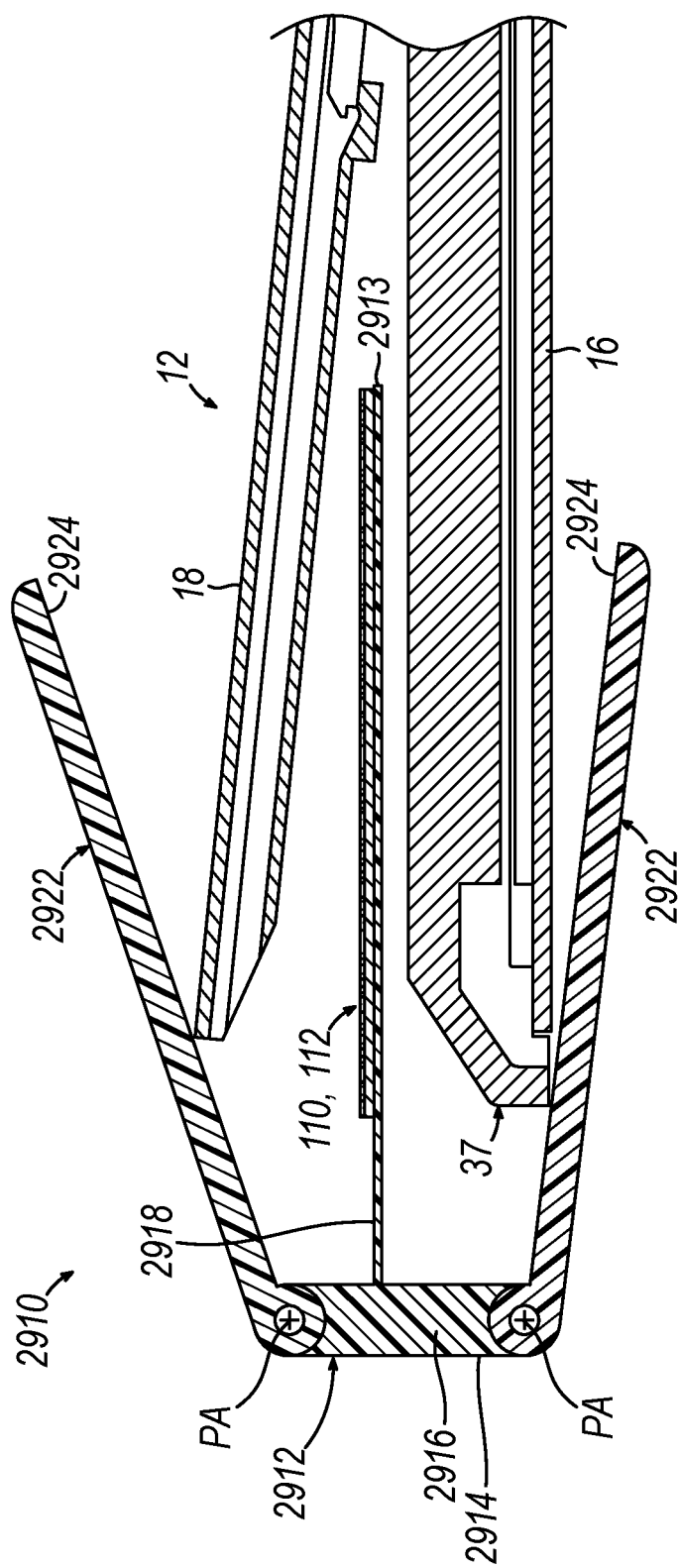
FIG. 61A depicts a side cross-sectional view of the adjunct applicator device of FIG. 60 positioned over the end effector of FIG. 3, showing pivotable lever arms of the adjunct applicator device in an open position.
Figure 61B:
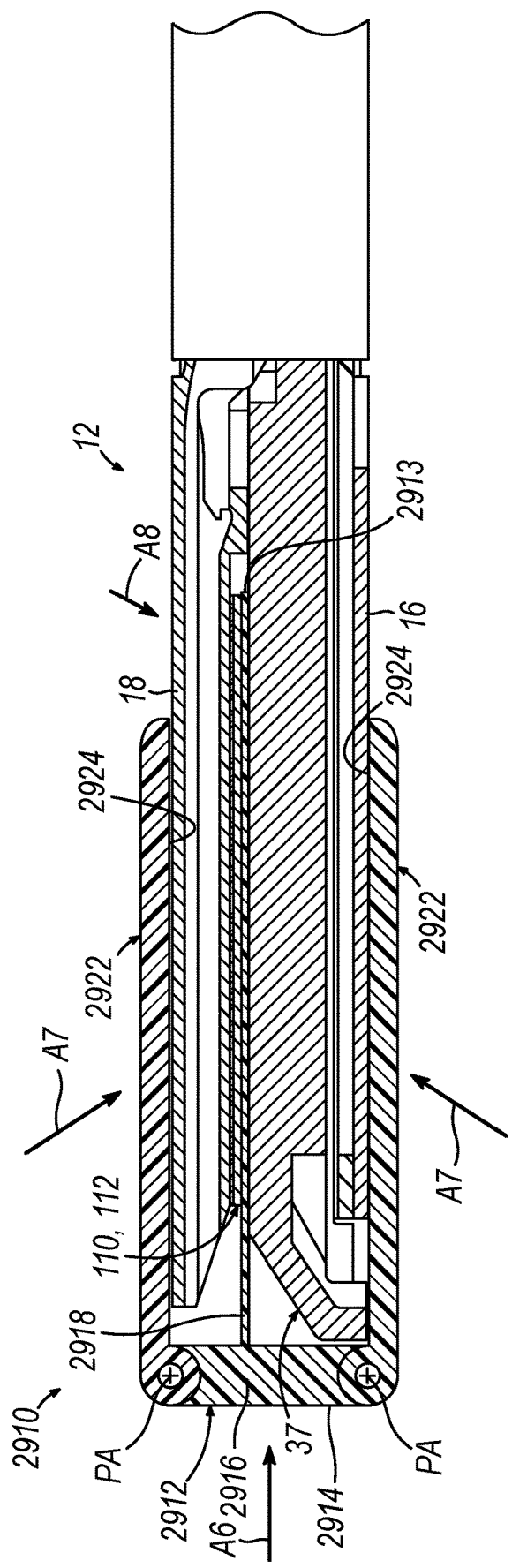
FIG. 61B depicts a side cross-sectional view of the adjunct applicator device of FIG. 60 positioned over the end effector of FIG. 3, showing the pivotable lever arms of the adjunct applicator device in a closed position for transitioning the end effector toward the closed state.

FIG. 61A shows adjunct applicator device (2910) in a configuration where lever arms (2922) are pivoted about the respective pivot axes (PA) from an open position toward a closed position such that closure surfaces (2924) mechanically engage the outer external surfaces of the respective jaws (16, 18) to thereby transition end effector (12) from the open state toward the closed state; while FIG. 61B shows adjunct applicator device (2910) in a configuration where lever arms (2922) are in the closed position such that closure surfaces (2924) mechanically engage the outer external surfaces of the respective jaws (16, 18) to thereby maintain end effector (12) in the closed state. To use adjunct applicator device (2910) to load end effector (12), the operator would first position adjunct applicator device (2910) and end effector (12) such that platform (2918) and buttress assembly (110, 112) are positioned between anvil (18) and staple cartridge (37) and such that end effector (12) is received between lever arms (2922) with lever arms (2922) at or near the open position as shown in FIG. 61A. The operator would then advance adjunct applicator device (2910) proximally relative to end effector (12) as indicated by sixth arrow (A6) in FIG. 61B and/or pivot lever arms (2922) toward the closed position (e.g., by pinching lever arms (2922) toward each other) as indicated by seventh arrows (A7) in FIG. 61B to mechanically engage closure surfaces (2924) with the outer external surfaces of the respective jaws (16, 18) until closure surfaces (2924) are generally parallel to the respective outer external surfaces as shown in FIG. 61B. End effector jaws (16, 18) may be back-driven closed on platform (2918) by such mechanical engagement (e.g., while closure trigger (26) of instrument (10) remains unactuated) as indicated by eighth arrow (A8) in FIG. 61B, thereby adhesively attaching buttress assembly (110, 112) to anvil (18) (e.g., to the stapling surface thereof). Buttress assembly (110, 112) may be released from platform (2918), such that end effector jaws (16, 18) may be disengaged from platform (2918) while buttress assembly (110, 112) remains adhered to anvil (18), such as by pivoting lever arms (2922) toward the open position. In one example, adjunct applicator device (2910) may be simultaneously advanced proximally relative to end effector (12) while lever arms (2922) are pivoted toward the closed position.

While adjunct applicator device (2910) is shown applying buttress assembly (110, 112) to anvil (18), adjunct applicator device (2910) may additionally or alternatively apply buttress assembly (110, 112) to lower jaw (16), such as to stapler cartridge (37) (e.g., to the stapling surface thereof).

In one example, adjunct applicator device (2910) may include a threshold force-application or pressure-application feature configured to prevent the end effector jaws (16, 18) from pivoting toward the open state until lever arms (2922) have applied a threshold force and/or pressure to the respective jaws (16, 18) sufficient to ensure proper seating of buttress assembly (110, 112) on anvil (18) (or lower jaw (16)). For example, each lever arm (2922) may include one or more notches configured to frictionally engage the respective jaws (16, 18) for inhibiting opening of jaws (16, 18) until lever arms (2922) are pivoted toward the open position. In addition or alternatively, adjunct applicator device (2910) may include a threshold force-notification or pressure-notification feature configured to provide a visual, haptic, and/or audible indication to a user that lever arms (2922) have applied a threshold force and/or pressure to the respective jaws (16, 18) sufficient to ensure proper seating of buttress assembly (110, 112) on anvil (18) (or lower jaw (16)).

Figure 62A:
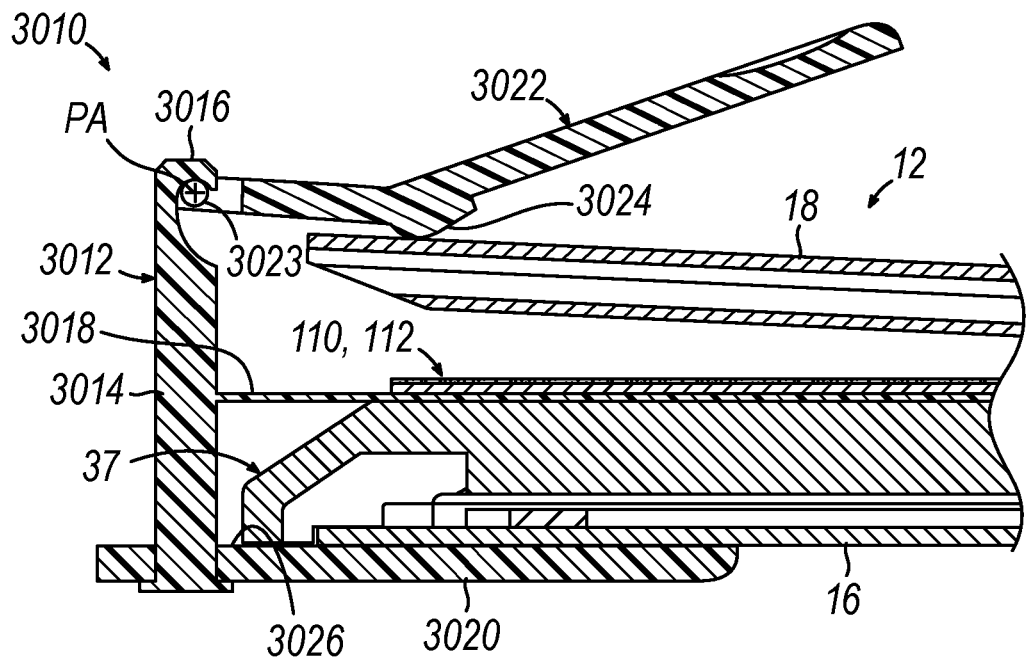
FIG. 62A depicts a side cross-sectional view of another exemplary adjunct applicator device that may be used to carry and apply the buttress assemblies of FIG. 8 positioned over the end effector of FIG. 3, showing a pivotable lever arm of the adjunct applicator device in an unactuated position.
Figure 62B:
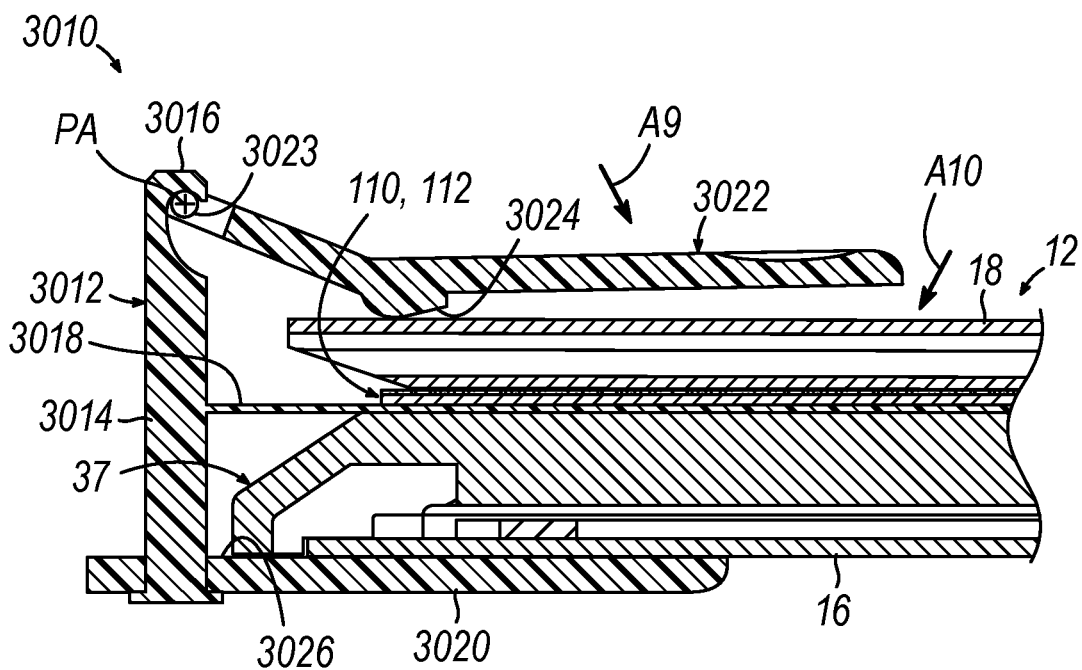
FIG. 62B depicts a side cross-sectional view of the adjunct applicator device of FIG. 62A positioned over the end effector of FIG. 3, showing the pivotable lever arm of the adjunct applicator device in an actuated position for transitioning the end effector toward the closed state.
Figure 63:
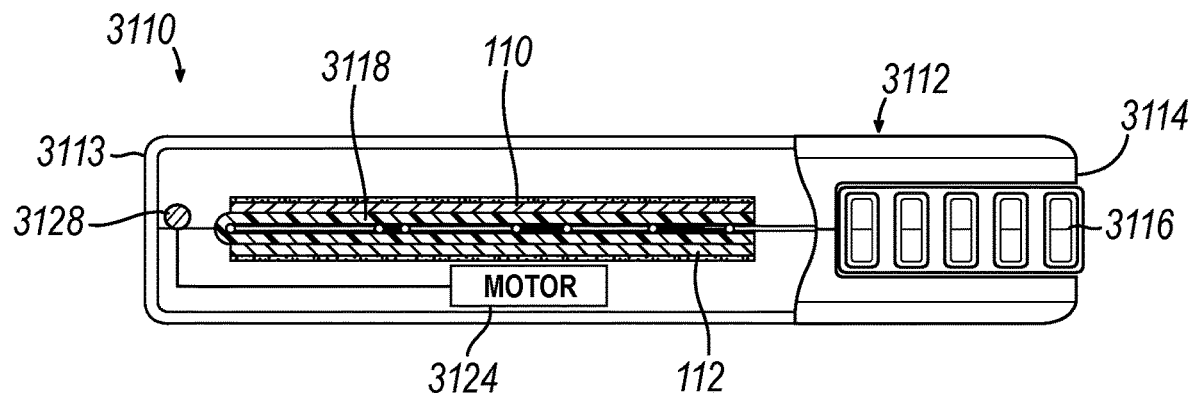
FIG. 63 depicts a schematic side cross-sectional view of another exemplary adjunct applicator device carrying the buttress assemblies of FIG. 8.
Figure 64:
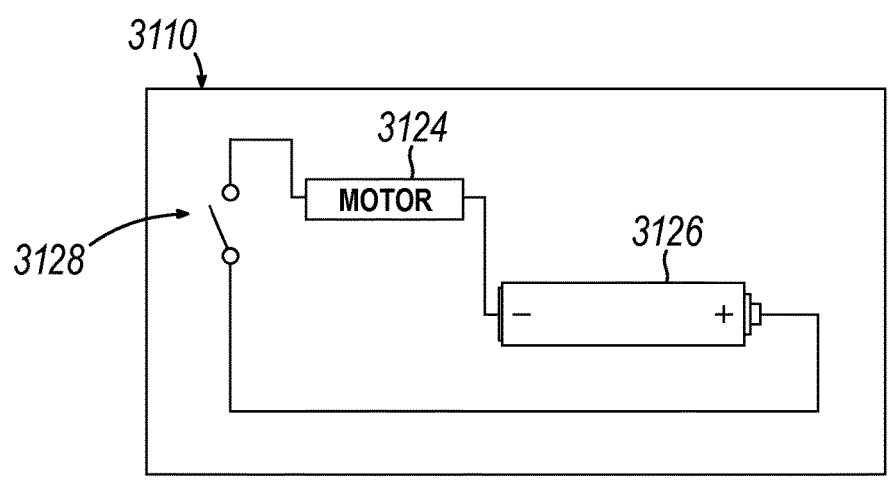
FIG. 64 depicts a schematic view of the adjunct applicator device of FIG. 63, showing various electrical components including an electrical switch configured to detect a tissue stop of the end effector of FIG. 3.

E. Exemplary Adjunct Applicator Device with Camming Lever Arm for Back-Driving End Effector Jaws FIGS. 62A-62B show another exemplary adjunct applicator device (3010) configured to force the jaws of an end effector to close onto a portion of adjunct applicator device (3010) supporting one or more buttress assemblies (110, 112), or otherwise "back-drive" the jaws of the end effector for applying buttress assemblies (110, 112) thereon. Applicator device (700) is similar to adjunct applicator devices (210, 2610, 2710, 2810, 2910) described above except as otherwise described below.

Adjunct applicator device (3010) of this example comprises a frame (3012) extending between a proximal end (not shown) and a distal end (3014). Frame (3012) includes a hinge knuckle (3016) positioned at or near distal end (3014) of frame (3012), a compression pad or platform (3018) extending proximally from knuckle (3016) to the proximal end of frame (3012), and a fixed arm (3020) extending proximally from knuckle (3016). Adjunct applicator device (3010) further comprises a movable member in the form of a pivotable lever arm (3022) coupled to knuckle (3016) via a hinge pin (3023) and configured to pivot relative to platform (3018) about a lateral pivot axis (PA) extending in a direction perpendicular to a longitudinal axis of platform (3018), and to selectively receive end effector (12) against fixed arm (3020) as will be described in greater detail below.

Platform (3018) of the present example is configured to support at least one buttress assembly (110, 112) on at least one side of platform (3018). In the example shown, platform (3018) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively. While platform (3018) is shown supporting buttress assembly (110, 112) on only a single side of platform (3018), platform (3018) may just as easily support buttress assemblies (110, 112) on both sides of platform (3018).

Lever arm (3022) is generally flat and includes a protruding tapered closure surface (3024) configured to selectively mechanically engage an outer external surface of one of end effector jaws (16, 18), while fixed arm (3020) is generally flat and includes a generally flat untapered closure surface (3026) configured to selectively mechanically engage an outer surface of the other of end effector jaws (16, 18) to thereby transition end effector (12) from an open state toward a closed state when platform (3018) is positioned between jaws (16, 18). In this regard, arms (3020, 3022) may be sized and configured relative to end effector (12) such that closure surfaces (3024, 3026) are collectively capable of at least partially circumferentially surrounding or encircling end effector (12) and to be in contact or near-contact with respective outer external surfaces of jaws (16, 18) for constricting end effector (12) in the closed state. For example, closure surfaces (3024, 3026) may collectively define a variable cross dimension capable of being substantially equal to or slightly greater than a distance between outer external surfaces of jaws (16, 18) when end effector (12) is in the closed state. It will be appreciated that tapered closure surface (3024) may alternatively be curved.

FIG. 62A shows adjunct applicator device (3010) in a configuration where lever arm (3022) is pivoted about the pivot axis (PA) from an open position toward a closed position such that tapered closure surface (3024) mechanically engages the outer external surface of anvil (18) while untapered closure surface (3026) mechanically engages the outer external surface of lower jaw (16) to thereby transition end effector (12) from the open state toward the closed state; while FIG. 62B shows adjunct applicator device (3010) in a configuration where lever arm (3022) is in the closed position such that closure surfaces (3024, 3026) mechanically engage the respective outer external surfaces of jaws (16, 18) to thereby maintain end effector (12) in the closed state. To use adjunct applicator device (3010) to load end effector (12), the operator would first position adjunct applicator device (3010) and end effector (12) such that platform (3018) and buttress assembly (110, 112) are positioned between anvil (18) and staple cartridge (37) and such that end effector (12) is received between arms (3020, 3022) with lever arm (3022) at or near the open position as shown in FIG. 62A. The operator would then pivot lever arm (3022) toward the closed position as indicated by ninth arrow (A9) in FIG. 62B to mechanically engage closure surface (3024) with the outer external surface of anvil (18) such that anvil (18) is cammed radially inwardly as indicated by tenth arrow (A10) in FIG. 62B. End effector jaws (16, 18) may be back-driven closed on platform (3018) by such mechanical engagement (e.g., while closure trigger (26) of instrument (10) remains unactuated) as shown in FIG. 62B, thereby adhesively attaching buttress assembly (110, 112) to anvil (18) (e.g., to the stapling surface thereof). Buttress assembly (110, 112) may be released from platform (3018), such that end effector jaws (16, 18) may be disengaged from platform (3018) while buttress assembly (110, 112) remains adhered to anvil (18). In one example, adjunct applicator device (3010) may be simultaneously advanced proximally relative to end effector (12) while lever arm (3022) is pivoted toward the closed position.

While adjunct applicator device (3010) is shown applying buttress assembly (110, 112) to anvil (18), adjunct applicator device (3010) may additionally or alternatively apply buttress assembly (110, 112) to lower jaw (16), such as to stapler cartridge (37) (e.g., to the stapling surface thereof).

VII. Exemplary Adjunct Applicator Devices that Detect Full Seating of Applicator Device in Surgical Stapler End Effector In some instances, it may be desirable to provide an adjunct applicator device that includes one or more features operable ensure that the applicator device is fully seated within and properly aligned with a surgical stapler end effector in an open state before applying an adjunct element (e.g., a buttress assembly or a tissue thickness compensator) to one or both jaws of the end effector. Each of the exemplary applicator devices described below in connection with FIGS. 63-66B provide such functionality.

A. Exemplary Applicator Device with Tissue Stop-Engaging Feature for Detecting Proper Seating in End Effector FIGS. 63-65B show an exemplary adjunct applicator device (3100) configured to prevent improperly loading buttress assemblies (110, 112) onto the jaws of an end effector while adjunct applicator device (3100) is longitudinally misaligned with the jaws, via a tissue stop-engaging feature. Adjunct applicator device (3100) is similar to adjunct applicator device (210) described above except as otherwise described below.

Adjunct applicator device (3100) of this example comprises a housing (3112) extending between a proximal end (3113) and a distal end (3114). Housing (3112) includes integral gripping features defining a handle (3116) positioned at or near distal end (3114) of housing (3112). Adjunct applicator device (3110) also comprises an expandable compression pad or platform (3118) configured to selectively transition between a collapsed or non-expanded state in which platform (3118) assumes a generally flat configuration (FIGS. 63 and 65A) and a deployed or expanded state in which platform (3118) assumes a generally wedge-shaped configuration (FIG. 65B). In this regard, adjunct applicator device (3110) further comprises a platform driver in the form of a threaded rod (3120) rotatably coupled to housing (3112) and extending between opposing folded halves of platform (3118), and a plurality of extendable arms or linkages (3122) positioned between threaded rod (3120) and the opposing folded halves of platform (3118) such that rotation of threaded rod (3120) in a predetermined direction causes linkages (3122) to extend radially outwardly from threaded rod (3120) for deploying platform (3118). In the example shown, adjunct applicator device (3110) further comprises an energy storage device in the form of a motor (3124) having a power source such as a battery (3126) selectively electrically coupled therewith and configured to selectively supply torque to threaded rod (3120) for deploying platform (3118). In this regard, adjunct applicator device (3110) also includes a detector in the form of an electrical probe or switch (3128) in electrical communication with motor (3124) and battery (3126) for controllably activating motor (3124) as will be described in greater detail below.

Platform (3118) of the present example is configured to support buttress assembly (110) on one opposing folded side of platform (3118) and another buttress assembly (112) on the other opposing folded side of platform (3118). In the example shown, platform (3118) supports wide versions of buttress assemblies (110, 112) that unitarily span across slots (42, 49) of anvil (18) and staple cartridge (37), respectively, though buttress assemblies (110, 112) may alternatively be provided in a respective pair of portions that are separated to avoid spanning across slots (42, 49) of anvil (18) and staple cartridge (37), respectively.

Electrical switch (3128) is positioned at or near proximal end (3113) of housing (3112) and is configured to detect a predetermined portion of end effector (12), such as a tissue stop (12a) defined by a side flange of anvil (18), when end effector (12) is properly positioned relative to adjunct applicator device (3110) for loading buttress assemblies (110, 112) onto end effector (12). For example, and with reference to FIG. 64, electrical switch (3128) may be configured to move from an open state to a closed state in response to contacting tissue stop (12a). Motor (3124) may be configured to activate for deploying platform (3118) in response to movement of electrical switch (3128) to the closed state. For example, movement of electrical switch (3128) to the closed state may selectively place motor (3124) in electrical communication with battery (3126) such that power is selectively supplied to motor (3124) from battery (3126) via electrical switch (3128). Thus, motor (3124) may be configured to selectively supply torque to threaded rod (3120) for deploying platform (3118) in response to detection of tissue stop (12a) by electrical switch (3128). In this manner, electrical switch (3128) may assist in providing proper longitudinal and lateral alignment of end effector (12) with adjunct applicator device (3110) during deployment of platform (3118). In one example, adjunct applicator device (3110) may include a pair of electrical switches (3128) configured to detect respective tissue stops (12a) defined by laterally opposed side flanges of anvil (18), and motor (3124) may be configured to selectively supply torque to threaded rod (3120) for deploying platform (3118) in response to detection of both tissue stops (12a) by the respective electrical switches (3128) (e.g., simultaneously). Such a pair of electrical switches (3128) may assist in providing proper angular alignment of end effector (12) with adjunct applicator device (3110) (e.g., relative to a longitudinal axis of end effector (12)) during deployment of platform (3118). In addition or alternatively, adjunct applicator device (3110) may include a laterally opposed pair of angled ramps or camming surfaces at or near proximal end (3113) of housing (3112) for catching tissue stops (12a) and angularly aligning end effector (12) with adjunct applicator device (3110) during distal advancement of end effector (12) relative to adjunct applicator device (3110).

Figure 65A:
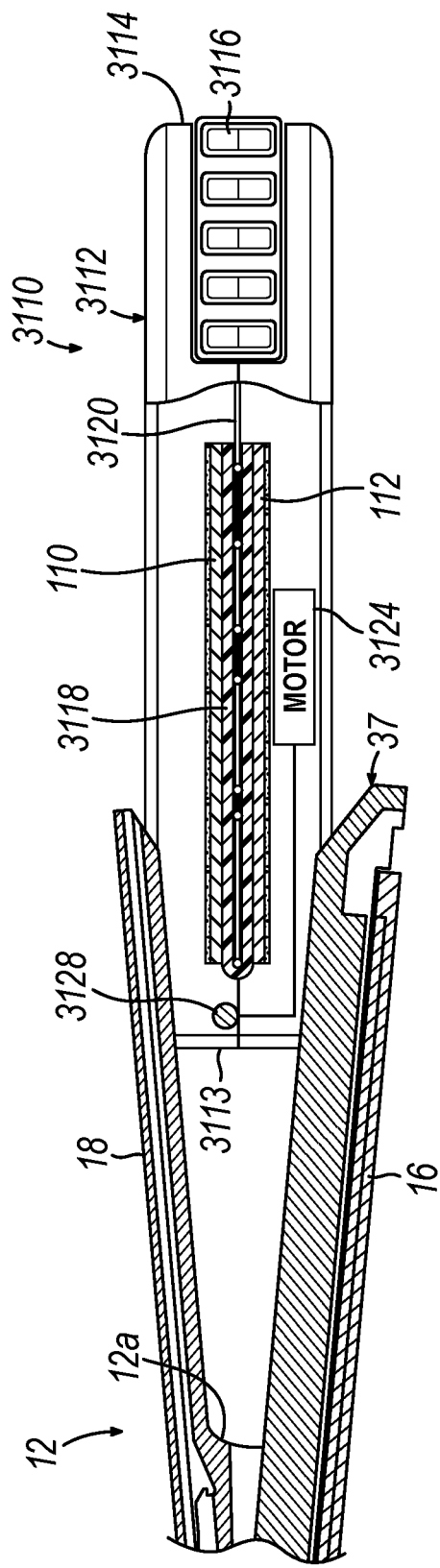
FIG. 65A depicts a side cross-sectional view of the end effector of FIG. 3 positioned over the adjunct applicator device of FIG. 63, showing an expandable platform of the adjunct applicator device in a collapsed state.
Figure 65B:
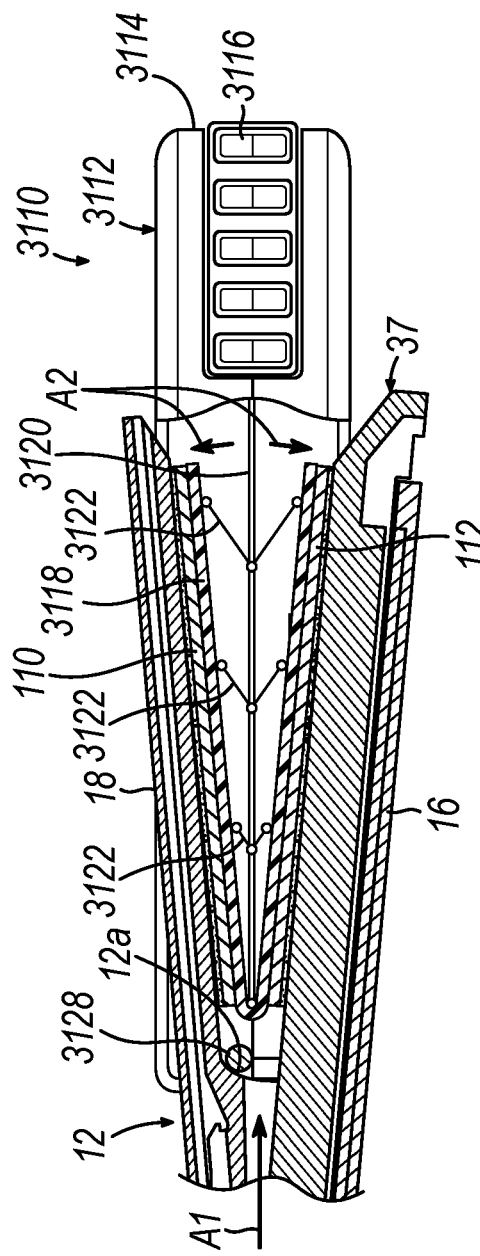
FIG. 65B depicts a side cross-sectional view of the end effector of FIG. 3 positioned over the adjunct applicator device of FIG. 63, showing the expandable platform of the adjunct applicator device in a deployed state for applying the buttress assemblies onto the end effector jaws in response to the tissue stop of the end effector contacting the electrical switch of the adjunct applicator device.

FIG. 65A shows end effector (12) in the open state and positioned relative to adjunct applicator device (3110) such that electrical switch (3128) is spaced apart from tissue stop (12a), thereby preventing platform (3118) from transitioning out of the collapsed state; while FIG. 65B shows end effector (12) positioned relative to adjunct applicator device (3110) such that electrical switch (3128) contacts tissue stop (12a) to thereby activate motor (3124) and consequently transition platform (3118) from the collapsed state toward the deployed state. To use adjunct applicator device (3110) to load end effector (12), the operator would first position adjunct applicator device (3110) and end effector (12) such that platform (3118) and buttress assemblies (110, 112) are positioned between anvil (18) and staple cartridge (37) with platform (3118) in the collapsed state as shown in FIG. 65A. The operator would then advance end effector (12) distally relative to adjunct applicator device (3110) to contact electrical switch (3128) with tissue stop (12a) as indicated by first arrow (A1) in FIG. 65B. Platform (3118) may be deployed by motor (3124) toward end effector jaws (16, 18) in response to such contact as indicated by second arrows (A2) in FIG. 65B, thereby adhesively attaching buttress assemblies (110, 112) to the respective jaws (16, 18). Buttress assemblies (110, 112) may be released from platform (3118), such that end effector jaws (16, 18) may be disengaged from platform (3118) while buttress assemblies (110, 112) remain adhered to the respective jaws (16, 18).

While deployment of platform (3118) has been described as being automated via motor (3124) and battery (3126), adjunct applicator device (3110) may be configured such that deployment of platform (3118) is performed manually via user input, such as by allowing a user to apply torque to threaded rod (3120). In such cases, adjunct applicator device (3110) may include a locking mechanism configured to transition between a locked state in which the locking mechanism inhibits rotation of threaded rod (3120) to thereby prevent deployment of platform (3118) and an unlocked state in which the locking mechanism allows rotation of threaded rod (3120) to thereby permit deployment of platform (3118) (e.g., upon application of torque by a user to threaded rod (3120). In one example, motor (3124) may be configured to selectively transition the locking mechanism from the locked state to the unlocked state in response to detection of tissue stop (12a) by electrical switch (3128). Alternatively, motor (3124), battery (3126), and electrical switch (3128) may be omitted, and adjunct applicator device (3110) may include a detector in the form of a mechanical switch such as a cammed feature configured to selectively transition the locking mechanism from the locked state to the unlocked state in response to contacting one or more tissue stops (12a). For example, such a cammed feature may be configured to rotate in response to contacting tissue stop(s) (12a), and such rotation of the cammed feature may allow rotation of threaded rod (3120) to thereby permit deployment of platform (3118) (e.g., upon application of torque by a user to threaded rod (3120).

Although adjunct applicator device (3110) has been described as including expandable platform (3118) and a platform driver in the form of threaded rod (3120) and linkages (3122) for deploying platform (3118), it will be appreciated that adjunct applicator device (3110) may include any other suitable types of platform and/or platform driver for deploying such platforms to attach buttress assemblies (110, 112) to the end effector jaws (16, 18). Likewise, although adjunct applicator device (3110) has been described as including a detector in the form of electrical switch (3128), it will be appreciated that adjunct applicator device (3110) may include any other suitable type of electrical and/or mechanical detector for detecting a predetermined portion of end effector (12) when adjunct applicator device (3110) is properly aligned therewith such that the platform driver may be configured to selectively deploy the platform only when the detector detects the predetermined portion of end effector (12) (e.g., either by automatically deploying the platform in response to such detection, or by transitioning a locking mechanism of the driver to an unlocked state to permit deployment of the platform in response to such detection). For example, the detector could be a contactless mechanism, such as a proximity sensor (e.g., optical, magnetic, etc.), configured to detect the presence of the predetermined portion of the end effector (12) without actually contacting the predetermined portion of the end effector (12).

Figure 66A:
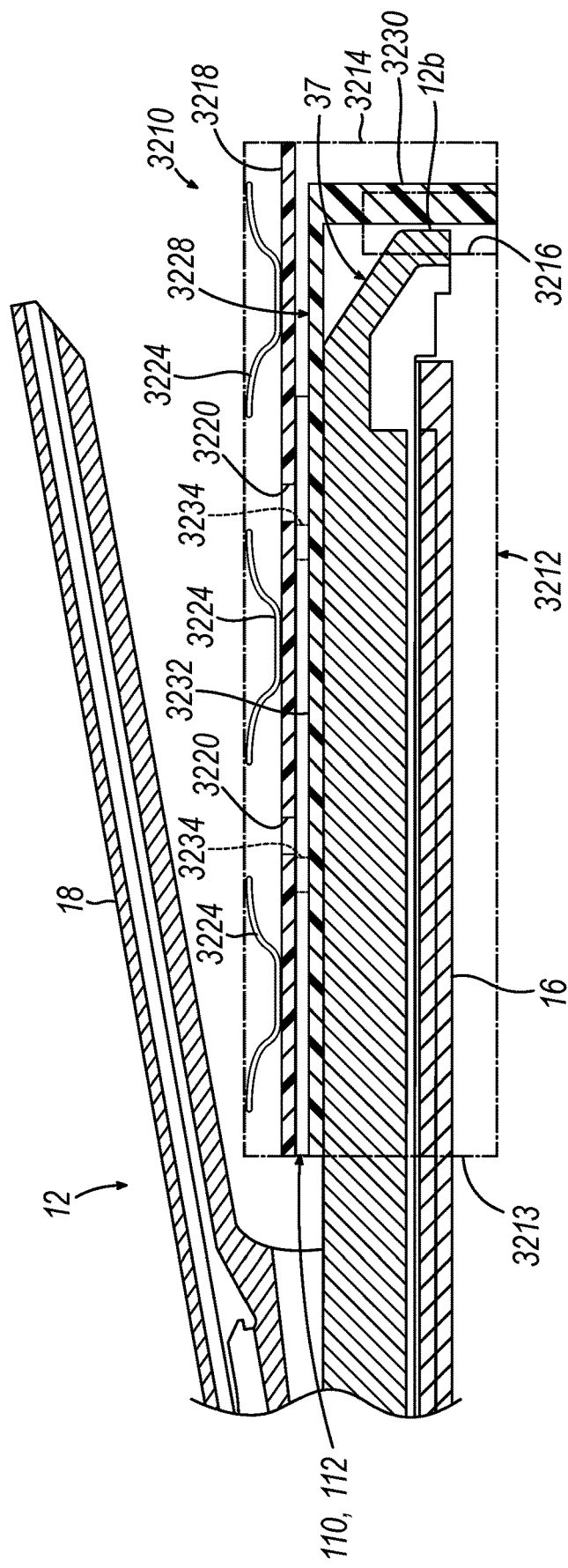
FIG. 66A depicts a side cross-sectional view of another exemplary adjunct applicator device carrying one of the buttress assemblies of FIG. 8 and positioned over the lower jaw of the end effector of FIG. 3, showing a movable platform of the adjunct applicator device in a retracted state.
Figure 66B:
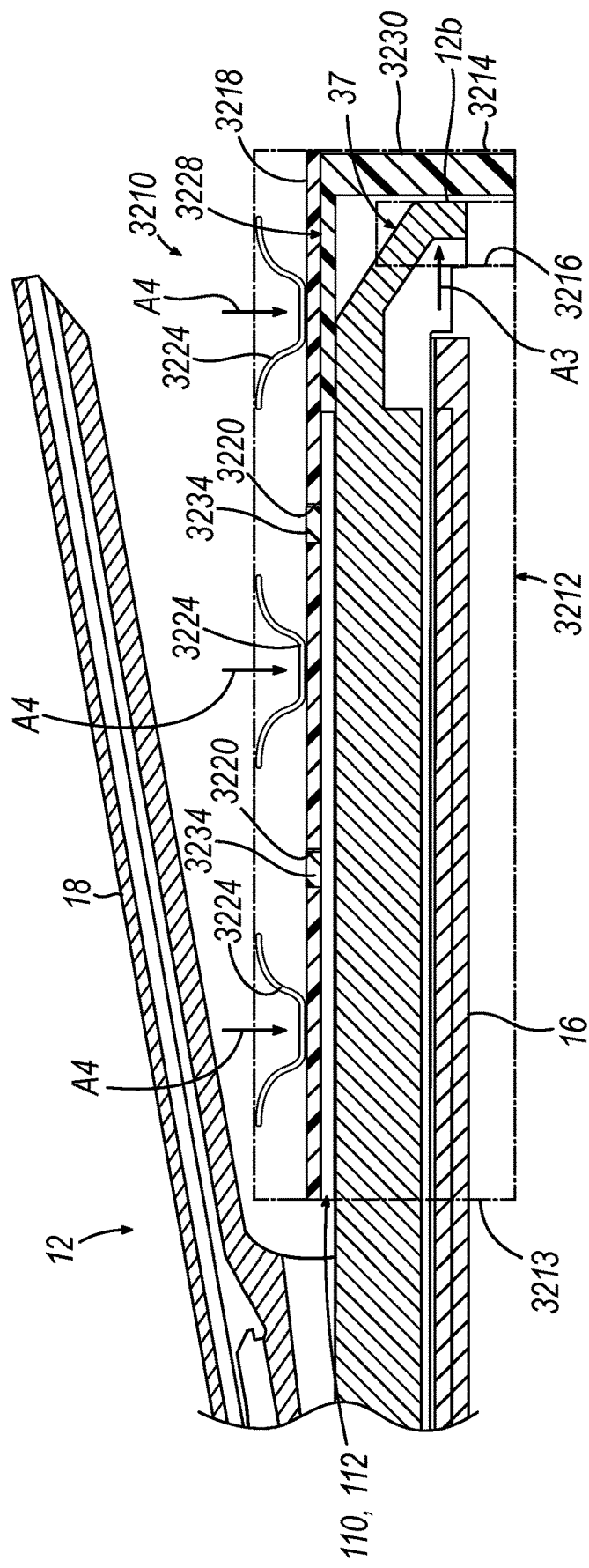
FIG. 66B depicts a side cross-sectional view of the adjunct applicator device of FIG. 66A positioned over the lower jaw of the end effector of FIG. 3, showing the movable platform of the adjunct applicator device in a deployed state for applying the buttress assembly onto the lower jaw of the end effector in response to the distal tip of the lower jaw contacting a translatable slide of the adjunct applicator device.

B. Exemplary Applicator Device with Distal Tip-Engaging Feature for Detecting Proper Seating in End Effector FIGS. 66A-66B show an exemplary adjunct applicator device (3210) configured to prevent improperly loading buttress assemblies (110, 112) onto the jaws of an end effector while adjunct applicator device (3210) is longitudinally misaligned with the jaws, via a distal tip-engaging feature. Adjunct applicator device (3210) is similar to adjunct applicator devices (210, 3110) described above except as otherwise described below.

Adjunct applicator device (3210) of this example comprises a housing (3212) extending between a proximal end (3213) and a distal end (3214). Housing (3212) includes a viewing window (3216) positioned at or near distal end (3214) of housing (3212) for permitting visual observation of internal components positioned within housing (3212) as will be described in greater detail below. Adjunct applicator device (3210) also comprises a generally flat floating compression pad or platform (3218) having a pair of slots (3220) and configured to selectively transition between a retracted state (FIG. 66A) and a deployed state (FIG. 66B). In this regard, adjunct applicator device (3210) further comprises a platform driver in the form of a plurality of energy storage devices including resilient members and, more particularly, compression leaf springs (3224) positioned between platform (3218) and housing (3212). Leaf springs (3224) are configured to selectively transition from a compressed state (FIG. 66A) to an expanded state (FIG. 66B) to thereby urge platform (3218) in an application direction in which the surface of platform (3218) configured to support buttress assembly (110, 112) faces (e.g., perpendicular to a longitudinal axis of platform (3218)) for deploying platform (3218). Adjunct applicator device (3210) also includes a detector in the form of a mechanical switch and, more particularly, a longitudinally translatable slide (3228) positioned on an opposite side of platform (3218) from leaf springs (3224) for restricting movement of platform (3218) in the application direction as will be described in greater detail below.

Platform (3218) of the present example is configured to support at least one buttress assembly (110, 112) on at least one side of platform (3218). In the example shown, platform (3218) supports a wide version of buttress assembly (110, 112) that unitarily spans across slot (42, 49) of anvil (18) or staple cartridge (37), though buttress assembly (110, 112) may alternatively be provided in a respective pair of portions that are separated to avoid spanning across slots (42, 49) of anvil (18) and staple cartridge (37), respectively.

Translatable slide (3228) includes an activation bar (3230) positioned at or near distal end (3214) of housing (3212) and a generally elongate support (3232) extending proximally from activation bar (3230) and parallel to platform (3218). Translatable slide (3228) further includes a pair of tabs (3234) protruding from support (3232) toward platform (3218) and configured to selectively abut platform (3218) to thereby prevent expansion of leaf springs (3224), and further configured to be selectively received by respective slots (3220) to thereby permit expansion of leaf springs (3224) for deploying platform (3218). Activation bar (3230) is configured to detect a predetermined portion of end effector (12), such as a distal tip (12b) defined by staple cartridge (37) of lower jaw (16), when end effector (12) is properly positioned relative to adjunct applicator device (3210) for loading buttress assembly (110, 112) onto end effector (12). For example, translatable slide (3228) may be configured to move from a proximal unactuated state to a distal actuated state in response to activation bar (3230) being pushed distally by or otherwise contacting distal tip (12b). Leaf springs (3224) may be configured to expand for deploying platform (3218) in response to movement of translatable slide (3228) to the actuated state. For example, movement of translatable slide (3228) to the actuated state may selectively longitudinally align tabs (3234) of support (3232) with slots (3220) of platform (3218) such that leaf springs (3224) are permitted to selectively urge platform (3218) in the application direction. Thus, leaf springs (3224) may be configured to selectively urge platform (3218) in the application direction for deploying platform (3218) in response to detection of distal tip (12b) by activation bar (3230) of translatable slide (3228). In this manner, translatable slide (3228) may assist in providing proper longitudinal and lateral alignment of end effector (12) with adjunct applicator device (3210) during deployment of platform (3218). In one example, movement of translatable slide (3228) to the actuated state may be observable through viewing window (3216) to thereby provide a visual indication of the deployment of platform (3218).

FIG. 66A shows end effector (12) in the open state with adjunct applicator device (3210) positioned over lower jaw (16) such that activation bar (3230) of translatable slide (3228) is spaced apart from distal tip (12b), thereby allowing tabs (3234) to abut platform (3218) for preventing platform (3218) from transitioning out of the retracted state; while FIG. 66B shows end effector (12) positioned relative to adjunct applicator device (3210) such that distal tip (12b) distally pushes or otherwise contacts activation bar (3230) to thereby translate slide (3228) distally such that tabs (3234) longitudinally align with slots (3220) and consequently cease abutting platform (3218) to allow leaf springs (3224) to transition platform (3218) from the retracted state toward the deployed state. To use adjunct applicator device (3210) to load end effector (12), the operator would first position adjunct applicator device (3210) and end effector (12) such that lower jaw (16) is received within housing (3212) with platform (3218) and buttress assembly (110, 112) positioned between anvil (18) and staple cartridge (37), and with platform (3218) in the retracted state as shown in FIG. 66A. The operator would then advance end effector (12) distally relative to adjunct applicator device (3210) to distally push or otherwise contact activation bar (3230) of translatable slide (3228) with distal tip (12b) as indicated by third arrow (A3) in FIG. 66B. Platform (3218) may be deployed by leaf springs (3224) toward lower jaws (16) in response to such contact as indicated by fourth arrows (A4) in FIG. 66B, thereby adhesively attaching buttress assembly (110, 112) to lower jaw (16). Buttress assembly (110, 112) may be released from platform (3218), such that lower jaw (16) may be disengaged from platform (3218) while buttress assembly (110, 112) remains adhered to lower jaw (16).

VIII. Exemplary Adjunct Applicator Devices with Authentication Features

In some instances, it may be desirable to provide an adjunct applicator device having certain features that promote alignment between the applicator device and the jaws of the end effector; prevent reuse of the applicator device, the end effector, or both; and/or authenticate the applicator device with a given end effector to promote use of the applicator device with only a specific predetermined type of end effector having a specific predetermined configuration. Each of the exemplary applicator devices described below in connection with FIGS. 67A-79B provide such functionality.

A. Exemplary Applicator Device with Lockout

Figure 67A:
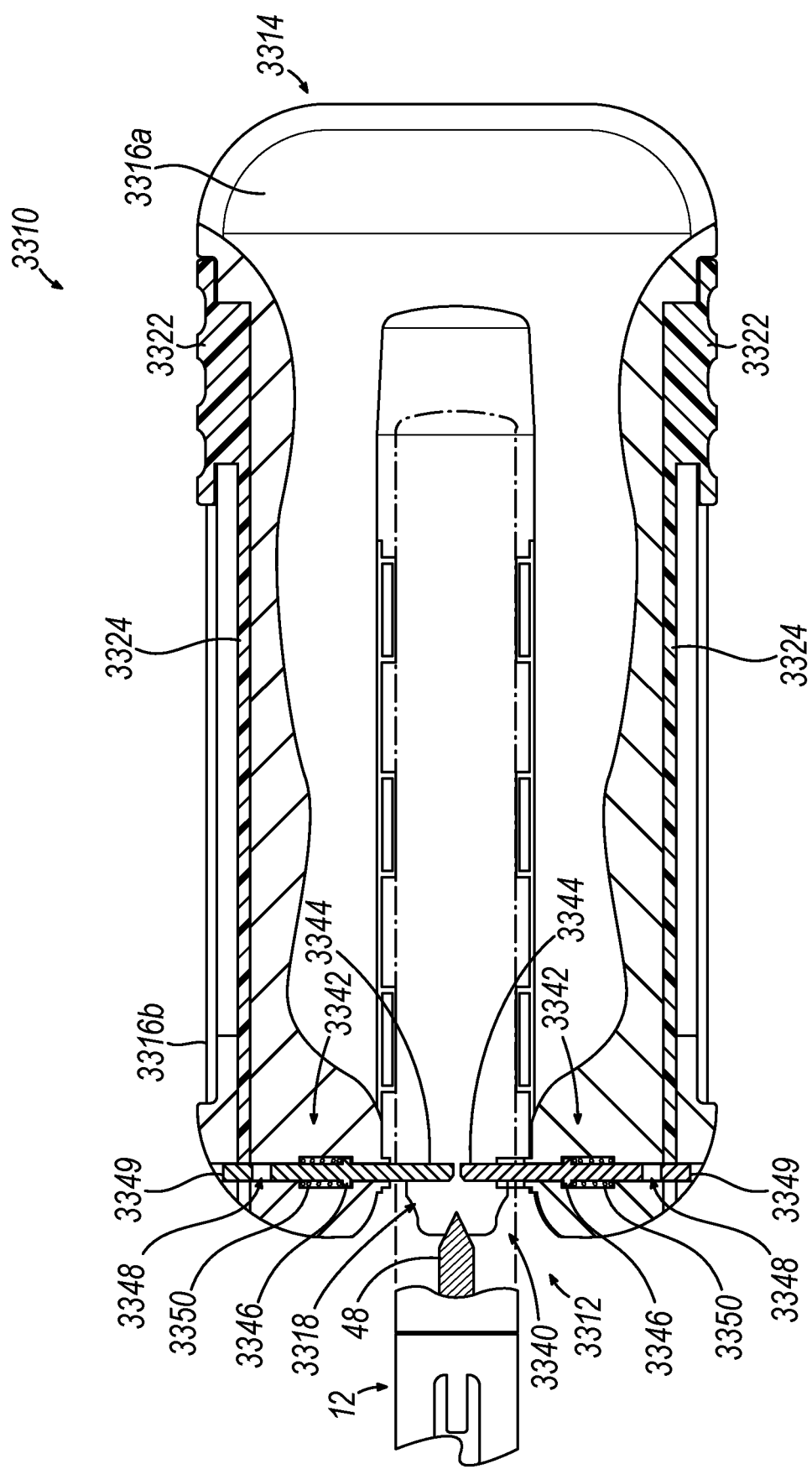
FIG. 67A depicts a top cutaway view of another exemplary adjunct applicator device that may be used to carry and apply the buttress assemblies of FIG. 8, with the adjunct applicator device in a locked configuration.

FIG. 67A shows an exemplary alternative adjunct applicator device (3310) (also referred to as a "buttress applicator") that may be used to support, protect, and apply adjunct material, such as buttress assemblies (110, 112), to end effector (12). Adjunct applicator device (3310) of the present example is substantially similar to applicator device (210) described above except where otherwise explicitly described herein. For instance, as with applicator device (210), applicator device (3310) of this example comprises an open end (3312) and a closed end (3314). As with open end (212) described above, open end (3312) of this example is configured to receive end effector (12) as will be described in greater detail below. Similarly, applicator device (3310) of this example further includes a first housing (416*a*) and a second housing (3316*b*), which each collectively generally define a "U" shape to present open end (3312). A platform (3318) is similarly interposed between first and second housings (3316*a*, 3316*b*).

As with platform (218) described above, platform (3318) of the present example is configured to support a pair of buttress assemblies (110) on one side of platform (3318) and another pair of buttress assemblies (112) on the other side of platform (3318). Platform (3318) is exposed in recesses that are formed between the prongs of the "U" configuration of first and second housings (3316*a*, 3316*b*). Each buttress assembly (110, 112) is provided in a respective pair of portions that are separated to avoid spanning across slots (42, 49) of anvil (18) and staple cartridge (37), respectively, though platform (3318) may just as easily support wide versions of buttress assemblies (110, 112) that unitarily span across slots (42, 49) of anvil (18) and staple cartridge (37), respectively.

Unlike platform (218) described above, platform (3318) of this example is generally configured to expand in one or more directions for application of buttress assemblies (110, 112). As will be described in greater detail below, this functionality may be achieved by platform (3318) operating as an expandable wedge. By way of example only, this functionality can be accomplished in some examples by configuring platform (3318) or other suitable features of applicator device (3310) in accordance with the teachings of U.S. patent application Ser. No. 17/022,209, entitled "Apparatus and Method to Apply Buttress to End Effector of Surgical Stapler via Driven Member," filed on Sep. 16, 2020, issued as U.S. Pat. No. 11,564,683 on Jan. 31, 2023, the disclosure of which is incorporated by reference herein.

As with applicator device (210) described above, first and second housings (3316*a*, 3316*b*) include gripping features (3322). However, unlike gripping features (222) described above, gripping features (3322) of the present example are movable to selectively expand platform (3318). As will be described in greater detail below, gripping features (3322) are generally configured for translation relative to housings (3316*a*, 3316*b*) to thereby activate expansion of platform (3318). As will also be described in greater detail below, it should be understood in certain configurations, gripping features (3322) can be locked to prevent expansion of platform or otherwise lockout application of buttress assemblies (110, 112) using applicator device (3310).

Unlike applicator device (210) described above, applicator device (3310) of the present example includes a lockout assembly (3340) disposed within housings (3316*a*, 3316*b*). Lockout assembly (3340) is generally configured to prevent expansion of platform (3218) until applicator device (3310) is properly positioned within end effector (12) to thereby prevent misapplication of buttress assemblies (110, 112). In other words, lockout assembly (3340) is generally configured to permit deployment of buttress assemblies (110, 112) only when a predetermined portion of end effector (12) engages lockout assembly (3340). Such engagement can then be used to permit movement of gripping features (3322) to activate expansion or other movement of platform (3318).

Lockout assembly (3340) of the present example is positioned proximate open end (3312) and includes two actuators (3342) extending inwardly into open end (3312) from either side of applicator device (3310) thereof. Each actuator (3342) includes an engagement portion (3344), a spring collar (3346), a release opening (3348), and a lock end (3349). Although not shown, it should be understood that each actuator (3342) in the present example is configured as an elongate rod, I-beam, or other elongate structure. Of course, various other suitable cross-sectional shapes may be used for each actuator (3342) as will be apparent to those of ordinary skill in the art in view of the teachings herein.

Engagement portion (3344) of each actuator (3342) defines a length suitable for extending into open end (3312) from housings (3316*a*, 3316*b*). In the present example, this length of extension for each engagement portion (3344) is generally equivalent to half of the lateral length of open end (3312). Thus, engagement portions (3344) of each actuator (3342) extend towards each other to collectively occupy the entire lateral length of open end (3312). Alternatively, engagement portions (3344) of each actuator (3342) may collectively occupy most of the lateral length of open end (3312) to define a slight gap at the end of each engagement portion (3344). As will be described in greater detail below, such a gap between engagement portions (3344) may be desirable to promote movement of each actuator (3342) through engagement with a portion of end effector (12).

Spring collar (3346) is positioned along the length of each actuator (3342) between a respective engagement portion (3344) and release opening (3348). Spring collar (3346) is generally configured to engage a spring (3350) disposed within one or more of housings (3316*a*, 3316*b*) to bias each actuator (3342) towards a predetermined position. In the present example, the combination of spring collar (3346) and spring (3350) is configured to bias each actuator (3342) towards a locked position corresponding to the configuration shown in FIG. 67A. As will be described in greater detail below, each actuator (3342) is positioned to prevent movement of a corresponding gripping feature (3322) when in the locked position.

Release opening (3348) is defined within each actuator (3342) proximate lock end (3349). As will be described in greater detail below, release opening (3348) is generally configured to receive a portion of a corresponding gripping feature (3322). To facilitation such a configuration, each release opening (3348) corresponding to each actuator (3342) extends through actuator (3342) from one side to another. Thus, each release opening (3348) is configured as a through hole extending through a corresponding actuator (3342).

Adjacent to release opening (3348), lock end (3349) of each actuator (3342) is positioned on the outermost end thereof. Each lock end (3349) is generally configured to block movement of a portion of a corresponding gripping feature (3322). Thus, it should be understood that lock end (3349) is of a generally solid configuration. As will be described in greater detail below, each actuator (3342) is generally configured to transition laterally within applicator device (3310) to transition engagement between a portion of gripping feature (3322) and lock end (3349), or the portion of gripping feature (3322) and release opening (3348).

To promote engagement between gripping features (3322) and lock assembly (3340), each gripping feature (3322), each gripping feature (3322) includes a lock arm (3324). In particular, each lock arm extends axially or proximally through applicator device (3310) from a body of each gripping feature (3322) towards each actuator (3342). Each lock arm (3324) is generally configured as an elongate rod or beam having a cross-section corresponding to the shape of a respective release opening (3348). As will be described in greater detail below, each lock arm (3324) is configured for receipt within a respective release opening (3348) to permit movement of gripping feature (3322).

As best seen in FIGS. 67A and 67B, lockout assembly (3340) is generally responsive to a predetermined portion of end effector (12) to lock and unlock movement of gripping features (3322). As can be seen in FIGS. 68A and 68B, the unlocking movement of gripping features (3322) permits activation of applicator device (3310) by gripping features (3322) to expand platform (3318). Thus, lockout assembly (3340) is configured to transition from a locked configuration shown in FIG. 67A to an unlocked configuration in FIG. 67B. This transition results in griping features (3322) being usable to activate expansion of platform (3318), as can be seen in FIG. 68B.

As can be seen in FIG. 67A, in the locked configuration, each actuator (3342) of lockout assembly (3340) is positioned inwardly such that each engagement portion (3344) is nearly in contact (or alternatively in contact) with the opposite engagement portion (3344). Correspondingly, each lock end (3349) is positioned adjacent to a proximal end of a corresponding lock arm (3324). Thus, each lock end (3349) blocks movement of each gripping feature (3322) via lock arm (3324) when lockout assembly (3340) is in the locked configuration. Additionally, it should be understood that lockout assembly (3340) is biased by spring (3350) and spring collar (3246) towards the locked configuration.

Transition of lockout assembly (3340) from the locked configuration to the unlocked configuration is shown in FIG. 67B. As can be seen, the transition of lockout assembly (3340) is driven by a predetermined portion of end effector (12). In the present example, this transition is driven by cutting edge (48) of end effector (12). Use of cutting edge (48) in the present example is generally desirable because the particular shape, size, and position of cutting edge (48) can be unique to end effector (12). Thus, use of cutting edge (48) as described herein can function as a lockout feature to promote use of applicator device (3310) with only certain specific end effectors corresponding to end effector (12) described above. In other words, end effectors having a different configuration than end effector (12) described above may not be useable with applicator device (3310). The use of cutting edge (48) as described herein is further desirable to prevent deployment of buttress assemblies (110, 112) until applicator device (3310) is properly positioned within end effector (12). Although cutting edge (48) is shown and described herein as being usable to drive lockout assembly (3340), it should be understood that in other examples, various alternative portions of end effector (12) can be used to drive the transition of lockout assembly (3340). As will be understood, suitable portions of end effectors (12) may include any portion of end effector (12) that is unique or varied relative to other end effector configurations or styles.

Returning to the present example, lockout assembly (3340) is transitioned by engagement between engagement portion (3344) of each actuator (3342) with cutting edge (48) of end effector (12). In particular, applicator device (3310) is inserted into/onto end effector (12) (or end effector (12) is inserted into/onto applicator device (3310)) to bring cutting edge (48) into contact with each engagement portion (3344). This contact pushes each actuator (3342) outwardly away from the opposite actuator (3342) by a predetermined distance. Once this predetermined distance is reached as shown in FIG. 67B, each release opening (3348) is positioned adjacent to the proximal end of a corresponding lock arm (3324). This permits each lock arm (3324) to be received within a corresponding release opening (3348). As a result, each gripping feature may be translated proximally relative to housings (3316a, 3316b).

As shown in FIG. 68B, once lockout assembly (3340) is transitioned to the unlocked configuration, each gripping feature (3322) can be moved proximally to activate expansion of platform (3318). This expansion pushes platform (3318) towards upper deck (72) and anvil (18) of end effector (12) for deployment of buttress assembly (110, 112) thereon. Although not shown, it should be understood that gripping features (3322) can be in communication with one or more features suitable to activate expansion of platform (3318). In the present example, gripping features (3322) are used to drive a linkage assembly to expand platform (3318). As discussed above, expansion of platform (3318) can be accomplished using a variety of mechanical and/or electrical configuration.

B. Exemplary Applicator Device with Keyed Release

Figure 69:
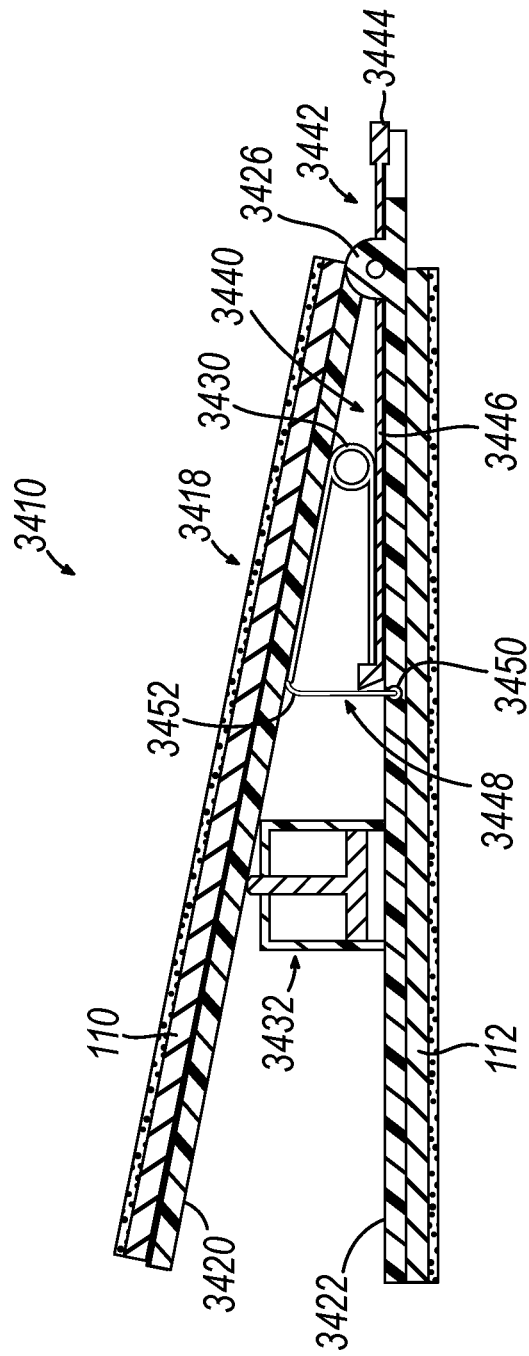
FIG. 69 depicts a side cross-sectional view of another exemplary adjunct applicator device that may be used to carry and apply the buttress assemblies of FIG. 8.

FIG. 69 shows another exemplary adjunct applicator device (3410) (also referred to as a "buttress applicator") that may be used to support, protect, and apply adjunct material, such as buttress assemblies (110, 112), to an end effector. Adjunct applicator device (3410) of the present example is substantially similar to adjunct applicator device (210, 3310) described above except where otherwise explicitly described herein. For instance, as with applicator device (3310), applicator device (3410) of this example comprises a housing (not shown) defining an open end (not shown) and a closed end (not shown). A platform (3418) is similarly interposed between one or more portions of the housing.

As with platform (3318) described above, platform (3418) of the present example is configured to support a pair of buttress assemblies (110) on one side of platform (3418) and another pair of buttress assemblies (112) on the other side of platform (3418). Also as with platform (3318), platform (3418) of the present example is generally configured to be expandable to apply buttress assemblies (110, 112). To support such expandability, platform (3418) includes an upper support (3420), and a lower support (3422) connected with a hinge (3426). Upper support (3420) comprises an elongate flat surface configured for support of buttress assembly (110). Meanwhile, lower support (3422) also comprises an elongate flat surface configured for support of buttress assembly (112).

Upper support (3420) is connected to lower support (3422) at hinge (3426). Hinge (3426) is positioned at the proximal end of each support (3420, 3422) such that hinge (3426) is generally configured for insertion into an end effector (3512), as will be described in greater detail below. Hinge (3426) is generally configured to permit pivoting of upper support (3420) relative to lower support (3422).

Platform (3418) of the present example is configured to expand automatically (e.g., without an operator pushing or pulling portions of platform (3418)). To facilitate such automatic expansion, platform (3418) of the present example further includes a resilient member or torsion spring (3430) and a dashpot (3432). Torsion spring (3430) is configured to provide an outward force against upper support (3420) and lower support (3422) to bias platform (3418) towards an expanded configuration. Meanwhile, dashpot (3432) is generally configured to provide a controlled force opposite of torsion spring (3430) (e.g., an inwardly oriented force). As will be understood, dashpot (3432) is generally configured to act as a damper to prevent torsion spring (3430) from expanding platform (3418) at an undesirable rate. By way of example only, this functionality can be accomplished in some examples by configuring platform (3418) or other suitable features of applicator device (3410) in accordance with the teachings of U.S. patent application Ser. No. 17/022,209, entitled "Apparatus and Method to Apply Buttress to End Effector of Surgical Stapler via Driven Member," filed on Sep. 16, 2020, issued as U.S. Pat. No. 11,564,683 on Jan. 31, 2023, the disclosure of which is incorporated by reference herein.

To activate expansion of platform (3418), applicator device (3410) of the present example further includes a release assembly (3440). Release assembly (3440) is generally configured to engage a predetermined portion of end effector (3512) to activate expansion of platform (3418) upon such engagement. Thus, release assembly (3440) is similar to lockout assembly (3340) described above in that release assembly (3440) promotes use of applicator device (3410) with only certain end effectors and also promote activation of applicator device (3410) only when applicator device (3410) is properly positioned within such end effectors.

Release assembly (3440) of the present example comprises a probe (3442) and a latch (3448). Probe (3442) includes a keyed end (3444) and an elongate pusher (3446) extending from keyed end (3444). A portion of probe (3442) extends proximally from hinge (3426) such that keyed end (3444) protrudes from a proximal end of applicator device (3410). As will be described in greater detail below, the particular position of probe (3442) is configured to permit engagement between keyed end (3444) and a predetermined portion of end effector (3510) when lower support (3422) is properly seated within end effector (3512).

Elongate pusher (3446) extends distally from hinge (3426) and keyed end (3444) towards torsion spring (3430) and latch (3448). Elongate pusher (3446) is generally responsive to movement of keyed end (3444) such that movement of keyed end (3444) results in corresponding movement of elongate pusher (3446). As will be described in greater detail below, movement of elongate pusher (3446) is configured to actuate latch (3448), which releases torsion spring (3430) and thereby expanding platform (3418).

Latch (3448) is generally configured to selectively engage torsion spring (3430) to hold torsion spring (3430) in a compressed configuration. In the present example, latch (3448) comprises an elongate rod, or wire that includes coupler (3450) and a release (3452). Coupler (3450) is pivotably coupled to lower support (3422) to permit latch (3448) to pivot relative to lower support (3422). Release (3452) is positioned opposite of coupler (3450) as is configured to releasably engage torsion spring (3430) and/or a portion of upper support (3420) to hold torsion spring (3430) in the compressed configuration. As will be described in greater detail below, elongate pusher (3446) is generally configured to engage latch (3448) to pivot latch (3448) about coupler (3450) to disengage release (3452) from torsion spring (3430) and/or a portion of upper support (3420).

Although release assembly (3440) is shown as having a specific configuration, it should be understood that in other examples, a variety of alternative configurations may be used. For instance, in some examples other mechanical release mechanisms can be used to permit selective expansion of platform (3418) via torsion spring (3430) or other mechanisms configured for storage of potential energy. In other examples, release assembly (3440) can use various electrical/mechanical components such as solenoids, motors, push-buttons, sensors, and/or etc. Of course, still various other suitable configurations for release assembly (3440) as will be apparent to those of ordinary skill in the art in view of the teachings herein.

Figure 70A:
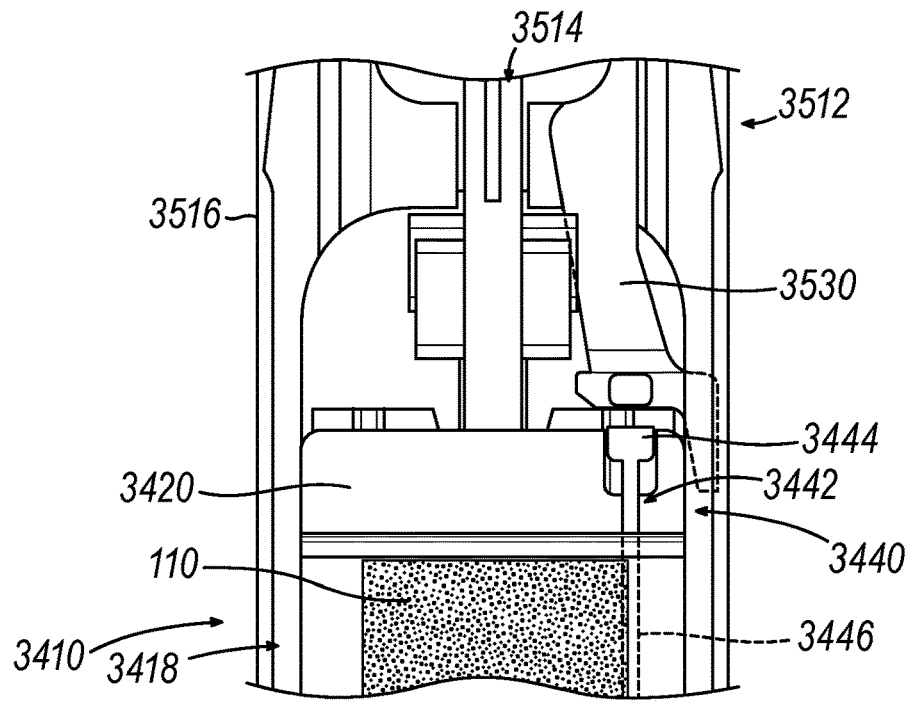
FIG. 70A depicts a top detailed plan view of the adjunct applicator device of FIG. 69, with an end effector being inserted into the adjunct applicator device and having select components omitted from view.

As can be seen in FIG. 70A, applicator device (3410) of the present example is configured for use with end effector (3512). End effector (3512) of the present example is substantially similar to end effector (12) described above except where otherwise explicitly noted herein. For instance, like with end effector (12) described above, end effector (3512) of the present example employs a firing beam (3514) that may be used to sever and staple tissue in a single stroke. As with firing beam (14) described above, firing beam (3514) of the present example may be driven relative to an anvil (not shown) (similar to anvil (18)) and an unspent staple cartridge (not shown) (similar to staple cartridge (37)) to sever and staple tissue. As with staple cartridge (37), the staple cartridge of end effector (3512) is removably installed into a channel of a lower jaw (3516).

Unlike end effector (12) described above, end effector (3512) of the present example includes a cartridge lockout (3530) integrated into end effector (3512). Lockout (3530) is generally configured to mate with certain corresponding components of a staple cartridge. Such a mating arrangement moves lockout (3530) into a predetermined position and unlocks certain operations of end effector (3512) such as movement of firing beam (3514) and closure of the anvil. Thus, it should be understood that lockout (3530) is configured to prevent use of end effector (3512) when no staple cartridge is installed, an improper (e.g., lacking mating features) staple cartridge is installed, or a staple cartridge is improperly installed. In some examples, lockout (3530) and other associated features of end effector (3512) and the staple cartridge can be configured in accordance with the teachings of U.S. patent application Ser. No. 16/453,273, entitled "Method for Providing an Authentication Lockout in a Surgical Stapler with a Replaceable Cartridge," filed on Jun. 26, 2019, issued as U.S. Pat. No. 11,298,129 on Apr. 12, 2022, the disclosure of which is incorporated by reference herein.

Figure 70B:
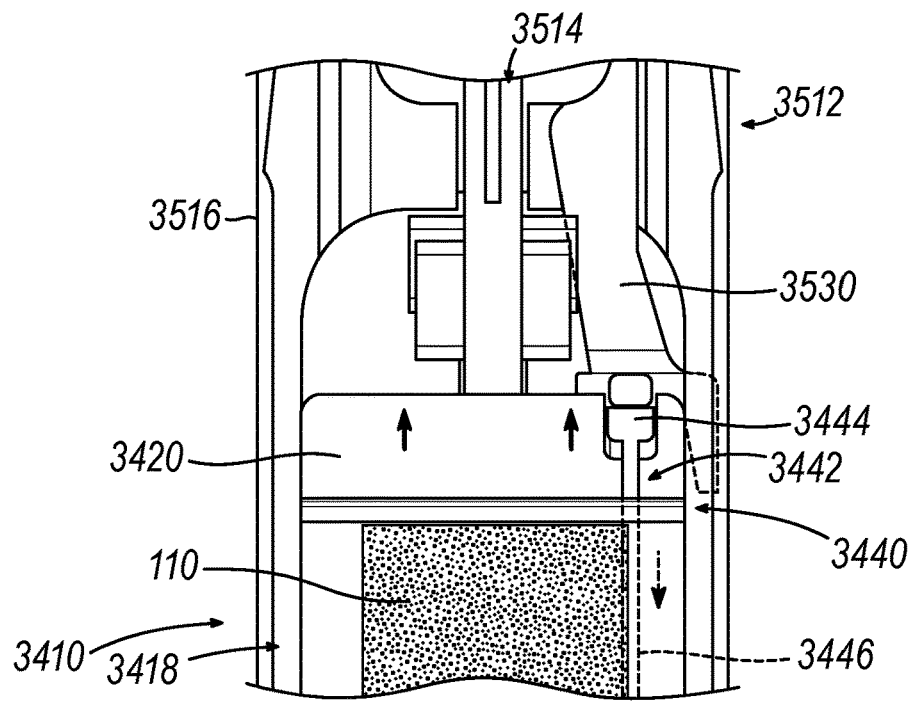
FIG. 70B depicts another top detailed plan view of the adjunct applicator device of FIG. 69, with the end effector of FIG. 70A fully inserted into the adjunct applicator device and having select components omitted from view.
Figure 71:
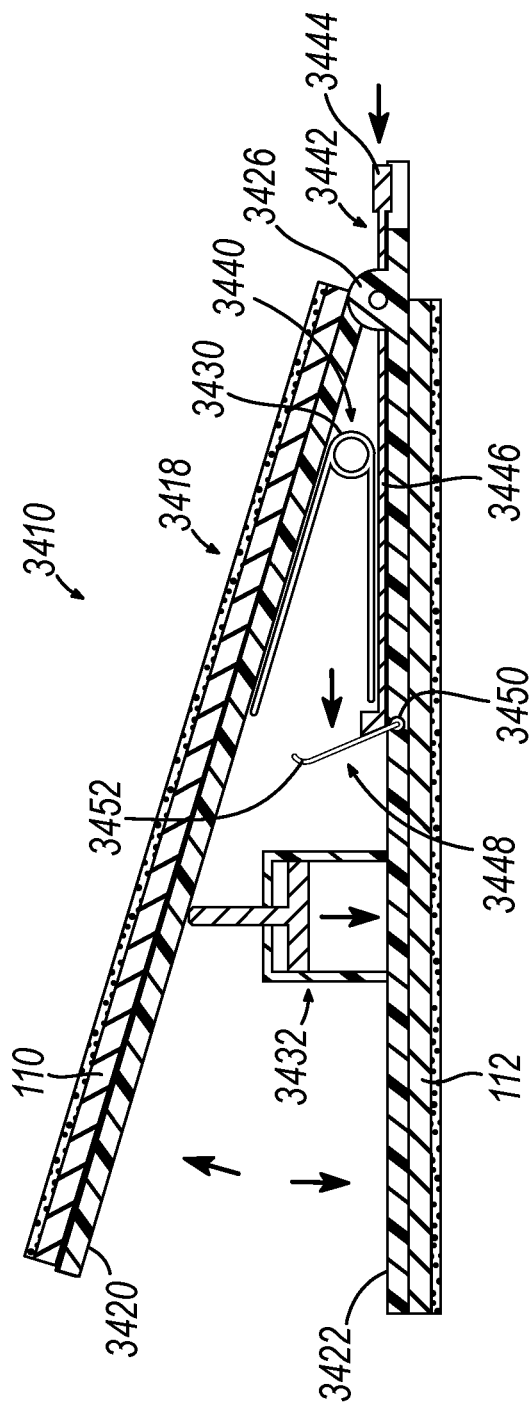
FIG. 71 depicts another side cross-sectional view of the adjunct applicator device of FIG. 69, with a platform of the adjunct applicator device in an expanded configuration.

Use of adjunct applicator device (3410) with end effector (3512) is shown in FIGS. 70A through 71. As can be best seen in FIG. 70A, applicator device (3410) may be first inserted into end effector (3512) to position lower support (3422) into alignment with lower jaw (3516) of end effector (3512). The direction of insertion is such that hinge (3426) and keyed end (3444) are inserted into end effector (3512) first towards lockout (3530).

Once applicator device (3410) is fully inserted into end effector (3512), keyed end (3444) engages a portion of lockout (3530) as can be seen in FIG. 70B. In some examples, the particular geometry of keyed end (3444) may be configured to correspond to a specific geometric feature of lockout (3530) to further promote precise positioning of applicator device (3410) relative to end effector (3512). Regardless, upon engagement between keyed end (3444) and lockout (3530), keyed end (3444) pushes probe (3442) distally.

As best seen in FIG. 71, upon distal movement of probe (3442), elongate pusher (3446) engages latch (3448). Latch (3448) is correspondingly pushed by elongate pusher (3446) to pivot about coupler (3450), thereby disengaging release (3452) from torsion spring (3430) and/or upper support (3420). With torsion spring (3430) released, platform (3418) can expand at a controlled pace using the force applied by torsion spring (3430) and dashpot (3432) to apply buttress assemblies (110, 112) to end effector (3512).

C. Exemplary Applicator Device with RFID Authentication

FIGS. 72A and 73A depict yet another exemplary alternative adjunct applicator device (3610) (also referred to as a "buttress applicator") that may be used to support, protect, and apply adjunct material, such as buttress assemblies (110, 112), to an end effector. Adjunct applicator device (3610) of the present example is substantially similar to adjunct applicator device (210, 3310, 3410) described above except where otherwise explicitly described herein. For instance, as with applicator device (3310), applicator device (3610) of this example comprises a housing (3616) defining an open end (3612) and a closed end (3614). A platform (3618) is similarly interposed between one or more portions of the housing.

As with platform (3318) described above, platform (3618) of the present example is configured to support a pair of buttress assemblies (110) on one side of platform (3618) and another pair of buttress assemblies (112) on the other side of platform (3618). Also as with platform (3318), platform (3618) of the present example is generally configured to be expandable to apply buttress assemblies (110, 112). To support such expandability, platform (3618) includes certain mechanisms generally configured to promote expansion thereof. By way of example only, platform (3618) of the present example includes an expandable wedge driven by a linkage mechanism similar to platform (3318) described above. However, it should be understood that in other examples, other suitable mechanisms may be used such as an expandable balloon, a spring-loaded wedge, a lead screw driven mechanism, and/or etc. In still other examples, platform (3618) may be configured in accordance with one or more of the teachings of U.S. patent application Ser. No. 17/022,209, entitled "Apparatus and Method to Apply Buttress to End Effector of Surgical Stapler via Driven Member," filed on Sep. 16, 2020, issued as U.S. Pat. No. 11,564,683 on Jan. 31, 2023, the disclosure of which is incorporated by reference herein.

Unlike platform (3318) described above, expandability of platform (3618) in the present example is motor driven rather than being manually driven by an operator. In particular, as best seen in FIG. 73A, the interior of applicator device (3610) includes a motor (3630), a power source (3634), and a switch (3638), all incorporated into a circuit. Although not shown, it should be understood that motor (36730) of the present example may be in communication with one or more features of platform (3618) to drive expansion of platform (3618). For instance, as noted above, platform (3618) of the present example can use a linkage mechanism to provide expansion thereof. Thus, in such an example, motor (3630) can be configured to rotate a lead screw or other drive mechanism to move platform (3618) from a flat configuration to an expanded configuration. Of course, in other configurations where alternative expansion mechanisms are used, motor (3630) may be varied as needed. For instance, in some examples motor (3630) can include a vacuum pump, a linear actuator, and/or etc.

Switch (3638) is in communication with motor (3630) and power source (3634) to selectively activate and deactivate power supplied to motor (3630) via power source (3634). Power source (3634) of the present example is shown as a battery, although any other suitable source of power may be used including direct and/or alternating current sources. Although not shown, it should be understood that motor (3630), power source (3634) and switch (3638) can be connected to other electrical circuitry such as microcontrollers, controllers, relays, diodes, capacitors, inductors, resistors, inverters, and/or etc.

Returning to FIG. 72A, applicator device (3610) further includes an RFID module (3640). As will be described in greater detail below, RFID module (3640) is generally configured to respond to one or more corresponding RFID components of end effector (3712). This relationship is generally desirable to provide both confirmation that applicator device (3610) is used with a suitable end effector similar to end effector (3712), and confirmation that applicator device (3610) is properly positioned prior to deployment of buttress assemblies (110, 112) via platform (3618).

As can be seen, RFID module (3640) is in communication with switch (3638). In the present example, RFID module (3640) is configured to trip or otherwise actuate switch between an open and closed circuit configuration. As will be understood, this configuration permits RFID module (3640) to activate motor (3630) and thereby expand platform (3618) for deployment of buttress assemblies (110, 112) only when RFID module (3640) is in proximity with certain corresponding features of end effector (3712).

RFID module (3640) of the present example is positioned adjacent to the proximal end of applicator device (3610) proximate open end (3612). Although only a single RFID module (3640) is visible, it should be understood that an additional RFID module (3640) may be disposed on each side of applicator device (3610) (e.g., one on the side out of the page in FIG. 72A and one on the side into the page in FIG. 72A). As will be described in greater detail below, this proximal positioning is generally desirable to confirm proper positioning of applicator device (3610) within end effector (3712). In other examples, any suitable number of RFID modules (3640) may be used. For instance, in some examples, four RFID modules (3640) can be used with two on the proximal end of applicator device (3610) and two on the distal end of applicator device (3610). Such a configuration may be desirable to provide improved position confirmation. Thus, in other examples, even more RFID modules (3640) may be used as will be apparent to those of ordinary skill in the art in view of the teachings herein. Additionally, it should be understood that in examples where multiple RFID modules (3640) are used, all such RFID modules (3370) may be in communication with switch (3638) such that all RFID models (3640) may be used to transition switch (3638) between the open and closed circuit configurations.

As seen in FIG. 72A, applicator device (3610) is usable with end effector (3712). End effector (3712) of the present example is substantially similar to end effector (12) described above except where otherwise explicitly noted herein. For instance, like with end effector (12) described above, end effector (3712) of the present example employs a firing beam (3714) that may be used to sever and staple tissue in a single stroke. As with firing beam (14) described above, firing beam (3714) of the present example may be driven relative to an anvil (3718) and an unspent staple cartridge (3737) to sever and staple tissue. As with staple cartridge (37), staple cartridge (3737) is removably installed into a channel of a lower jaw (3716).

Unlike end effector (12) described above, end effector (3712) of the present example includes an RFID module (3740) positioned adjacent to the crotch formed by anvil (3718) and lower jaw (3716). RFID module (3740) of end effector (3712) is generally configured to communicate with RFID module (3640) of applicator device (3610). By way of example only, RFID module (3740) of end effector (3712) is configured as an RFID sensor or antenna. Meanwhile, RFID module (3640) of applicator device (3610) is configured as an RFID chip or transmitter for transmission of radio frequencies to RFID module (3740) of end effector (3712). Of course, in other examples, this configuration can be reversed and RFID module (3740) can be configured as a chip or transmitter, while RFID module (3640) can be configured as a sensor or antenna.

Although end effector (3712) of the present example is shown as having a single RFID module (3740), it should be understood that in other examples, end effector (3712) can include any suitable number of RFID modules (3740). For instance, in some examples, an array of RFID modules (3740) can be used in end effector (3712), with groups of RFID modules (3740) being configured to serve certain specific purposes. In such configurations, one group of RFID modules (3740) may be used to detect and authenticate the presence of a specific staple cartridge similar to staple cartridge (3737). Meanwhile, another group of RFID modules (3740) may be used to detect and authenticate the presence of a specific adjunct applicator device similar to adjunct applicator device (3610). Still another group of RFID modules (3740) may be used to detect other and authenticate the presence (or lack thereof) of other ancillary components such as staple cartridge retainer. In some examples, suitable configurations for RFID module (3740) may be in accordance with at least some of the teachings of U.S. patent application Ser. No. 16/458,108, entitled "Surgical Instrument System Comprising an RFID System," filed on Jun. 30, 2019, issued as U.S. Pat. No. 11,376,098 on Jul. 5, 2022, the disclosure of which is incorporated by reference herein.

An exemplary use of the present example is shown in FIGS. 72A through 73B. As can be seen, end effector (3712) is initially moved relatively to applicator device (3610) to insert applicator device (3610) into end effector (3712). FIG. 73A shows switch (3638) of applicator device (3610) as being in the open configuration during insertion. This open configuration corresponds to platform (3618) being in a non-expanded configuration. Although not shown, it should be understood that in some uses, end effector (3712) may be electronically locked prior to and during insertion of applicator device (3610). For instance, RFID module (3740) may generate a signal corresponding to applicator device (3610) not being detected. This signal may then be communicated with electronic circuitry within end effector (3712) or other portions of the instrument (not shown) to physically or electronically lock portions of the instrument or end effector (3712) from moving (e.g., to prevent distal advancement of firing beam (3714)).

Once applicator device (3610) is fully inserted into end effector (3712), RFID module (3640) of applicator device (3610) is adjacent to RFID module (3740) of end effector (3712) as can be seen in FIG. 72B. RFID module (3640) then responds to the presence of RFID module (3740) by transitioning switch (3638) from the open configuration to the closed configuration as shown in FIG. 73B. This transition of switch (3638) causes motor (3630) to activate and thereby expand platform (3618), which results in application of buttress assemblies (110, 112) to anvil (3718) and staple cartridge (3737) of end effector (3712).

In some uses, RFID module (3740) may also respond to the presence of RFID module (3640). For instance, RFID module (3740) may generate one or more signals upon detection of the presence of RFID module (3640). Such signals may then be transmitted to other portions of end effector (3712) or the instrument to release or otherwise disengage certain lockout features. Alternatively, such lockout features may remain active, but may be disengaged after either a predetermined amount of time or until the presence of RFID module (3640) is no longer detected.

D. Exemplary Applicator Device with External Power Input

FIG. 74A depicts yet another exemplary alternative adjunct applicator device (3810) (also referred to as a "buttress applicator") that may be used to support, protect, and apply adjunct material, such as buttress assemblies (110, 112), to an end effector. Adjunct applicator device (3710) of the present example is substantially similar to adjunct applicator device (210, 3310, 3410, 3610) described above except where otherwise explicitly described herein. For instance, as with applicator device (3310), applicator device (3810) of this example comprises a housing (916) defining an open end (3812) and a closed end (3814). A platform (3818) is similarly interposed between one or more portions of housing (3816).

As with platform (3318) described above, platform (3818) of the present example is configured to support a pair of buttress assemblies (110) on one side of platform (3818) and another pair of buttress assemblies (112) on the other side of platform (3818). Also as with platform (3318), platform (3818) of the present example is generally configured to be expandable to apply buttress assemblies (110, 112). To support such expandability, platform (3818) includes certain mechanisms generally configured to promote expansion thereof. By way of example only, platform (3818) of the present example includes an expandable wedge driven by a linkage mechanism similar to platform (3318) described above. However, it should be understood that in other examples, other suitable mechanisms may be used such as an expandable balloon, a spring-loaded wedge, a lead screw driven mechanism, and/or etc. In still other examples, platform (3818) may be configured in accordance with one or more of the teachings of U.S. patent application Ser. No. 17/022,209, entitled "Apparatus and Method to Apply Buttress to End Effector of Surgical Stapler via Driven Member," filed on Sep. 16, 2020, issued as U.S. Pat. No. 11,564,683 on Jan. 31, 2023, the disclosure of which is incorporated by reference herein.

Unlike platform (3318) described above, expandability of platform (3818) in the present example is motor driven rather than being manually driven by an operator. In particular, as best seen in FIG. 74A, applicator device (3810) includes a power input or keyed driver (3830). Power input (3830) is shown as being in communication with one or more features of platform (3818) to drive expansion of platform (3818). Such features of platform (3818) can be driven by power input (3830) in a variety of ways. For instance, as noted above, platform (3818) of the present example can use a linkage mechanism to provide expansion thereof. Thus, in such an example, power input (3830) can be configured to rotate a lead screw or other drive mechanism to move platform (3818) from a flat configuration to an expanded configuration. Of course, in other configurations where alternative expansion mechanisms are used, power input (3830) may be varied as needed. For instance, in some examples power input (3830) can include a vacuum pump, a linear actuator, and/or etc.

Power input (3830) is configured to communicate with certain features of an end effector (3912). As will be described in greater detail below, in some examples, end effector (3912) can include certain power output or rotary drive features that can be used to power, drive, or actuate certain accessory components configured for use with end effector (3912). Accordingly, it should be understood that applicator device (3810) of the present example does not need an internal power source to operate. Instead, applicator device (3810) can be driven by an external power source including, but not limited to, certain rotary drive components integrated into end effector (3912).

As seen in FIG. 74A, applicator device (3810) is usable with end effector (3912). End effector (3912) of the present example is substantially similar to end effector (12) described above except where otherwise explicitly noted herein. For instance, like with end effector (12) described above, end effector (3912) of the present example employs a firing beam (3914) that may be used to sever and staple tissue in a single stroke. As with firing beam (14) described above, firing beam (3914) of the present example may be driven relative to an anvil (1018) and an unspent staple cartridge (3937) to sever and staple tissue. As with staple cartridge (37), staple cartridge (3937) is removably installed into a channel of a lower jaw (3916).

Unlike end effector (12) described above, end effector (3912) of the present example includes a power output (3940) or rotary driver positioned adjacent to the crotch formed by anvil (3918) and lower jaw (3916). Power output (3940) of end effector (3912) is generally configured to engage power input (3830) of applicator device (3810) to transfer power from end effector (3912) to applicator device (3810). By way of example only, power output (3940) of the present example is configured to communicate rotary motion to applicator device (3810) via power input (3830). As best seen in FIG. 75, both power input (3830) and power output (3940) are keyed relative to each other to facilitate communication of such rotary motion.

Although power input (3830) and power output (3940) of the present example are configured for communication of mechanical rotary power, it should be understood that in other examples various forms of energy can be communicated between power input (3830) and power output (3940). For instance, in some examples, power output (3940) may be configured to transmit translational motion to power input (3830). In other examples, power output (3940) may be configured to transmit electrical, hydraulic, or pneumatic power to power input (3830). In such examples, applicator device (3810) can include other components suitable to use such electrical, hydraulic, or pneumatic power such as motors, pumps, valves, filters, and/or etc. Of course, in still other examples, various alternative power transfer mechanisms may be used as will be apparent to those of ordinary skill in the art in view of the teachings herein.

FIGS. 74A and 74B show an exemplary use of adjunct applicator device (3810) with end effector (3912). As can be seen in FIG. 74A, applicator device (3810) and end effector (3912) are initially separated. In the position, platform (3818) is in the flat configuration. In addition, power input (3830) is not in communication with power output (3940), so platform (3818) cannot be transitioned to the expanded configuration. Thus, when applicator device (3810) and end effector (3912) are initially separated, power input (3830) and power output (3940) functionally act as a functional lockout feature to prevent inadvertent or premature deployment of buttress assemblies (110, 112).

Next, as can be seen in FIG. 74B, applicator device (3810) is moved into position within end effector (3912) by either moving end effector (3912) relative to applicator device (3810) or cartridge relative to end effector (3912). In this position, open end (3812) of applicator device (3810) is inserted into end effector (3912) to permit engagement between power input (3830) and power output (3940). Once power input (3830) and power output (3940) are engaged, platform (3818) can be expanded by rotating power input (3830) via power output (3940) to deploy buttress assemblies (110, 112) onto anvil (3918) and staple cartridge (3937). Because engagement between power input (3830) and power output (3940) is needed for expansion of platform (3818), it should be understood that power input (3830) and power output (3940) act as an alignment features to promote proper placement of buttress assemblies (110, 112).

In some uses, power output (3940) may be incorporated into the drive for firing beam (3914) and/or other operational components of end effector (3912). In such examples, it should be understood that power output (3940) may rotate in one direction to drive firing beam (3914) and/or other operational components of end effector (3912). Meanwhile, power output (3940) may rotate in an opposite direction to drive expansion of platform (3818) via power input (3830). In some examples, such an operational feature may be desirable to prevent inadvertent operation of end effector (3912) (e.g., firing of firing beam (3914)) prematurely such as during deployment of buttress assemblies (110, 112).

E. Exemplary Applicator Device with Locating Features

FIG. 76 shows another exemplary adjunct applicator device (4010) (also referred to as a "buttress applicator") that may be used to support, protect, and apply adjunct material, such as buttress assemblies (110, 112), to an end effector. Adjunct applicator device (4010) of the present example is substantially similar to adjunct applicator device (3410) described above except where otherwise explicitly described herein. For instance, as with applicator device (3410), applicator device (4010) of this example comprises a platform (4018) configured to expand or otherwise move to apply buttress assemblies (110, 112) to an end effector. Although not shown, it should be understood that in other examples, applicator device (4010) may also include other additional features similar to housing.

As with platform (3418) described above, platform (4018) of the present example is configured to support a pair of buttress assemblies (110) on one side of platform (4018) and another pair of buttress assemblies (112) on the other side of platform (4018). Also as with platform (3418), platform (4018) of the present example is generally configured to be expandable to apply buttress assemblies (110, 112). To support such expandability, platform (4018) includes an upper support (4020), and a lower support (4022) connected with a hinge (4026). Upper support (4020) comprises an elongate flat surface configured for support of buttress assembly (110). Meanwhile, lower support (4022) also comprises an elongate flat surface configured for support of buttress assembly (112).

Upper support (4020) is connected to lower support (4022) at hinge (4026). Hinge (4026) is positioned at the proximal end of each support (4020, 4022) such that hinge (4026) is generally configured for insertion into an end effector (12), as will be described in greater detail below. Hinge (4026) is generally configured to permit pivoting of upper support (4020) relative to lower support (4022).

Unlike platform (3418) described above, platform (4018) of the present example is configured to expand manually through actuation by an operator. To facilitate such manual expansion, platform (4018) of the present example further includes a manipulation tab (4030) and a lock tab (4032). Manipulation tab (4030) extends distally from upper support (4020) and is generally configured for gasping by an operator to manually pull or otherwise manipulate upper support (4020) about hinge (4026).

Lock tab (4032) extends distally from lower support (4022). As will be described in greater detail below, lock tab (4032) is generally configured to fasten to staple cartridge (37) of end effector (12) to secure lower support (4022) to staple cartridge (37). To facilitate such fastening, lock tab (4032) is generally shaped to correspond to the shape of the distal end of staple cartridge (37). In addition, lock tab (4032) includes a lock tooth (4034) extending proximally from a distal end of lock tab (4032). As will be understood, lock tooth (4034) is generally configured to engage a portion of staple cartridge (37) to releasably secure lock tab (4032) to staple cartridge (37).

Platform (4018) further includes an upper insert (4040) and a lower insert (4042) extending from upper support (4020) and lower support (4022), respectively. As will be described in greater detail below, both upper insert (4040) and lower insert (4042) are configured to engage portions of end effector (12)/staple cartridge (37) to provide a locating feature or mechanical ground to ensure proper positioning of applicator device (4010) within end effector (12). Lower support (4022) is additionally beneficial to detect certain features of end effector (12) (e.g., wedge sled (41)) to prevent use of applicator device (4010) with end effector (12) in an improper state (e.g., after firing of wedge sled (41)).

Upper insert (4040) extends upwardly from an upper surface of upper support (4020). The particular size and shape of upper insert (4040) is generally configured to permit receipt of upper insert (4040) into longitudinal anvil slot (42) of anvil (18). As will be understood, this configuration permits upper insert (4040) to ensure proper positioning of upper support (4020) relative to anvil (18) for proper application of buttress assembly (110). In other words, upper insert (4040) is configured to act similarly to a go-no-go gauge to prevent application of buttress assembly (110) when applicator device (4010) is misaligned or used with an improper end effector (12) entirely.

Lower insert (4042) extends downwardly from a lower surface of lower support (4022). The particular size and shape of lower insert (4042) is generally configured to permit receipt of lower insert (4042) into vertical slot (49) of staple cartridge (37). As will be understood, this configuration permits lower insert (4042) to ensure proper positioning of lower support (4022) relative to staple cartridge (37). In addition, lower insert (4042) is configured to prevent use of applicator device (4010) when staple cartridge (37) is in a fired state. As will be understood, this functionality is generally provided by lower insert (4042) being shaped to avoid wedge sled (41) when wedge sled (41) is in a home or unfired position. Meanwhile, lower insert (4042) is also shaped to contact wedge sled (41) when wedge sled (41) is in a fired position to thereby block full insertion of applicator device (4010) into end effector (12).

Figure 77A:
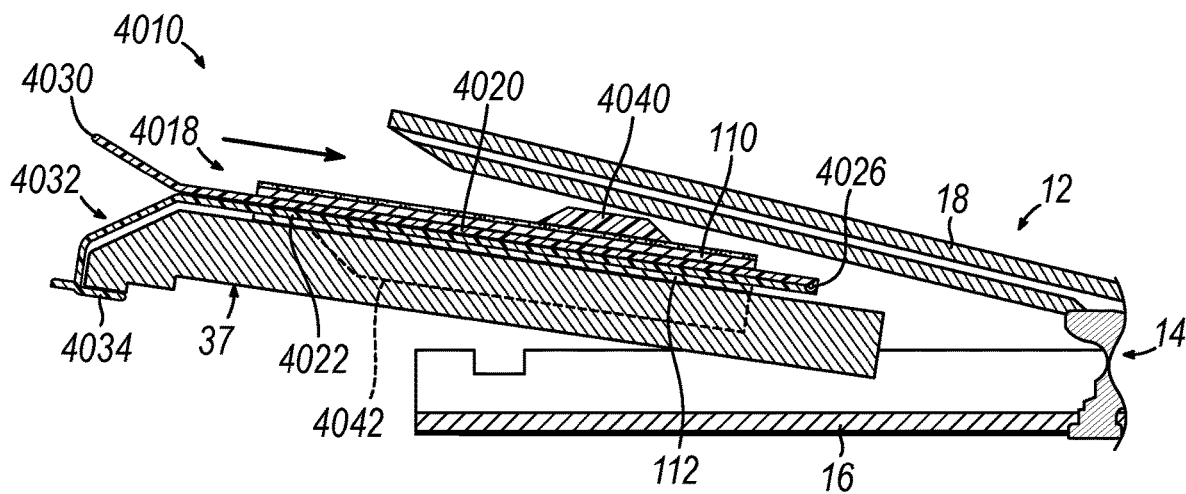
Figure 77B:
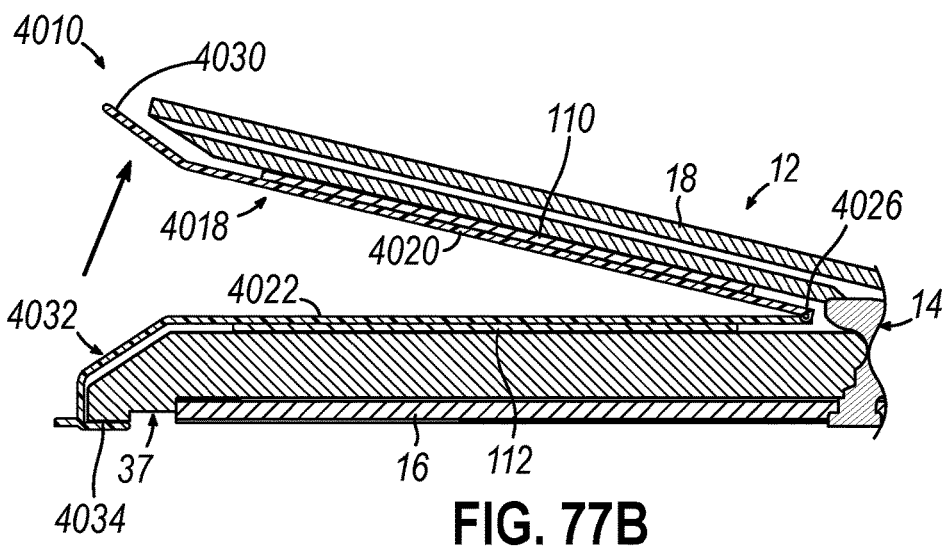
Figure 77C:
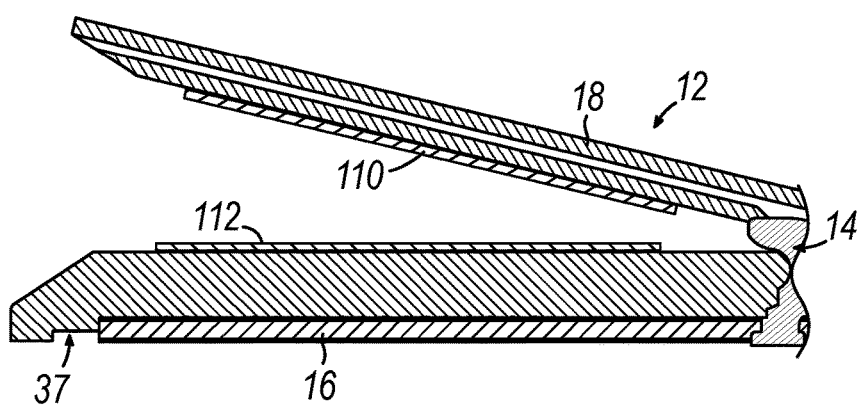

FIGS. 77A through 77C show an exemplary use of applicator device (4010) with end effector (12) to apply buttress assemblies (110, 112) to end effector (12)/staple cartridge (37). As can be seen in FIG. 77A, applicator device (4010) can initially be installed onto staple cartridge (37) prior to insertion of staple cartridge (37) into lower jaw (16) of end effector (12). Applicator device (4010) can be installed onto staple cartridge (37) by inserting lower insert (4042) into vertical slot (49) of staple cartridge (37) and then snapping lock tab (4032) onto the distal end of staple cartridge (37). Incidentally, the step of installing applicator device (4010) onto staple cartridge (37) may also include application of buttress assembly (112) to upper deck (72) of staple cartridge (37).

Although the present use shows applicator device (4010) being installed onto staple cartridge (37) prior to insertion of staple cartridge (37) into lower jaw (16) of end effector (12), it should be understood that in other uses, staple cartridge (37) may be readily inserted into lower jaw (16) first. In such an alternative use, applicator device (4010) may then be installed onto staple cartridge (37) once staple cartridge (37) is inserted into lower jaw (16).

Regardless of the particular order of installation of applicator device (4010) to staple cartridge (37) and staple cartridge (37) to lower jaw (16), once both components are installed, upper support (4020) of applicator device (4010) may be used to apply buttress assembly (110). In particular, and as best seen in FIG. 77B, buttress assembly (110) can be applied by an operator grasping manipulation tab (4030) and pivoting upper support (4020) about hinge (4026) upwardly towards anvil (18). Upper insert (4040) can then be received by longitudinal anvil slot (42) to ensure proper alignment between upper support (4020) and anvil (18). Upon receipt of upper insert (4040) into longitudinal anvil slot (42), upper support (4020) may be further pivoted about hinge (4026) to apply buttress assembly (110) to anvil (18).

After buttress assembly (110) is applied to anvil (18) as described above, applicator device (4010) can be removed from end effector (12) as shown in FIG. 77C. With applicator device (4010) removed, end effector (12) may then be used in a procedure.

F. Exemplary Applicator Device with Reuse Lockout Feature

Figure 78:
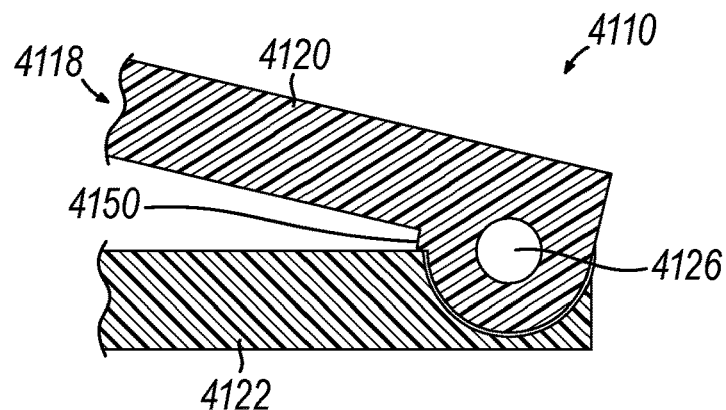

In some adjunct applicator devices similar to adjunct applicator device (4010) described above, it may be desirable to include certain features to prevent or discourage reuse of the cartridge after application of buttress assemblies (110, 112). FIG. 78 shows an exemplary alternative adjunct applicator device (4110) that is substantially similar to adjunct applicator device (4010) described above unless otherwise explicitly described herein. For instance, like with applicator device (4010), applicator device (4110) of this example includes a platform (4118) having an upper support (4120) and a lower support (4122). Although not shown, it should be understood that upper support (4120) and lower support (4122) may include structures similar manipulation tab (4030), lock tab (4032), upper insert (4040) and lower insert (4042).

Applicator device (4110) also includes a hinge (4126) similar to hinge (4026) described above. However, unlike hinge (4026), hinge (4126) of the present example includes a one-way stop (4150). One-way stop (4150) is generally configured to act as a ratchet mechanism by permitting hinge (4126) to open, while preventing complete re-closure after opening. In the present example, one-way stop (4150) is configured as a protrusion or detent feature integrated into a portion of hinge (4126) to permit rotation of upper support (4120) in one direction, but prevent rotation of upper support (4120) in another direction after upper support (4120) has passed a certain predetermined point of rotation.

Although one-way stop (4150) is shown in the present example as being integrated into hinge (4126), it should be understood that in other examples, one-way stop (4150) can be readily integrated into other components of applicator device (4110). Alternatively, in other examples, one-way stop (4150) can be an entirely separate component attached to one or more elements of applicator device (4110). Various alternative configurations for one-way stop (4150) will be apparent to those of ordinary skill in the art in view of the teachings herein.

In use, applicator device (4110) can be used as similarly described above with respect to applicator device (4010). For instance, applicator device (4110) can be first installed onto staple cartridge (37). The combination of applicator device (4110) and staple cartridge (37) can then be inserted into lower jaw (16) of end effector (12). Upper support (4120) can then be pivoted about hinge relative to lower support (4122) to apply buttress assembly (110). However, unlike the use described above, it should be understood that once support (4120) is pivoted past a certain point, one-way stop (4150) functions to prevent pivoting in the reverse direction. Thus, upon removal of applicator device (4110) after application of buttress assemblies (110, 112), applicator device (4110) may remain in an at least partially open state to provide an affirmative indication of previous use and thereby discourage reuse thereof. Although one-way stop (4150) prevents some reverse pivoting of upper support (4120), it should be understood that at least some reverse pivoting may still be permitted to permit removal of applicator device (4110) from end effector (12) after application of buttress assemblies (110, 112).

G. Exemplary Applicator Device with Liner

In examples, it may be desirable to use buttress assemblies (110, 112) described above with a single-use pre-applied liner. Such a liner may be desirable to protect buttress assemblies (110, 112) until application thereof onto an end effector. As can be seen in FIG. 79A shows adjunct applicator device (4010) described above with an added liner (4050) disposed over buttress assembly (110). Although liner (4050) is described herein as being used with applicator device (4010), it should be understood that liner (4050) described below can be alternatively used with any other applicator device (210, 3310, 3410, 3610, 3710, 4110) described herein.

Liner (4050) of the present example is a single material covering that is configured to cover buttress assembly (110). In the present example, liner (4050) comprises a material of paper or polymer. In other examples, various alterative materials can be used. Additionally, in addition or in the alternative, such materials of liner (4050) can be coated with one or more coating layers of various materials such as wax, polymer, alloy, combinations of different materials, and/or etc.

Liner (4050) includes a cover portion (4052) and an excess portion (4054). Cover portion (4052) corresponds to the size and shape of buttress assembly (110) to cover buttress assembly (110). Meanwhile, excess portion (4054) extends proximally from buttress assembly (110). As will be described in greater detail below, excess portion (4054) is generally configured to engage a portion of end effector (12) to provide a visual cue for removal of liner (4050).

FIGS. 79A and 79B show an exemplary use of applicator device (4010) with liner (4050). It should be understood that use of applicator device (4010) with liner (4050) is substantially similar to the use described above with respect to FIGS. 77A through 77C, unless otherwise explicitly described herein. For instance, as described above, applicator device (4010) may be first installed onto staple cartridge (37) and then both applicator device (4010) and staple cartridge (37) can be inserted into lower jaw (16) of end effector (12). However, unlike the use described above, in the use here, liner (4050) is pre-applied to applicator device (4010) such that liner (4050 is also inserted into lower jaw (16) along with applicator device (4010) and staple cartridge (37) as can be seen in FIG. 79A.

As applicator device (4010) is inserted into lower jaw (16), excess portion (4054) engages the crotch of end effector (12) formed at the intersection of lower jaw (16) and anvil (18). This engagement causes excess portion (4054) of liner (4050) to compact, roll, or bunch-up in the space between the crotch of end effector (12) and buttress assembly (110). This change of excess portion (4054) may provide an operator with a visual cue to remind the operator to remove liner (4050) prior to proceeding. Although not show, it should be understood that in some examples such functionality of excess portion (4045) can be added by excess portion (4045) including a T-shaped or otherwise expanded proximal end to avoid the possibility of excess portion (4045) remaining longitudinally extended by entering portions of end effector (12).

Liner (4050) can next be removed by an operator gasping excess portion (4045) or other portions of liner (4050) configured to aid removal (e.g., a removal tab). Once liner (4050) is removed, buttress assembly (110) can then be applied to anvil (18) by an operator gasping manipulation tab (4030) and pivoting upper support (4020) as similarly described above with respect to FIG. 77B. Applicator device (4010) can then be removed and end effector (12) can be readily used in a procedure.

IX. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of applying an adjunct element to an end effector of a surgical stapler using an applicator, wherein the end effector includes a first stapling surface having a plurality of staple openings and a second stapling surface having a plurality of staple forming pockets, the method comprising: (a) providing the end effector in an open state in which the first and second stapling surfaces are spaced apart from one another; (b) with the end effector in the open state, positioning at least a portion of the applicator between the first and second stapling surfaces; (c) without engaging a closure system input feature of the surgical stapler, compressively engaging a portion of the end effector with the applicator to thereby secure the adjunct element to one of the first stapling surface or the second stapling surface; and (d) withdrawing the applicator and the end effector relatively away from one another so that the adjunct element remains attached to the one of the first stapling surface or the second stapling surface of the end effector.

Example 2

The method of Example 1, wherein the adjunct element is releasably attached to the applicator.

Example 3

The method of Example 2, wherein the adjunct element comprises a first adjunct element, wherein the applicator further includes a second adjunct element, wherein the method further comprises securing the first adjunct element to the first stapling surface and securing the second adjunct element to the second stapling surface.

Example 4

The method of any of the preceding Examples, wherein the applicator is configured to transition between a plurality of angular orientations in each of which the applicator defines a distally opening angle.

Example 5

The method of Example 4, wherein the applicator includes a base and a body configured to releasably couple with the base in each of the angular orientations.

Example 6

The method of any of the preceding Examples, wherein the method further comprises transitioning the applicator from a non-expanded state to an expanded state to thereby advance the adjunct element in a direction toward the one of the first stapling surface or the second stapling surface, wherein the applicator defines a distally opening angle in the expanded state.

Example 7

The method of Example 6, wherein the applicator includes a first contact feature and a second contact feature that are movable relative to one another between the non-expanded state and the expanded state, wherein the first contact feature is configured to engage the first stapling surface and the second contact member is configured to engage the second stapling surface.

Example 8

The method of any of Examples 6 through 7, wherein transitioning the applicator from the non-expanded state to the expanded state comprises actuating the applicator with a motor.

Example 9

The method of any of Examples 6 through 8, wherein transitioning the applicator from the non-expanded state to the expanded state comprises inflating a portion of the applicator with a fluid.

Example 10

The method of any of Examples 6 through 9, wherein the end effector includes a first jaw that defines the first stapling surface and a second jaw that defines the second stapling surface, wherein the applicator includes a first contact feature and a second contact feature movable relative to one another, wherein compressively engaging a portion of the end effector with the applicator comprises engaging one of the first or second stapling surfaces with the first contact feature and simultaneously engaging an outer jaw surface disposed opposite the one of the first or second stapling surfaces with the second contact feature.

Example 11

The method of Example 10, wherein the first and second contact features are resiliently biased toward one another.

Example 12

The method of any Examples 6 through 11, further comprising engaging a first predetermined portion of the end effector with a second predetermined portion of the applicator, wherein the act of engaging the first and second predetermined portions with one another permits the applicator to transition from the non-expanded state to the expanded state, wherein the applicator remains in the non-expanded state prior to engagement of the first and second predetermined portions with one another.

Example 13

The method of any of Example 12, wherein the applicator further includes an actuator, wherein the method further comprises transitioning the applicator from the non-expanded state to the expanded state with the actuator in response to the first and second predetermined portions engaging one another.

Example 14

The method of any of the preceding Examples, wherein the end effector includes a first jaw that defines the first stapling surface and a second jaw that defines the second stapling surface, wherein compressively engaging a portion of the end effector includes engaging an outer jaw surface of one of the first jaw or the second jaw with the applicator to urge the end effector toward a closed state in which the adjunct element is compressed against the one of the first stapling surface or the second stapling surface.

Example 15

The method of Example 14, wherein the applicator includes a translatable member, wherein engaging the outer jaw surface of the applicator includes actuating the translatable member distally relative to the end effector to thereby engage the outer jaw surface.

Example 16

A method of applying first and second adjunct elements to an end effector of a surgical stapler using an applicator, wherein the end effector includes a first stapling surface having a plurality of staple openings and a second stapling surface having a plurality of staple forming pockets, the method comprising: (a) providing the end effector in an open state in which the first and second stapling surfaces are spaced apart from one another; (b) with the end effector in the open state, positioning the applicator at least partially between the first and second stapling surfaces such that the first adjunct element faces toward the first stapling surface and the second adjunct element faces toward the second stapling surface; (c) with the end effector in the open state, advancing the applicator and the end effector relatively toward one another so that the first adjunct element engages the first stapling surface and the second adjunct element engages the second stapling surface; and (d) with the end effector in the open state, withdrawing the applicator and the end effector relatively away from one another so that the first and second adjunct elements separate from the applicator while remaining attached to the first and second stapling surfaces, respectively, of the end effector.

Example 17

The method of Example 16, wherein the applicator includes a first contact member that supports the first adjunct element and a second contact member that supports the second adjunct element.

Example 18

The method of any of Examples 16 through 17, wherein the first and second contact members of the applicator are configured to define a distally opening angle.

Example 19

A method of applying an adjunct element to an end effector of a surgical stapler using an applicator, wherein the end effector includes a first stapling surface having a plurality of staple openings and a second stapling surface having a plurality of staple forming pockets, the method comprising: (a) providing the end effector in an open state in which the first and second stapling surfaces are spaced apart from one another; (b) with the end effector in the open state, positioning at least a portion of the applicator between the first and second stapling surfaces; (c) transitioning the applicator from a non-expanded state to an expanded state to advance the adjunct element in a direction toward one of the first or second stapling surfaces; (d) with the end effector in the open state and the applicator in the expanded state, engaging the one of the first or second stapling surfaces with the adjunct element and thereby securing the adjunct element to the one of the first or second stapling surfaces; and (e) with the end effector in the open state, withdrawing the applicator and the end effector relatively away from one another so that the adjunct element separates from the applicator while remaining attached to the end effector.

Example 20

The method of Example 19, further comprising engaging a first predetermined portion of the end effector with a second predetermined portion of the applicator, wherein the act of engaging the first and second predetermined portions with one another permits the applicator to transition from the non-expanded state to the expanded state.

X. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/022,186, entitled "Apparatus and Method to Apply Buttress to End Effector of Surgical Stapler via Fixed Base," filed on Sep. 16, 2020, published as U.S. Pub. No. 2022/0079592 on Mar. 17, 2022; U.S. patent application No. 17/022,209, entitled "Apparatus and Method to Apply Buttress to End Effector of Surgical Stapler via Driven Member," filed on Sep. 16, 2020, issued as U.S. Pat. No. 11,564,683 on Jan. 31, 2023; U.S. patent application Ser. No. 17/022,214, entitled "Apparatus and Method to Apply Buttresses Separately to Jaws of End Effector of Surgical Stapler," filed on Sep. 16, 2020, issued as U.S. Pat. No. 11,452,523 on Sep. 27, 2022; U.S. patent application No. 17/022,414, entitled "Apparatus and Method to Close End Effector of Surgical Stapler onto Buttress," filed on Sep. 16, 2020, issued as U.S. Pat. No. 11,419,605 on Aug. 23, 2022; U.S. patent application Ser. No. 17/022,419, entitled "Apparatus and Method to Detect Full Seating of Adjunct applicator device in End Effector of Surgical Stapler," filed on Sep. 16, 2020, issued as U.S. Pat. No. 11,559,306 on Jan. 24, 2023; and/or U.S. patent application Ser. No. 17/022,442, entitled "Apparatus and Method to Apply Buttress to End Effector of Surgical Stapler with Authentication," filed on Sep. 16, 2020, issued as U.S. Pat. No. 11,413,040 on Aug. 16, 2022. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of applying an adjunct element to an end effector of a surgical stapler using an applicator, wherein the end effector includes a first stapling surface having a plurality of staple openings and a second stapling surface having a plurality of staple forming pockets, the method comprising:
   (a) providing the end effector in an open state in which the first and second stapling surfaces are presented by the end effector and are spaced apart from one another and from the applicator;
   (b) with the end effector in the open state, positioning at least a portion of the applicator between the first and second stapling surfaces;
   (c) inflating a portion of the applicator with a fluid to transition the applicator from a non-expanded state to an expanded state to thereby advance the adjunct element in a direction toward one of the first stapling surface or the second stapling surface, wherein the applicator defines a distally opening angle in the expanded state;
   (d) without engaging a closure system input feature of the surgical stapler, compressively engaging a portion of the end effector with the applicator to thereby secure the adjunct element to one of the first stapling surface or the second stapling surface; and
   (e) withdrawing the applicator and the end effector relatively away from one another so that the adjunct element remains attached to the one of the first stapling surface or the second stapling surface of the end effector.

2. The method of claim 1, wherein the adjunct element is releasably attached to the applicator.

3. The method of claim 2, wherein the adjunct element comprises a first adjunct element, wherein the applicator further includes a second adjunct element, wherein the method further comprises securing the first adjunct element to the first stapling surface and securing the second adjunct element to the second stapling surface.

4. The method of claim 1, wherein the applicator is configured to transition between a plurality of angular orientations in each of which the applicator defines a distally opening angle.

5. The method of claim 4, wherein the applicator includes a base and a body configured to releasably couple with the base in each of the angular orientations.

6. The method of claim 1, wherein the applicator includes a first contact feature and a second contact feature that are movable relative to one another between the non-expanded state and the expanded state, wherein the first contact feature is configured to engage the first stapling surface and the second contact member is configured to engage the second stapling surface.

7. The method of claim 1, wherein transitioning the applicator from the non-expanded state to the expanded state comprises actuating the applicator with a motor.

8. The method of claim 1, wherein the end effector includes a first jaw that defines the first stapling surface and a second jaw that defines the second stapling surface, wherein the applicator includes a first contact feature and a second contact feature movable relative to one another, wherein compressively engaging a portion of the end effector with the applicator comprises engaging one of the first or second stapling surfaces with the first contact feature and simultaneously engaging an outer jaw surface disposed opposite the one of the first or second stapling surfaces with the second contact feature.

9. The method of claim 8, wherein the first and second contact features are resiliently biased toward one another.

10. The method of claim 1, further comprising engaging a first predetermined portion of the end effector with a second predetermined portion of the applicator, wherein the act of engaging the first and second predetermined portions with one another permits the applicator to transition from the non-expanded state to the expanded state, wherein the applicator remains in the non-expanded state prior to engagement of the first and second predetermined portions with one another.

11. The method of claim 10, wherein the applicator further includes an actuator, wherein the method further comprises transitioning the applicator from the non-expanded state to the expanded state with the actuator in response to the first and second predetermined portions engaging one another.

12. The method of claim 1, wherein the end effector includes a first jaw that defines the first stapling surface and a second jaw that defines the second stapling surface, wherein compressively engaging a portion of the end effector includes engaging an outer jaw surface of one of the first jaw or the second jaw with the applicator to urge the end effector toward a closed state in which the adjunct element is compressed against the one of the first stapling surface or the second stapling surface.

13. A method of applying first and second adjunct elements to an end effector of a surgical stapler using an applicator having a body portion and a base portion, wherein the end effector includes a first stapling surface having a plurality of staple openings and a second stapling surface having a plurality of staple forming pockets, the method comprising:
   (a) providing the end effector in an open state in which the first and second stapling surfaces are spaced apart from one another;

(b) with the end effector and the applicator spaced apart from one another, removably coupling the body portion of the applicator with the base portion of the applicator in a predefined position, wherein the body portion supports the first and second adjunct elements and is configured to removably couple with the base portion in a plurality of predefined positions and define a respective predefined angle in each of the predefined positions;

(c) with the end effector in the open state, positioning the body portion of the applicator at least partially between the first and second stapling surfaces such that the first adjunct element faces toward the first stapling surface and the second adjunct element faces toward the second stapling surface;

(d) with the end effector in the open state, advancing the applicator and the end effector relatively toward one another so that the first adjunct element engages and overlies the first stapling surface and the second adjunct element engages and overlies the second stapling surface while the body portion remains stationary relative to the base portion; and (e) with the end effector in the open state, withdrawing the applicator and the end effector relatively away from one another so that the first and second adjunct elements separate from the applicator while remaining attached to the first and second stapling surfaces, respectively, of the end effector.

14. The method of claim 13, wherein the body portion of the applicator includes a first contact member that supports the first adjunct element and a second contact member that supports the second adjunct element.

15. The method of claim 14, wherein the first and second contact members of the applicator are configured to define the respective distally opening angle in each of the predefined positions.

16. A method of applying an adjunct element to an end effector of a surgical stapler using an applicator having a flexible body with a hollow interior, wherein the end effector includes a first stapling surface having a plurality of staple openings and a second stapling surface having a plurality of staple forming pockets, the method comprising:

(a) providing the end effector in an open state in which the first and second stapling surfaces are presented by the end effector and are spaced apart from one another and from the applicator;

(b) with the end effector in the open state, positioning at least a portion of the applicator between the first and second stapling surfaces;

(c) inflating the hollow interior to thereby transition the applicator from a non-expanded state to an expanded state to advance the adjunct element in a direction toward one of the first or second stapling surfaces, wherein the applicator defines a distally opening angle in the expanded state;

(d) with the end effector in the open state and the applicator in the expanded state, engaging the one of the first or second stapling surfaces with the adjunct element and thereby securing the adjunct element to the one of the first or second stapling surfaces; and (e) with the end effector in the open state, withdrawing the applicator and the end effector relatively away from one another so that the adjunct element separates from the applicator while remaining attached to the end effector.

17. The method of claim 16, further comprising engaging a first predetermined portion of the end effector with a second predetermined portion of the applicator, wherein the act of engaging the first and second predetermined portions with one another permits the applicator to transition from the non-expanded state to the expanded state.

18. The method of claim 1, wherein the applicator is wedge shaped to allow for compressive engagement with both the first and second stapling surfaces.

19. The method of claim 1, wherein the step of inflating a portion of the applicator is performed using a syringe.

20. The method of claim 1, wherein the step of inflating a portion of the applicator is performed using a pump.

* * * * *